(12) United States Patent
Corti et al.

(10) Patent No.: US 11,723,977 B2
(45) Date of Patent: *Aug. 15, 2023

(54) BROADLY NEUTRALIZING ANTIBODIES DIRECTED AGAINST THE RABIES VIRUS GLYCOPROTEIN AND USES THEREOF

(71) Applicants: HUMABS BIOMED SA, Bellinzona (CH); INSTITUT PASTEUR, Paris (FR)

(72) Inventors: Davide Corti, Bellinzona (CH); Hervé Bourhy, Chaville (FR)

(73) Assignees: Institut Pasteur, Paris (FR); Humabs Biomed SA, Bellinzona (CH)

(*) Notice: Subject to any disclaimer, the term of this patent is extended or adjusted under 35 U.S.C. 154(b) by 315 days.

This patent is subject to a terminal disclaimer.

(21) Appl. No.: 16/882,359

(22) Filed: May 22, 2020

(65) Prior Publication Data

US 2020/0354436 A1    Nov. 12, 2020

Related U.S. Application Data

(62) Division of application No. 15/527,511, filed as application No. PCT/EP2015/002305 on Nov. 18, 2015, now Pat. No. 10,703,801.

(51) Int. Cl.
| | |
|---|---|
| *A61K 39/42* | (2006.01) |
| *C07K 16/10* | (2006.01) |
| *A61K 39/00* | (2006.01) |
| *A61P 31/14* | (2006.01) |

(52) U.S. Cl.
CPC .............. *A61K 39/42* (2013.01); *C07K 16/10* (2013.01); *A61K 2039/505* (2013.01); *A61K 2039/507* (2013.01); *A61P 31/14* (2018.01); *C07K 2317/21* (2013.01); *C07K 2317/33* (2013.01); *C07K 2317/34* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/76* (2013.01); *C07K 2317/92* (2013.01); *C12N 2760/20111* (2013.01)

(58) Field of Classification Search
CPC ................................ A61K 39/42; C07K 16/10
See application file for complete search history.

(56) References Cited

FOREIGN PATENT DOCUMENTS

| WO | 2006/084006 A1 | 8/2006 |
|---|---|---|
| WO | 2011/080765 A2 | 7/2011 |

OTHER PUBLICATIONS

Traggiai, E., et al., Aug. 2004, An efficient method to make human monoclonal antibodies from memory B cells: potent neutralization of SARS coronavirus, Nat. Med. 10(8):871-875.*

Tiller, T., et al., 2008, Efficient generation of monoclonal antibodies from single human B cells by single cell RT-PCR and expression vector cloning, J. Immunol. Meth. 329:112-124.*

"Scientific Report 2013-2014 Institute for Research in Biomedicine", Jul. 1, 2015 (Jul. 1, 2015), XP055244996, Retrieved from the Internet: URL: http://www.irb.usi.ch/sites/www.irb.usi/ch/files/media/attachments/scientific_report_2013-2014.pdf [retrieved on Jan. 26, 2016].

Bakker, A. B. H. et al: "Novel Human Monoclonal Antibody Combination Effectively Neutralizing Natural Rabies Virus Variants and Individual In Vitro Escape Mutants", Journal of Virology, The American Society for Microbiology, US, vol. 79, No. 14, Jul. 1, 2005 (Jul. 1, 2005), pp. 9062-9068.

Both, L. et al: "Production, characterization, and antigen specificity of recombinant 62-71-3, a candidate monoclonal antibody for rabies prophylaxis in humans", The FASB Journal, vol. 27, No. 5, Jan. 31, 2013 (Jan. 31, 2013), pp. 2055-2065.

Cai, K. et al: "Fine mapping and interaction analysis of a linear rabies virus neutralizing epitope", Microbes and Infection, Elsevier, Paris, FR, vol. 12, No. 12-13, Nov. 1, 2010 (Nov. 1, 2010}, pp. 948-955.

Corti, D. et al: "Broadly Neutralizing

(56) References Cited

OTHER PUBLICATIONS

Winkler et al., "Changing the Antigen Binding Specificity by Single Point Mutations of an Anti-p24 (HIV-1) Antibody[1]," *J. Immunol.* 765:4505-4514, 2000.

Xiang et al., "Light-chain framework region residue Tyr71 of chimeric B72.3 antibody plays an important role in influencing the TAG72 antigen binding," *Protein Engineering* 12(5):417-421, Feb. 10, 1999.

\* cited by examiner

| Isolate name | Host species | Country of origin | Year | Viral species | Phylogroup | Lineage | Accession number |
|---|---|---|---|---|---|---|---|
| 9704 | Tadarida brasiliensis (Mexican free-tailed bat) | Argentina | 1997 | RABV | I | Bat (American Indigenous) | |
| Botswana/dog/BNVL2009-3580/V5493-2010 | Canis familiaris (dog) | Botswana | 2009 | RABV | I | Cosmopolitan (ex Africa 1) | |
| Botswana/honey badger/BNVL2009-6665/V5493-2010 | Mellivora capensis (honey badger) | Botswana | 2009 | RABV | I | Africa 3 | |
| Burkina Faso/dog/139-2007/V6155-2007 | Canis familiaris (dog) | Burkina Faso | 2007 | RABV | I | Africa 2 | |
| Burkina Faso/dog/9-2007/V6155-2007 | Canis familiaris (dog) | Burkina Faso | 2007 | RABV | I | Africa 2 | |
| 2045 | Canis familiaris (dog) | China | 2002 | RABV | I | Asian 1 or 2a (China) | |
| France/red fox/GS7 1-11-1990/V1039-2011 | Vulpes vulpes (red fox) | France | 1990 | RABV | I | Cosmopolitan-Western Europe | |
| Pasteur Virus (PV)-Paris-93127 | na | France | na | RABV | I | na | |
| 9001 | Canis familiaris (from vampire bat virus) | French Guyana | 1990 | RABV | I | Bat (American Indigenous) | |
| Italy/dog/V3425/2009 | Canis familiaris (dog) | Italy | 2009 | RABV | I | Cosmopolitan-Western Europe | |
| Italy/human/V117/1996 (Nepal) | Homo sapiens | Italy | 1996 | RABV | I | Arctic-like-1 | |
| Italy/red fox/V673/2011 | Vulpes vulpes (red fox) | Italy | 2011 | RABV | I | Cosmopolitan-Western Europe | |
| Brazil/bat/260-08/RS1249-2013 | Bat/Mus musculus* | Brazil | 2008 | RABV | I | Bat (American indigenous) | |
| Brazil/bovine/303-2011/RS1040-2012 | Bos taurus (cows) | Brazil | 2011 | RABV | I | Bat (American indigenous) | |
| Brazil/kinkajou/RS3609-5-2011 | Potos flavus (kinkajou) | Brazil | 2008 | RABV | I | Bat (American indigenous) | |
| Challenge virus strain (CVS)-11 | na | Lab strain | na | RABV | I | na | EU352767 |
| 9508SAD BERN | na | Lab strain | na | RABV | I | na | |
| Niger/Dog/105-251-2007/V6097-2007 | Canis familiaris (dog) | Niger | 2007 | RABV | I | Africa 2 | |
| 4030 | Homo sapiens | Phillipines | 2004 | RABV | I | Asian 2b (Philippines) | |
| Poland/racoon dog/1985/V3229-2009 | Nyctereutes procyonoides (racoon dog) | Poland | 1985 | RABV | I | Cosmopolitan, North-Eastern Europe | |
| 9141 | Vulpes lagopus (arctic fox) | Siberia, Russia | 1988 | RABV | I | Arctic 2 (Siberia) | |
| Spain/dog/201020958-2010/RS639-2012 | Canis familiaris (dog) | Spain (ex Morocco) | 2010 | RABV | I | Cosmopolitan (ex Africa 1) | |
| 8743 | Homo sapiens | Thailand | 1983 | RABV | I | Asian 2c (south East Asia) | |
| Tunisia/dog/ARIANA2-1991/V3951-2010 | Canis familiaris (dog) | Tunisia | 1991 | RABV | I | Cosmopolitan (ex Africa 1) | |
| ERA (Evelyn Rokitniki Abelseth) | na | na | na | RABV | I | na | |
| CVS 9.13 | | Lab strain | | RABV | I | na | |
| RV250 | Urocitellus undulatus (long-tailed ground squirrel) | Russia (Tuva) | | RABV | I | Arctic-like | |
| RV193 | Canis familiaris (dog) | Pakistan | 1989 | RABV | I | Arctic-like | |
| RV277 | Capra aegagrus hircus (goat) | Pakistan | | RABV | I | Arctic-like | |
| RV61 | Canis familiaris (dog) | India | 1987 | RABV | I | Arctic-like | |
| 93033ISR | Canis familiaris (dog) | Israel | 1993 | RABV | I | Cosmopolitan, Middle East | |
| 86081IRA | Canis familiaris (dog) | Iran | 1985 | RABV | I | Cosmopolitan, Middle East | |
| 91004USA | Mephitis mephitis (skunk) | USA | 1991 | RABV | I | Arctic related, arctic 1 | |
| Mauritania/dog/2019-2006/V6235-2007 | Canis familiaris (dog) | Mauritania | 2007 | RABV | I | Africa 2 | |
| Pittman More strain (PM) (PV12?) | Canis familiaris (dog) | USA? (lab strain) | na | RABV | I | na | |

Figure 1

| Isolate name | Host species | Country of origin | Year | Viral species | Phylogroup | Lineage | Accession number |
|---|---|---|---|---|---|---|---|
| 87006TU | Vulpes vulpes (fox) | Turkey | 1987 | RABV | I | Cosmopolitan, America | |
| 91001USA | Mephitis mephitis (skunk) | USA | 1991 | RABV | I | Cosmopolitan, America | |
| 91035OMA | Vulpes vulpes (fox) | Oman | 1991 | RABV | I | Arctic related, arctic like 1b | |
| 98011CHI | Canis familiaris (dog) | Chile | 1998 | RABV | I | Asia, China, Clade II | |
| 09029NEP | Bubalus arnee (wild water buffalo) | Nepal | 2003 | RABV | I | Indian subcontinent | |
| 02052AFG | Canis familiaris (dog) | Afghanistan | 2002 | RABV | I | Cosmopolitan, Middle East | |
| FLRCC90148 | Nycterutes procyonoides (racoon dog) | USA | 2009 | RABV | I | Cosmopolitan, America | AGE31951 |
| RV/R3.PHL/2008/TRa-065 | Canis familiaris (dog) | Phillipines | 2008 | RABV | I | Asian 2b (Philippines) | BAN14123 |
| ABLV/Australia/bat/98:0AUS-1998/V1039-2011 | Pteropus alecto (Black flying fox) | Australia | 1996 | ABLV | I | | NA |
| 98010 | Saccolaimus flaviventris (Insectivorous bat) | Australia | 1996 | ABLV | I | | AAD47899.1 |
| 1301 Bokeloh bat lyssavirus | Myotis nattererii (Natterer's bat) | France | 2013 | BBLV | I | | NA |
| 86132SA | Homo sapiens | South Africa | 1971 | DUVV | I | | NA |
| DUVV/SouthAfrica/human/96132SA-1971/RS639-2012 | Homo sapiens | South Africa | ? | DUVV | I | | NA |
| EBLV1a/France/bat/122938-2002/V3951-2009 | Eptesicus serotine (serotine bat) | France | 2002 | EBLV-1 | I | | NA |
| EBLV1b/France/bat/8918-1989 | Eptesicus serotine (serotine bat) | France | 1989 | EBLV-1 | I | | EU293112 |
| EBLV2/UK/bat/RV1332-2002/V3951-2009 | Myotis daubentonii (Daubenton's bat) | UK | 2002 | EBLV-2 | I | | NA |
| 94112 | Myotis dasycneme (pond bat) | Netherainds | 1989 | EBLV-2 | I | | NA |
| 2053 | Myotis daubentonii (Daubenton's bat) | Switzerland | 2002 | EBLV-2 | I | | NA |
| 8619 | Eidolon helvum (straw-coloured fruit bat) | Nigeria | 1956 | LBV | II | | NA |
| MOK | Felis catus (domestic cat) | Zimbabwe | 1981 | MOK | II | | NA |
| Shimoni bat Virus | Hipposideros commersoni (leaf-nosed bat) | Kenya | 2009 | SHIBV | II | | NA |
| West Caucasian bat Virus | Miniopterus schreibersi (common bent-wing bat) | Russia | 2002 | WCBV | III | | NA |
| Australian bat lyssavirus/RV634 | Pteropus alecto (black flying fox) | Australia | 1996 | ABLV | I | | AAP86775.1 |
| Aravan Virus | Myotis blythi (Lesser mouse-eared bat) | Kyrgyzstan | 1991 | ARAV | I | | EU623444 |
| Duvenhage Virus RSA2006 | Homo sapiens | South Africa | 2006 | DUVV | I | | NA |
| Duvenhage Virus ZIM86-RV131 | Nycteris thebaica (Egyptian slit-faced bat) | Zimbabwe | 1986 | DUVV | I | | NA |
| European bat lyssavirus 1.RV20 | Eptesicus serotinus (serotine bat) | Denmark | 1986 | EBLV-1 | I | | EU352768 |
| European bat lyssavirus 1.RV9 | Eptesicus serotinus (serotine bat) | Germany | 1968 | EBLV-1 | I | | NA |
| EBLV1a/France/bat/122938-2002/V3951-2009 | Eptesicus serotinus (serotine bat) | France | 2002 | EBLV-1 | I | | NA |
| EBLV2/UK/bat/RV1332-2002/V3951-2009* | Myotis daubentonii (Daubenton's bat) | UK | 2002 | EBLV-2 | I | | NA |
| European bat lyssavirus 2.RV1787 | Myotis daubentonii (Daubenton's bat) | UK | 2004 | EBLV-2 | I | | EU352769 |
| European bat lyssavirus 2.RV628 | Myotis daubentonii (Daubenton's bat) | UK | 1996 | EBLV-2 | I | | NA |
| Irkut Virus | Murina leucogaster ( greater tube-nosed bat) | Russia | 2002 | IRKV | I | | NA |
| Khujand Virus | Myotis mystacinus (whiskered bat) | Tajikistan | 2001 | KHUV | I | | AAP86779.1 |
| 8619 | Eidolon helvum (straw-coloured fruit bat) | Nigeria | 1956 | LBV | II | | NA |
| Lagos Bat Virus NIG56-RV1 | Eidolon helvum (straw-coloured fruit bat) | Nigeria | 1956 | LBV | II | | EF547431 |
| Lagos Bat Virus SA2004 | Epomophorus wahlbergi (Wahlberg's epauletted fruit b | South Africa | 2004 | LBV | II | | EF547428 |
| Mokola Virus NIG68.RV4 | Crocidura sp. (white-toothed shrews) | Nigeria | 1968 | MOK | II | | HM623780 |
| Mokola Virus 98/071 RA361 | Felis catus (domestic cat) | South Africa | 1998 | MOK | II | | GQ500108 |
| Ikoma virus | Civettictis civetta (African civet) | Tanzania | 2009 | IKOV | IV | | AFQ62097 |

| | | Isotype | HEAVY CHAIN | | | | | LIGHT CHAIN | | | | CVS-11 pp-neutralization | WB | |
|---|---|---|---|---|---|---|---|---|---|---|---|---|---|---|
| | Donor | | VH | % nts | JH | % nts | DH | VL/VK | % nts | JL/JK | % nts | (IC90 ng/ml) | Non-red. | Red. |
| CR057 | | IgG1 λ | V1-69*01 | na | J5*02 | na | D3-10*02 | VL2-11*02 | na | JL2*01 | na | 1 | ++ | - |
| CR4098 | | IgG1 κ | V3-33*03 | na | J4*02 | na | D6-19*01 | VK1-17*01 | na | JK1*01 | na | 8 | ++ | - |
| RVA122 | A | IgG1 λ | V4-59*03 | 95% | J6*02 | 89% | D4-17*01 | VL1-47*01 | 94% | JL3*02 | 92% | 0,03 | + | - |
| RVA144 | A | IgG3 λ | V4-39*01 | 92% | J5*02 | 84% | D4-4*01 | VL1-40*01 | 97% | JL2*01 | 92% | 0,09 | + | - |
| RVA125 | A | IgG1 κ | V3-30*03 | 88% | J6*02 | 72% | D3-10*01 | VK7-43*01 | 88% | JK3*02 | 84% | 0,5 | + | - |
| RVB185 | B | IgG1 λ | V4-39*01 | 89% | J4*02 | 85% | D3-9*01 | VL1-44*01 | 95% | JL3*02 | 97% | 0,3 | ++ | - |
| RVB492 | B | IgG1 λ | V3-23*01 | 90% | J4*02 | 98% | D3-10*01 | VL-2-11*01 | 97% | JL2*01 | 97% | 0,2 | - | - |
| RVB143 | B | IgG1 λ | V1-46*01 | 93% | J6*02 | 90% | D2-21*01 | VL2-14*01 | 94% | JL2*01 | 84% | 317 | ++ | + |
| RVB161 | B | IgG1 λ | V4-39*07 | 96% | J4*02 | 88% | D4-17*01 | VL1-44*01 | 98% | JL3*02 | 100% | 0,08 | - | - |
| RVB181 | B | IgG3 λ | V3-30*02 | 91% | J6*02 | 82% | D1-26*01 | VL1-40*01 | 94% | JL2*01 | 89% | 1,4 | + | - |
| RVB686 | B | IgG1 κ | V3-30*04 | 95% | J2*01 | 94% | D6-6*01 | VK1-5*01 | 93% | JK1*01 | 97% | 0,6 | + | - |
| RVC03 | C | IgG1 κ | V3-23*01 | 91% | J4*02 | 94% | D3-3*01 | VK1-44*01 | 96% | JK3*02 | 97% | 1 | + | - |
| RVC20 | C | IgG3 κ | V4-31*06 | 96% | J4*02 | 90% | D3-3*01 | VK1-16*01 | 98% | JK4*01 | 100% | 0,1 | ++ | - |
| RVC21 | C | IgG3 λ | V4-39*01 | 93% | J5*01 | 80% | D4-17*01 | VL1-51*01 | 96% | JL1*01 | 100% | 0,04 | + | - |
| RVC38 | C | IgG3 κ | V1-69*06 | 91% | J4*02 | 85% | D5-24*01 | VK1-9*01 | 96% | JK4*04 | 100% | 0,01 | - | - |
| RVC44 | C | IgG3 κ | V3-21*01 | 92% | J3*02 | 86% | D6-19*01 | VK1-39*01 | 95% | JK1*01 | 100% | 0,7 | ++ | + |
| RVC58 | C | IgG1 λ | V3-23*04 | 96% | J6*02 | 95% | D2-15*01 | VL2-14*01 | 99% | JL2*01 | 94% | 0,01 | - | - |
| RVC68 | C | IgG1 κ | V4-59*01 | 93% | J6*03 | 89% | D4-17*01 | VK1-12*01 | 96% | JK2*01 | 94% | 9 | + | + |
| RVC111 | C | IgG1 κ | V3-30*04 | 98% | J4*02 | 94% | D1-14*01 | VK1-5*01 | 96% | JK1*01 | 95% | 0,6 | - | - |
| RVC04 | C | IgG3 λ | V3-30*03 | 95% | J6*02 | 77% | D1-7*01 | VL1-40*01 | 96% | JL3*01 | 97% | 0,02 | + | - |
| RVC56 | C | IgG3 κ | V3-7*01 | 98% | J6*02 | 98% | D3-10*01 | VK-1*5*03 | 98% | JK2*01 | 97% | 0,03 | - | - |
| RVC69 | C | IgG3 κ | V1-69*01 | 92% | J4*02 | 92% | D5-24*01 | VK1-9*01 | 94% | JK4*01 | 95% | 0,13 | ND | - |
| RVD74 | D | IgG1 | V3-48*02 | 94% | J4*02 | 98% | D5-5*01 | VL2-14*01 | 92% | JL2*01 | 91% | 0,03 | ++ | - |

Figure 3

| | CR57 | RVA125 | RVC3 | RVC20 | RVD74 | CR4098 | RVA122 | RVA144 | RVB492 | RVC4 | RVC69 | RVC38 | RVC58 | RVB181 | RVC56 | RVB185 | RVC21 | RVC161 | RVC111 | RVB686 | RVC44 | RVB143 | RVC68 | |
|---|---|---|---|---|---|---|---|---|---|---|---|---|---|---|---|---|---|---|---|---|---|---|---|---|
| CR057 | 100 | 89 | 90 | 100 | 99 | 1 | -137 | -188 | -328 | -6 | -71 | 11 | -262 | -23 | -29 | -186 | -110 | -78 | -62 | -50 | 9 | 15 | -8 | |
| RVA125 | 100 | 100 | 100 | 100 | 100 | -4 | -58 | -83 | -221 | -6 | -90 | -172 | -107 | 10 | -38 | -137 | -157 | -39 | -5 | 16 | 17 | 20 | 12 | |
| RVC3 | 100 | 99 | 100 | 100 | 99 | -22 | -72 | -113 | -265 | -19 | -96 | -174 | -171 | -7 | -54 | -122 | -142 | -80 | -22 | -9 | 8 | 14 | 4 | I |
| RVC20 | 94 | 89 | 95 | 100 | 99 | -16 | -40 | -64 | -156 | 8 | -93 | -166 | -115 | 13 | -22 | -96 | -142 | -25 | 20 | 26 | 28 | 36 | 41 | |
| RVD74 | 99 | 66 | 73 | 99 | 100 | 4 | 2 | -112 | -525 | -3 | -53 | -106 | -125 | -27 | 40 | -96 | -140 | -63 | 39 | 47 | 15 | 16 | 10 | |
| CR4098 | 17 | -3 | -10 | 26 | 4,4 | 100 | 95 | 88 | 96 | 99 | 97 | 98 | 97 | 99 | 96 | 87 | 97 | 67 | 98 | -88 | 11 | 5 | -10 | |
| RVA122 | -3 | -9 | -9 | -24 | -6 | 95 | 100 | 88 | 100 | 78 | 97 | 98 | 100 | 96 | 95 | 90 | 96 | 63 | 98 | 8 | 20 | 4 | 4 | |
| RVA144 | -10 | -18 | -13 | -20 | 2 | 74 | 92 | 100 | 92 | 60 | 69 | 82 | 92 | 92 | 94 | 98 | 96 | 67 | 98 | 12 | 36 | 9 | 10 | |
| RVB492 | -9 | -2 | -9 | -23 | -2 | 93 | 100 | 74 | 100 | 74 | 96 | 98 | 99 | 97 | 95 | 72 | 88 | 63 | 99 | 7 | 16 | 14 | 10 | III |
| RVC04 | 9 | 12 | 8 | 15 | 16 | 100 | 99 | 92 | 99 | 100 | 98 | 98 | 97 | 101 | 96 | 94 | 95 | 72 | 99 | 10 | 14 | 15 | 12 | |
| RVC69 | -4 | -3 | -9 | -7 | 11 | 91 | 101 | 76 | 96 | 89 | 100 | 99 | 98 | 99 | 95 | 76 | 76 | 63 | 97 | 14 | -2 | 16 | 10 | |
| RVC38 | -11 | 9 | 4 | 14 | 21 | 95 | 101 | 87 | 100 | 93 | 99 | 100 | 100 | 101 | 96 | 87 | 93 | 72 | 99 | 37 | 32 | 20 | 12 | |
| RVC58 | -15 | 4 | -17 | -17 | 6 | 64 | 97 | 65 | 97 | 52 | 80 | 93 | 100 | 88 | 95 | 49 | 84 | 67 | 97 | 23 | 14 | 12 | 4 | |
| RVB181 | -7 | -9 | -12 | 15 | 8 | 22 | 91 | 61 | 85 | 78 | 57 | 76 | 77 | 100 | 83 | 15 | 79 | 66 | 94 | 7 | 22 | 2 | 4 | |
| RVC56 | -10 | 2 | -13 | 1 | 3 | 8 | 76 | 33 | 58 | 21 | 19 | 57 | 59 | 53 | 100 | 21 | 51 | 69 | 92 | 13 | 24 | 9 | 3 | |
| RVB185 | -2 | -9 | -12 | -7 | 2 | 25 | 63 | 70 | 64 | 10 | 0 | -3 | 33 | 36 | 95 | 100 | 91 | 64 | 97 | -1 | -9 | 8 | 1 | III.2 |
| RVC21 | -7 | -5 | 2 | 1 | 5 | 31 | 74 | 94 | 69 | 46 | 20 | 34 | 67 | 93 | 94 | 96 | 100 | 66 | 97 | 8 | 39 | 7 | 2 | |
| RVB161 | -4 | -11 | -9 | 7 | 4 | 26 | 62 | 33 | 38 | -3 | -36 | -30 | -9 | 24 | 85 | 5 | 86 | 68 | 94 | 2 | -2 | 3 | 2 | |
| RVC111 | -1 | -2 | -5 | 4 | 10 | 5 | 64 | 30 | -17 | 5 | -5 | 37 | 18 | -6 | 90 | 27 | 53 | 73 | 100 | 13 | -6 | 11 | 1 | |
| RVB686 | 82 | 43 | 13 | 74 | 91 | 86 | 100 | 37 | 99 | 66 | 98 | 100 | 99 | 94 | 96 | 3 | 58 | 74 | 92 | 100 | 24 | 23 | 10 | A |
| RVC44 | 18 | 8 | 16 | 55 | 31 | -2 | 6 | 11 | -48 | 34 | 17 | -66 | -42 | 61 | 6 | -11 | -16 | 59 | 26 | 38 | 100 | 27 | 19 | B |
| RVB143 | 9 | -11 | -3 | 21 | 8 | 32 | 43 | -8 | -41 | -5 | 1 | -14 | 1 | 17 | 15 | -39 | -27 | 1 | 29 | 8 | -5 | 100 | 98 | C |
| RVC68 | -6 | 3 | -16 | 27 | 5 | 15 | 20 | -17 | -40 | 5 | -13 | -30 | -18 | 21 | -7 | -44 | -45 | 8 | 10 | -1 | -10 | 98 | 100 | |
| Berirab | 97 | 93 | 87 | 100 | 99 | 99 | 99 | 97 | 102 | 98 | 97 | 99 | 98 | 99 | 100 | 96 | 98 | 97 | 99 | 91 | 66 | 53 | 39 | |

Figure 4

| Phylogroup | Virus | Strain | I RVC3 | I RVC20 | I CR57 | III RVA122 | III RVA144 | III RVB492 | III RVC38 | III RVC58 | III CR4098 | III RAB1 | III.2 RVC21 | III.2 RVB185 | III.2 RVC111 | B RVC44 | C RVC68 | Berirab |
|---|---|---|---|---|---|---|---|---|---|---|---|---|---|---|---|---|---|---|
| Phylogroup I | RABV | CVS-11 | 1,05 | 0,13 | 0,99 | 0,03 | 0,09 | 0,19 | 0,01 | 0,01 | 7,87 | 48,00 | 0,04 | 0,34 | 0,61 | 0,65 | 8,91 | 987,00 |
| Phylogroup I | RABV | ERA | 0,40 | 0,30 | 0,99 | 0,10 | 0,90 | 0,30 | 0,10 | 0,30 | 0,70 | 1,00 | 29,00 | 0,70 | 0,61 | 1,50 | 12,90 | 1086,00 |
| Phylogroup I | DUVV | RSA2006 | 13,10 | 0,70 | 116,10 | 0,20 | 2,70 | 0,10 | 0,04 | 0,20 | - | - | 3,50 | 0,05 | 1159,00 | 5,70 | 45,80 | - |
| Phylogroup I | DUVV | RV131 | 12,60 | 2,60 | 14,80 | 0,30 | 8,70 | 0,20 | 0,30 | 1,20 | - | - | 7860,00 | 1,20 | 2,30 | 11,70 | 32,60 | - |
| Phylogroup I | EBLV-1 | 122938 | 5,36 | 16,24 | - | 0,46 | 5,04 | 0,07 | 0,05 | 0,07 | - | - | 34,45 | 2,15 | 2246,00 | 28,96 | 84,00 | 10925,00 |
| Phylogroup I | EBLV-1 | RV9 | 3,00 | 3,60 | - | 2,00 | 8,60 | 2,60 | 0,20 | 1,20 | - | - | 792,20 | 8,50 | 6,90 | 63,50 | 309,70 | - |
| Phylogroup I | EBLV-1 | RV20 | 0,40 | 0,30 | - | 0,20 | 2,30 | 0,20 | 0,02 | 0,10 | - | - | 240,00 | 0,60 | 1,50 | 0,60 | 3,20 | - |
| Phylogroup I | EBLV-2 | RV1332 | - | 0,23 | 13,45 | 2,62 | 2,24 | 0,09 | 0,39 | 1,75 | - | - | 5,09 | 3,60 | 1358,00 | 3,65 | 16,22 | 19501,00 |
| Phylogroup I | EBLV-2 | RV628 | 0,10 | 0,40 | 1,70 | 0,40 | 10,10 | 0,20 | 0,30 | 0,60 | - | - | 54,60 | 2,10 | 3,70 | 8,50 | 79,40 | - |
| Phylogroup I | EBLV-2 | RV1787 | 0,30 | 0,10 | 2,10 | 0,10 | 10,00 | 0,10 | 0,06 | 0,20 | - | - | 217,40 | 0,60 | 0,30 | 0,10 | 22,10 | - |
| Phylogroup I | ABLV | RV634 | 0,20 | 0,10 | 0,10 | 0,10 | 0,10 | 0,07 | 0,10 | 0,10 | 3,20 | 10,00 | 44,80 | 0,08 | 0,40 | 0,40 | 0,30 | 265,60 |
| Phylogroup I | IRKV | | - | 23,26 | 68,62 | 0,17 | 34,46 | 0,05 | 2,43 | 0,06 | - | - | 2,40 | 45,80 | 1983,00 | 23,66 | 317,26 | 34510,00 |
| Phylogroup I | KHUV | | 0,10 | 0,79 | 4,42 | 0,10 | 7,61 | 0,17 | 0,10 | 0,10 | - | 6700,00 | 371,00 | 1,45 | 9,09 | 287,00 | 259,00 | - |
| Phylogroup I | ARAV | | 0,10 | 0,10 | 0,13 | 0,10 | 0,55 | - | 0,10 | 0,10 | 1757,00 | 140,00 | 18,55 | 0,10 | 0,53 | 22,40 | 19,21 | 67,85 |
| Phylogroup II | LBV | 8619 | - | - | - | - | - | - | - | - | - | nd | - | - | - | 465,00 | 219,00 | - |
| Phylogroup II | LBV | RV1 | - | - | - | - | - | - | - | - | 396,90 | - | - | - | - | 48,20 | 2,10 | - |
| Phylogroup II | LBV | SA2004 | - | - | - | - | - | - | - | - | - | - | - | - | - | - | 100,60 | - |
| Phylogroup II | MOKV | RV4 | - | - | - | - | - | - | - | - | - | nd | - | - | - | - | 56,30 | - |
| Phylogroup II | MOKV | RA36 | - | - | - | - | - | - | - | - | - | - | - | - | - | - | 76,00 | - |
| Phylogroup II | SHIBV | | - | 28,00 | - | - | - | - | - | - | - | - | - | - | - | 135,00 | 110,00 | - |
| III | WCBV | | - | - | - | - | - | - | - | - | - | - | - | - | - | - | - | - |
| IV | IKOV | | nd | 11,00 | - | - | - | - | - | - | - | - | - | - | - | nd | nd | - |

| Phylogroup | Virus | Strain | I RVC3 | I RVC20 | I CR57 | III RVA122 | III RVA144 | III RVB492 | III RVC38 | III RVC58 | III CR4098 | III RAB1 | III.2 RVC21 | III.2 RVB185 | III.2 RVC111 | B RVC44 | C RVC68 | Berirab |
|---|---|---|---|---|---|---|---|---|---|---|---|---|---|---|---|---|---|---|
| I | RABV | V6155 | 318 | 234 | 648 | 17 | 39 | 30 | 19 | 21 | - | 484 | 45 | 160 | 2513 | 153 | - | 5075 |
| I | RABV | BW/badger | 36 | 46 | 7 | 40 | 98 | 30 | 28 | 21 | 27 | 13 | 31 | 35 | 934 | 232 | 2958 | nd |
| I | RABV | Niger/Dog | 919 | 27 | 515 | 18 | 57 | 29 | 28 | 21 | 4593 | nd | 41 | 34 | 934 | 376 | 7604 | nd |
| I | RABV | 9704 | 83 | 83 | 63 | 6 | 83 | 83 | 9 | 6 | 83 | 5 | 71 | 71 | 1285 | 63 | 214 | 9211 |
| I | RABV | 86132SA | 63 | 83 | 5900 | 80 | 250 | 21 | 21 | 60 | - | nd | 21 | 210 | 30 | - | 2000 | - |
| I | RABV | RS639 | nd | - | - | nd | nd | nd | nd | 415 | - | nd | nd | nd | nd | nd | nd | - |
| I | DUVV | 8918 | - | 83 | - | 0,5 | 29 | 20 | 15 | 21 | - | - | 229 | 18 | 7947 | 3435 | - | - |
| I | DUVV | 122938 | 105 | 569 | - | 46 | 460 | 850 | 909 | 815 | 21 | nd | 372 | 349 | - | 5960 | 30 | - |
| I | EBLV-1 | 02053 | 206 | 33 | 21 | 1750 | 5200 | - | 5900 | 250 | 28 | nd | 5900 | - | 29 | 750 | 200 | 21 |
| I | EBLV-1 | 94112 | 0,5 | 1562 | 28 | - | - | - | - | 500 | - | - | - | - | 30 | 1080 | nd | 0,5 |
| I | EBLV-2 | RV1332 | nd | 29 | 1888 | nd | nd | nd | nd | 66 | - | - | nd | nd | nd | nd | - | 33685 |
| I | EBLV-2 | 98010 | - | - | - | - | - | 2000 | 200 | 800 | - | nd | - | - | - | 700 | - | - |
| I | ABLV | V1039 | 36 | 397 | 875 | 18 | 43 | 30 | 28 | 21 | 96 | 309 | 31 | 34 | 2115 | 394 | 30 | - |
| I | BBLV | 1301 | nd | 22 | 54 | nd | nd | nd | nd | 24 | - | nd | nd | nd | nd | nd | 200 | - |
| II | LBV | 8619 | - | - | - | - | - | - | - | - | - | nd | - | - | - | 210 | nd | - |
| II | MOKV | (strain?) | 200 | 7 | - | - | - | - | - | - | - | - | - | - | 24 | - | 588 | - |

Figure 7

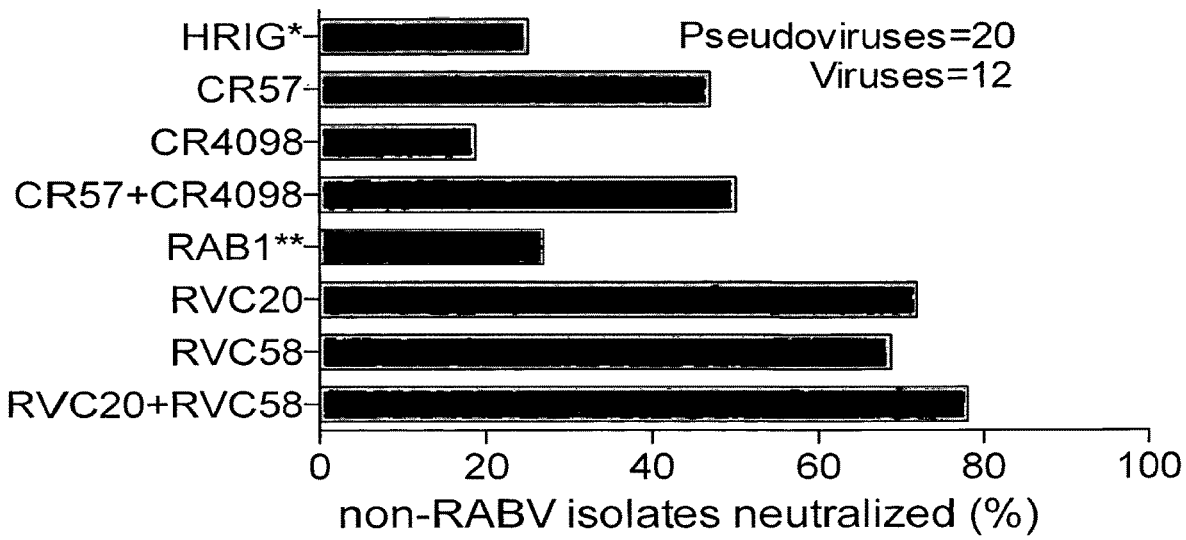
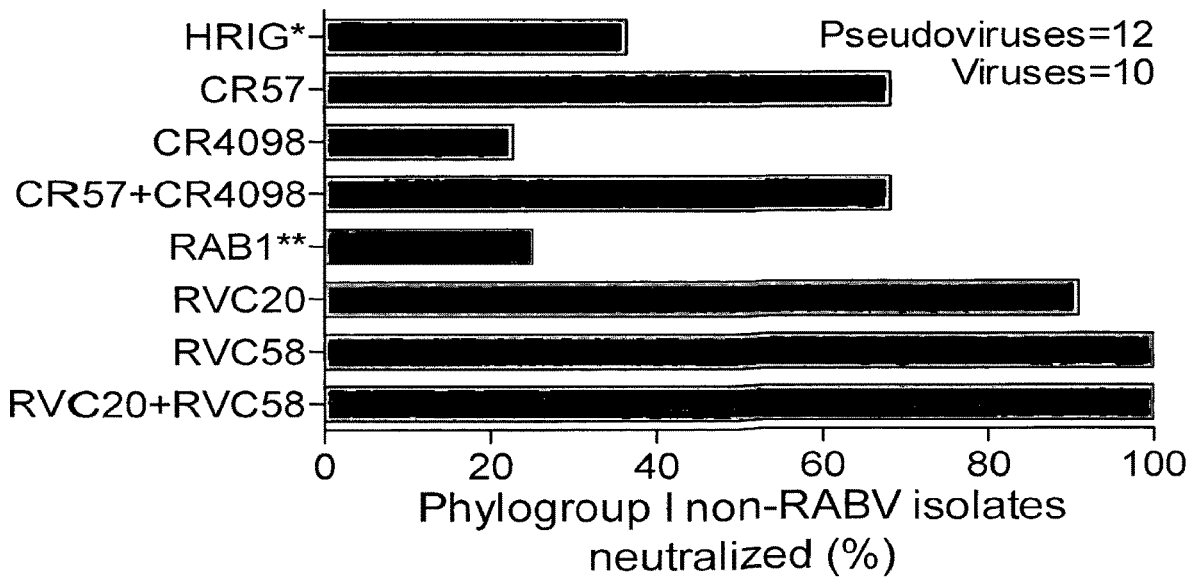
Figure 8

A
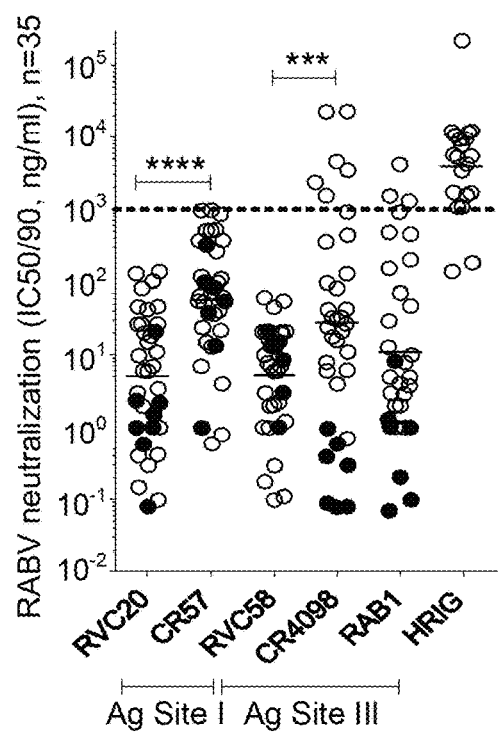
B
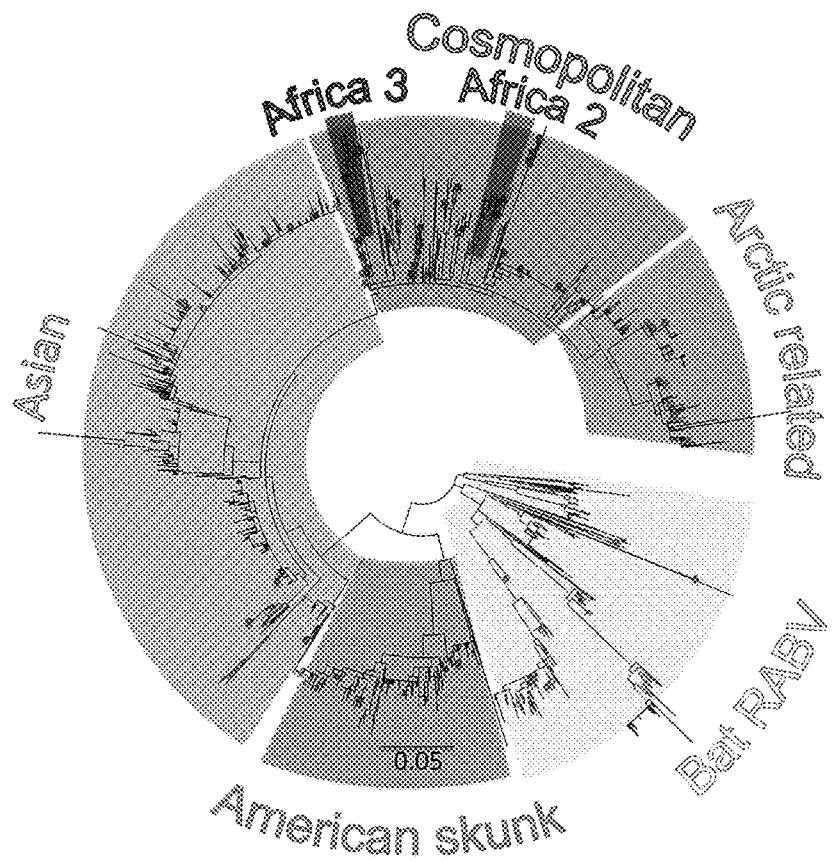
Figure 10

| Isolate name | RVC58 | RVC20 | CR57 | CR4098 | RAB1 | HRIG (Berirab) | Neutralization assay used |
|---|---|---|---|---|---|---|---|
| 9704 | 6 | 83 | 63 | 83 | 5 | 188 | RFFIT |
| Botswana/dog/BNVL2009-3580/V5493-2010 | 2 | 18 | 15 | 6 | 10 | ND | FAVN |
| Botswana/honey badger/BNVL2009-6665/V5493-2010 | 21 | 46 | 7 | 27 | 13 | ND | FAVN |
| Burkina Faso/dog/139-2007/V6155-2007 | 46 | 27 | 855 | 3524 | ND | ND | FAVN |
| Burkina Faso/dog/9-2007/V6155-2007 | 0,18 | 0,42 | 262 | 2376 | 483 | 12000 | FAVN |
| 02045 | 1 | 133 | 4 | 445 | 1 | 1604 | RFFIT |
| France/red fox/GS7 1-11-1990/V1039-2011 | 21 | 46 | 515 | 43 | ND | ND | FAVN |
| Pasteur Virus (PV)-Paris-93127 | 56 | 1 | 56 | 24 | ND | 14 | RFFIT |
| 9001 | 63 | 140 | 41 | 130 | ND | 140 | RFFIT |
| Italy/dog/V3425/2009 | 3 | 43 | 74 | 33 | ND | 12315 | FAVN |
| Italy/human/V117/1996 (Nepal) | 1 | 0,41 | 55 | 18 | 3 | 7894 | RFFIT |
| Italy/red fox/V673/2011 | 21 | 105 | 378 | 43 | 30 | ND | FAVN |
| Brazil/bat/260-08/RS1249-2013 | 7,9 | 6,15 | 969 | 11 | 460 | 3464 | RFFIT |
| Brazil/bovine/303-2011/RS1040-2012 | 1,23 | 9,8 | 96 | 31 | 73 | 1080 | RFFIT |
| Brazil/kinkajou/RS3609-5-2011 | 2 | 2 | 520 | 1571 | 4153 | 5509 | FAVN |
| Challenge virus strain (CVS)-11 | 0,01 | 0,13 | 0,99 | 7,87 | 48 | 987 | PV |
| Challenge virus strain (CVS)-11 | 16 | 20 | 37 | 21 | 4,2 | 5778 | RFFIT |
| Challenge virus strain (CVS)-11 | 13 | 1171 | 2841 | 56 | ND | 58054 | FAVN |
| 9508SAD BERN | 7 | 1 | 1000 | 23600 | 1 | 221300 | RFFIT |
| Niger/Dog/105-251-2007/V6097-2007 | 21 | 27 | 515 | 4593 | ND | ND | FAVN |
| 04030 | 6 | 6 | 13 | 543 | 2 | 4233 | RFFIT |
| Poland/racoon dog/1985/V3229-2009 | 20 | 27 | 377 | 33 | 154 | ND | FAVN |
| 9141 | 10 | 11 | 22 | 930 | 1294 | 10965 | RFFIT |
| Spain/dog/201020958-2010/RS639-2012 | 2,23 | 3,4 | 121 | 6,2 | 3 | 5288 | RFFIT |
| 8743 | 7 | 3 | 66 | 99 | 2 | 1700 | RFFIT |
| Tunisia/dog/ARIANA2-1991/V3951-2010 | 21 | 15 | 113 | 16 | 8 | ND | FAVN |
| ERA (Evelyn Rokitniki Abelseth) | 0,3 | 0,3 | 0,8 | 0,7 | <7 | 1086 | PV |
| CVS 9.13 | 21 | 7 | 24 | 23600 | ND | 1700 | RFFIT |
| RV250 | 21,5 | 2,2 | 84,5 | 0,6 | 0,2 | ND | PV |
| RV193 | 12,8 | 0,6 | 38,4 | 0,4 | 1,4 | ND | PV |
| RV277 | 13,9 | 1,5 | 100,3 | 0,3 | 1,3 | ND | PV |
| RV61 | 15,1 | 0,08 | 54,7 | 0,09 | 0,07 | ND | PV |
| 93033ISR | 3,1 | 2,4 | 13,5 | <0.08 | 0,1 | ND | PV |
| 86081IRA | <7 | <7 | <7 | <7 | <7 | ND | PV |
| 91004USA | 8,7 | 21 | 319,5 | 0,08 | 8,4 | ND | PV |
| Mauritania/dog/2019-2006/V6235-2007 | 0,15 | 0,11 | 100 | 359 | 206 | 9704 | FAVN |
| Pittman More strain (PM) (PV12?) | 66 | NA | 100 | 21 | NA | 11200 | RFFIT |
| 87006TU* | + | + | + | + | + | ND | FACS |
| 91001USA* | + | + | + | + | - | ND | FACS |
| 91035OMA* | + | + | + | + | + | ND | FACS |
| 98011CHI* | + | + | + | + | + | ND | FACS |
| 09029NEP* | + | + | - | + | + | ND | FACS |
| 02052AFG* | + | + | + | + | + | ND | FACS |
| FLRC090148* | +/- | + | +/- | + | + | ND | FACS |
| RV/R3.PHL/2008/TRa-065* | + | + | - | + | + | ND | FACS |

* tested for binding to G-protein trasfectants

Figure 11

| Isolate name | Host species | Country of origin | Year | Viral species | Phylogroup | Lineage | RVC58 | RVC20 | CR57 | CR4098 | HRIG (Berirab) | Neutralization assay used* |
|---|---|---|---|---|---|---|---|---|---|---|---|---|
| 9704 | Tadarida brasiliensis (bat) | Argentina | 1997 | RABV | I | Bat (American Indigenous) | 6 | 83 | 63 | 83 | 188 | RFFIT |
| Botswana/dog/BNVL2009-3580/V5493-2010 | Dog | Botswana | 2009 | RABV | I | Cosmopolitan (ex Africa 1) | 2 | 18 | 15 | 6 | n.e. | FAVN |
| Botswana/honey badger/BNVL2009-6665/V5493-2010 | Badger | Botswana | 2009 | RABV | I | Africa 3 | 21 | 46 | 7 | 27 | n.e. | FAVN |
| Burkina Faso/dog/139-2007/V6155-2007 | Dog | Burkina Faso | 2007 | RABV | I | Africa 2 | 46 | 27 | 855 | 3524 | n.e. | FAVN |
| Burkina Faso/dog/9-2007/V6155-2007 | Dog | Burkina Faso | 2007 | RABV | I | Africa 2 | 21 | 234 | 648 | 45926 | 5075 | FAVN |
| 02045 | Dog | China | 2002 | RABV | I | Asian 1 or 2a (China) | 1 | 133 | 4 | 445 | 1604 | RFFIT |
| France/red fox/GS7 1-11-1990/V1039-2011 | Red fox | France | 1990 | RABV | I | Cosmopolitan-Western Europe | 21 | 46 | 515 | 43 | n.e. | FAVN |
| Pasteur Virus (PV)-Paris-93127 | na | France | na | RABV | I | na | 56 | 1 | 56 | 24 | 14 | RFFIT |
| 9001 | Dog (vampire bat virus) | French Guyana | 1990 | RABV | I | Bat (American Indigenous) | 63 | 140 | 41 | 130 | 140 | RFFIT |
| Italy/dog/V3425/2009 | Dog | Italy | 2009 | RABV | I | Cosmopolitan-Western Europe | 3 | 43 | 74 | 33 | 12315 | FAVN |
| Italy/human/V117/1996 (Nepal) | Human | Italy | 1996 | RABV | I | Arctic-like-1 | 21 | 3704 | 48 | 31 | 269 | FAVN |
| Italy/red fox/V673/2011 | Red fox | Italy | 2011 | RABV | I | Cosmopolitan-Western Europe | 21 | 105 | 378 | 43 | n.e. | FAVN |
| Brazil/bat/260-08/RS1249-2013 | Bat/Mus musculus* | Latin America | 2008 | RABV | I | Bat (American indigenous) | 415 | 873 | 678 | 60 | 12192 | FAVN |
| Brazil/bovine/303-2011/RS1040-2012 | Vampire bat | Latin America | 2011 | RABV | I | Bat (American indigenous) | 140 | 678 | 224 | 60 | 12192 | FAVN |
| Brazil/kinkajou/RS3609-5-2011 | Unknown | Latin America | 2008 | RABV | I | Bat (American indigenous) | 2 | 2 | 520 | 1571 | 5509 | FAVN |
| Challenge virus strain (CVS)-11 | na | na | na | RABV | I | na | 13/16/0.1 | 1171, 20, 0.1 | 2841 | 56/4408/4 | 58054/5778/987 | FAVN/RFFIT/PV |
| 9508SAD BERN | na | na | na | RABV | I | na | 7 | 1 | 1000 | 23600 | 221300 | RFFIT |
| Niger/Dog/105-251-2007/V6097-2007 | Dog | Niger | 2007 | RABV | I | Africa 2 | 21 | 27 | 515 | 4593 | n.e. | FAVN |
| 04030 | Human bitten by Dog | Phillipines | 2004 | RABV | I | Asian 2b (Philippines) | 6 | 6 | 13 | 543 | 4233 | RFFIT |
| Poland/racoon dog/1985/V3229-2009 | Racoon dog | Poland | 1985 | RABV | I | Cosmopolitan, North-Eastern Europe | 20 | 27 | 377 | 33 | n.e. | FAVN |
| 9141 | Arctic fox | Siberia, Russia | 1988 | RABV | I | Arctic 2 (Siberia) | 10 | 11 | 22 | 930 | 10965 | RFFIT |
| Spain/dog/201020958-2010/RS639-2012 | Dog | Spain (ex Morocco) | 2010 | RABV | I | Cosmopolitan (ex Africa 1) | 415 | 172 | 97 | 36 | 7179 | FAVN |
| 8743 | Human | Thailand | 1983 | RABV | I | Asian 2c (south East Asia) | 7 | 3 | 66 | 99 | 1700 | RFFIT |
| Tunisia/dog/ARIANA2-1991/V3951-2010 | Dog | Tunisia | 1991 | RABV | I | Cosmopolitan (ex Africa 1) | 21 | 15 | 113 | 16 | n.e. | FAVN |
| ERA (Evelyn Rokitniki Abelseth) | na | na | na | RABV | I | na | 0.3 | 0.3 | 0.8 | 0.7 | 1086 | PV |
| CVS 9.13 | | | | RABV | I | na | 21 | 7 | 24 | 23600 | 1700 | RFFIT |

Figure 12

| Isolate name | Host species | Country of origin | Year | Viral species | Phylogroup | RVC58 | RVC20 | CR57 | CR4098 | HRIG (Berirab) | Neutralization assay used* | Accession number |
|---|---|---|---|---|---|---|---|---|---|---|---|---|
| ABLV/Australia/bat/9810AUS-1998/V1039-2011 | *Pteropus alecto* (Black flying fox) | Australia | 1996 | ABLV | I | 21 | 397 | 875 | 96 | - | FAVN | NA |
| 98010 | Insectivorous bat | Australia | 1996 | ABLV | I | 800 | - | 15600 | - | - | RFFIT | AAD47899.1 |
| 1301 Bokeloh bat lyssavirus | Myotis nattererii (bat) | France | 2013 | BBLV | I | 24 | 22 | 54 | 38106 | - | RFFIT | NA |
| 86132SA | Human | South Africa | 1971 | DUVV | I | 60 | 83 | 5900 | - | - | RFFIT | NA |
| DUVV/SouthAfrica/human/96132SA-1971/RS639-2012 | Human | South Africa | ? | DUVV | I | 415 | 52650 | 17433 | - | 251821 | FAVN | NA |
| EBLV1a/France/bat/122938-2002/V3951-2009 | Eptesicus serotinus (bat) | France | 2002 | EBLV-1 | I | 815 | 569 | - | - | NA | FAVN | NA |
| EBLV1b/France/bat/8918-1989 | Eptesicus serotinus (bat) | France | 1989 | EBLV-1 | I | 7 | 129 | - | - | 49101 | RFFIT | EU293112 |
| EBLV2/UK/bat/RV1332-2002/V3951-2009 | Myotis daubentonii (bat) | UK | 2002 | EBLV-2 | I | 919 | 52649 | 17433 | - | - | FAVN | NA |
| 94112 | Myotis dasycneme (pond bat) | Netheralnds | 1989 | EBLV-2 | I | 500 | 1562 | 28 | 28 | NA | RFFIT | NA |
| 02053 | Bat (Myotis daubentonii) | Switzerland | 2002 | EBLV-2 | I | 250 | 33 | 21 | 21 | NA | RFFIT | NA |
| MOK | Cat | Zimbabwe | 1981 | MOK | II | - | 7 | - | - | - | RFFIT | NA |
| Shimoni bat Virus | Hipposideros commersoni (bat) | Kenya | 2009 | SHIBV | II | - | 28 | - | - | - | PV | NA |
| West Caucasian bat Virus | Miniopterus schreibersi (bat) | Russia | 2002 | WCBV | III | - | - | - | - | - | PV | NA |
| Australian bat lyssavirus/RV634 | Pteropus alecto (bat) | Australia | 1996 | ABLV | I | 0.1 | 0.1 | 0.1 | 3 | 266 | PV | NA |
| Aravan Virus | Myotis blythi (bat) | Kyrgyzstan | 1991 | ARAV | I | 0.1 | 0.1 | 0.1 | 1757 | - | PV | AAP86775.1 |
| Duvenhage Virus RSA2006 | ? | South Africa | 2006 | DUVV | I | 0.2 | 0.7 | 116 | - | - | PV | EU623444 |
| Duvenhage Virus ZIM86-RV131 | Bat | Zimbawe | 1986 | DUVV | I | 1 | 3 | 15 | - | - | PV | NA |
| European bat lyssavirus 1.RV20 | Bat | Germany | 1986 | EBLV-1 | I | 0.1 | 0.3 | - | - | 49101 | PV | NA |
| European bat lyssavirus 1.RV9 | Bat | Germany | 1968 | EBLV-1 | I | 1 | 4 | - | - | - | PV | EU352768 |
| EBLV1a/France/bat/122938-2002/V3951-2009* | Eptesicus serotinus (bat) | France | 2002 | EBLV-1 | I | 0.1 | 16 | 26579 | - | 10925 | PV | NA |
| EBLV2/UK/bat/RV1332-2002/V3951-2009* | Myotis daubentonii (bat) | UK | 2002 | EBLV-2 | I | 1,75 | 0,23 | 13,45 | 11197 | 19501 | PV | NA |
| European bat lyssavirus 2.RV1787 | Myotis daubentoni (bat) | UK | 2004 | EBLV-2 | I | 0.2 | 0.1 | 2 | - | - | PV | EU352769 |
| European bat lyssavirus 2.RV628 | Bat | UK | 1996 | EBLV-2 | I | 0.6 | 0.4 | 2 | - | - | PV | NA |
| Irkut Virus | Murina leucogaster (bat) | Russia | 2002 | IRKV | I | 0.06 | 23 | 69 | - | 34510 | PV | NA |
| Khujand Virus | Myotis mystacinus (bat) | Tajikistan | 2001 | KHUV | I | 0.1 | 0.8 | 4 | 77056 | 72951 | PV | AAP86779.1 |
| 8619* | Eidolon helvum (bat) | Nigeria | 1956 | LBV | II | - | - | - | - | - | RFFIT | NA |
| Lagos Bat Virus NIG56-RV1 | Eidolon helvum (bat) | Nigeria | 1956 | LBV | II | - | - | - | - | - | PV | EF547431 |
| Lagos Bat Virus SA2004 | Eptesicus wahlbergi (bat) | South Africa | 2004 | LBV | II | - | - | - | 397 | - | PV | EF547428 |
| Mokola Virus NIG68.RV4 | Crocidura sp. (Shrew) | Nigeria | 1968 | MOK | II | - | - | - | - | - | PV | HM623780 |
| Mokola Virus 98/071 RA36 | Feline | South Africa | 1998 | MOK | II | - | - | - | - | - | PV | GQ500108 |

Figure 13

| Group | Antibody | CVS-11 | K226E | K226N | G229E | N336D | N336S |
|---|---|---|---|---|---|---|---|
| I | CR57 | ■ |  |  |  | ▨ | ▨ |
| I | RVC3 | ■ | ▨ | ▨ | ▨ | ▨ | nd |
| I | RVC20 | ■ |  |  |  | ▨ | ▨ |
| III | CR4098 | ■ | ▨ | ▨ | ▨ | ▨ | ▨ |
| III | RVA122 | ■ | ▨ | ▨ | ▨ | ▨ | nd |
| III | RVA144 | ■ | ▨ | ▨ | ▨ | ▨ | nd |
| III | RVB185 | ■ | ▨ | ▨ | ▨ | ▨ | nd |
| III | RVC21 | ■ | ▨ | ▨ | ▨ | ▨ | nd |
| III | RVC58 | ■ | ▨ | ▨ | ▨ | ▨ | ▨ |
| III | RVB492 | ■ | ▨ | ▨ | ▨ | ▨ | nd |
| III | RVC38 | ■ | ▨ | ▨ | ▨ | ▨ | nd |
| III | RAB1 | ■ | nd | nd | nd | nd | ░ |
| III.2 | RVC111 | ■ | ▨ | ▨ | ▨ | ░ | nd |
| B | RVC44 | ■ | ▨ | ▨ | ▨ | ▨ | nd |
| C | RVC68 | ■ | ▨ | ▨ | ▨ | ░ | nd |

RVA122:

VH: <u>IGHV4-59*03</u> (95.09%), <u>IGHJ6*02 (a)</u> (88.71%), <u>IGHD4-17*01</u>

| | |
|---|---|
| CAGGTGCACCTGCAGGAGTCGGGCCCAGGACTGGTGAAGCCTTCGGAGACCCT<br>GTCCCTCACCTGCACTGTCTCTGGTGACTCCATGAATAATTTCTACTGGGGCT<br>GGATCCGGCAGCCCGCAGGGAAGGGACTGGAGTGGATTGGATATATCTATTAC<br>AGTGGGACCACCAACTACAACCCCTCCCTCAAGAGTCGAGTCACCATATCAAT<br>AGACACGTCCAAGAACCAATTCTCCCTGAAGGTGAACTCTGTGACCGCTGCGG<br>ACACGGCCGTGTATTATTGTGCGAGAGACTCCGGTGACTACGTCAGCTACTAC<br>TATTATGGTATGGACGTCTGGGGCCCAGGGACCACGGTCACCGTCTCCTCAG | SEQ ID<br>NO: 17 |
| QVHLQESGPGLVKPSETLSLTCTVSGDSMNNFYWGWIRQPAGKGLEWIGYIY<br>YSGTTNYNPSLKSRVTISIDTSKNQFSLKVNSVTAADTAVYYCARDSGDYVS<br>YYYYGMDVWGPGTTVTVSS | SEQ ID<br>NO: 15 |

VL: <u>IGLV1-47*01</u> (94.04%), <u>IGLJ3*02</u> (91.89%)

| | |
|---|---|
| CAGTCTGTGCTGACTCAGTCACCCTCAGCGTCTGATACCCCCGGGCAGAGGG<br>TCACCATCTCTTGTTCTGGAAGCAGCTCCAACATCGGAAGTAATTATGTGTA<br>TTGGTACCAGCAGTTCCCAGGAACGGCCCCCAAACTCCTTATTTACAAGAGT<br>GATAGCGGCCCTCAGGGGTCCCTGACCGATTCTCTGGCTCCACGTCTGGCA<br>CCTCAGCCTCCCTGGCCATCAGTGGGCTCCGGTCCGAAGATGAGGCTGATTA<br>TTACTGTGCAGCATGGGATAACAGGCTGAGTGGTTGGCTCTTCGGCGGAGGG<br>ACGAAGCTGACCGTCCTAG | SEQ ID<br>NO: 18 |
| QSVLTQSPSASDTPGQRVTISCSGSSSNIGSNYVYWYQQFPGTAPKLLIYKS<br>DKRPSGVPDRFSGSTSGTSASLAISGLRSEDEADYYCAAWDNRLSGWLFGGG<br>TKLTVL | SEQ ID<br>NO: 16 |

Figure 22

RVA144:

VH: <u>IGHV4-39*01</u> (92.44%), <u>IGHJ5*02</u> (84.31%), <u>IGHD4-4*01</u>

CAGCTGCAGCTGCAGGAGTCGGGCCCAGGACTGGTGAAGCCCTCGGAGACCCT
GTCCCTCACTTGCACTGTCTCTGGTGGTTCCATCAGCAGTACTATTTTCTACT
GGGGCTGGATCCGCCAGCCCCAGGGAAGGGACTGGAGTGGATTGGGAGTGTC
TATTATAATGGACACACCTACTACAATCCGTCCCTCAAGAGTCGAGTCGCCAT
ATCCATTGACAAGTCCAAGAACCAGTTCTCCCTGAGGCTTAACTCTGTGACCG
CCGCGGACACGGCTGTATATTACTGTGCGAGACCCTCAACATATGACTACAGT
ATTGGGCGCTGGGGCCAGGGAACCCTGGTCACCGTCTCCTCAG

SEQ ID NO: 35

QLQLQESGPGLVKPSETLSLTCTVSGGSISSTIFYWGWIRQPPGKGLEWIGS<u>V</u>
YYNGHTYYNPSLKSRV<u>A</u>IS<u>I</u>DKSKNQFSL<u>R</u>L<u>N</u>SVTAADTAVYYCARPSTYDYS
IGRWGQGTLVTVSS

SEQ ID NO: 33

VL: <u>IGLV1-40*01</u> (98.88%), <u>IGLJ2*01 or IGLJ3*01 or</u>
<u>IGLJ3*2</u> (91.67%)

CAGTCCGTGCTGACGCAGCCGCCCTCAGTGTCTCGGGCCCCAGGGCAGAGGGT
CACCATCTCCTGCACTGGGAGCAGCTCCAACATCGGGGCAGGTTATGATGTCC
ACTGGTACCAGCAACTTCCAGGAACAGCCCCCAAACTCCTCATCTATGGTAAC
ACCAAGCGGCCCTCAGGGGTCCCTGACCGATTCTCTGGCTCCAAGTCTGGCAC
CTCAGCCTCCTGGCCATCACTGGGCTCCTGACTGAGGATGAGGCTGATTATT
ACTGCCAGTCCTTTGACAGCAGCCTGAGTGCTTGGGTATTCGGCGGAGGGACC
AAACTGACCGTCCTGG

SEQ ID NO: 36

QSVLTQPPSVS<u>R</u>APGQRVTISCTGSSSNIGAGYDVHWYQQLPGTAPKLLIYGN
TKRPSGVPDRFSGSKSGTSASLAITGLL<u>T</u>EDEADYYCQS<u>F</u>DSSL<u>A</u>WVFGGGT
KLTVL

SEQ ID NO: 34

Figure 23

RVB185:

VH: IGHV4-39*01 (88.85%), IGHJ4*02 (85.42%), IGHD3-9*01

CAGGTGCAGCTGCAGGAGTCGGGCCCAGGACTGGTGAAGCCTTCGGAGACCCT SEQ ID
GTCCCTCACCTGCAGTGTCTCCGGTGCCCCCGTCAGTGGTGTTAACTCCTACT NO: 53
GGGTGTGGATCCGCCAGCCCCCGGGAAGGGGCTGGAGTGGATTGCGACTATC
AAGTACAGTGGGAGCACCCACCGTAGCCCGTCGCTCAGGAGTCGAGTCACCAT
ATCCGTAGCACGTCCAAGAATCAGTTCTCCCTGGAGCTGAGCTCTGTGACCG
CCGCTGACACGGCTGTATATTACTGTGCCAGACAAAGTACTATGACGGGCCGG
GACTACTGGGGCCAGGGAACCCTGGTCACCGTCTCCTCAG

QVQLQESGPGLVKPSETLSLTCS<u>VS</u>GAPVSGVNSYWVWIRQPPGKGLEWIATI SEQ ID
KYSGSTHRSPSLRSRVTISVDTSKNQFSLELSSVTAADTAVYYCARQSTMTGR NO: 51
DYWGQGTLVTVSS

VL: IGLV1-44*01 (96.09%), IGLJ3*02 (97.37%)

CAGTCTGTGCTGACTCAGCCACCCTCAGCGTCTGGGACCCCCGGGCAGAGGGT SEQ ID
CACCATCTCTTGTTCTGGAAGCAGATCCAACATCGGAAGCCATCCTGTAAACT NO: 54
GGTACCAGCAGCTCCCGGGAGCGGCCCCCAAGCTCCTCATCTATGGTGATAGT
CAGCGACCCTCAGGGGTCCCTGACCGATTCTCTGGCTCCAAGTCTGGCCCCTC
AGCCTCCCTGGCCATCAGTGGACTCCAGTCTGAAGATGAGGCTGATTATTACT
GTGCAGCATGGGATGACAGCCTGAGTGGCCTTTGGGTGTTCGGCGGAGGGACC
AAGCTGACCGTCCTAA

QSVLTQPPSASGTPGQRVTISCSGSRSNIGSHPVNWYQQLPGAAPKLLIYGDS SEQ ID
QRPSGVPDRFSGSKSGPSASLAISGLQSEDEADYYCAAWDDSLSGLWVFGGGT NO: 52
KLTVL

Figure 24

RVB492:

VH-variant1: IGHV3-23*01, or IGHV3-23*D4 or IGHV3-23-23*05 (90.28%), IGHJ4*02 (97.92%), IGHD3-10*01

GAGGTGCAGCTGATGGAGTCTGGGGGAGGCCTGGTACAGCCGGGGGGTCCAT SEQ ID
GAGACTCTACTGTGCAGCCTCTGGATTCAGCTTTAGCAGCTATGCCATGAGCT NO: 72
GGGTCCGCCAGGCTCCAGGGAAGGGGCTCGAGTGGGTCTCAAGT**CTTAATTCT
ATTGATCATAGAACA**GACTATGCAGACTCCGTGAAGGGCCGGTTCACCATCTC
CAGAGACAATTCCAAGAACACCCTGTATTTACAAATGGACAGCCTGAGAGTCG
AGGACTCGGCCATGTATTACTGT**GCTCGGGGGGTGGGACTATGGTTCGGTGAA
TTATCCTGGAATTACTTTGACTAC**TGGGGCCAGGGAACCCTGGTCACCGTCTC
CTCAG

EVQLMESGGGLVQPGGSMRLYCAASGFSFSSYAMSWVRQAPGKGLEWVSSLNS SEQ ID
IDHRTDYADSVKGRFTISRDNSKNTLYLQMDSLRVEDSAMYYCARGVGLWFGE NO: 69
LSWNYFDYWGQGTLVTVSS

VH-variant2: IGHV3-23*04 (90.24%), IGHJ4*02 (97.92%), IGHD3-10*01

GAGGTGCAGCTGGTGCAGTCTGGGGGAGGCCTGGTACAGCCGGGGGGTCCAT SEQ ID
GAGACTCTACTGTGCAGCCTCTGGATTCAGCTTTAGCAGCTATGCCATGAGCT NO: 73
GGGTCCGCCAGGCTCCAGGGAAGGGGCTCGAGTGGGTCTCAAGT**CTTAATTCT
ATTGATCATAGAACA**GACTATGCAGACTCCGTGAAGGGCCGGTTCACCATCTC
CAGAGACAATTCCAAGAACACCCTGTATTTACAAATGGACAGCCTGAGAGTCG
AGGACTCGGCCATGTATTACTGT**GCTCGGGGGGTGGGACTATGGTTCGGTGAA
TTATCCTGGAATTACTTTGACTAC**TGGGGCCAGGGAACCCTGGTCACCGTCTC
CTCAG

EVQLVQSGGGLVQPGGSMRLYCAASGFSFSSYAMSWVRQAPGKGLEWVSSLNS SEQ ID
IDHRTDYADSVKGRFTISRDNSKNTLYLQMDSLRVEDSAMYYCARGVGLWFGE NO: 70
LSWNYFDYWGQGTLVTVSS

VL: IGLV2-11*01 (96.88%), IGLJ2*01, or IGLJ3*01 (96.88%)

CAGTCTGCCCTGACTCAGCCTCGCTCAGTGTCCGGGTCTCCTGGACAGTCAGT SEQ ID
CACCATCTCCTGCACTGGAACCAGCAATGATATTGGTGGTTATAACTATGTCT NO: 74
CCTGGTACCAACAACACCCAGGCAAAGCCCCCAAACTCATGATTTTT**TATGTC
AAT**AAGCGGCCCTCAGGGGTCCCTGATCGCTTCTCTGGCTCCAAGTCTGGCAA
CACGGCCTCCCTGACCATCTCTGGGCTCCAGGCTGAGGATGAAGCTGATTATT
ACTGCTGCTCATTTGCAGGCAGTTACTCCTTATTCGGCAGAGGGACCAAGCTG
ACCGTCCTAG

QSALTQPRSVSGSPGQSVTISCTGTSNDIGGYNYVSWYQQHPGKAPKLMIFYV SEQ ID
NKRPSGVPDRFSGSKSGNTASLTISGLQAEDEADYYCCSFAGSYSLFGRGTKL NO: 71
TVL

Figure 25

RVC3:

VH: <u>IGHV3-23*01</u> (90.97%), <u>IGHJ4*02 (a)</u> (93.75%), <u>IGHD3-3*01</u>

GAGGTGCAGCTGTTGGAGTCTGGGGGAGGCCTGGTGCAGCCGGGGGGGTCCCTGA    SEQ ID
GACTCTCCTGTGCAGCCTCTACATTCACGTTTAGAAACTATGCCATGTCCTGGGT    NO: 91
CCGCCAGGCTCCAGGGAAGGGGCTGGACTGGGTCTCAGG**GATTAGTGCTAGTGGT
AGTAGCACG**AATTATGCAGCCTCCCTGAAGGGCCGATTTACCATCTCCAGAGACA
ATTCCAAGAACACATTGTATCTGCAAATGAACAGCCTGAGAGCCGAGGACACGGC
CGTCTATTACTGT**GCGAAATTTGCTCACGATTTTTGGAGTGGTTATTCTTACTTT
GACTCC**TGGGGCCAGGGAACCCTGGTCACCGTCTCCTCAG

EVQLLESGGGLVQPGGSLRLSCAASTFTFRNYAMSWVRQAPGKGLDWVSGISASG    SEQ ID
SSTNYAASLKGRFTISRDNSKNTLYLQMNSLRAEDTAVYYCAKFAHDFWSGYSYF    NO: 89
DSWGQGTLVTVSS

VK: <u>IGKV3-15*01</u>(98.21%), <u>IGKJ5*01</u> (100%)

GAAATAGTGATGACGCAGTCTCCAGCCACCCTGTCTGTGTCTCCAGGGGAAAGAG    SEQ ID
CCACCCTCTCCTGCAGGGCCGGTCAGAGTGTTAACAGCAACTTAGCCTGGTACCA    NO: 92
GCAGAAACCTGGGCAGGCTCCCAGACTCCTCATCTATGGTGCATCCACCAGGGCC
ACTGGTATCCCAGCCAGGTTCAGTGGCAGTGGGTCTGGGACAGAGTTCACTCTCA
CCATCAGCAGCCTGCAGTCTGAAGATTTTGCAGTTTATTACTGT**CAGCAGTATAA
TAATTGGGTTTCGATCACC**TTCGGCCAAGGGACACGACTGGAGATTAAAC

EIVMTQSPATLSVSPGERATLSCRAGQSVNSNLAWYQQKPGQAPRLLIYGASTRA    SEQ ID
TGIPARFSGSGSGTEFTLTISSLQSEDFAVYYCQQYNNWVSITFGQGTRLEIK    NO: 90

Figure 26

RVC20:

VH: IGHV4-31*06 (95.86%), IGHJ4*02 (89.58%), IGHD3-3*01

CAGGTGCAGCTGCAGGAGTCGGGCCCAGGACTGGTGAAGCCTTCACAGACCCTG  SEQ ID
TCCCTCACCTGCACTGTCTCCGGTGGCTCCTTCAGCAGTGGAAGTTACTCCTGG  NO: 109
AACTGGATCCGCCAGCACCCAGGGAAGGGCCTGGAGTGGATTGGGTACATCTAT
TACAGTGGGAGCACTTATTACAACCCGTCCCTCAAGAGTCGAGTTACCATGTCA
GTACACACGTCTAAGAACCAGTTCTCCCTGAAGCTGAACTCTATAACTGCCGCG
GACACGGCCGTGTATTACTGTGCGAGAGGCACGTATTCCGATTTTTGGAGTGGT
TCCCCTTTAGACTACTGGGGCCAGGGAACCCTGGTCACCGTCTCCTCAG

QVQLQESGPGLVKPSQTLSLTCTVSGGSFSSGSYSWNWIRQHPGKGLEWIGYIY SEQ ID
YSGSTYYNPSLKSRVTMSVHTSKNQFSLKLNSITAADTAVYYCARGTYSDFWSG NO: 107
SPLDYWGQGTLVTVSS

VK: IGKV1-16*01(98.21%), IGKJ4*01 (100%)

GACATCCAGATGACCCAGTCTCCATCCTCACTGTCTGCATCTGTAGGAGACAGA  SEQ ID
GTCACCATCACTTGTCGGGCGAGTCAGGGCATTAGCAATTATTTAGCCTGGTTT  NO: 110
CAGCAGAAACCAGGGAAAGCCCCTAAGTCCCTGATCTATGCTGCATCCAGTTTG
CAAAGTGGGGTCCCATCAAGGTTCAGCGGCAGTGGATCTGGGACAGATTTCACT
CTCACCATCAACAGCCTGCAGCCTGAAGATTTTGTAACTTATTTCTGCCAACAG
TATGATACTTACCCTCTCACTTTCGGCGGAGGGACCAAGGTGGAGATCAAAC

DIQMTQSPSSLSASVGDRVTITCRASQGISNYLAWFQQKPGKAPKSLIYAASSL SEQ ID
QSGVPSRFSGSGSGTDFTLTINSLQPEDFVTYFCQQYDTYPLTFGGGTKVEIK NO: 108

Figure 27

RVC21:

VH: IGHV4-39*01 (92.78%), IGHJ5*01, or IGHJ5*02 (a) (80.39%), IGHD4-17*01

CAGCTGCAGCTGCAGGAGTCGGGCCCAGGACTGGTGAAGCCTTCGGAGACCCTGTC  SEQ ID
CCTCACGTGCACTGTCTCTGGTGGCTCCATCAGCAACCCTAACTACTACTGGGGCT  NO: 127
GGATCCGCCAGCCCCAGGGAAGGGTCTGGAATGGATTGGGAGTATCTATTATAAT
GGGTACACCTACTACAACCCGTCCCTCAAGAGTCGAGTTACCATATCCGTGGACAA
GTCCAAGGACCAGTTCTTTCTGAAGATGACCTCTCTGACCGCCGCAGACACGGCTG
TGTATTACTGTGCGACGCAATCTACGATGACTACCATAGCGGGCCACTACTGGGGC
CAGGGAACCCTGGTCACCGTCTCCTCAG

QLQLQESGPGLVKPSETLSLTCTVSGGSISNPNYYWGWIRQPPGKGLEWIGSIYYN  SEQ ID
GYTYYNPSLKSRVTISVDKSKDQFFLKMTSLTAADTAVYYCATQSTMTTIAGHY**WG  NO: 125
QGTLVTVSS

VL: IGLV1-51*01 (96.49%), IGLJ1*01 (100%)

CAGTCTGTATTGACGCAGGCGCCCTCAGTGTCTGCGGCCCCAGGACTAAAGGTCAC  SEQ ID
CATCTCCTGCTCTGGAAGCACATCCAACATTGGGAATTCTTATGTATCCTGGTACC  NO: 128
AGCAGCTCCCAGGAACAGCCCCCAAACTCCTCATTTATGACAATAATAAGCGACCC
TCAGGGATTCCTGACCGATTCTCTGGCTCCAAGTCTGACACGTCAGCCACCCTGGG
CATCACCGGACTCCAGACTGGGGACGAGGCCGATTATTACTGCGGAACATGGGACA
GCAGCCTGAATGCTTATGTCTTCGGAACTGGGACCAAGGTCACCGTCCTAG

QSVLTQAPSVSAAPGLKVTISCSGSTSNIGNSYVSWYQQLPGTAPKLLIYDNNKRP  SEQ ID
SGIPDRFSGSKSDTSATLGITGLQTGDEADYYCGTWDSSLNAYVFGTGTKVTVL  NO: 126

Figure 28

RVC38:

VH: IGHV1-69*06 (91.32%), IGHJ4*02 (85.42%), IGHD5-24*01

GAGGTGCAGCTGGTGCAGTCTGGGGCTGAGGTGAAGAAGCCTGGGTCCTCGGTGAG SEQ ID
GGTCTCCTGCAAGGCTTCTGGAGGCACCTTCAGCAGCTATGCCATCAGCTGGGTGC NO: 145
GACAGGCCCCTGGGCTAGGGCTTGAGTGGATGGGAGGGATCATGCCTATGTTTGTG
GCGGCAAACTACGCACAGAACTTCCAGGGCAGAGTCACGGTTTCTGTGGACAAATC
CACGAACACCGCCTATATGGAGATGCACAACCTGAGATCTGACGACACGGCCATGT
ATTACTGTGCGAGAGGGGATGGCTACAATTACAAGTGGTATTTTGACCTTTGGGGC
CAGGGAACCCTAGTCACCGTCTCCTCAG

EVQLVQSGAEVKKPGSSVRVSCKASGGTFSSYAISWVRQAPGLGLEWMGGIMPMFV SEQ ID
AANYAQNFQGRVTVSVDKSTNTAYMEMHNLRSDDTAMYYCARGDGYNYKWYFDLWG NO: 143
QGTLVTVSS

VK: IGKV1-9*01(96.06%), IGKJ4*01 (100%)

GACATCCAGTTGACCCAGTCTCCATCCTTCCTGTCTGCATCTGTAGGAGACAGAGT SEQ ID
CACCATCACTTGCCGGGCCAGTCAGGACATTAGTAATTATTTAGCCTGGTATCAGC NO: 146
AAAAACCAGGGAAGCCCCCTAAACTCCTGATCTATGCTGCATCCACTTTGCAAAGG
GGGGTCCCATCAAGGTTCAGTGGCAGTGGATCTGGGTCAGAATTCACTCTCACAAT
CAGCAGCCTGCAGCCTGAAGATTTTGCAACTTATTACTGTCAACAGCTTGATACTT
ACGTCGCGCTCACTTTCGGCGGAGGGACCAAGGTGGAGATCAAAC

DIQLTQSPSFLSASVGDRVTITCRASQDISNYLAWYQQKPGKPPKLLIYAASTLQR SEQ ID
GVPSRFSGSGSGSEFTLTISSLQPEDFATYYCQQLDTYVALTFGGGTKVEIK NO: 144

Figure 29

RVC44:

VH: IGHV3-21*01 (92.36%), IGHJ3*02 (86%), IGHD6-19*01

GAGGTGCAGCTGGTGCAGTCTGGGGGAGGCCTGGTCAAGCCTGGGGGGTCCCTGAG SEQ ID
ACTCTCCTGTGCAGCCTCTGGCTTCACCTTTAGTAGTTATAGTATGAGTTGGGTCC NO: 163
GCCAGGCTCCAGGGAAGGGCCTGGAGTGGGTCTCATCC**ATCAGTACTACTGGTACT
TACATA**TACTACGCAGACTCAGTGGAGGGCCGATTCTCCATTTCCAGAGACAGCGC
CAGGAGCTCTCTGTTTCTGCAAATGAACAGCCTGAGAGCCGAGGACACGGCTGTCT
ATTACTGT**GCGAGACGGTCGGCCATAGCACTGGCTGGTACGCAGCGTGCTTTTGAT
AT**CTGGGGCCAGGGACAAACGTCATCGTCTCTTCAG

EVQLVQSGGGLVKPGGSLRLSCAASGFTFSSYSMSWVRQAPGKGLEWVSSISTTGT SEQ ID
YIYYADSVEGRFSISRDSARSSLFLQMNSLRAEDTAVYYCARRSAIALAGTQRAFD NO: 161
IWGPGTNVIVSS

VK: IGKV1-39*01, or IGKV1D-39*01 (95.34%), IGKJ1*01 (100%)

GACATCCAGATGACCCAGTCTCCATCTTCCCTGTCTGCATCTGTAGGAGACAGAGT SEQ ID
CACCATCACTTGCCGGGCAAGTCAGAACATTAACAACTATTAAATTGGTATCAGC NO: 164
AGAAACTAGGGAAAGCCCCTAAGCTCCTGATCTATGCTGCATCCAGTTTACATAGT
GGGGTCCCATCAAGGTTCAGTGCCAGTGGATCTGGGACAGATTTCATTCTGACCAT
CAGTAATCTGCAACCTGAAGATTGTGAACTTACTACTGT**CAACAGAGTTACAGTA
ACCCTTGGACG**TTCGGCCAAGGGACCAAGGTGGAAATCAAAC

DIQMTQSPSSLSASVGDRVTITCRASQNINNYLNWYQQKLGKAPKLLIYAASSLHS SEQ ID
GVPSRFSASGSGTDFILTISNLQPEDCATYYCQQSYSNPWTFGQGTKVEIK NO: 162

Figure 30

RVC58:

VH: IGHV3-23*04 (96.18%), IGHJ6*02 (a) (95.16%), IGHD2-15*01

GAGGTGCAGCTGGTGGAGTCTGGGGGAGGCTTGGTACAGCCTGGGGGGTCCCTGAG SEQ ID
ACTCTCCTGTGCGGCCTCTGGATTCACCTTTAGCACCTATGCCATGAATTGGGTCC NO: 181
GCCAGGCTCCAGGGAAGGGGCTGGAGTGGGTCTCAGGT**ATTAGTGATAGAGGTGGT
AGTAGA**TACTACGCAGGCTCCGTGAAGGGCCGGTTCACCATCTCCAGAGACAATTC
CAAGAACACGCTGTTTCTGCAAATGAACAGCCTGAGAGCCGAGGACACGGCCGTAT
ATTACTGT**GCGAGAGATATTGCCCCCCATATAACTACTACTTCTACGGTATGGAC
GTC**TGGGGCCGAGGGACCACGGTCACCGTCTCCTCAG

EVQLVESGGGLVQPGGSLRLSCAASGFTFSTYAMNWVRQAPGKGLEWVSGISDRGG SEQ ID
SRYYAGSVKGRFTISRDNSKNTLFLQMNSLRAEDTAVYCARDIAPPYNYYFYGMD NO: 179
VWGRGTTVTVSS

VL: IGLV2-14*01 (97.57%), IGLJ2*01, or IGLJ3*01 (94.44%)

CAGTCTGCCCTGACTCAGCCTGCCTCCGTGTCTGGGTCTCCTGGACAGTCGATCAC SEQ ID
CATCTCCTGCACTGGTACCAGCAGTGACATTGGTGCTTTTAACTATGTCTCTTGGT NO: 182
ACCAACAGCACCCAGGCAAAGCCCCCAAACTCATAATTTATGAGGTCAGTAATCGG
CCCTCAGGGGTTTCTAATCGCTTCTCTGGCTCCAAGTCTGGCAACACGGCCTCCCT
GACCATCTCTGGGCTCCAGGCTGAGGACGAGGCTGATTATTACTGC**AACTCATATA
CAAGCAGCAGCACTCAGTTA**TTCGGCGGAGGGACCAAGCTGACCGTCCTAG

QSALTQPASVSGSPGQSITISCTGTSSDIGAFNYVSWYQQHPGKAPKLIIYEVSNR SEQ ID
PSGVSNRFSGSKSGNTASLTISGLQAEDEADYYCNSYTSSSTQLFGGGTKLTVL NO: 180

Figure 31

RVC68:

VH: IGHV4-59*01 (92.63%), IGHJ6*03 (a) (88.71%), IGHD4-17*01

CAGGTGCAGCTACAGGAGTCGGGCCCAAGACTGGTGAAGCCCTCGGAGACCCTGTC SEQ ID
CCTCACCTGCACTTTCTCTGGTGGCTCCATTAGTGAGCACCACTGGAGCTGGCTCC NO: 199
GGCAGTCCCCAGGGAAGGGACTGGAGTGGATTGGATATATCTTTCACAGTGGGAGT
ACCAACTACAACCCCTCCCTCAAGAGTCGAGTCAACATATCATTAGACAAGTCCAA
GAACCAGTTCTCCCTGAAGCTGAGTTCTGTGACCGCTGCGGACACGGCCGTGTATT
TCTGTGCGAGAGCGGTGTCTACTTACTACTACTATTACATAGACGTCTGGGGCCAA
GGGACCACGGTCACCGTCTCCTCAG

QVQLQESGPRLVKPSETLSLTCTFSGGSISEHHWSWLRQSPGKGLEWIGYIFHSGS SEQ ID
TNYNPSLKSRVNISLDKSKNQFSLKLSSVTAADTAVYFCARAVSTYYYYYIDVWGQ NO: 197
GTTVTVSS

VK: IGKV1-12*01, or IGKV1-12*02 or IGKV1D-12*02 (95.70%),
IGKJ2*01, or IGKJ2*02 (94.44%)

GACATCCAGATGACCCAGTCTCCATCTTCCGTGTCTGCATCTGTAGGAGACAGAGT SEQ ID
CACCATCACTTGTCGGGCGAGTCAGGATATTAGCAACTGGTTAGCCTGGTATCAGC NO: 200
AGAAACCAGGGAAAGCCCCTAAACTCCTGATCTATGCTGCGTCCAGTTTGCAAAGT
GGGATCTCATCTAGGTTCAGCGGCGGTGGCTCTGGGACAGATTTCACTCTCACCAT
CAGCAGCCTGCAGCCTGAAGATTTTGCAAGTTACTACTGTCAACAGGCTAAGAGTT
TCCCTCTTACTTTTGGCCAGGGGACCAAGCTGGAGATCAAAC

DIQMTQSPSSVSASVGDRVTITCRASQDISNWLAWYQQKPGKAPKLLIYAASSLQS SEQ ID
GISSRFSGGGSGTDFTLTISSLQPEDFASYYCQQAKSFPLTFGQGTKLEIK NO: 198

Figure 32

RVC111:

VH: IGHV3-30*04 (97.57%), IGHJ4*02 (93.75%), IGHD1-14*01

CAGGTGCAACTGGTGGAGTCTGGGGGAGGCGTGGTCCAGCCTGGGAGGTCCCTGAG  SEQ ID
ACTCTCCTGTGCAGCCTCTGGATTCTCCTTCAGTAGCTATGTTATGTACTGGGTCC  NO: 217
GCCAGGCTCCAGGCAAGGGGCTGGAGTGGGTGACAATT**ATATCATATGATGGAAGT
AATAAA**TACTACGCAGACTCCGTGAAGGGCCGATTCACCATCTCCAGAGACAATTC
CAAGAACACGCTGTATCTGCAAATGAACAGCCTGAGAGCTGAGGACACGGCTGTCT
ATTACTGTGCGAGAGGGTCCGGAACCCAAACTCCCCTCTTTGACTACTGGGGCCAG
GGAACCCTGGTCACCGTCTCCTCAG

QVQLVESGGGVVQPGRSLRLSCAASGFSFSSYVMYWVRQAPGKGLEWVTIISYDGS  SEQ ID
NKYYADSVKGRFTISRDNSKNTLYLQMNSLRAEDTAVYYCARGSGTQTPLFDYWGQ  NO: 215
GTLVTVSS

VK: IGKV1-5*01 (95.70%), IGKJ1*01 (94.74%)

GACATCCAGATGACCCAGTCTCCTTCCACCCTGTCTGCATCTGTGGGAGACAGAGT  SEQ ID
CACCATCACTTGCCGGGCCAATCAGAGTATTACTAGCTGGGTGGCCTGGTATCAGC  NO: 218
AGATGCCAGGGAGAGCCCCTAAACTCCTGATCTATGATGACTCCACTTTGGAAAGT
GGGGTCCCATCAAGGTTCAGCGGCAGTGGATCTGGGACAGAATTCACTCTCACCAT
CAGCAGCCTGCAGCCTGATGATTTTGCAACTTATTACTGC**CAACAGTATGAGAGTT
ATTCAGGGACG**TTCGGCCAAGGGACCAAGGTGGAAATCAAAC

DIQMTQSPSTLSASVGDRVTITCRANQSITSWVAWYQQMPGRAPKLLIYDDSTLES  SEQ ID
GVPSRFSGSGSGTEFTLTISSLQPDDFATYYCQQYESYSGTFGQGTKVEIK       NO: 216

Figure 33

BROADLY NEUTRALIZING ANTIBODIES DIRECTED AGAINST THE RABIES VIRUS GLYCOPROTEIN AND USES THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 470082_404 D2_SEQUENCE_LISTING.txt. The text file is 70.5 KB, was created on May 22, 2020, and is being submitted electronically via EFS-Web.

The present invention relates to antibodies, and antigen binding fragments thereof, that potently neutralize infection of both rabies virus (RABV) and non-RABV lyssaviruses. The invention also relates to antigenic sites to which the antibodies and antigen binding fragments bind, as well as to nucleic acids that encode and immortalized B cells and cultured plasma cells that produce such antibodies and antibody fragments. In addition, the invention relates to the use of the antibodies and antibody fragments of the invention in screening methods as well as in the diagnosis, prophylaxis and treatment of RABV infection and infection with non-RABV lyssaviruses.

Rabies is a viral infection, that causes acute inflammation of the brain. Rabies is distributed nearly worldwide and affects principally wild and domestic animals, but also involves humans, resulting in a devastating disease, which is nearly 100% invariably fatal in individuals who do not receive post-exposure prophylaxis (PEP). Early symptoms of rabies can include fever and tingling at the site of exposure. These symptoms are followed by one or more of the following symptoms: violent movements, uncontrolled excitement, fear of water, an inability to move parts of the body, confusion, and loss of consciousness. After symptoms appear, rabies almost always results in death. The time period between contracting the disease and the start of symptoms is usually one to three months. However, this time period can vary from less than one week to more than one year. The time period depends on the distance the virus must travel to reach the central nervous system.

Rabies is caused by a number of lyssaviruses including rabies virus and other lyssaviruses, for example European bat lyssavirus.

Lyssaviruses have helical symmetry, with a length of about 180 nm and a cross-section of about 75 nm. These viruses are enveloped and have a single-stranded RNA genome with negative sense. The genetic information is packed as a ribonucleoprotein complex in which RNA is tightly bound by the viral nucleoprotein. The RNA genome of the virus encodes five genes whose order is highly conserved: nucleoprotein (N), phosphoprotein (P), matrix protein (M), glycoprotein (G), and the viral RNA polymerase (L).

The Lyssavirus genus is subdivided into three phylogroups. Phylogroup I includes the species Rabies virus (RABV), European bat lyssavirus type 1 (EBLV-1) and type 2 (EBLV-2), Duvenhage virus (DUVV), Australian bat lyssavirus (ABLV), Aravan virus (ARAV), Khujand virus (KHUV), Bokeloh bat lyssavirus (BBLV) and Irkut virus (IRKV). Phylogroup II includes Lagos bat virus (LBV), Mokola virus (MOKV), and Shimoni bat virus (SHIV or SHIBV). The remaining viruses, West Caucasian bat virus (WCBV) and Ikoma lyssavirus (IKOV) cannot be included in either of these phylogroups but are related phylogenetically to each other, however, their genetic distances are greater than the distances between phylogroups I and II (Bourhy, H., et al. Journal of Clinical Microbiology 30, 2419-2426, 1992; Bourhy, H., et al. Virology 194, 70-81, 1993; Amengual, B., et al. J Gen. Virol 78, 2319-2328, 1997; Hooper, P. T. et al. Bulletin de l'Institut Pasteur 95, 209-218, 1997; Kuzmin, I. V. et al. Virus Res 149, 197-210, 2010; Badrane, H., et al. J Virol 75, 3268-3276, 2001; Marston, D. A. et al. Emerg Infect Dis 18, 664-667, 2012). Importantly, all genotypes of these lyssaviruses have caused human and/or animal deaths in nature (Badrane, H., et al. J Virol 75, 3268-3276, 2001).

Rabies virus (RABV) was the first of the fourteen lyssavirus genotypes to be identified. The rabies virus is a large bullet-shaped, enveloped, single stranded RNA virus classified and the genome of rabies virus codes for five viral proteins: RNA-dependent RNA polymerase (L); a nucleoprotein (N); a phosphorylated protein (P); a matrix protein (M) located on the inner side of the viral envelope; and an external surface glycoprotein (G). The G protein (62-67 kDa) is a type-I glycoprotein composed of 505 amino acids that has two to four potential N-glycosylation sites. The G protein covers the outer surface of the virion envelope and is the only target antigen, which is able to induce virus-neutralizing antibodies.

Rabies is widespread across the globe and approximately 10 million people a year are treated after exposure to rabies, usually following a bite from infected animals (dogs, bats, foxes, cats, monkeys raccoons, skunks, cattle, wolves, coyotes and others domestic and wild animals). Some 40,000 to 70,000 people are estimated to die of the disease each year, mainly in Africa, China and India, and 50% cases of rabies worldwide occur in children. These data highlight the significant unmet medical need for a safe, effective and affordable rabies treatment.

Rabies prevention is achieved either by pre- or post-exposure vaccination, mostly using modern, tissue culture-based vaccines. Immunizing before exposure (Pre-exposure prophylaxis (PrEP)) is recommended for those who are at high risk and is achieved by administration of a rabies vaccine (active immunization). The high-risk group includes people who work with bats or who spend prolonged periods in areas of the world where rabies is common. Furthermore, the anti-rabies vaccine is recommended for people travelling to countries in Africa and Asia, where rabies is endemic.

Currently available rabies vaccines include the most widely used but highly risk-prone nerve tissue vaccines, or the safer but more costly cell culture and embryonated egg vaccines (CCEEVs). In Germany e.g. only two anti-rabies vaccines are on the market, Rabipur® and "Tollwut-Impfstoff (human diploid cell [HDC]) inaktiviert". These vaccines contain inactivated rabies virus. Both vaccines are recommended for pre- and postexposure use.

After exposure to the virus, a post-exposure prophylaxis (PEP) with the rabies vaccine and a rabies immunoglobulin (RIG) are the standard treatment preventing the disease, if the person receives the treatment as early as possible after infection, i.e. during the first days after the infection. If left untreated until the start of the symptoms, rabies is nearly 100% fatal. Thus, currently, there is no treatment for rabies.

The currently used "treatment" when someone is assumed to be infected by the virus is post-exposure prophylaxis (PEP), which combines rabies immunoglobulin (RIG), in particular human or equine rabies immunoglobulins (HRIG and ERIG, respectively), with a rabies vaccine. In particular, patients receive one dose of RIG (passive immunization) and several doses of rabies vaccine (active immunization)

according to the information of the rabies vaccine manufacturer. In a widely used standard therapy, for example, five doses of the vaccine are administered over a twenty-eight day period, i.e. the first dose of rabies vaccine is given as soon as possible after exposure, preferably day 0, with additional doses on days 3, 7, 14, and 28 after the first (cf rki.de/DE/Content/Infekt/EpidBull/Merkblaetter/Ratgeber_Tollwut.html, retrieved at Nov. 12, 2014). In contrast, rabies immunoglobulin (RIG) for passive immunization is administered only once, preferably at, or as soon as possible after, the initiation of post-exposure vaccination. The dose of human rabies immunoglobulin (HRIG) proposed by the WHO is 20 IU/kg body weight; for equine immunoglobulin (ERIG) and F(ab')2 products it is 40 IU/kg body weight (cf. who.int/rabies/human/WHO_strategy_pre-post_exposure/en/indexi.html #, retrieved at Nov. 12, 2014). In particular, higher doses can reduce vaccine efficacy. All of the rabies immunoglobulin, or as much as anatomically possible to avoid possible compartment syndrome, should be administered into or around the wound site or sites. The remaining immunoglobulin, if any, should be injected intramuscularly at a site distant from the site of vaccine administration. Rabies immunoglobulin may be diluted to a volume sufficient for all wounds to be effectively and safely infiltrated (cf. who.int/rabies/human/WHO_strategy_pre-post_exposure/en/indexi.html #, retrieved at Nov. 12, 2014). This is usually successful if administered up to 24-48 hours following exposure. The HRIG is widely used, especially in developed countries, and is considered safer than ERIG. The high cost of HRIG and its limited availability prohibit its wide use in developing countries. Moreover, the vaccine and HRIG or ERIG do not effectively protect against infection with different lyssavirus species (protection is inversely related to the genetic distance with the vaccine strain). Thus, the need to replace HRIG with at least an equally potent and a safer rabies antibody-based product is considered to be important to improve the access to rabies biologicals, in particular in developing countries.

To this end, mouse monoclonal antibodies as well as human monoclonal antibodies have been developed in the last decade with two products in advanced clinical trials. Namely, CL184 (produced by Crucell), which is a cocktail of two human antibodies called CR57 and CR4098, was developed to replace HRIGs in clinical trials up to phase III (Bakker, A. B. H. et al., J Virol 79, 9062-9068, 2005; Goudsmit J, Marissen W E, Weldon W C, Niezgoda M, Hanlon C A, Rice A B, Kruif J, Dietzschold B, Bakker A B, Rupprecht C E (2006) Comparison of an anti-rabies human monoclonal antibody combination with human polyclonal anti-rabies immune globulin. J Infect Dis 193: 796-801). However, recently the trial was stopped because of the lack of neutralizing activity of the cocktail, or one of the two antibodies of the cocktail, against some circulating RABV isolates. Another human monoclonal antibody, which is presently tested in clinical phase III in India is RAB1, which is produced by Mass Biologics and Serum Institute of India and which is based on a single monoclonal antibody (Sloan S E, Hanlon C, Weldon W, Niezgoda M, Blanton J, Self J, Rowley K J, Mandell R B, Babcock G J, Thomas W D, Jr, et al (2007) Identification and characterization of a human monoclonal antibody that potently neutralizes a broad panel of rabies virus isolates. Vaccine 25: 2800-2810; Nagarajan T, Marissen W E, Rupprecht C E (2014) Monoclonal antibodies for the prevention of rabies: theory and clinical practice. Antibody Technology Journal 4: 1-12). However, RABV isolates that are not neutralized by each of these monoclonal antibodies (CR57, CR4098 and RAB1) have been identified (Kuzimina N A, Kuzmin I V, Ellison J A, Rupprecht C E (2013) Conservation of binding epitopes for monoclonal antibodies on the rabies virus glycoprotein. Journal of Antiviral and Antiretrovirals 5: 37-43, Marissen W E, Kramer R A, Rice A, Weldon W C, Niezgoda M, Faber M, Slootstra J W, Meloen R H, Clijsters-van der Horst M, Visser T J, et al (2005) Novel rabies virus-neutralizing epitope recognized by human monoclonal antibody: fine mapping and escape mutant analysis. J Virol 79: 4672-4678). In the case of the RAM antibody, two out of 25 isolates tested were not neutralized and three were poorly neutralized (Sloan S E, Hanlon C, Weldon W, Niezgoda M, Blanton J, Self J, Rowley K J, Mandell R B, Babcock G J, Thomas W D, Jr, et al (2007) Identification and characterization of a human monoclonal antibody that potently neutralizes a broad panel of rabies virus isolates. Vaccine 25: 2800-2810). In this case the risk of PEP failure is, at least in principle, higher than in the case of the CR57 and CR4098 antibody cocktail. These studies indicate that CR4098 and RAB1 have a limited breadth of reactivity towards non-RABV isolates and that a significant fraction of the RABV isolates tested are not or only poorly neutralized by these antigenic site III antibodies. Indeed, for the lack of large RABV coverage the development of CL184 was recently halted, while RAM in still under development in a Phase 2/3 in India.

Accordingly, there is still a need to replace HRIG with an at least equally potent and safer antibody-based product. Moreover, there is a need for a product capable of preventing as well as treating or attenuating infection with different lyssaviruses with high potency and efficacy, i.e. a product which is not limited to neutralize RABV only, in particular since in some countries, e.g. in Europe and Australia, rabies is mainly transmitted by bats. Further, it is important to have antibodies that target different epitopes and different antigenic sites on the various strains in order to avoid appearance of resistant virus strains and to prevent the escape of resistant variants of the virus.

Moreover, since there is currently no treatment for rabies, there is a need of a product which is effective in treating or attenuating infection, even if the exposure to the virus was more than 24 to 48 hours before the first treatment with the product. The development of such a treatment would be of benefit in particular for at least two classes of patients: those with known exposure to RABV but who have failed to receive prompt post-exposure prophylaxis due to circumstances and who are at increased risk of developing RABV infection, and those who did not recognize contact with the virus and present signs (of different severity) of the disease (e.g. individuals infected by unnoticed contacts with infected bats; RABV of bat origin where dog rabies is controlled has become the leading cause of human rabies). The development of a product of potent and broadly neutralizing antibodies may thus help to expand the post-exposure treatment window for human RABV infection, that is currently limited to the first days after infection. In these individuals the RABV might has already reached the CNS tissues and early or late signs of the disease might have also appeared. These patients could benefit from a treatment with highly potent neutralizing antibodies that can leak across the blood brain barrier (or administered directly in the CSN) delivering a sufficient amount of antibodies capable of effectively neutralizing the virus replication in the CNS tissue.

In view of the above, it is the object of the present invention to provide an antibody-based product, which is at least equally potent, but safer and more cost-effective compared to HRIG. Moreover, it is the object of the present invention to provide a product which is capable of preventing as well as treating or attenuating infection with different lyssaviruses with high potency and efficacy, i.e. a product which is not limited to neutralize RABV only. Furthermore, it is the object of the present invention to provide a product which is effective in treating or attenuating infection, even if the exposure to the virus was more than 24 to 48 hours before the first treatment with the product. In summary, it is the object of the present invention to provide improved antibodies, or antigen binding fragments thereof, as well as related nucleic acid molecules, vectors and cells and pharmaceutical compositions, which overcome the above discussed disadvantages of the prior art by a cost-effective and straight-forward approach.

The object underlying the present invention is solved by the claimed subject matter.

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

As used herein, reference to "treatment" of a subject or patient is intended to include prevention, prophylaxis, attenuation, amelioration and therapy. The terms "subject" or "patient" are used interchangeably herein to mean all mammals including humans. Examples of subjects include humans, cows, dogs, cats, horses, goats, sheep, pigs, and rabbits. In one embodiment, the patient is a human.

As used herein, the terms "antigen binding fragment," "fragment," and "antibody fragment" are used interchangeably to refer to any fragment of an antibody of the invention that retains the antigen-binding activity of the antibody. Examples of antibody fragments include, but are not limited to, a single chain antibody, Fab, Fab', F(ab')$_2$, Fv or scFv. Further, the term "antibody" as used herein includes both antibodies and antigen binding fragments thereof.

As used herein, a "neutralizing antibody" is one that can neutralize, i.e., prevent, inhibit, reduce, impede or interfere with, the ability of a pathogen to initiate and/or perpetuate an infection in a host. The terms "neutralizing antibody" and "an antibody that neutralizes" or "antibodies that neutralize" are used interchangeably herein. These antibodies can be used alone, or in combination, as prophylactic or therapeutic agents upon appropriate formulation, in association with active vaccination, as a diagnostic tool, or as a production tool as described herein.

Doses are often expressed in relation to the bodyweight. Thus, a dose which is expressed as [g, mg, or other unit]/kg (or g, mg etc.) usually refers to [g, mg, or other unit] "per kg (or g, mg etc.) bodyweight", even if the term "bodyweight" is not explicitly mentioned.

The term "specifically binding" and similar reference does not encompass non-specific sticking.

The term "vaccine" as used herein is typically understood to be a prophylactic or therapeutic material providing at least one antigen, preferably an immunogen. The antigen or immunogen may be derived from any material that is suitable for vaccination. For example, the antigen or immunogen may be derived from a pathogen, such as from bacteria or virus particles etc., or from a tumor or cancerous tissue. The antigen or immunogen stimulates the body's adaptive immune system to provide an adaptive immune response. In particular, an "antigen" or an "immunogen" refers typically to a substance which may be recognized by the immune system, preferably by the adaptive immune system, and which is capable of triggering an antigen-specific immune response, e.g. by formation of antibodies and/or antigen-specific T cells as part of an adaptive immune response. Typically, an antigen may be or may comprise a peptide or protein which may be presented by the MHC to T-cells.

As used herein, "sequence variant" refers to any alteration in a reference sequence, whereby a reference sequence is any of the sequences listed in the "Table of Sequences and SEQ ID Numbers" (sequence listing), i.e. SEQ ID NO: 1 to SEQ ID NO:218. Thus, the term "sequence variant" includes nucleotide sequence variants and amino acid sequence variants. Of note, the sequence variants referred to herein are in particular functional sequence variants, i.e. sequence variants maintaining the biological function of, for example, the antibody. In the context of the present invention such a maintained biological function is preferably the binding of the antibody to the RABV (and non-RABV) G protein.

Sequence identity is usually calculated with regard to the full length of the reference sequence (i.e. the sequence recited in the application). Percentage identity, as referred to herein, can be determined, for example, using BLAST using the default parameters specified by the NCBI (the National Center for Biotechnology Information; ncbi.nlm.nih.gov/) [Blosum 62 matrix; gap open penalty=11 and gap extension penalty=1].

As used herein, a "nucleotide sequence variant" has an altered sequence in which one or more of the nucleotides in the reference sequence is deleted, or substituted, or one or more nucleotides are inserted into the sequence of the reference nucleotide sequence. Nucleotides are referred to hereinby the standard one-letter designation (A, C, G, or T). Due to the degeneracy of the genetic code, a "nucleotide sequence variant" can either result in a change in the respective reference amino acid sequence, i.e. in an "amino acid sequence variant" or not. Preferred sequence variants are such nucleotide sequence variants, which do not result in amino acid sequence variants (silent mutations), but other non-silent mutations are within the scope as well, in particular mutant nucleotide sequences, which result in an amino acid sequence, which is at least 80%, preferably at least 90%, more preferably at least 95% sequence identical to the reference sequence.

An "amino acid sequence variant" has an altered sequence in which one or more of the amino acids in the reference sequence is deleted or substituted, or one or more amino acids are inserted into the sequence of the reference amino acid sequence. As a result of the alterations, the amino acid sequence variant has an amino acid sequence which is at least 80% identical to the reference sequence, preferably, at least 90% identical, more preferably at least 95% identical, most preferably at least 99% identical to the reference sequence. Variant sequences which are at least 90% identical have no more than 10 alterations, i.e. any combination of deletions, insertions or substitutions, per 100 amino acids of the reference sequence.

While it is possible to have non-conservative amino acid substitutions, it is preferred that the substitutions be conservative amino acid substitutions, in which the substituted amino acid has similar structural or chemical properties with the corresponding amino acid in the reference sequence. By way of example, conservative amino acid substitutions involve substitution of one aliphatic or hydrophobic amino acids, e.g. alanine, valine, leucine and isoleucine, with another; substitution of one hydoxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include the fusion to the N- or C-terminus of an amino acid sequence to a reporter molecule or an enzyme.

Importantly, the alterations in the sequence variants do not abolish the functionality of the respective reference sequence, in the present case, e.g., the functionality of a sequence of an antibody, or antigen binding fragment thereof, to bind to the same epitope and/or to sufficiently neutralize infection of RABV and non-RABV lyssaviruses. Guidance in determining which nucleotides and amino acid residues, respectively, may be substituted, inserted or deleted without abolishing such functionality are found by using computer programs well known in the art.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

It is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

The invention is based, amongst other findings, on the discovery and isolation of antibodies that are highly potent in neutralizing RABV and non-RABV lyssaviruses, as well as of antigenic sites and epitopes to which the antibodies of the invention bind. Such antibodies are desirable, as only small quantities of the antibodies are required in order to neutralize RABV and non-RABV lyssavirus infection by one single antibody. Each single antibody according to the present invention is highly effective in preventing as well as treating or attenuating RABV and non-RABV lyssavirus infection. Thereby, costs of production of medicaments comprising the antibodies for the treatment of RABV and non-RABV lyssavirus infection are reduced. Moreover, the antibodies according to the present invention neutralize not only RABV, but also non-RABV lyssaviruses, which also cause rabies, in a potent and effective way. In respect to RABV the antibodies according to the present invention recognize broad variations, which occur naturally in the epitopes, thus avoiding resistant RABV strains. In addition, the peptidic antigenic sites or immunogenic polypeptides comprising epitopes recognized by the antibodies of the invention may be a component of a vaccine or a combination therapy capable of inducing protection against RABV and non-RABV lyssavirus (reflecting active immunization).

In a first aspect, the present invention provides an isolated antibody, antibody variants and antigen binding fragments thereof, that neutralize lyssavirus infection by (i) RABV and (ii) at least 50% of non-RABV lyssaviruses selected from the group consisting of DUVV, EBLV-1, EBLV-2, ABLV, IRKV, KHUV, ARAV, LBV, MOK, SHIV, BBLV and WCBV, with an $IC_{50}$ of less than 10000 ng/ml.

Thereby, "with an $IC_{50}$ of less than 10000 ng/ml" means that each species neutralized by an inventive antibody is inhibited by the above $IC_{50}$ value.

"At least 50% of non-RABV lyssaviruses selected from the group consisting of DUVV, EBLV-1, EBLV-2, ABLV, IRKV, KHUV, ARAV, LBV, MOK, SHIV, BBLV and WCBV" refers to at least 50% of the species Duvenhage virus (DUVV), European bat lyssavirus type 1 (EBLV-1) and type 2 (EBLV-2), Australian bat lyssavirus (ABLV), Irkut virus (IRKV), Khujand virus (KHUV), Aravan virus (ARAV), Lagos bat virus (LBV), Mokola virus (MOKV), Shimoni bat virus (SHIV or SHIBV), Bokeloh bat lyssavirus (BBLV), and West Caucasian bat virus (WCBV), i.e. at least 6 species among the above mentioned 12 species.

Preferably, the isolated antibody, antibody variants and antigen binding fragments thereof, neutralize lyssavirus infection by (i) RABV and (ii) at least 50% of non-RABV lyssaviruses selected from the group consisting of DUVV, EBLV-1, EBLV-2, ABLV, IRKV, KHUV, ARAV, LBV, MOK, SHIV, BBLV, WCBV and IKOV, with an $IC_{50}$ of less than 10000 ng/ml.

"At least 50% of non-RABV lyssaviruses selected from the group consisting of DUVV, EBLV-1, EBLV-2, ABLV, IRKV, KHUV, ARAV, LBV, MOK, SHIV, BBLV, WCBV and IKOV" refers to at least 50% of the species Duvenhage virus (DUVV), European bat lyssavirus type 1 (EBLV-1) and type 2 (EBLV-2), Australian bat lyssavirus (ABLV), Irkut virus (IRKV), Khujand virus (KHUV), Aravan virus (ARAV), Lagos bat virus (LBV), Mokola virus (MOKV), Shimoni bat virus (SHIBV), Bokeloh bat lyssavirus (BBLV), West Caucasian bat virus (WCBV) and Ikoma lyssavirus (IKOV) i.e. at least 7 species among the above mentioned 13 species.

Each single lyssavirus species is considered as being neutralized with an $IC_{50}$ of less than 10000 ng/ml, whenever at least one isolate of any such lyssavirus species is neutralized with an $IC_{50}$ of less than 10000 ng/ml. Preferably, at least two isolates of any such lyssavirus species are neutralized with an $IC_{50}$ of less than 10000 ng/ml.

Preferably, the $IC_{50}$ of less than 10000 ng/ml is achieved with infectious viruses, i.e. in particular not with pseudotyped viruses.

Thus, the antibodies, antibody variants and antigen binding fragments thereof, according to the present invention are able to neutralize a broad spectrum of lyssaviruses.

Preferably, the isolated antibody, antibody variants and antigen binding fragments thereof neutralizes lyssavirus infection of at least 55%, more preferably at least 60%, even more preferably at least 65%, most preferably at least 68% and particularly preferably at least 70% of the non-RABV lyssaviruses selected from the group consisting of DUVV, EBLV-1, EBLV-2, ABLV, IRKV, KHUV, ARAV, LBV, MOK, SHIV, BBLV and WCBV with an $IC_{50}$ below 10000 ng/ml.

More preferably, the isolated antibody, antibody variants and antigen binding fragments thereof neutralizes lyssavirus infection of at least 55%, more preferably at least 60%, even more preferably at least 65%, most preferably at least 68% and particularly preferably at least 70% of the non-RABV lyssaviruses selected from the group consisting of DUVV, EBLV-1, EBLV-2, ABLV, IRKV, KHUV, ARAV, LBV, MOK, SHIV, BBLV, WCBV and IKOV with an $IC_{50}$ below 10000 ng/ml.

Moreover, the present invention also provides an isolated antibody, antibody variants and antigen binding fragments thereof, that neutralize lyssavirus infection by (i) RABV and (ii) at least 50% of all isolates of non-RABV lyssaviruses selected from the group consisting of DUVV, EBLV-1, EBLV-2, ABLV, IRKV, KHUV, ARAV, LBV, MOK, SHIV, BBLV and WCBV, with an $IC_{50}$ of less than 10000 ng/ml. Preferably, the isolated antibody, antibody variants and antigen binding fragments thereof, neutralize lyssavirus infection by (i) RABV and (ii) at least 50% of all isolates of non-RABV lyssaviruses selected from the group consisting of DUVV, EBLV-1, EBLV-2, ABLV, IRKV, KHUV, ARAV, LBV, MOK, SHIV, BBLV, WCBV and IKOV, with an $IC_{50}$ of less than 10000 ng/ml.

Thereby, "at least 50% of isolates of non-RABV lyssaviruses selected from the group consisting of DUVV, EBLV-1, EBLV-2, ABLV, IRKV, KHUV, ARAV, LBV, MOK, SHIV, BBLV and WCBV" refers to all isolates of the above 12 species considered and "at least 50% of all isolates of non-RABV lyssaviruses selected from the group consisting of DUVV, EBLV-1, EBLV-2, ABLV, IRKV, KHUV, ARAV, LBV, MOK, SHIV, BBLV, WCBV and IKOV" refers to all isolates of the above 13 species considered (i.e. all isolates considered represent 100% and the number of isolates neutralized with an $IC_{50}$ of less than 10000 ng/ml represents the respective percentage). Preferably, the following first 31 isolates are considered to reflect 100% isolates (cf. Table 1, all isolates except IKOV), more preferably all 32 isolates shown in Table 1 (including IKOV) are considered to reflect 100% isolates:

TABLE 1 non-RABV lyssavirus isolates

| Isolate name | Viral species | Phylogroup |
|---|---|---|
| ABLY/Australia/bat/9810AUS-1998/V1039-2011 | ABLV | I |
| 98010 | ABLY | I |
| 1301 Bokeloh bat lyssavirus | BBLV | I |
| 86132SA | DUVV | I |
| DUW/SouthAfrica/human/96132SA-1971/RS639-2012 | DUVV | I |
| EBLV1a/France/bat/122938-2002/V3951-2009 | EBLV-1 | I |
| EBLV1b/France/bat/8918-1989 | EBLV-1 | I |
| EBLV2/UK/bat/RV1332-2002/V3951-2009 | EBLV-2 | I |
| 94112 | EBLV-2 | I |
| 02053 | EBLV-2 | I |
| 8619 | LBV | II |
| MOK | MOK | II |
| Shimoni bat Virus | SHIV | II |
| West Caucasian bat Virus | WCBV | III |
| Australian bat lyssavirus/RV634 | ABLV | I |
| Aravan Virus | ARAV | I |
| Duvenhage Virus RSA2006 | DUVV | I |
| Duvenhage Virus ZIM86-RV131 | DUVV | I |
| European bat lyssavirus 1.RV20 | EBLV-1 | I |
| European bat lyssavirus 1.RV9 | EBLV-1 | I |
| EBLV1a/France/bat/122938-2002/V3951-2009* | EBLV-1 | I |
| EBLV2/UK/bat/RV1332-2002/V3951-2009* | EBLV-2 | I |
| European bat lyssavirus 2.RV1787 | EBLV-2 | I |
| European bat lyssavirus 2.RV628 | EBLV-2 | I |
| Irkut Virus | IRKV | I |
| Kbujand Virus | KHUV | I |
| 8619* | LBV | II |
| Lagos Bat Virus NIG56-RV1 | LBV | II |
| Lagos Bat Virus SA2004 | LBV | II |
| Mokola Virus NIG68.RV4 | MOK | II |
| Mokola Virus 98/071 RA36 | MOK | II |
| Ikoma lyssavirus | IKOV | IV |

*same isolate tested as pseudovirus and infectious virus.

A more detailed description of the non-RABV lyssavirus isolates shown in Table 1 (as well as of various RABV isolates) is shown in FIG. 1. This includes—in addition to isolate name, viral species and phylogroup (as shown in Table 1)—host species, country and year of origin, lineage and the GenBank accession number of the amino acid and/or nucleotide sequence of the glycoprotein G of that isolate, if available (cf. FIG. 1).

Accordingly, if at least 16 of the first 31 isolates specified in Table 1 (i.e. all isolates except IKOV) are neutralized by the antibody, antibody variant or antigen binding fragment thereof, with an $IC_{50}$ of less than 10000 ng/ml, the antibody, antibody variant or antigen binding fragment thereof neutralizes infection of at least 50% of isolates of non-RABV lyssaviruses selected from the group consisting of DUVV, EBLV-1, EBLV-2, ABLV, IRKV, KHUV, ARAV, LBV, MOK, SHIV, BBLV and WCBV, with an $IC_{50}$ of less than 10000 ng/ml. Moreover, if at least 16 of the 32 isolates specified in Table 1 are neutralized by the antibody, antibody variant or antigen binding fragment thereof, with an $IC_{50}$ of less than 10000 ng/ml, the antibody, antibody variant or antigen binding fragment thereof neutralizes infection of at least 50% of isolates of non-RABV lyssaviruses selected from the group consisting of DUVV, EBLV-1, EBLV-2, ABLV, IRKV, KHUV, ARAV, LBV, MOK, SHIV, BBLV, WCBV and IKOV with an $IC_{50}$ of less than 10000 ng/ml.

Preferably, the isolated antibody, antibody variants and antigen binding fragments thereof neutralizes lyssavirus infection of at least 55%, more preferably at least 60%, even more preferably at least 65%, most preferably at least 68% and particularly preferably at least 70% of isolates of the non-RABV lyssaviruses selected from the group consisting of DUVV, EBLV-1, EBLV-2, ABLV, IRKV, KHUV, ARAV, LBV, MOK, SHIV, BBLV and WCBV with an $IC_{50}$ of less than 10000 ng/ml. More preferably, the isolated antibody, antibody variants and antigen binding fragments thereof neutralizes lyssavirus infection of at least 55%, more preferably at least 60%, even more preferably at least 65%, most preferably at least 68% and particularly preferably at least 70% of all isolates of the non-RABV lyssaviruses selected from the group consisting of DUVV, EBLV-1, EBLV-2, ABLV, IRKV, KHUV, ARAV, LBV, MOK, SHIV, BBLV, WCBV and IKOV with an $IC_{50}$ below 10000 ng/ml.

Preferably, the first 12 isolates mentioned in Table 1 (i.e. from ABLV/Australia/bat/98 10A US-1998/V/039-2011 to MOK/MOK) are tested as infectious viruses, whereas the other isolates mentioned in Table 1 (i.e. from Shimoni bat Virus/SHIV to Ikoma lyssavirus/IKOV) are preferably tested as pseudotyped viruses. Thereby, it is preferred to consider an isolate as neutralizing a certain virus for infectious viruses, if the $IC_{50}$ is less than 10000 ng/ml and for pseudotyped viruses, if the $IC_{90}$ is less than 10000 ng/ml.

Thus, in a preferred embodiment the present invention provides an isolated antibody, antibody variants and antigen binding fragments thereof, that neutralize lyssavirus infection by (i) RABV and (ii) at least 50% of all isolates of non-RABV lyssaviruses selected from the group consisting of A BLV/Australia/bat/9810A US-1998/V1039-2011/ABLV, 98010/ABLV, 1301 Bokeloh bat lyssavirus/BBLV, 86132SA/DUVV, DUVV/SouthAfrica/human/96132SA-1971/RS639-2012/DUVV, EBLV 1a/France/bat/122938-2002/V3951-2009/EBLV-1, EBLV1b/France/bat/8918-1989/EBLV-1, EBLV2/UK/bat/RV1332-2002/V3951-2009/EBLV-2, 94112/EBLV-2, 02053/EBLV-2, 8619/LBV, MOK/MOK, Shimoni bat Virus/SHIV, West Caucasian bat Virus/WCBV, Australian bat lyssavirus/RV634/ABLV, Aravan Virus/ARAV, Duvenhage Virus RSA2006/DUVV, Duvenhage Virus ZIM86-RV 131/DUVV, European bat lyssavirus 1.RV20/EBLV-1, European bat lyssavirus 1.RV9/EBLV-1, EBLV1a/France/bat/122938-2002/V3951-2009/EBLV-1, EBLV2/UR/bat/RV 1332-2002/V3951-2009/EBLV-2, European bat lyssavirus 2.RV1787/EBLV-2, European bat Lyssavirus 2.RV628/EBLV-2, Irkut Virus/IRKV, Khujand Virus/KHUV, 8619/LBV, Lagos Bat Virus NIG56-RV1/LBV, Lagos Bat Virus SA2004/LBV, Mokola Virus NIG68.RV4IMOK, Mokola Virus 98/071 RA36/MOK and Ikoma lyssavirus/IKOV with an $IC_{50}$ of less than 10000 ng/ml for ABLV/Australia/bat/98 10A US-1998/V1039-2011/ABLV, 98010/ABLV, 1301 Bokeloh bat lyssavirus/BBLV, 86132SA/DUVV, DUVV/SouthAfrica/human/96132SA-19711 RS639-2012/DUVV, EBLV1a/France/bat/122938-2002/V3951-2009/EBLV-1, EBLV1b/France/bat/8918-1969/EBLV-1, EBLV2/UK/bat/RV1332-2002/V3951-2009/EBLV-2, 94112/EBLV-2, 02053/EBLV-2, 8619/LBV, MOK/MOK tested as infectious viruses and with an $IC_{90}$ of less than 10000 ng/ml for Shimoni bat Virus/SHIV, West Caucasian bat Virus/WCBV, Australian bat lyssavirus/RV634/ABLV, Aravan Virus/ARAV, Duvenhage Virus RSA2006/DUVV, Duvenhage Virus ZIM86-RV131/DUVV, European bat lyssavirus 1.RV20/EBLV-1, European bat lyssavirus 1.RV9/EBLV-1, EBLV1a/France/bat/122938-2002/V3951-2009/EBLV-1, EBLV2/UK/bat/RV1332-2002/V3951-2009/EBLV-2, European bat lyssavirus 2.RV1787/EBLV-2, European bat Lyssavirus 2.RV628/EBLV-2, Irkut Virus/IRKV, Khujand Virus/KHUV, 8619/LBV, Lagos Bat Virus NIG56-RV1/LBV, Lagos Bat Virus SA2004/LBV, Mokola Virus NIG68.RV1/MOK, Mokola Virus 98/071 RA36/MOK and Ikoma lyssavirus/IKOV tested as pseudotyped viruses.

The following description of the present invention, in particular all preferred embodiments and further aspects, relates to both, the isolated antibody, or an antigen binding fragment thereof, that neutralizes lyssavirus infection by (i) RABV and (ii) at least 50% of non-RABV lyssaviruses selected from the group consisting of DUVV, EBLV-1, EBLV-2, ABLV, IRKV, KHUV, ARAV, LBV, MOK, SHIV, BBLV and WCBV, with an $IC_{50}$ of less than 10000 ng/ml as described above (including the above described preferred embodiments thereof) as well as to the isolated antibody, or an antigen binding fragment thereof, that neutralizes lyssavirus infection by (i) RABV and (ii) at least 50% of (all) isolates of non-RABV lyssaviruses selected from the group consisting of DUVV, EBLV-1, EBLV-2, ABLV, IRKV, KHUV, ARAV, LBV, MOK, SHIV, BBLV and WCBV, with an $IC_{50}$ of less than 10000 ng/ml as described above (including the above described preferred embodiments thereof).

Preferably, the antibody, or the antigen binding fragment thereof, according to the present invention binds to the G protein (glycoprotein G) of RABV. More preferably the antibody, or the antigen binding fragment thereof, according to the present invention binds also to the G protein (glycoprotein G) of non-RABV lyssaviruses.

The antibody, antibody variant or antigen binding fragment thereof, according to the present invention have very low $IC_{50}$ values. In particular, antibodies with $IC_{50}$ values of 10000 ng/ml or more are unlikely to be effective in vivo. Thus, the antibodies according to the present invention have a particular high or strong affinity for RABV and non-RABV lyssaviruses and are therefore particularly suitable for counteracting and/or at least in part preventing a RABV- and/or non-RABV-lyssavirus-infection and/or adverse effects of a RABV- and/or non-RABV-lyssavirus infection.

To determine the $IC_{50}$ value in a neutralization assay, pseudoviruses and/or infectious viruses may be used. Respective neutralization assays are known to the person skilled in the art. However, preferably the neutralization assay according to Wright, E. et al., Vaccine 27, 7178-7186, 2009, which is incorporated by reference herein, is used for assessing pseudoviruses (PV). For infectious viruses preferably the "fluorescent-antibody virus neutralization test" (FAVN) according to Cliquet, F., et al., J. Immunol Methods 212, 79-87, 1998., which is incorporated by reference herein, or "the rapid fluorescent focus inhibition test" (RFFIT) according to Smith, J. S., et al., Bull. World Health Organ. 48, 535-541, 1973, which is also incorporated by reference herein, is used.

In general, a neutralization assay typically measures the loss of infectivity of the virus through reaction of the virus with specific antibodies. Typically, a loss of infectivity is caused by interference by the bound antibody with any of the virus replication steps including binding to target cells, entry, and/or viral release. In the following a non-limiting example of a neutralization assay is given to illustrate the principle: a given amount of a virus, e.g. 50-100 TCDID50 (50% tissue culture infective dose), and different concentrations of the antibodies are mixed under appropriate conditions, e.g. for 1 hour at room temperature, and then inoculated into an appropriate target cell culture, e.g. Hep-2 cells or BHK-21 (baby hamster kidney 21) cells. Values may be typically provided per ml cell culture. The presence of unneutralized virus is detected for example after a predetermined amount of time, e.g. 1, 2, 3, 4, 5, 6, or 7 days, by measuring the cytopathic effect of the (unneutralized) virus on target cells, e.g. by using a colorimetric assay for the quantification of cellular viability, like for instance the WST-1 reagent. The more target cells are rescued from cell death or are measured to be viable, the more virus was neutralized by the antibodies. The effects measured are usually dose-dependent: The higher the antibody titer, the more cells are rescued. Depending on the neutralizing character of the antibody, the $TCID_{50}$ values vary, e.g. an antibody of significant neutralizing character will require lower amounts (of the antibody) to be added (for, e.g., achieving the same amount of "rescued" target cells in the assay, i.e. cells measured to be viable) than another antibody of less pronounced neutralizing character.

Preferably, for the antibody according to the present invention the $IC_{50}$ value (i.e. 50% neutralization) in an infectious virus neutralization assay as described above is less than 10000 ng/ml, i.e. regarding infectious viruses, whereas for the same antibody the $IC_{90}$ value (i.e. 90% neutralization) in a pseudovirus neutralization assay as described above is less than 10000 ng/ml, i.e. regarding pseudoviruses.

Moreover, it is preferred that the antibody, or the antigen binding fragment thereof, according to the present invention neutralizes lyssavirus infection by at least 70% of non-RABV phylogroup I lyssaviruses selected from the group consisting of DUVV, EBLV-1, EBLV-2, ABLV, IRKV, KHUV, and ARAV, with an $IC_{50}$ of less than 10000 ng/ml. Thereby, "at least 70%" of the above mentioned species means at least 5 out of the 7 species. Infection of one lyssavirus species is considered as neutralized with an $IC_{50}$ of less than 10000 ng/ml, if infection of at least one isolate of this lyssavirus species is neutralized with an $IC_{50}$ of less than 10000 ng/ml. Preferably, the isolated antibody, antibody variants and antigen binding fragments thereof neutralizes lyssavirus infection by at least 70% of non-RABV phylogroup I lyssaviruses selected from the group consisting of DUVV, EBLV-1, EBLV-2, ABLV, IRKV, KHUV, ARAV and BBLV with an $IC_{50}$ of less than 10000 ng/ml. Thereby, "at least 70%" of the above mentioned species means at least 6 out of the 8 species. Infection of one lyssavirus species is considered as neutralized with an $IC_{50}$ of less than 10000 ng/ml, if infection of at least one isolate of this lyssavirus species is neutralized with an $IC_{50}$ of less than 10000 ng/ml.

Preferably, the isolated antibody, antibody variants and antigen binding fragments thereof neutralizes lyssavirus infection of at least 75%, more preferably at least 80%, even more preferably at least 82%, of the non-RABV phylogroup I lyssaviruses selected from the group consisting of DUVV, EBLV-1, EBLV-2, ABLV, IRKV, KHUV, and ARAV, with an $IC_{50}$ of less than 10000 ng/ml. More preferably, the isolated antibody, antibody variants and antigen binding fragments thereof neutralizes lyssavirus infection of at least 75%, more preferably at least 80%, even more preferably at least 82%, of the non-RABV phylogroup I lyssaviruses selected from the group consisting of DUVV, EBLV-1, EBLV-2, ABLV, IRKV, KHUV, ARAV and BBLV with an $IC_{50}$ of less than 10000 ng/ml.

According to another preferred embodiment, the antibody, or the antigen binding fragment thereof, according to the present invention neutralizes lyssavirus infection by at least 70% of isolates of non-RABV phylogroup I lyssaviruses selected from the group consisting of DUVV, EBLV-1, EBLV-2, ABLV, IRKV, KHUV, and ARAV, with an $IC_{50}$ of less than 10000 ng/ml. Thereby, "at least 70% of isolates of non-RABV lyssaviruses selected from the group consisting of DUVV, EBLV-1, EBLV-2, ABLV, IRKV, KHUV, and ARAV" refers to all isolates of the above 7 species considered (i.e. all isolates considered represent 100% and the number of isolates neutralized with an $IC_{50}$ of less than 10000 ng/ml represents the respective percentage). More preferably, the antibody, or the antigen binding fragment thereof, according to the present invention neutralizes lyssavirus infection by at least 70% of isolates of non-RABV phylogroup I lyssaviruses selected from the group consisting of DUVV, EBLV-1, EBLV-2, ABLV, IRKV, KHUV, ARAV and BBLV with an $IC_{50}$ of less than 10000 ng/ml. Thereby, "at least 70% of isolates of non-RABV lyssaviruses selected from the group consisting of DUVV, EBLV-1, EBLV-2, ABLV, IRKV, KHUV ARAV and BBLV" refers to all isolates of the above 8 species considered (i.e. all isolates considered represent 100% and the number of isolates neutralized with an $IC_{50}$ of less than 10000 ng/ml represents the respective percentage). Preferably, the 22 isolates mentioned in Table 1 regarding phylogroup I species are considered to calculate the percentage. Accordingly, if at least 16 out of these 22 isolates mentioned in Table 1 regarding phylogroup I species are neutralized by the antibody, antibody variant or antigen binding fragment thereof, with an $IC_{50}$ of less than 10000 ng/ml, the antibody, antibody variant or antigen binding fragment thereof neutralizes infection of at least 70% of isolates of non-RABV phylogroup I lyssaviruses selected from the group consisting of DUVV, EBLV-1, EBLV-2, ABLV, IRKV, KHUV, ARAV and, preferably BBLV, with an $IC_{50}$ of less than 10000 ng/ml. Preferably, the isolated antibody, antibody variants and antigen binding fragments thereof neutralizes lyssavirus infection of at least 75%, more preferably at least 80%, even more preferably at least 82%, of isolates of the non-RABV phylogroup I lyssaviruses selected from the group consisting of DUVV, EBLV-1, EBLV-2, ABLV, IRKV, KHUV, ARAV and, preferably, BBLV with an $IC_{50}$ of less than 10000 ng/ml.

It is particularly preferred that the isolated antibody, antibody variants and antigen binding fragments thereof, according to the present invention neutralizes lyssavirus infection by at least 70% of the isolates of non-RABV phylogroup I lyssaviruses selected from the group consisting of ABLV/Australia/bat/9810AUS-1998/V1039-201/ABLV, 98010/ABLV, 1301 Bokeloh bat lyssavirus/BBLV, 86132SA/DUVV, DUVV/SouthAfrica/hurnan/196132 SA-1971/RS639-2012/DUVV, EBLV France/bat/122938-2002/V3951-2009/EBLV-1, EBLV1b/France/bat/8918-1989/EBLV-1, EBLV2/UK/bat/RV1332-2002/V3951-2009/ EBLV-2, 94112/EBLV-2, 02053/EBLV-2, Australian bat lyssavirus/RV634/ABLV, Aravan Virus/ARAV, Duvenhage Virus RSA2006/DUVV, Duvenhage Virus ZIM86-RV 131/ DUVV, European bat lyssavirus 1.RV20/EBLV-1, European bat lyssavirus 1.RV9/EBLV-1, EBLV1a/France/bat/122938-2002/V3951-2009/EBLV-1, EBLV2/UK/bat/RV1332-2002/ V3951-2009/EBLV-2, European bat lyssavirus 2.RV1787/ EBLV-2 and European bat lyssavirus 2.RV628/EBLV-2, Irkut Virus/IRKV, Khujand Virus/KHUV, with an $IC_{50}$ of less than 10000 ng/ml for ABLV/Australia/bat/98 10 A US-1998/V1039-2011/ABLV, 98010/ABLV, 1301 Bokeloh bat lyssavirus/BBLV, 86132SA/DUVV, DUVV/South-Africa/human/96132SA-1971/RS639-2012/DUVV, EBLV France/bat/122938-2002/V3951-2009/EBLV-1, EBLV113/ France/bat/8918-1989/EBLV-1, EBLV2/UK/bat/RV332-2002/V3951-2009/EBLV-2, 94412/EBLV-2 and 02053/ EBLV-2, tested as infectious viruses and with an $IC_{90}$ of less than 10000 ng/ml for Australian bat lyssavi RV634/ABLV, Aravan Virus/ARAV, Duvenhage Virus RSA2006/DUVV, Duvenhage Virus ZIM86-RV131/DUVV, European bat lyssavirus 1.RV20/EBLV-1, European bat lyssavirus 1.RV9/ EBLV-1, EBLV1a/France/bat/122938-2002/V3951-2009/ EBLV-1, EBLV2/UK/bat/RV1332-2002/V3951-2009/ EBLV-2, European bat lyssavirus 2.RV1787/EBLV-2, European bat lyssavirus 2.RV628/EBLV-2, Irkut Virus/ IRKV and Khujand Virus/KIIUV tested as pseudotyped viruses.

Among the lyssaviruses, and in particular the phylogroup I lyssaviruses, it is particularly preferred that the antibody, or the antigen binding fragment thereof, according to the present invention neutralizes infection of EBLV-1. In particular, the antibody, or the antigen binding fragment thereof, according to the present invention neutralizes infection of at least one isolate of EBLV-1, more preferably of at least two, even more preferably of at least three EBLV-1 isolates, e.g. the EBLV-1 isolates mentioned in Table 1, with an $IC_{50}$ below 10000 ng/ml. Thereby, it is particularly preferred if the one or more EBLV-1 isolates are neutralized in both, in a pseudovirus neutralization assay as described above and in an infectious virus neutralization assay as described above. Even more preferably, the $IC_{50}$ value in the infectious virus neutralization assay is below 10000 ng/ml and the $IC_{50}$ value in the pseudovirus neutralization assay is below 10000 ng/ml.

Of note, none of the prior art human monoclonal antibodies CR57, CR4098 and RAM neutralizes EBLV-1 (cf. FIGS. 5 and 6). However, rabies due to European Bat Lyssavirus type 1 is present in many European countries and bats are listed as protected species across Europe. The disease is fatal in humans and has been described in Europe following a bat bite. Rabies pre-exposure vaccination and post-exposure treatment is recommended for occupationally exposed persons and treatment of international travellers after bat bites is also recommended (Stantic-Pavlinic M. (2005) Eurosurveillance, Volume 10, Issue ii), however, as shown in FIGS. 5 and 6, HRIG hardly neutralizes EBLV-1. Therefore, there is a need for (human) antibodies neutralizing EBLV-1.

It is also preferred that the antibody, or the antigen binding fragment thereof, according to the present invention neutralizes infection by RABV CVS-11 with an $IC_{90}$ of 400 ng/ml or less, more preferably with an $IC_{90}$ of 100 ng/ml or less, even more preferably with an $IC_{90}$ of 50 ng/ml or less and particularly preferably with an $IC_{90}$ of 1 ng/ml or less. In other words, the concentration of the antibody, or the antigen binding fragment thereof, according to the present invention required for 90% neutralization ($IC_{90}$) of the RABV isolate CVS-11 (challenge virus strain 11) is 400 ng/ml or less, preferably 100 ng/ml or less, more preferably 50 ng/ml or less, even more preferably 1 ng/ml or less, in particular in a pseudovirus neutralization assay as described above, and preferably also in a RFFIT infectious virus neutralization assay as described above.

In general, it is preferred that the antibody, or the antigen binding fragment thereof, according to the present invention is a monoclonal antibody or antigen binding fragment thereof. In contrast to polyclonal antibodies, monoclonal antibodies are monospecific antibodies, i.e. they bind to a specific epitope. Therefore, unexpected binding is largely avoided and monoclonal antibodies are considered as safer compared to polyclonal antibodies.

Preferably, the antibody according to the present invention, or the antigen binding fragment thereof, is a human antibody, a monoclonal antibody, a human monoclonal antibody, a purified antibody, a single chain antibody, Fab, Fab', F(ab')2, Fv or scFv.

The antibodies of the invention may thus be human antibodies, monoclonal antibodies, human monoclonal antibodies, recombinant antibodies or purified antibodies. The invention also provides fragments of the antibodies of the invention, particularly fragments that retain the antigen-binding activity of the antibodies. Such fragments include, but are not limited to, single chain antibodies, Fab, Fab', F(ab')2, Fv or scFv. Although the specification, including the claims, may, in some places, refer explicitly to antigen binding fragment(s), antibody fragment(s), variant(s) and/or derivative(s) of antibodies, it is understood that the term "antibody" or "antibody of the invention" includes all categories of antibodies, namely, antigen binding fragment(s), antibody fragment(s), variant(s) and derivative(s) of antibodies.

Fragments of the antibodies of the invention can be obtained from the antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. Antibody "fragments" include Fab, Fab', F(ab')2 and Fv fragments. The invention also encompasses single-chain Fv fragments (scFv) derived from the heavy and light chains of an antibody of the invention. For example, the invention includes a scFv comprising the CDRs from an antibody of the invention. Also included are heavy or light chain monomers and dimers, single domain heavy chain antibodies, single domain light chain antibodies, as well as single chain antibodies, e.g., single chain Fv in which the heavy and light chain variable domains are joined by a peptide linker.

Antibody fragments of the invention may impart monovalent or multivalent interactions and be contained in a variety of structures as described above. For instance, scFv molecules may be synthesized to create a trivalent "triabody" or a tetravalent "tetrabody." The scFv molecules may include a domain of the Fc region resulting in bivalent minibodies. In addition, the sequences of the invention may be a component of multispecific molecules in which the sequences of the invention target the epitopes of the invention and other regions of the molecule bind to other targets. Exemplary molecules include, but are not limited to, bispecific Fab2, trispecific Fab3, bispecific scFv, and diabodies (Holliger and Hudson, 2005, *Nature Biotechnology* 9: 1126-1136).

In general, the antibody according to the present invention, or the antigen binding fragment thereof, preferably comprises (at least) three CDRs on the heavy chain and (at least) three CDRs on the light chain. In general, complementarity determining regions (CDRs) are the hypervariable regions present in heavy chain variable domains and light chain variable domains. Typically, the CDRs of a heavy chain and the connected light chain of an antibody together form the antigen receptor. Usually, the three CDRs (CDR1, CDR2, and CDR3) are arranged non-consecutively in the variable domain. Since antigen receptors are typically composed of two variable domains (on two different polypeptide chains, i.e. heavy and light chain), there are six CDRs for each antigen receptor (heavy chain: CDRH1, CDRH2, and CDRH3; light chain: CDRL1, CDRL2, and CDRL3). A single antibody molecule usually has two antigen receptors and therefore contains twelve CDRs. The CDRs on the heavy and/or light chain may be separated by framework regions, whereby a framework region (FR) is a region in the variable domain which is less "variable" than the CDR. For example, a chain (or each chain, respectively) may be composed of four framework regions, separated by three CDR.

Preferably, the CDRs, in particular CDRH3, of the antibody according to the present invention are derived from an antibody developed in a human. In particular, the CDRs, in particular the CDRH3, of the antibody according to the present invention are of human origin or functional sequence variants thereof.

The sequences of the heavy chains and light chains of several antibodies of the invention, each comprising three CDRs on the heavy chain and three CDRs on the light chain have been determined. The position of the CDR amino acids are defined according to the IMGT numbering system (IMGT: imgt.org/; cf Lefranc, M.-P. et al. (2009) Nucleic Acids Res. 37, D1006-D1012). The sequences of the CDRs, heavy chains, light chains as well as the sequences of the nucleic acid molecules encoding the CDRs, heavy chains, light chains of the antibodies of the invention, i.e. of several antibodies according to the invention, are disclosed in the sequence listing. The CDRs of the antibody heavy chains are also referred to as CDRH1, CDRH2 and CDRH3, respectively. Similarly, the CDRs of the antibody light chains are also referred to as CDRL1, CDRL2 and CDRL3, respectively.

Preferably, the antibody according to the present invention, or the antigen binding fragment thereof, comprises a heavy chain comprising CDRH1, CDRH2 and CDRH3 and a light chain comprising CDRL1, CDRL2 and CDRL3, wherein the heavy chain CDRH3 comprises an amino acid sequence that is at least 80%, preferably at least 90%, identical to SEQ ID NOs: 3, 21, 39, 57, 77, 95, 113, 131, 149, 167, 185, or 203, whereby amino acid sequences that are at least 80%, preferably at least 90%, identical to SEQ ID NOs: 95 or 167 are particularly preferred. More preferably, the heavy chain CDRH3 of the antibody, or of the antigen binding fragment thereof, comprises the amino acid sequence of SEQ ID NOs: 3, 21, 39, 57, 77, 95, 113, 131, 149, 167, 185, or 203, more preferably of SEQ ID NOs: 95 or 167. In more general terms, the present invention also comprises an antibody, or an antigen binding fragment thereof, comprising a heavy chain comprising CDRH1, CDRH2 and CDRH3 and a light chain comprising CDRL1, CDRL2 and CDRL3, wherein the heavy chain CDRH3 comprises an amino acid sequence variant to SEQ ID NOs: 3, 21, 39, 57, 77, 95, 113, 131, 149, 167, 185, or 203, whereby amino acid sequence variants to SEQ ID NOs: 95 or 167 are particularly preferred. More preferably the heavy chain comprises at least two CDRH3 with one heavy chain CDRH3 comprising an amino acid sequence that is at least 80%, preferably at least 90%, identical to SEQ ID NO: 95 and one heavy chain CDRH3 comprising an amino acid sequence that is at least 80%, preferably at least 90%, identical to SEQ ID NO: 167. The sequence variants referred to above are in particular functional sequence variants, e.g. wherein the binding of the antibody to the RABV (and non-RABV) G protein (glycoprotein G) is maintained.

It is also preferred that, the isolated antibody of the invention, or the antigen binding fragment thereof, comprises a heavy chain comprising CDR1, CDR2 and CDR3 and a light chain comprising CDR1, CDR2 and CDR3, wherein the heavy chain CDR3 comprises an amino acid sequence that is at least 90%, for example, 90%, 91%, 92%, 93%, 94%, 95%, 96%, 97%, 98%, 99% or 100% identical to SEQ ID NOs: 3, 21, 39, 57, 77, 95, 113, 131, 149, 167, 185, or 203, preferably to SEQ ID NOs: 95 or 167. More preferably the heavy chain comprises at least two CDRH3 with one heavy chain CDRH3 comprising an amino acid sequence of SEQ ID NO: 95 and one heavy chain CDRH3 comprising an amino acid sequence of SEQ ID NO: 167. The sequence variants referred to above are in particular functional sequence variants, e.g. wherein the binding of the antibody to the RABV (and non-RABV) G protein (glycoprotein G) is maintained.

Table 2 provides the SEQ ID numbers for the amino acid sequences of the six CDRs of the heavy and light chains, respectively, of exemplary antibodies of the invention.

TABLE 2

SEQ ID Numbers for CDR Polypeptides of exemplary antibodies of the invention.

| | SEQID NOs. for CDR Polypeptides | | | | | |
|---|---|---|---|---|---|---|
| | CDRH1 | CDRH2 | CDRH3 | CDRL1 | CDRL2 | CDRL3 |
| RVA122 | 1 | 2 | 3 | 4 | 5/6 | 7 |
| RVA144 | 19 | 20 | 21 | 22 | 23/24 | 25 |
| RVB185 | 37 | 38 | 39 | 40 | 41/42 | 43 |
| RVB492 | 55 | 56 | 57 | 58 | 59/60 | 61 |
| RVC3 | 75 | 76 | 77 | 78 | 79/80 | 81 |
| RVC20 | 93 | 94 | 95 | 96 | 97/98 | 99 |
| RVC21 | 111 | 112 | 113 | 114 | 115/116 | 117 |
| RVC38 | 129 | 130 | 131 | 132 | 133/134 | 135 |
| RVC44 | 147 | 148 | 149 | 150 | 151/152 | 153 |
| RVC58 | 165 | 166 | 167 | 168 | 169/170 | 171 |
| RVC68 | 183 | 184 | 185 | 186 | 187/188 | 189 |
| RVC111 | 201 | 202 | 203 | 204 | 205/206 | 207 |

Variant antibodies are also included within the scope of the invention. Thus, variants of the sequences recited in the application are also included within the scope of the invention. The variants referred to herein are in particular functional, e.g. wherein the binding of the antibody to the RABV (and non-RABV) G protein (glycoprotein G) is maintained. Such variants include natural variants generated by somatic mutation in vivo during the immune response or in vitro upon culture of immortalized B cell clones. Alternatively, variants may arise due to the degeneracy of the genetic code or may be produced due to errors in transcription or translation.

Further variants of the antibody sequences having improved affinity and/or potency may be obtained using methods known in the art and are included within the scope of the invention. For example, amino acid substitutions may be used to obtain antibodies with further improved affinity. Alternatively, codon optimization of the nucleotide sequence may be used to improve the efficiency of translation in expression systems for the production of the antibody. Further, polynucleotides comprising a sequence optimized for antibody specificity or neutralizing activity by the application of a directed evolution method to any of the nucleic acid sequences of the invention are also within the scope of the invention.

Preferably, variant antibody sequences may share 70% or more (i.e. 75%, 80%, 85%, 88%, 90%, 92%, 95%, 96%, 97%, 98%, 99% or more) amino acid sequence identity with the sequences recited in the application. Such variants usually have a greater homology to the sequences listed herein in the CDRs of the heavy chain variable region ($V_H$) and light chain variable region ($V_L$) than in the framework region. As is known to one of skill in the art, mutations are more tolerated, i.e., limited or no loss of function (e.g., specificity or neutralization ability) in the framework regions than in the CDRs.

The invention thus comprises an antibody, or an antigen binding fragment thereof, wherein the variation from the sequences provided herein is preferably in the framework region(s) of the antibody or in the nucleic acid residues that encode the framework region(s) of the antibody.

In the present invention, such (variant) antibodies are preferred, in which the number of somatic mutations is reduced (i.e. "germlined" antibodies: reverted back to the "germline" configuration). Germline sequences of antibodies may be determined, for example, with reference to IMGT database (e.g., according to the IMGT VDJ and VJ assignments and rearrangement interpretation: imgt.org/; cf Lefranc, M.-P. et al. (2009) Nucleic Acids Res. 37, D1006-D1012) and "germlined" antibody variants may be produced, for example, by gene synthesis or by site-directed mutagenesis. A low level of somatic mutations reduces the potential risk of antibody immunogenicity. Preferably, the number of somatic mutations is reduced in the framework regions (FR) (i.e. "framework regions germlined" antibodies, also referred to herein as FR-GL variants). (Variant) antibodies, or an antigen binding fragment thereof, and FR-GL variants, respectively, without any somatic mutations in the framework regions (FR) are more preferred. Particularly preferred are such (variant) antibodies, or an antigen binding fragment thereof, and FR-GL variants, respectively, with as few somatic mutations as possible, whereby on the other hand the neutralizing activity is not impaired (as compared to the reference antibody/fragment containing (more) somatic mutations). Such antibodies are on the one hand not impaired in their neutralizing activities, thus showing a very high potency and breadth. On the other hand, a potential risk of antibody immunogenicity is significantly reduced.

In a preferred embodiment, the isolated antibody or antibody fragment of the invention comprises at least one CDR with a sequence that has at least 95% sequence identity to any one of SEQ ID NOs: 1-7, 19-25, 37-43, 55-61, 75-81, 93-99, 111-117, 129-135, 147-153, 165-171, 183-189, or 201-207. The amino acid sequences of the heavy and light chain variable regions of the antibodies of the invention as well as the nucleic acid sequences that encode them are provided in the Table of Sequences and SEQ ID Numbers below. The amino acid residues corresponding to the six CDRs and the nucleic acid residues that encode them are highlighted in bold text.

Preferably, an isolated antibody, or antigen binding fragment thereof, according to the present invention comprises more than one CDR with a sequence that has at least 95% sequence identity to any one of SEQ ID NOs: 1-7, 19-25, 37-43, 55-61, 75-81, 93-99, 111-117, 129-135, 147-153, 165-171, 183-189, and 201-207.

Preferably, the antibody, or antigen binding fragment thereof, comprises two CDRs with a sequence that has at least 95% sequence identity to any one of SEQ ID NOs: 1-7, 19-25, 37-43, 55-61, 75-81, 93-99, 111-117, 129-135, 147-153, 165-171, 183-189, or 201-207. Thereby it is preferred that the antibody, or antigen binding fragment thereof, comprises (i) a CDRH1 that has at least 95% sequence identity to any one of SEQ ID NOs: 1, 19, 37, 55, 75, 93, 111, 129, 147, 165, 183 or 201 and a CDRL1 that has at least 95% sequence identity to any one of SEQ ID NOs: 4, 22, 40, 58, 78, 96, 114, 132, 150, 168, 186, or 204; (ii) a CDRH2 that has at least 95% sequence identity to any one of SEQ ID NOs: 2, 20, 38, 56, 76, 94, 112, 130, 148, 166, 184, or 202, and a CDRL2 that has at least 95% sequence identity to any one of SEQ ID NOs: 5, 6, 23, 24, 41, 42, 59, 60, 79, 80, 97, 98, 115, 116, 133, 134, 151, 152, 169, 170, 187, 188, 205, or 206; or (iii) a CDRH3 that has at least 95% sequence identity to any one of SEQ ID NOs: 3, 21, 39, 57, 77, 95, 113, 131, 149, 167, 185, or 203, and a CDRL3 that has at least 95% sequence identity to any one of SEQ ID NOs: 7, 25, 43, 61, 81, 99, 117, 135, 153, 171, 189, or 201.

Preferably, the antibody, or antigen binding fragment thereof, comprises three CDRs with a sequence that has at least 95% sequence identity to any one of SEQ ID NOs: 1-7, 19-25, 37-43, 55-61, 75-81, 93-99, 111-117, 129-135, 147-153, 165-171, 183-189, and 201-207. Thereby it is preferred that the antibody, or antigen binding fragment thereof, comprises (i) a CDRH1 that has at least 95% sequence identity to any one of SEQ ID NOs: 1, 19, 37, 55, 75, 93, 111, 129, 147, 165, 183 or 201, a CDRH2 that has at least 95% sequence identity to any one of SEQ ID NOs: 2, 20, 38, 56, 76, 94, 112, 130, 148, 166, 184, or 202, and a CDRH3 that has at least 95% sequence identity to any one of SEQ ID NOs: 3, 21, 39, 57, 77, 95, 113, 131, 149, 167, 185, or 203; or (ii) a CDRL1 that has at least 95% sequence identity to any one of SEQ ID NOs: 4, 22, 40, 58, 78, 96, 114, 132, 150, 168, 186, or 204, a CDRL2 that has at least 95% sequence identity to any one of SEQ ID NOs: 5, 6, 23, 24, 41, 42, 59, 60, 79, 80, 97, 98, 115, 116, 133, 134, 151, 152, 169, 170, 187, 188, 205, or 206, and a CDRL3 that has at least 95% sequence identity to any one of SEQ ID NOs: 7, 25, 43, 61, 81, 99, 117, 135, 153, 171, 189, or 201.

Preferably, the antibody, or antigen binding fragment thereof, comprises four CDRs with a sequence that has at least 95% sequence identity to any one of SEQ ID NOs: 1-7, 19-25, 37-43, 55-61, 75-81, 93-99, 111-117, 129-135, 147-153, 165-171, 183-189, and 201-207. Thereby it is preferred that the antibody, or antigen binding fragment thereof, comprises (i) a CDRH1 that has at least 95% sequence identity to any one of SEQ ID NOs: 1, 19, 37, 55, 75, 93, 111, 129, 147, 165, 183 or 201, a CDRH2 that has at least 95% sequence identity to any one of SEQ ID NOs: 2, 20, 38, 56, 76, 94, 112, 130, 148, 166, 184, or 202, a CDRH3 that has at least 95% sequence identity to any one of SEQ ID NOs: 3, 21, 39, 57, 77, 95, 113, 131, 149, 167, 185, or 203, and a CDRL that has at least 95% sequence identity to any one of SEQ ID NOs: 4-6, 20-22, 36-38, or 52-54; (ii) a CDRL1 that has at least 95% sequence identity to any one of SEQ ID NOs: 4, 22, 40, 58, 78, 96, 114, 132, 150, 168, 186, or 204, a CDRL2 that has at least 95% sequence identity to any one of SEQ ID NOs: 5, 6, 23, 24, 41, 42, 59, 60, 79, 80, 97, 98, 115, 116, 133, 134, 151, 152, 169, 170, 187, 188, 205, or 206, a CDRL3 that has at least 95% sequence identity to any one of SEQ ID NOs: 7, 25, 43, 61, 81, 99, 117, 135, 153, 171, 189, or 201, and a CDRH that has at least 95% sequence identity to any one of SEQ ID NOs: 1-3, 19-21, 37-39, 55-57, 75-77, 93-95, 111-113, 129-131, 147-149, 165-167, 183-185 or 201-203, whereby a CDRH3 that has at least 95% sequence identity to any one of SEQ ID NOs: 3, 21, 39, 57, 77, 95, 113, 131, 149, 167, 185, or 203 is particularly preferred; (iii) a CDRH1 that has at least 95% sequence identity to any one of SEQ ID NOs: 1, 19, 37, 55, 75, 93, 111, 129, 147, 165, 183 or 201, a CDRL1 that has at least 95% sequence identity to any one of SEQ ID NOs: 4, 22, 40, 58, 78, 96, 114, 132, 150, 168, 186, or 204, a CDRH2 that has at least 95% sequence identity to any one of SEQ ID NOs: 2, 20, 38, 56, 76, 94, 112, 130, 148, 166, 184, or 202, and a CDRL2 that has at least 95% sequence identity to any one of SEQ ID NOs: 5, 6, 23, 24, 41, 42, 59, 60, 79, 80, 97, 98, 115, 116, 133, 134, 151, 152, 169, 170, 187, 188, 205, or 206; (iv) a CDRH1 that has at least 95% sequence identity to any one of SEQ ID NOs: 1, 19, 37, 55, 75, 93, 111, 129, 147, 165, 183 or 201, a CDRL1 that has at least 95% sequence identity to any one of SEQ ID NOs: 4, 22, 40, 58, 78, 96, 114, 132, 150, 168, 186, or 204, a CDRH3 that has at least 95% sequence identity to any one of SEQ ID NOs: 3, 21, 39, 57, 77, 95, 113, 131, 149, 167, 185, or 203, and a CDRL3 that has at least 95% sequence identity to any one of SEQ ID NOs: 7, 25, 43, 61, 81, 99, 117, 135, 153, 171, 189, or 201; or (v) a CDRH2 that has at least 95% sequence identity to any one of SEQ ID NOs: 2, 20, 38, 56, 76, 94, 112, 130, 148, 166, 184, or 202, a CDRL2 that has at least 95% sequence identity to any one of SEQ ID NOs: 5, 6, 23, 24, 41, 42, 59, 60, 79, 80, 97, 98, 115, 116, 133, 134, 151, 152, 169, 170, 187, 188, 205, or 206, a CDRH3 that has at least 95% sequence identity to any one of SEQ ID NOs: 3, 21, 39, 57, 77, 95, 113, 131, 149, 167, 185, or 203, and a CDRL3 that has at least 95% sequence identity to any one of SEQ ID NOs: 7, 25, 43, 61, 81, 99, 117, 135, 153, 171, 189, or 201.

Preferably, the antibody, or antigen binding fragment thereof, comprises five CDRs with a sequence that has at least 95% sequence identity to any one of SEQ ID NOs: 1-7, 19-25, 37-43, 55-61, 75-81, 93-99, 111-117, 129-135, 147-153, 165-171, 183-189, and 201-207. Thereby it is preferred that the antibody, or antigen binding fragment thereof, comprises five CDRs selected from the group of a CDRH1 that has at least 95% sequence identity to any one of SEQ ID NOs: 1, 19, 37, 55, 75, 93, 111, 129, 147, 165, 183 or 201, a CDRH2 that has at least 95% sequence identity to any one of SEQ ID NOs: 2, 20, 38, 56, 76, 94, 112, 130, 148, 166, 184, or 202, a CDRH3 that has at least 95% sequence identity to any one of SEQ ID NOs: 3, 21, 39, 57, 77, 95, 113, 131, 149, 167, 185, or 203, a CDRL1 that has at least 95% sequence identity to any one of SEQ ID NOs: 4, 22, 40, 58, 78, 96, 114, 132, 150, 168, 186, or 204, a CDRL2 that has at least 95% sequence identity to any one of SEQ ID NOs: 5, 6, 23, 24, 41, 42, 59, 60, 79, 80, 97, 98, 115, 116, 133, 134, 151, 152, 169, 170, 187, 188, 205, or 206, and a CDRL3 that has at least 95% sequence identity to any one of SEQ ID NOs: 7, 25, 43, 61, 81, 99, 117, 135, 153, 171, 189, or 201.

Preferably, the antibody, or antigen binding fragment thereof, comprises six CDRs with a sequence that has at least 95% sequence identity to any one of SEQ ID NOs: 1-7, 19-25, 37-43, 55-61, 75-81, 93-99, 111-117, 129-135, 147-153, 165-171, 183-189, and 201-207. Thereby it is preferred that the antibody, or antigen binding fragment thereof, comprises six CDRs selected from the group of a CDRH1 that has at least 95% sequence identity to any one of SEQ ID NOs: 1, 19, 37, 55, 75, 93, 111, 129, 147, 165, 183 or 201, a CDRH2 that has at least 95% sequence identity to any one of SEQ ID NOs: 2, 20, 38, 56, 76, 94, 112, 130, 148, 166, 184, or 202, a CDRH3 that has at least 95% sequence identity to any one of SEQ ID NOs: 3, 21, 39, 57, 77, 95, 113, 131, 149, 167, 185, or 203, a CDRL1 that has at least 95% sequence identity to any one of SEQ ID NOs: 4, 22, 40, 58, 78, 96, 114, 132, 150, 168, 186, or 204, a CDRL2 that has at least 95% sequence identity to any one of SEQ ID NOs: 5, 6, 23, 24, 41, 42, 59, 60, 79, 80, 97, 98, 115, 116, 133, 134, 151, 152, 169, 170, 187, 188, 205, or 206, and a CDRL3 that has at least 95% sequence identity to any one of SEQ ID NOs: 7, 25, 43, 61, 81, 99, 117, 135, 153, 171, 189, or 201. More preferably, the antibody, or antigen binding fragment thereof, comprises: (i) heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 1-5 and 7 or to the amino acid sequences of SEQ ID NOs: 1-4 and 6-7, respectively; (ii) heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 19-23 and 25 or to the amino acid sequences of SEQ ID NOs: 19-22 and 24-25, respectively; (iii) heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 37-41 and 43 or to the amino acid sequences of SEQ ID NOs: 37-40 and 42-43, respectively; (iv) heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 55-59 and 61 or to the amino acid sequences of SEQ ID NOs: 55-58 and 60-61, respectively; (v) heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 75-79 and 81 or to the amino acid sequences of SEQ ID NOs: 75-78 and 80-81, respectively; (vi) heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 93-97 and 99 or to the amino acid sequences of SEQ ID NOs: 93-96 and 98-99, respectively; (vii) heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 111-115 and 117 or to the amino acid sequences of SEQ ID NOs: 111-114 and 116-117, respectively; (viii) heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 129-133 and 135 or to the amino acid sequences of SEQ ID NOs: 129-132 and 134-135, respectively; (ix) heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 147-151 and 153 or to the amino acid sequences of SEQ ID NOs: 147-150 and 152-153, respectively; (x) heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 165-169 and 171 or to the amino acid sequences of SEQ ID NOs: 165-168 and 170-171, respectively; (xi) heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 183-187 and 189 or to the amino acid sequences of SEQ ID NOs: 183-186 and 188-189, respectively; or (xii) heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 201-205 and 207 or to the amino acid sequences of SEQ ID NOs: 201-204 and 206-207, respectively.

In a particularly preferred embodiment the isolated antibody or antigen binding fragment thereof, according to the invention comprises heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 93-97 and 99 or to the amino acid sequences of SEQ ID NOs: 93-96 and 98-99, respectively.

In another particularly preferred embodiment the isolated antibody or antigen binding fragment thereof, according to the invention comprises heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 165-169 and 171 or to the amino acid sequences of SEQ ID NOs: 165-168 and 170-171, respectively.

Even more preferably, the isolated antibody or antigen binding fragment thereof, according to the invention comprises: (i) heavy chain CDRH1, CDRH2, and CDRH3 amino acid sequences and light chain CDRL1, CDRL2, and CDRL3 amino acid sequences as set forth in SEQ ID NOs: 1-5 and 7 or in SEQ ID NOs: 1-4 and 6-7, respectively; (ii) heavy chain CDRH1, CDRH2, and CDRH3 amino acid sequences and light chain CDRL1, CDRL2, and CDRL3 amino acid sequences as set forth in SEQ ID NOs: 19-23 and 25 or in SEQ ID NOs: 19-22 and 24-25, respectively; (iii) heavy chain CDRH1, CDRH2, and CDRH3 amino acid sequences and light chain CDRL1, CDRL2, and CDRL3 amino acid sequences as set forth in SEQ ID NOs: 37-41 and 43 or in SEQ ID NOs: 37-40 and 42-43, respectively; (iv) heavy chain CDRH1, CDRH2, and CDRH3 amino acid sequences and light chain CDRL1, CDRL2, and CDRL3 amino acid sequences as set forth in SEQ ID NOs: 55-59 and 61 or in SEQ ID NOs: 55-58 and 60-61, respectively; (v) heavy chain CDRH1, CDRH2, and CDRH3 amino acid sequences and light chain CDRL1, CDRL2, and CDRL3 amino acid sequences as set forth in SEQ ID NOs: 75-79 and 81 or in SEQ ID NOs: 75-78 and 80-81, respectively; (vi) heavy chain CDRH1, CDRH2, and CDRH3 amino acid sequences and light chain CDRL1, CDRL2, and CDRL3 amino acid sequences as set forth in SEQ ID NOs: 93-97 and 99 or in SEQ ID NOs: 93-96 and 98-99, respectively; (vii) heavy chain CDRH1, CDRH2, and CDRH3 amino acid sequences and light chain CDRL1, CDRL2, and CDRL3 amino acid sequences as set forth in SEQ ID NOs: 111-115 and 117 or in SEQ ID NOs: 111-114 and 116-117, respectively; (viii) heavy chain CDRH1, CDRH2, and CDRH3 amino acid sequences and light chain CDRL1, CDRL2, and CDRL3 amino acid sequences as set forth in SEQ ID NOs: 129-133 and 135 or in SEQ ID NOs: 129-132 and 134-135, respectively; (ix) heavy chain CDRH1, CDRH2, and CDRH3 amino acid sequences and light chain CDRL1, CDRL2, and CDRL3 amino acid sequences as set forth in SEQ ID NOs: 147-151 and 153 or in SEQ ID NOs: 147-150 and 152-153, respectively; (x) heavy chain CDRH1, CDRH2, and CDRH3 amino acid sequences and light chain CDRL1, CDRL2, and CDRL3 amino acid sequences as set forth in SEQ ID NOs: 165-169 and 171 or in SEQ ID NOs: 165-168 and 170-171, respectively; (xi) heavy chain CDRH1, CDRH2, and CDRH3 amino acid sequences and light chain CDRL1, CDRL2, and CDRL3 amino acid sequences as set forth in SEQ ID NOs: 183-187 and 189 or in SEQ ID NOs: 183-186 and 188-189, respectively; or (xii) heavy chain CDRH1, CDRH2, and CDRH3 amino acid sequences and light chain CDRL1, CDRL2, and CDRL3 amino acid sequences as set forth in SEQ ID NOs: 201-205 and 207 or in SEQ ID NOs: 201-204 and 206-207, respectively.

Among the embodiments described above of the antibody, or antigen binding fragment thereof, of the invention having at least one CDR, i.e. one, two, three, four, five six CDRs as described above, such an embodiment of the antibody, or antigen binding fragment thereof, is preferred, which comprises a CDRH3 that has at least 95% sequence identity to any one of SEQ ID NOs: 3, 21, 39, 57, 77, 95, 113, 131, 149, 167, 185, or 203.

It is also preferred that, the isolated antibody or antigen binding fragment of the invention comprises a heavy chain CDR1 with the amino acid sequence of SEQ ID NOs: 1, 19, 37, 55, 75, 93, 111, 129, 147, 165, 183 or 201 or sequence variants thereof; a heavy chain CDR2 with the amino acid sequence of SEQ ID NOs: 2, 20, 38, 56, 76, 94, 112, 130, 148, 166, 184, or 202 or sequence variants thereof; and a heavy chain CDR3 with the amino acid sequence of SEQ ID NOs: 3, 21, 39, 57, 77, 95, 113, 131, 149, 167, 185, or 203 or sequence variants thereof. In certain embodiments, an antibody or antibody fragment as provided herein comprises a heavy chain comprising the amino acid sequence of (i) SEQ ID NO: 1 for CDRH1, SEQ ID NO: 2 for CDRH2 and SEQ ID NO: 3 for CDRH3, (ii) SEQ ID NO: 19 for CDRH1, SEQ ID NO: 20 for CDRH2, and SEQ ID NO: 21 for CDRH3, (iii) SEQ ID NO: 37 for CDRH1, SEQ ID NO: 38 for CDRH2, and SEQ ID NO: 39 for CDRH3, (iv) SEQ ID NO: 55 for CDRH1, SEQ ID NO: 56 for CDRH2, and SEQ ID NO: 57 for CDRH3; (v) SEQ ID NO: 75 for CDRH1, SEQ ID NO: 76 for CDRH2, and SEQ ID NO: 77 for CDRH3; (vi) SEQ ID NO: 93 for CDRH1, SEQ ID NO: 94 for CDRH2, and SEQ ID NO: 95 for CDRH3; (vii) SEQ ID NO: 111 for CDRH1, SEQ ID NO: 112 for CDRH2, and SEQ ID NO: 113 for CDRH3; (viii) SEQ ID NO: 129 for CDRH1, SEQ ID NO: 130 for CDRH2, and SEQ ID NO: 131 for CDRH3; (ix) SEQ ID NO: 147 for CDRH1, SEQ ID NO: 148 for CDRH2, and SEQ ID NO: 149 for CDRH3; (x) SEQ ID NO: 165 for CDRH1, SEQ ID NO: 166 for CDRH2, and SEQ ID NO: 167 for CDRH3; (xi) SEQ ID NO: 183 for CDRH1, SEQ ID NO: 184 for CDRH2, and SEQ ID NO: 185 for CDRH3; or (xii) SEQ ID NO: 201 for CDRH1, SEQ ID NO: 202 for CDRH2, and SEQ ID NO: 203 for CDRH3.

Preferably, the antibody or antigen binding fragment of the invention comprises a light chain CDR1 with the amino acid sequence of SEQ ID NOs: 4, 22, 40, 58, 78, 96, 114, 132, 150, 168, 186, or 204 or sequence variants thereof; a light chain CDR2 with the amino acid sequence of SEQ ID NOs: 5, 6, 23, 24, 41, 42, 59, 60, 79, 80, 97, 98, 115, 116, 133, 134, 151, 152, 169, 170, 187, 188, 205, or 206 or sequence variants thereof; and a light chain CDR3 with the amino acid sequence of SEQ ID NO: 7, 25, 43, 61, 81, 99, 117, 135, 153, 171, 189, or 201 or sequence variants thereof. In certain embodiments, an antibody or antibody fragment as provided herein comprises a light chain comprising the amino acid sequence of (i) SEQ ID NO: 4 for CDRL1, SEQ ID NO: 5 or 6 for CDRL2, and SEQ ID NO: 7 for CDRL3; (ii) SEQ ID NO: 22 for CDRL1, SEQ ID NO: 23 or 24 for CDRL2, and SEQ ID NO: 25 for CDRL3; (iii) SEQ ID NO: 40 for CDRL1, SEQ ID NO: 41 or 42 for CDRL2, and SEQ ID NO: 43 for CDRL3; (iv) SEQ ID NO: 58 for CDRL1, SEQ ID NO: 59 or 60 for CDRL2, and SEQ ID NO: 61 for CDRL3; (v) SEQ ID NO: 78 for CDRL1, SEQ ID NO: 79 or 80 for CDRL2, and SEQ ID NO: 81 for CDRL3; (vi) SEQ ID NO: 96 for CDRL1, SEQ ID NO: 97 or 98 for CDRL2, and SEQ ID NO: 99 for CDRL3; (vii) SEQ ID NO: 114 for CDRL1, SEQ ID NO: 115 or 116 for CDRL2, and SEQ ID NO: 117 for CDRL3; (viii) SEQ ID NO: 132 for CDRL1, SEQ ID NO: 133 or 134 for CDRL2, and SEQ ID NO: 135 for CDRL3; (ix) SEQ ID NO: 150 for CDRL1, SEQ ID NO: 151 or 152 for CDRL2, and SEQ ID NO: 152 for CDRL3; (x) SEQ ID NO: 168 for CDRL1, SEQ ID NO: 169 or 170 for CDRL2, and SEQ ID NO: 171 for CDRL3; (xi) SEQ ID NO: 186 for CDRL1, SEQ ID NO: 187 or 188 for CDRL2, and SEQ ID NO: 189 for CDRL3; or (xii) SEQ ID NO: 204 for CDRL1, SEQ ID NO: 205 or 206 for CDRL2, and SEQ ID NO: 207 for CDRL3.

In another embodiment of the invention, the invention comprises an isolated antibody or antigen binding fragment thereof, comprising heavy chain CDR1, CDR2 and CDR3 and light chain CDR1, CDR2, and CDR3 amino acid sequences that are at least 80%, for example, 80%, 81%, 82%, 83%, 84%, 85%, 86%, 87%, 88%, 89%, 90%, 91%, 92%, 93%, 94%, 95%, 96%, 97%, 98%, 99% or 100% identical to the amino acid sequences of SEQ ID NOs: 1-7, 19-25, 37-43, 55-61, 75-81, 93-99, 111-117, 129-135, 147-153, 165-171, 183-189, and 201-207, respectively.

Preferably, the antibody, or the antigen binding fragment thereof, is according to gRVA122, gRVA144, gRVB185, gRVB492, gRVC3, gRVC20, gRVC21, gRVC38, gRVC44, gRVC58, gRVC68, or gRVC111, preferably it is according to gRVC20 or gRVC58. More preferably, the antibody, or the antigen binding fragment thereof, is RVA122, RVA44, RVB185, RVB492, RVC3, RVC20, RVC21, RVC38, RVC44, RVC58, RVC68, or RVC111, preferably RVC20 or RVC58.

The present inventors have isolated twelve monoclonal antibodies (mAbs), which are referred to herein as RVA122, RVA144, RVB185, RVB492, RVC3, RVC20, RVC21, RVC38, RVC44, RVC58, RVC68, and RVC111 (cf. Examples 1 to 4). Based on the antibodies RVA122, RVA44, RVB185, RVB492, RVC3, RVC20, RVC21, RVC38, RVC44, RVC58, RVC68, and RVC111, in particular on the VH and VL genes of RVA22, RVA44, RVB185, RVB492, RVC3, RVC20, RVC21, RVC38, RVC44, RVC58, RVC68, and RVC111, the terms gRVA122, gRVA144, gRVB185, gRVB492, gRVC3, gRVC20, gRVC21, gRVC38, gRVC44, gRVC58, gRVC68, or gRVC111, as used herein, refer to respective "generic" antibodies, or antigen binding fragments thereof, having the specific amino acid sequences, encoded by the specific nucleotide sequences, as outlined below.

As used herein, "gRVA122" refers to an antibody, or antigen binding fragment thereof, having a CDRH1 amino acid sequence according to SEQ ID NO: 1, which is encoded by a CDRH1 nucleotide sequence according to SEQ ID NO: 8, a CDRH2 amino acid sequence according to SEQ ID NO: 2, which is encoded by a CDRH2 nucleotide sequence according to SEQ ID NO: 9, a CDRH3 amino acid sequence according to SEQ ID NO: 3, which is encoded by a CDRH3 nucleotide sequence according to SEQ ID NO: 10, a CDRL1 amino acid sequence according to SEQ ID NO: 4, which is encoded by a CDRL1 nucleotide sequence according to SEQ ID NO: 11, a CDRL2 amino acid sequence according to SEQ ID NO: 5 or 6, which is encoded by a CDRL2 nucleotide sequence according to SEQ ID NO: 12 or 13, and a CDRL3 amino acid sequence according to SEQ ID NO: 7, which is encoded by a CDRL3 nucleotide sequence according to SEQ ID NO: 14. The heavy chain variable region ($V_H$) of "gRVA122" has an amino acid sequence according to SEQ ID NO: 15, which is encoded by a nucleotide sequence according to SEQ ID NO: 17, and the light chain variable region ($V_L$) of "gRVA122" has an amino acid sequence according to SEQ ID NO: 16, which is encoded by a nucleotide sequence according to SEQ ID NO: 18.

As used herein, "gRVA144" refers to an antibody, or antigen binding fragment thereof, having a CDRH1 amino acid sequence according to SEQ ID NO: 19, which is encoded by a CDRH1 nucleotide sequence according to SEQ ID NO: 26, a CDRH2 amino acid sequence according to SEQ ID NO: 20, which is encoded by a CDRH2 nucleotide sequence according to SEQ ID NO: 27, a CDRH3 amino acid sequence according to SEQ ID NO: 21, which is encoded by a CDRH3 nucleotide sequence according to SEQ ID NO: 28, a CDRL1 amino acid sequence according to SEQ ID NO: 22, which is encoded by a CDRL1 nucleotide sequence according to SEQ ID NO: 29, a CDRL2 amino acid sequence according to SEQ ID NO: 23 or 24, which is encoded by a CDRL2 nucleotide sequence according to SEQ ID NO: 30 or 31, and a CDRL3 amino acid sequence according to SEQ ID NO: 25, which is encoded by a CDRL3 nucleotide sequence according to SEQ ID NO: 32. The heavy chain variable region ($V_H$) of "gRVA144" has an amino acid sequence according to SEQ ID NO: 33, which is encoded by a nucleotide sequence according to SEQ ID NO: 35, and the light chain variable region ($V_L$) of "gRVA144" has an amino acid sequence according to SEQ ID NO: 34, which is encoded by a nucleotide sequence according to SEQ ID NO: 36.

As used herein, "gRVB185" refers to an antibody, or antigen binding fragment thereof, having a CDRH1 amino acid sequence according to SEQ ID NO: 37, which is encoded by a CDRH1 nucleotide sequence according to SEQ ID NO: 44, a CDRH2 amino acid sequence according to SEQ ID NO: 38, which is encoded by a CDRH2 nucleotide sequence according to SEQ ID NO: 45, a CDRH3 amino acid sequence according to SEQ ID NO: 39, which is encoded by a CDRH3 nucleotide sequence according to SEQ ID NO: 46, a CDRL1 amino acid sequence according to SEQ ID NO: 40, which is encoded by a CDRL1 nucleotide sequence according to SEQ ID NO: 47, a CDRL2 amino acid sequence according to SEQ ID NO: 41 or 42, which is encoded by a CDRL2 nucleotide sequence according to SEQ ID NO: 48 or 49, and a CDRL3 amino acid sequence according to SEQ ID NO: 43, which is encoded by a CDRL3 nucleotide sequence according to SEQ ID NO: 50. The heavy chain variable region ($V_H$) of "gRVB185" has an amino acid sequence according to SEQ ID NO: 51, which is encoded by a nucleotide sequence according to SEQ ID NO:

53, and the light chain variable region (V$_L$) of "gRVB185" has an amino acid sequence according to SEQ ID NO: 52, which is encoded by a nucleotide sequence according to SEQ ID NO: 54.

As used herein, "gRVB492" refers to an antibody, or antigen binding fragment thereof, having a CDRH1 amino acid sequence according to SEQ ID NO: 55, which is encoded by a CDRH1 nucleotide sequence according to SEQ ID NO: 62, a CDRH2 amino acid sequence according to SEQ ID NO: 56, which is encoded by a CDRH2 nucleotide sequence according to SEQ ID NO: 63, a CDRH3 amino acid sequence according to SEQ ID NO: 57, which is encoded by a CDRH3 nucleotide sequence according to SEQ ID NO: 64, a CDRL1 amino acid sequence according to SEQ ID NO: 58, which is encoded by a CDRL1 nucleotide sequence according to SEQ ID NO: 65, a CDRL2 amino acid sequence according to SEQ ID NO: 59 or 60, which is encoded by a CDRL2 nucleotide sequence according to SEQ ID NO: 66 or 67, and a CDRL3 amino acid sequence according to SEQ ID NO: 61, which is encoded by a CDRL3 nucleotide sequence according to SEQ ID NO: 68. The heavy chain variable region (V$_H$) of "gRVB492" has an amino acid sequence according to SEQ ID NO: 69 or 70, which is encoded by a nucleotide sequence according to SEQ ID NO: 72 or 73, and the light chain variable region (V$_L$) of "gRVB492" has an amino acid sequence according to SEQ ID NO: 71, which is encoded by a nucleotide sequence according to SEQ ID NO: 74.

As used herein, "gRVC3" refers to an antibody, or antigen binding fragment thereof, having a CDRH1 amino acid sequence according to SEQ ID NO: 75, which is encoded by a CDRH1 nucleotide sequence according to SEQ ID NO: 82, a CDRH2 amino acid sequence according to SEQ ID NO: 76, which is encoded by a CDRH2 nucleotide sequence according to SEQ ID NO: 83, a CDRH3 amino acid sequence according to SEQ ID NO: 77, which is encoded by a CDRH3 nucleotide sequence according to SEQ ID NO: 84, a CDRL1 amino acid sequence according to SEQ ID NO: 78, which is encoded by a CDRL1 nucleotide sequence according to SEQ ID NO: 85, a CDRL2 amino acid sequence according to SEQ ID NO: 79 or 80, which is encoded by a CDRL2 nucleotide sequence according to SEQ ID NO: 86 or 87, and a CDRL3 amino acid sequence according to SEQ ID NO: 81, which is encoded by a CDRL3 nucleotide sequence according to SEQ ID NO: 88. The heavy chain variable region (V$_H$) of "gRVC3" has an amino acid sequence according to SEQ ID NO: 89, which is encoded by a nucleotide sequence according to SEQ ID NO: 91, and the light chain variable region (V$_L$) of "gRVC3" has an amino acid sequence according to SEQ ID NO: 90, which is encoded by a nucleotide sequence according to SEQ ID NO: 92.

As used herein, "gRVC20" refers to an antibody, or antigen binding fragment thereof, having a CDRH1 amino acid sequence according to SEQ ID NO: 93, which is encoded by a CDRH nucleotide sequence according to SEQ ID NO: 100, a CDRH2 amino acid sequence according to SEQ ID NO: 94, which is encoded by a CDRH2 nucleotide sequence according to SEQ ID NO: 101, a CDRH3 amino acid sequence according to SEQ ID NO: 95, which is encoded by a CDRH3 nucleotide sequence according to SEQ ID NO: 102, a CDRL1 amino acid sequence according to SEQ ID NO: 96, which is encoded by a CDRL1 nucleotide sequence according to SEQ ID NO: 103, a CDRL2 amino acid sequence according to SEQ ID NO: 97 or 98, which is encoded by a CDRL2 nucleotide sequence according to SEQ ID NO: 104 or 105, and a CDRL3 amino acid sequence according to SEQ ID NO: 99, which is encoded by a CDRL3 nucleotide sequence according to SEQ ID NO: 106. The heavy chain variable region (V$_H$) of "gRVC20" has an amino acid sequence according to SEQ ID NO: 107, which is encoded by a nucleotide sequence according to SEQ ID NO: 109, and the light chain variable region (V$_L$) of "gRVC20" has an amino acid sequence according to SEQ ID NO: 108, which is encoded by a nucleotide sequence according to SEQ ID NO: 110.

As used herein, "gRVC21" refers to an antibody, or antigen binding fragment thereof, having a CDRH1 amino acid sequence according to SEQ ID NO: 111, which is encoded by a CDRH1 nucleotide sequence according to SEQ ID NO: 118, a CDRH2 amino acid sequence according to SEQ ID NO: 112, which is encoded by a CDRH2 nucleotide sequence according to SEQ ID NO: 119, a CDRH3 amino acid sequence according to SEQ ID NO: 113, which is encoded by a CDRH3 nucleotide sequence according to SEQ ID NO: 120, a CDRL1 amino acid sequence according to SEQ ID NO: 114, which is encoded by a CDRL1 nucleotide sequence according to SEQ ID NO: 121, a CDRL2 amino acid sequence according to SEQ ID NO: 115 or 116, which is encoded by a CDRL2 nucleotide sequence according to SEQ ID NO: 122 or 123, and a CDRL3 amino acid sequence according to SEQ ID NO: 117, which is encoded by a CDRL3 nucleotide sequence according to SEQ ID NO: 124. The heavy chain variable region (V$_H$) of "gRVC21" has an amino acid sequence according to SEQ ID NO: 125, which is encoded by a nucleotide sequence according to SEQ ID NO: 127, and the light chain variable region (V$_L$) of "gRVC21" has an amino acid sequence according to SEQ ID NO: 126, which is encoded by a nucleotide sequence according to SEQ ID NO: 128.

As used herein, "gRVC38" refers to an antibody, or antigen binding fragment thereof, having a CDRH1 amino acid sequence according to SEQ ID NO: 129, which is encoded by a CDRH1 nucleotide sequence according to SEQ ID NO: 136, a CDRH2 amino acid sequence according to SEQ ID NO: 130, which is encoded by a CDRH2 nucleotide sequence according to SEQ ID NO: 137, a CDRH3 amino acid sequence according to SEQ ID NO: 131, which is encoded by a CDRH3 nucleotide sequence according to SEQ ID NO: 138, a CDRL1 amino acid sequence according to SEQ ID NO: 132, which is encoded by a CDRL1 nucleotide sequence according to SEQ ID NO: 139, a CDRL2 amino acid sequence according to SEQ ID NO: 133 or 134, which is encoded by a CDRL2 nucleotide sequence according to SEQ ID NO: 140 or 141, and a CDRL3 amino acid sequence according to SEQ ID NO: 135, which is encoded by a CDRL3 nucleotide sequence according to SEQ ID NO: 142. The heavy chain variable region (V$_H$) of "gRVC38" has an amino acid sequence according to SEQ ID NO: 143, which is encoded by a nucleotide sequence according to SEQ ID NO: 145, and the light chain variable region (V$_L$) of "gRVC38" has an amino acid sequence according to SEQ ID NO: 144, which is encoded by a nucleotide sequence according to SEQ ID NO: 146.

As used herein, "gRVC44" refers to an antibody, or antigen binding fragment thereof, having a CDRH1 amino acid sequence according to SEQ ID NO: 147, which is encoded by a CDRH1 nucleotide sequence according to SEQ ID NO: 154, a CDRH2 amino acid sequence according to SEQ ID NO: 148, which is encoded by a CDRH2 nucleotide sequence according to SEQ ID NO: 155, a CDRH3 amino acid sequence according to SEQ ID NO: 149, which is encoded by a CDRH3 nucleotide sequence according to SEQ ID NO: 156, a CDRL1 amino acid sequence according to SEQ ID NO: 150, which is encoded by a CDRL1 nucleotide sequence according to SEQ ID NO: 157, a CDRL2 amino acid sequence according to SEQ ID NO: 151 or 152, which is encoded by a CDRL2 nucleotide sequence according to SEQ ID NO: 158 or 159, and a CDRL3 amino acid sequence according to SEQ ID NO: 153, which is encoded by a CDRL3 nucleotide sequence according to SEQ ID NO: 160. The heavy chain variable region ($V_H$) of "gRVC44" has an amino acid sequence according to SEQ ID NO: 161, which is encoded by a nucleotide sequence according to SEQ ID NO: 163, and the light chain variable region ($V_L$) of "gRVC44" has an amino acid sequence according to SEQ ID NO: 162, which is encoded by a nucleotide sequence according to SEQ ID NO: 164.

As used herein, "gRVC58" refers to an antibody, or antigen binding fragment thereof, having a CDRH1 amino acid sequence according to SEQ ID NO: 165, which is encoded by a CDRH1 nucleotide sequence according to SEQ ID NO: 172, a CDRH2 amino acid sequence according to SEQ ID NO: 166, which is encoded by a CDRH2 nucleotide sequence according to SEQ ID NO: 173, a CDRH3 amino acid sequence according to SEQ ID NO: 167, which is encoded by a CDRH3 nucleotide sequence according to SEQ ID NO: 174, a CDRL1 amino acid sequence according to SEQ ID NO: 168, which is encoded by a CDRL1 nucleotide sequence according to SEQ ID NO: 175, a CDRL2 amino acid sequence according to SEQ ID NO: 169 or 170, which is encoded by a CDRL2 nucleotide sequence according to SEQ ID NO: 176 or 177, and a CDRL3 amino acid sequence according to SEQ ID NO: 171, which is encoded by a CDRL3 nucleotide sequence according to SEQ ID NO: 178. The heavy chain variable region ($V_H$) of "gRVC58" has an amino acid sequence according to SEQ ID NO: 179, which is encoded by a nucleotide sequence according to SEQ ID NO: 181, and the light chain variable region ($V_L$) of "gRVC58" has an amino acid sequence according to SEQ ID NO: 180, which is encoded by a nucleotide sequence according to SEQ ID NO: 182.

As used herein, "gRVC68" refers to an antibody, or antigen binding fragment thereof, having a CDRH1 amino acid sequence according to SEQ ID NO: 183, which is encoded by a CDRH1 nucleotide sequence according to SEQ ID NO: 190, a CDRH2 amino acid sequence according to SEQ ID NO: 184, which is encoded by a CDRH2 nucleotide sequence according to SEQ ID NO: 191, a CDRH3 amino acid sequence according to SEQ ID NO: 185, which is encoded by a CDRH3 nucleotide sequence according to SEQ ID NO: 192, a CDRL1 amino acid sequence according to SEQ ID NO: 186, which is encoded by a CDRL1 nucleotide sequence according to SEQ ID NO: 193, a CDRL2 amino acid sequence according to SEQ ID NO: 187 or 188, which is encoded by a CDRL2 nucleotide sequence according to SEQ ID NO: 194 or 195, and a CDRL3 amino acid sequence according to SEQ ID NO: 189, which is encoded by a CDRL3 nucleotide sequence according to SEQ ID NO: 196. The heavy chain variable region ($V_H$) of "gRVC68" has an amino acid sequence according to SEQ ID NO: 197, which is encoded by a nucleotide sequence according to SEQ ID NO: 199, and the light chain variable region ($V_L$) of "gRVC68" has an amino acid sequence according to SEQ ID NO: 198, which is encoded by a nucleotide sequence according to SEQ ID NO: 200.

As used herein, "gRVC111" refers to an antibody, or antigen binding fragment thereof, having a CDRH1 amino acid sequence according to SEQ ID NO: 201, which is encoded by a CDRH1 nucleotide sequence according to SEQ ID NO: 208, a CDRH2 amino acid sequence according to SEQ ID NO: 202, which is encoded by a CDRH2 nucleotide sequence according to SEQ ID NO: 209, a CDRH3 amino acid sequence according to SEQ ID NO: 203, which is encoded by a CDRH3 nucleotide sequence according to SEQ ID NO: 210, a CDRL1 amino acid sequence according to SEQ ID NO: 204, which is encoded by a CDRL1 nucleotide sequence according to SEQ ID NO: 211, a CDRL2 amino acid sequence according to SEQ ID NO: 205 or 206, which is encoded by a CDRL2 nucleotide sequence according to SEQ ID NO: 212 or 213, and a CDRL3 amino acid sequence according to SEQ ID NO: 207, which is encoded by a CDRL3 nucleotide sequence according to SEQ ID NO: 214. The heavy chain variable region ($V_H$) of "gRVC111" has an amino acid sequence according to SEQ ID NO: 215, which is encoded by a nucleotide sequence according to SEQ ID NO: 217, and the light chain variable region ($V_L$) of "gRVC111" has an amino acid sequence according to SEQ ID NO: 216, which is encoded by a nucleotide sequence according to SEQ ID NO: 218.

Preferably, the antibodies according to gRVA122, gRVA144, gRVB185, gRVB492, gRVC3, gRVC20, gRVC21, gRVC38, gRVC44, gRVC58, gRVC68, or gRVC111, preferably it is according to gRVC20 and gRVC58 are of the IgG1 type.

Preferably, the isolated antibody or antigen binding fragment according to the present invention comprises a heavy chain comprising one or more (i.e., one, two or all three) heavy chain CDRs from gRVA122, gRVA144, gRVB185, gRVB492, gRVC3, gRVC20, gRVC21, gRVC38, gRVC44, gRVC58, gRVC68, or gRVC111, preferably it is according to gRVC20 and gRVC58.

It is also preferred that the isolated antibody or antigen binding fragment according to the present invention comprises light chain CDRs from gRVA122, gRVA144, gRVB185, gRVB492, gRVC3, gRVC20, gRVC21, gRVC38, gRVC44, gRVC58, gRVC68, or gRVC111, preferably it is according to gRVC20 and gRVC58.

Preferably, the isolated antibody or antigen binding fragment according to the present invention comprises all of the CDRs of antibody RVC20 as listed in Table 2 or all of the CDRs of antibody RVC58 as listed in Table 2. Alternatively, the isolated antibody or antigen binding fragment according to the present invention may also preferably all of the CDRs of antibody RVA122 as listed in Table 2. Alternatively, the isolated antibody or antigen binding fragment according to the present invention may also preferably all of the CDRs of antibody RVA144 as listed in Table 2. Alternatively, the isolated antibody or antigen binding fragment according to the present invention may also preferably all of the CDRs of antibody RVB185 as listed in Table 2. Alternatively, the isolated antibody or antigen binding fragment according to the present invention may also preferably all of the CDRs of antibody RVB492 as listed in Table 2. Alternatively, the isolated antibody or antigen binding fragment according to the present invention may also preferably all of the CDRs of antibody RVC3 as listed in Table 2. Alternatively, the isolated antibody or antigen binding fragment according to the present invention may also preferably all of the CDRs of antibody RVC21 as listed in Table 2. Alternatively, the isolated antibody or antigen binding fragment according to the present invention may also preferably all of the CDRs of antibody RVC38 as listed in Table 2. Alternatively, the isolated antibody or antigen binding fragment according to the present invention may also preferably all of the CDRs of antibody RVC44 as listed in Table 2. Alternatively, the isolated antibody or antigen binding fragment according to the present invention may also preferably all of the CDRs of antibody RVC68 as listed in Table 2. Alternatively, the isolated antibody or antigen binding fragment according to the present invention may also preferably all of the CDRs of antibody RVC111 as listed in Table 2.

The SEQ ID numbers for the amino acid sequence for the heavy chain variable region (V$_H$) and the light chain variable region (V$_L$) of exemplary antibodies of the invention as well as the SEQ ID numbers for the nucleic acid sequences encoding them are listed in Table 3.

TABLE 3

SEQ ID Numbers for V$_H$ and V$_L$ amino acid and nucleic acid residues for exemplary antibodies according to the present invention.

|  | V$_H$ amino acid | V$_L$ amino acid | V$_H$ nucleic acid | V$_L$ nucleic acid |
| --- | --- | --- | --- | --- |
| RVA122 | 15 | 16 | 17 | 18 |
| RVA144 | 33 | 34 | 35 | 36 |
| RVB185 | 51 | 52 | 53 | 54 |
| RVB492 | 69 or 70 | 71 | 72 or 73 | 74 |
| RVC3 | 89 | 90 | 91 | 92 |
| RVC20 | 107 | 108 | 109 | 110 |
| RVC21 | 125 | 126 | 127 | 128 |
| RVC38 | 143 | 144 | 145 | 146 |
| RVC44 | 161 | 162 | 163 | 164 |
| RVC58 | 179 | 180 | 181 | 182 |
| RVC68 | 197 | 198 | 199 | 200 |
| RVC111 | 215 | 216 | 217 | 218 |

Preferably, the isolated antibody or antigen binding fragment according to the present invention comprises a heavy chain variable region having an amino acid sequence that is about 70%, 75%, 80%, 85%, 88%, 90%, 92%, 95%, 96%, 97%, 98%, 99% or 100% identical to the sequence recited in any one of SEQ ID NOs: 15, 33, 51, 69, 70, 89, 107, 125, 143, 161, 179, 197, or 215. In another embodiment, the antibody or antibody fragment comprises a light chain variable region having an amino acid sequence that is about 70%, 75%, 80%, 85%, 90%, 85%, 88%, 90%, 92%, 95%, 96%, 97%, 98%, 99% or 100% identical to the sequence recited in SEQ ID NOs: 16, 34, 52, 71, 90, 108, 126, 144, 162, 180, 198, or 216. In yet another preferred embodiment, the antibody or antibody fragment comprises a heavy chain or a light chain variable region having an amino acid sequence that is about 70%, 75%, 80%, 85%, 88%, 90%, 92%, 95%, 96%, 97%, 98%, 99% or 100% identical to the sequences provided in FIGS. 22 to 33.

FIGS. 22 to 33 show the amino acid sequences for the heavy and light chains of antibodies RVA122, RVA144, RVB185, RVB492, RVC3, RVC20, RVC21, RVC38, RVC44, RVC58, RVC68, and RVC111, respectively, as well as the nucleic acid sequences that encode them. The amino acid sequences of the CDRs and the nucleic acid sequences that encode the CDRs are in bold text whereas the amino acid sequences of the framework region and the nucleic acid sequences that encode the framework region are in plain text.

Preferably, the isolated antibody or antigen binding fragment according to the present invention comprises (i) a heavy chain variable region having at least 80%, for example, 85%, 88%, 90%, 92%, 95%, 96%, 97%, 98%, 99% or 100% sequence identity to the amino acid sequence of SEQ ID NO: 15 and a light chain variable region having at least 80%, for example, 85%, 88%, 90%, 92%, 95%, 96%, 97%, 98%, 99% or 100% sequence identity to the amino acid sequence of SEQ ID NO: 16; or (ii) a heavy chain variable region having at least 80%, for example, 85%, 88%, 90%, 92%, 95%, 96%, 97%, 98%, 99% or 100% sequence identity to the amino acid sequence of SEQ ID NO: 33 and a light chain variable region having at least 80%, for example, 85%, 88%, 90%, 92%, 95%, 96%, 97%, 98%, 99% or 100% sequence identity to the amino acid sequence of SEQ ID NO: 34; (iii) or a heavy chain variable region having at least 80%, for example, 85%, 88%, 90%, 92%, 95%, 96%, 97%, 98%, 99% or 100% sequence identity to the amino acid sequence of SEQ ID NO: 51 and a light chain variable region having at least 80%, for example, 85%, 88%, 90%, 92%, 95%, 96%, 97%, 98%, 99% or 100% sequence identity to the amino acid sequence of SEQ ID NO: 52; or (iv) a heavy chain variable region having at least 80%, for example, 85%, 88%, 90%, 92%, 95%, 96%, 97%, 98%, 99% or 100% sequence identity to the amino acid sequence of SEQ ID NO: 69 and a light chain variable region having at least 80%, for example, 85%, 88%, 90%, 92%, 95%, 96%, 97%, 98%, 99% or 100% sequence identity to the amino acid sequence of SEQ ID NO: 71; or (v) a heavy chain variable region having at least 80%, for example, 85%, 88%, 90%, 92%, 95%, 96%, 97%, 98%, 99% or 100% sequence identity to the amino acid sequence of SEQ ID NO: 70 and a light chain variable region having at least 80%, for example, 85%, 88%, 90%, 92%, 95%, 96%, 97%, 98%, 99% or 100% sequence identity to the amino acid sequence of SEQ ID NO: 71; or (vi) a heavy chain variable region having at least 80%, for example, 85%, 88%, 90%, 92%, 95%, 96%, 97%, 98%, 99% or 100% sequence identity to the amino acid sequence of SEQ ID NO: 89 and a light chain variable region having at least 80%, for example, 85%, 88%, 90%, 92%, 95%, 96%, 97%, 98%, 99% or 100% sequence identity to the amino acid sequence of SEQ ID NO: 90; or (vii) a heavy chain variable region having at least 80%, for example, 85%, 88%, 90%, 92%, 95%, 96%, 97%, 98%, 99% or 100% sequence identity to the amino acid sequence of SEQ ID NO: 107 and a light chain variable region having at least 80%, for example, 85%, 88%, 90%, 92%, 95%, 96%, 97%, 98%, 99% or 100% sequence identity to the amino acid sequence of SEQ ID NO: 108; or (viii) a heavy chain variable region having at least 80%, for example, 85%, 88%, 90%, 92%, 95%, 96%, 97%, 98%, 99% or 100% sequence identity to the amino acid sequence of SEQ ID NO: 125 and a light chain variable region having at least 80%, for example, 85%, 88%, 90%, 92%, 95%, 96%, 97%, 98%, 99% or 100% sequence identity to the amino acid sequence of SEQ ID NO: 126; or (ix) a heavy chain variable region having at least 80%, for example, 85%, 88%, 90%, 92%, 95%, 96%, 97%, 98%, 99% or 100% sequence identity to the amino acid sequence of SEQ ID NO: 143 and a light chain variable region having at least 80%, for example, 85%, 88%, 90%, 92%, 95%, 96%, 97%, 98%, 99% or 100% sequence identity to the amino acid sequence of SEQ ID NO: 144; or (x) a heavy chain variable region having at least 80%, for example, 85%, 88%, 90%, 92%, 95%, 96%, 97%, 98%, 99% or 100% sequence identity to the amino acid sequence of SEQ ID NO: 161 and a light chain variable region having at least 80%, for example, 85%, 88%, 90%, 92%, 95%, 96%, 97%, 98%, 99% or 100% sequence identity to the amino acid sequence of SEQ ID NO: 162; or (xi) a heavy chain variable region having at least 80%, for example, 85%, 88%, 90%, 92%, 95%, 96%, 97%, 98%, 99% or 100% sequence identity to the amino acid sequence of SEQ ID NO: 179 and a light chain variable region having at least 80%, for example, 85%, 88%, 90%, 92%, 95%, 96%, 97%, 98%, 99% or 100% sequence identity to the amino acid sequence of SEQ ID NO: 180; or (xii) a heavy chain variable region having at least 80%, for example, 85%, 88%, 90%, 92%, 95%, 96%, 97%, 98%, 99% or 100% sequence identity to the amino acid sequence of SEQ ID NO: 197 and a light chain variable region having at least 80%, for example, 85%, 88%, 90%, 92%, 95%, 96%, 97%, 98%, 99% or 100% sequence identity to the amino acid sequence of SEQ ID NO: 198; or (xiii) a heavy chain variable region having at least 80%, for example, 85%, 88%, 90%, 92%, 95%, 96%, 97%, 98%, 99% or 100% sequence identity to the amino acid sequence of SEQ ID NO: 215 and a light chain variable region having at least 80%, for example, 85%, 88%, 90%, 92%, 95%, 96%, 97%, 98%, 99% or 100% sequence identity to the amino acid sequence of SEQ ID NO: 216.

More preferably, the antibody or the antigen binding fragment according to the present invention comprises: (i) a heavy chain variable region comprising the amino acid sequence of SEQ ID NO: 15 and a light chain variable region comprising the amino acid sequence of SEQ ID NO: 16; or (ii) a heavy chain variable region comprising the amino acid sequence of SEQ ID NO: 33 and a light chain variable region comprising the amino acid sequence of SEQ ID NO: 34; or (iii) a heavy chain variable region comprising the amino acid sequence of SEQ ID NO: 51 and a light chain variable region comprising the amino acid sequence of SEQ ID NO: 52; or (iv) a heavy chain variable region comprising the amino acid sequence of SEQ ID NO: 69 and a light chain variable region comprising the amino acid sequence of SEQ ID NO: 71; or (v) a heavy chain variable region comprising the amino acid sequence of SEQ ID NO: 70 and a light chain variable region comprising the amino acid sequence of SEQ ID NO: 71; or (vi) a heavy chain variable region comprising the amino acid sequence of SEQ ID NO: 89 and a light chain variable region comprising the amino acid sequence of SEQ ID NO: 90; or (vii) a heavy chain variable region comprising the amino acid sequence of SEQ ID NO: 107 and a light chain variable region comprising the amino acid sequence of SEQ ID NO: 108; or (viii) a heavy chain variable region comprising the amino acid sequence of SEQ ID NO: 125 and a light chain variable region comprising the amino acid sequence of SEQ ID NO: 126; or (ix) a heavy chain variable region comprising the amino acid sequence of SEQ ID NO: 143 and a light chain variable region comprising the amino acid sequence of SEQ ID NO: 144; or (x) a heavy chain variable region comprising the amino acid sequence of SEQ ID NO: 161 and a light chain variable region comprising the amino acid sequence of SEQ ID NO: 162; or (xi) a heavy chain variable region comprising the amino acid sequence of SEQ ID NO: 179 and a light chain variable region comprising the amino acid sequence of SEQ ID NO: 180; or (xii) a heavy chain variable region comprising the amino acid sequence of SEQ ID NO: 197 and a light chain variable region comprising the amino acid sequence of SEQ ID NO: 198; or (xiii) a heavy chain variable region comprising the amino acid sequence of SEQ ID NO: 215 and a light chain variable region comprising the amino acid sequence of SEQ ID NO: 216.

Examples of antibodies of the invention include, but are not limited to, RVA122, RVA144, RVB185, RVB492, RVC3, RVC20, RVC21, RVC38, RVC44, RVC58, RVC68, or RVC111, preferably RVC20 or RVC58. Preferably, the antibody, or the antigen binding fragment thereof, is according to gRVA122, gRVA144, gRVB185, gRVB492, gRVC3, gRVC20, gRVC21, gRVC38, gRVC44, gRVC58, gRVC68, or gRVC111, preferably it is according to gRVC20 or gRVC58.

The antibody, or the antigen binding fragment thereof, according to the present invention may be used in the prophylaxis, treatment or attenuation of infection by RABV and/or non-RABV lyssaviruses, preferably RABV and/or non-RABV phylogroup I lyssaviruses, more preferably RABV and/or EBLV-1. Further details for this use are described below, e.g. directly below and in the context of a pharmaceutical composition and of a medical use.

Preferably, the use of the antibody, or the antigen binding fragment thereof according to the present invention as described above, comprises administering said antibody in combination with another isolated monoclonal antibody that neutralizes lyssavirus infection and that comprises a heavy chain CDRH3 comprising an amino acid sequence that is at least 80%, preferably at least 90%, identical to SEQ ID NO: 95 or to SEQ ID NO: 167 and wherein both antibodies bind specifically to different epitopes on the glycoprotein G of RABV. The other antibody, i.e. the antibody that neutralizes lyssavirus infection and that comprises a heavy chain CDRH3 comprising an amino acid sequence that is at least 80%, preferably at least 90%, identical to SEQ ID NO: 95 or to SEQ ID NO: 167, is preferably also an antibody according to the present invention.

Preferably, the other antibody, i.e. the antibody that neutralizes lyssavirus infection and that comprises a heavy chain CDRH3 comprising an amino acid sequence that is at least 80%, preferably at least 90%, identical to SEQ ID NO: 95 or to SEQ ID NO: 167, comprises preferably (i) heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 93-97 and 99 or to the amino acid sequences of SEQ ID NOs: 93-96 and 98-99, respectively, or (ii) heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 165-169 and 171 or to the amino acid sequences of SEQ ID NOs: 165-168 and 170-171, respectively. More preferably, the other antibody, i.e. the antibody that neutralizes lyssavirus infection and that comprises a heavy chain CDRH3 comprising an amino acid sequence that is at least 80%, preferably at least 90%, identical to SEQ ID NO: 95 or to SEQ ID NO: 167, comprises a heavy chain variable region having at least 80%, preferably at least 90%, sequence identity to the amino acid sequence of SEQ ID NO: 107 or of SEQ ID NO: 179. Even more preferably, the other antibody, i.e. the antibody that neutralizes lyssavirus infection and that comprises a heavy chain CDRH3 comprising an amino acid sequence that is at least 80%, preferably at least 90%, identical to SEQ ID NO: 95 or to SEQ ID NO: 167, comprises (i) a heavy chain variable region having at least 80% sequence identity to the amino acid sequence of SEQ ID NO: 107 and a light chain variable region having at least 80% sequence identity to the amino acid sequence of SEQ ID NO: 108; or (ii) a heavy chain variable region having at least 80% sequence identity to the amino acid sequence of SEQ ID NO: 179 and a light chain variable region having at least 80% sequence identity to the amino acid sequence of SEQ ID NO: 180.

Thereby, a combination of antibodies is provided for the prophylaxis, treatment or attenuation of infection by RABV and/or non-RABV lyssaviruses, preferably RABV and/or non-RABV phylogroup I lyssaviruses, more preferably RABV and/or EBLV-1, with at least one broadly antibody, including EBLV-1 neutralization.

Preferably, the antibody, or the antigen binding fragment thereof, for use according to the present invention as described herein, binds to antigenic site I or III on the glycoprotein G of RABV and the other antibody, which is administered in combination, binds to the other of antigenic sites I or III on the glycoprotein G of RABV.

Interestingly, human anti-rabies antibodies most often recognize antigenic sites I or III on the glycoprotein G of RABV, whereas for example mouse anti-rabies antibodies most often recognize antigenic site II on the glycoprotein G of RABV. It is assumed that the immunogenic dominance of antigenic site II is lower in humans than in mice (Kramer R A, Marissen W E, Goudsmit J, Visser T J, Clijsters-Van der Horst M, Bakker A Q, de Jong M, Jongeneelen M, Thijsse S, Backus H H, Rice A B, Weldon W C, Rupprecht C E, Dietzschold B, Bakker A B, de Kruif J (2005) The human antibody repertoire specific for rabies virus glycoprotein as selected from immune libraries. Eur J Immunol. 35(7):2131-45). Accordingly, a combination of antibodies recognizing antigenic sites I and III on the glycoprotein G of RABV are believed to be more effective than for example a combination involving an antibody recognizing antigenic site II on the glycoprotein G of RABV.

Preferably, the antibody, or the antigen binding fragment thereof, for use according to the present invention as described herein, comprises a heavy chain CDRH3 comprising an amino acid sequence that is at least 80%, preferably at least 90%, identical to SEQ ID NO: 95 and wherein the other antibody administered in combination comprises a heavy chain CDRH3 comprising an amino acid sequence that is at least 80%, preferably at least 90%, identical to SEQ ID NO: 167.

Preferably, the antibody, or the antigen binding fragment thereof, for use according to the present invention as described herein, comprises heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 93-97 and 99 or to the amino acid sequences of SEQ ID NOs: 93-96 and 98-99, respectively, and the other antibody administered in combination comprises heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 165-169 and 171 or to the amino acid sequences of SEQ ID NOs: 165-168 and 170-171, respectively. More preferably, the antibody, or the antigen binding fragment thereof, for use according to the present invention as described herein, comprises a heavy chain variable region having at least 80% sequence identity to the amino acid sequence of SEQ ID NO: 107 and a light chain variable region having at least 80% sequence identity to the amino acid sequence of SEQ ID NO: 108 and the other antibody administered in combination comprises a heavy chain variable region having at least 80% sequence identity to the amino acid sequence of SEQ ID NO: 179 and a light chain variable region having at least 80% sequence identity to the amino acid sequence of SEQ ID NO: 180. Even more preferably, the antibody, or the antigen binding fragment thereof, for use according to the present invention as described herein, is according to gRVC20 and wherein the other antibody administered in combination is according to gRVC58.

Preferably, the antibody, or the antigen binding fragment thereof, for use according to the present invention as described herein and the other antibody, which is administered in combination, are administered simultaneously or consecutively.

Of note, the antibody, or the antigen binding fragment thereof, for use according to the present invention as described herein and the other antibody, which is administered in combination, may be administered separately, for example in separate pharmaceutical compositions, or together, i.e. as antibody "cocktail", for example in the same pharmaceutical composition.

Preferably, the antibody, or the antigen binding fragment thereof, for use according to the present invention as described herein and the other antibody, which is administered in combination, are administered separately. Thereby, the antibody, or the antigen binding fragment thereof, for use according to the present invention as described herein and the other antibody, which is administered in combination, may be administered either simultaneously or consecutively. For consecutive administration of both antibodies the time between (the end of) administration of the first antibody and (the beginning of) administration of the second antibody, e.g. in post-exposure prophylaxis or treatment of lyssavirus infection, is preferably no more than one week, more preferably no more than 5 days, even more preferably no more than 3 days, most preferably no more than 2 days and particularly preferably no more than one day (24 h). In a preferred embodiment thereof, the time between (the end of) administration of the first antibody and (the beginning of) administration of the second antibody is no more than 12 h, preferably no more than 6 h, more preferably no more than 3 h, even more preferably no more than 1 h, most preferably no more than 30 min and particularly preferably no more than 10 min. A consecutive administration wherein one antibody is administered immediately after administration of the other antibody is particularly preferred (this means in particular that the administration of one of the antibodies begins less than 10 min after the end of administration of the other antibody). In consecutive administration as described above it is preferred that the antibody, or the antigen binding fragment thereof, for use according to the present invention as described herein is administered first and the other antibody, which is administered in combination, is administered thereafter. In consecutive administration as described above it is also preferred that the other antibody, which is administered in combination, is administered first and the antibody, or the antigen binding fragment thereof, for use according to the present invention as described herein is administered thereafter. In one preferred embodiment thereof, an antibody, which is according to gRVC20, is administered first and an antibody, which is according to gRVC58, is administered thereafter as described above. In another preferred embodiment thereof, an antibody, which is according to gRVC58, is administered first and an antibody, which is according to gRVC20, is administered thereafter as described above.

It is also preferred that the antibody, or the antigen binding fragment thereof, for use according to the present invention as described herein and the other antibody, which is administered in combination, are administered as an antibody cocktail, e.g. in the same pharmaceutical composition as described herein.

Preferably, the antibody, or the antigen binding fragment thereof, for use according to the present invention as described herein and the other antibody, which is administered in combination, are administered at equimolar amounts.

The invention further comprises an antibody, or fragment thereof, that binds to the same epitope as an antibody or antigen binding fragment of the invention, or an antibody that competes with an antibody or antigen binding fragment of the invention.

Preferably, this epitope is antigenic site 111.2, B, or C of the RABV G protein (glycoprotein G). Neither of the antibodies CR57 and CR4098 binds to these epitopes, but they bind to antigenic site I and III, respectively. However, several antibodies according to the present invention, namely RVB181, RVC56, RVB185, RVC21, RVB161 and RVC111 bind to antigenic site 111.2 of RABV G protein. The novel antigenic site 111.2 is likely proximal to antigenic site III on the RABV G protein (cf. Example 3). Following the same criteria three additional novel antigenic sites were defined named A, B and C. Site B is defined by antibody RVC44, whose binding is not blocked by any other antibody of the panel. Similarly, site C is defined by antibodies RVB143 and RVC68, which also recognize a unique and distinct epitope as compared to all the other antibodies. Of note, RVC44, RVB143 and RVC68 are the only antibodies of this panel capable of binding by western blot to G protein under reducing conditions, suggesting that they recognize a linear epitope on RABV G protein (cf. Example 3).

Preferably, the antibody, or the antigen binding fragment thereof, according to the present invention that binds to the same epitope as the antibody as described above, also neutralizes infection of RABV and infection of at least 50% of the non-RABV lyssaviruses DUVV, EBLV-1, EBLV-2, ABLV, IRKV, KHUV, ARAV, LBV, MOK, SHIV, BBLV and WCBV with an $IC_{50}$ below 10000 ng/ml, whereby the preferred embodiments described above for the antibody, or the antigen binding fragment thereof, according to the present invention that neutralizes infection of RABV and infection of at least 50% of the non-RABV lyssaviruses DUVV, EBLV-1, EBLV-2, ABLV, IRKV, KHUV, ARAV, LBV, MOK, SHIV, BBLV and WCBV with an $IC_{50}$ below 10000 ng/ml also apply to the antibody, or the antigen binding fragment thereof, according to the present invention that binds to the same epitope as the antibody as described above.

Antibodies of the invention also include hybrid antibody molecules that neutralize infection of RABV and infection of at least 50% of the non-RABV lyssaviruses DUVV, EBLV-1, EBLV-2, ABLV, IRKV, KHUV, ARAV, LBV, MOK, SHIV, BBLV and WCBV with an $IC_{50}$ below 10000 ng/ml as described above and that comprise one or more CDRs from an antibody of the invention and one or more CDRs from another antibody to the same epitope. In one embodiment, such hybrid antibodies comprise three CDRs from an antibody of the invention and three CDRs from another antibody to the same epitope. Exemplary hybrid antibodies comprise (i) the three heavy chain CDRs from an antibody of the invention and the three light chain CDRs from another antibody to the same epitope, or (ii) the three light chain CDRs from an antibody of the invention and the three heavy chain CDRs from another antibody to the same epitope.

In another aspect, the invention also provides a nucleic acid molecule comprising a polynucleotide encoding the antibody, or the antigen binding fragment thereof, according to the present invention as described above. Nucleic acid sequences encoding part or all of the light and heavy chains and CDRs of the antibodies of the present invention are preferred. Preferably provided herein are thus nucleic acid sequences encoding part or all of the light and heavy chains and CDRs of exemplary antibodies of the invention. The above table 3 provides the SEQ ID numbers for the nucleic acid sequences encoding the heavy chain and light chain variable regions of some examples of antibodies of the invention. Table 4 below provides the SEQ ID numbers for the nucleic acid sequences encoding the CDRs of some examples of the antibodies of the invention. Due to the redundancy of the genetic code, variants of these nucleic acid sequences will exist that encode the same amino acid sequences.

Thus, the present invention also comprises a nucleic acid molecule comprising a polynucleotide encoding the antibody, or the antigen binding fragment thereof, according to the present invention.

A nucleic acid molecule is a molecule comprising, preferably consisting of nucleic acid components. The term nucleic acid molecule preferably refers to DNA or RNA molecules. It is preferably used synonymous with the term "polynucleotide". Preferably, a nucleic acid molecule is a polymer comprising or consisting of nucleotide monomers which are covalently linked to each other by phosphodiester-bonds of a sugar/phosphate-backbone. The term "nucleic acid molecule" also encompasses modified nucleic acid molecules, such as base-modified, sugar-modified or backbone-modified etc. DNA or RNA molecules.

TABLE 4

SEQ ID Numbers for CDR Polynucleotides of exemplary antibodies according to the present invention.

| | SEQ ID NOs. for CDR Polynucleotides | | | | | |
|---|---|---|---|---|---|---|
| | CDRH1 | CDRH2 | CDRH3 | CDRL1 | CDRL2 | CDRL3 |
| RVA122 | 8 | 9 | 10 | 11 | 12 or 13 | 14 |
| RVA144 | 26 | 27 | 28 | 29 | 30 or 31 | 32 |
| RVB185 | 44 | 45 | 46 | 47 | 48 or 49 | 50 |
| RVB492 | 62 | 63 | 64 | 65 | 66 or 67 | 68 |
| RVC3 | 82 | 83 | 84 | 85 | 86 or 87 | 88 |
| RVC20 | 100 | 101 | 102 | 103 | 104 or 105 | 106 |
| RVC21 | 118 | 119 | 120 | 121 | 122 or 123 | 124 |
| RVC38 | 136 | 137 | 138 | 139 | 140 or 141 | 142 |
| RVC44 | 154 | 155 | 156 | 157 | 158 or 159 | 160 |
| RVC58 | 172 | 173 | 174 | 175 | 176 or 177 | 178 |
| RVC68 | 190 | 191 | 192 | 193 | 194 or 195 | 196 |
| RVC111 | 208 | 209 | 210 | 211 | 212 or 213 | 214 |

Preferably, the polynucleotide sequence of the nucleic acid molecule according to the invention is at least 75% identical to the nucleic acid sequence of any one of SEQ ID NOs: 8-14, 17, 18, 26-32, 35, 36, 44-50, 53, 54, 62-68, 72-74, 82-88, 91, 92, 100-106, 109, 110, 118-124, 127, 128, 136-142, 145, 146, 154-160, 163, 164, 172-178, 181, 182, 190-196, 199, 200, 208-214, 217 or 218. Preferably, the nucleotide sequence of the nucleic acid molecule according to the invention is according to any one of SEQ ID NOs: 8-14, 17, 18, 26-32, 35, 36, 44-50, 53, 54, 62-68, 72-74, 82-88, 91, 92, 100-106, 109, 110, 118-124, 127, 128, 136-142, 145, 146, 154-160, 163, 164, 172-178, 181, 182, 190-196, 199, 200, 208-214, 217 or 218, or sequence variants thereof.

It is also preferred that, nucleic acid sequences according to the invention include nucleic acid sequences having at least 70%, at least 75%, at least 80%, at least 85%, at least 88%, at least 90%, at least 92%, at least 95%, at least 96%, at least 97%, at least 98% or at least 99% identity to the nucleic acid encoding the variable region of a heavy or light chain of an antibody of the invention. In another embodiment, a nucleic acid sequence of the invention has the sequence of a nucleic acid encoding a heavy or light chain CDR of an antibody of the invention. For example, a nucleic acid sequence according to the invention comprises a sequence that is at least 75%, at least 80%, at least 85%, at least 88%, at least 90%, at least 92%, at least 95%, at least 96%, at least 97%, at least 98% or at least 99% identical to the nucleic acid sequences of SEQ ID NOs: 8-14, 17, 18, 26-32, 35, 36, 44-50, 53, 54, 62-68, 72-74, 82-88, 91, 92, 100-106, 109, 110, 118-124, 127, 128, 136-142, 145, 146, 154-160, 163, 164, 172-178, 181, 182, 190-196, 199, 200, 208-214, 217 or 218.

In yet another preferred embodiment, nucleic acid sequences according to the invention include nucleic acid sequences having at least 70%, at least 75%, at least 80%, at least 85%, at least 88%, at least 90%, at least 92%, at least 95%, at least 96%, at least 97%, at least 98% or at least 99% identity to the nucleic acid encoding a heavy or light chain of an antibody of the invention as provided in FIGS. 22 to 33.

In general, the nucleic acid molecule may be manipulated to insert, delete or alter certain nucleic acid sequences. Changes from such manipulation include, but are not limited to, changes to introduce restriction sites, to amend codon usage, to add or optimize transcription and/or translation regulatory sequences, etc. It is also possible to change the nucleic acid to alter the encoded amino acids. For example, it may be useful to introduce one or more (e.g., 1, 2, 3, 4, 5, 6, 7, 8, 9, 10, etc.) amino acid substitutions, deletions and/or insertions into the antibody's amino acid sequence. Such point mutations can modify effector functions, antigen-binding affinity, post-translational modifications, immunogenicity, etc., can introduce amino acids for the attachment of covalent groups (e.g., labels) or can introduce tags (e.g., for purification purposes). Mutations can be introduced in specific sites or can be introduced at random, followed by selection (e.g., molecular evolution). For instance, one or more nucleic acids encoding any of the CDR regions, heavy chain variable regions or light chain variable regions of antibodies of the invention can be randomly or directionally mutated to introduce different properties in the encoded amino acids. Such changes can be the result of an iterative process wherein initial changes are retained and new changes at other nucleotide positions are introduced. Further, changes achieved in independent steps may be combined. Different properties introduced into the encoded amino acids may include, but are not limited to, enhanced affinity.

Further included within the scope of the invention are vectors, for example, expression vectors, comprising a nucleic acid sequence according to the invention. Preferably, a vector comprises a nucleic acid molecule according to the invention, for example a nucleic acid molecule as described above.

The term "vector" refers to a nucleic acid molecule, preferably to an artificial nucleic acid molecule, i.e. a nucleic acid molecule which does not occur in nature. A vector in the context of the present invention is suitable for incorporating or harboring a desired nucleic acid sequence. Such vectors may be storage vectors, expression vectors, cloning vectors, transfer vectors etc. A storage vector is a vector which allows the convenient storage of a nucleic acid molecule. Thus, the vector may comprise a sequence corresponding, e.g., to a desired antibody or antibody fragment thereof according to the present invention. An expression vector may be used for production of expression products such as RNA, e.g. mRNA, or peptides, polypeptides or proteins. For example, an expression vector may comprise sequences needed for transcription of a sequence stretch of the vector, such as a promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector which is suitable for transferring nucleic acid molecules into cells or organisms, for example, viral vectors. A vector in the context of the present invention may be, e.g., an RNA vector or a DNA vector. Preferably, a vector is a DNA molecule. For example, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector.

Cells transformed with such vectors are also included within the scope of the invention. Examples of such cells include but are not limited to, eukaryotic cells, e.g., yeast cells, animal cells or plant cells. In one embodiment the cells are mammalian, e.g., human, CHO, HEK293T, PER.C6, NS0, myeloma or hybridoma cells. Accordingly, the present invention also relates to a cell expressing the antibody, or the antigen binding fragment thereof, according to the present invention; or comprising the vector according to the present invention.

In particular, the cell may be transfected with a vector according to the present invention, preferably with an expression vector. The term "transfection" refers to the introduction of nucleic acid molecules, such as DNA or RNA (e.g. mRNA) molecules, into cells, preferably into eukaryotic cells. In the context of the present invention, the term "transfection" encompasses any method known to the skilled person for introducing nucleic acid molecules into cells, preferably into eukaryotic cells, such as into mammalian cells. Such methods encompass, for example, electroporation, lipofection, e.g. based on cationic lipids and/or liposomes, calcium phosphate precipitation, nanoparticle based transfection, virus based transfection, or transfection based on cationic polymers, such as DEAE-dextran or polyethylenimine etc. Preferably, the introduction is non-viral.

The invention also relates to monoclonal antibodies that bind to an epitope capable of binding the antibodies or antigen binding fragments of the invention. Accordingly, the present invention comprises an isolated or purified immunogenic polypeptide comprising an epitope that specifically binds to the antibody, or the antigen binding fragment thereof, according to the present invention. Such an immunogenic peptide according to the present invention may also be used for a vaccine, for example for a vaccine which is used in combination with the antibodies according to the present invention.

The invention provides novel epitopes to which the neutralizing antibodies of the invention bind. These epitopes, in particular antigenic site 111.2, B and C, are found on the RABV G protein (glycoprotein G) as described above.

The epitopes to which the antibodies of the invention bind may be linear (continuous) or conformational (discontinuous). Preferably, the antibodies and antibody fragments of the invention bind a conformational epitope, more preferably the conformational epitope is present only under non-reducing conditions. However, in particular with regard to antigenic sites B and C as described above, antibodies and antibody fragments of the invention may also bind a linear epitope, more preferably the linear epitope is present under both, non-reducing conditions and reducing conditions.

Monoclonal and recombinant antibodies are particularly useful in identification and purification of the individual polypeptides or other antigens against which they are directed. The antibodies of the invention have additional utility in that they may be employed as reagents in immunoassays, radioimmunoassays (RIA) or enzyme-linked immunosorbent assays (ELISA). In these applications, the antibodies can be labeled with an analytically-detectable reagent such as a radioisotope, a fluorescent molecule or an enzyme. The antibodies may also be used for the molecular identification and characterization (epitope mapping) of antigens.

Antibodies of the invention can also be coupled to a drug for delivery to a treatment site or coupled to a detectable label to facilitate imaging of a site comprising cells of interest, such as cells infected with RABV and/or non-RABV lyssaviruses. Methods for coupling antibodies to drugs and detectable labels are well known in the art, as are methods for imaging using detectable labels. Labeled antibodies may be employed in a wide variety of assays, employing a wide variety of labels. Detection of the formation of an antibody-antigen complex between an antibody of the invention and an epitope of interest (an epitope of RABV and/or non-RABV) can be facilitated by attaching a detectable substance to the antibody. Suitable detection means include the use of labels such as radionuclides, enzymes, coenzymes, fluorescers, chemiluminescers, chromogens, enzyme substrates or co-factors, enzyme inhibitors, prosthetic group complexes, free radicals, particles, dyes, and the like. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material is luminol; examples of bioluminescent materials include luciferase, luciferin, and aequorin; and examples of suitable radioactive material include 125I, 131I, 35S, or 3H. Such labeled reagents may be used in a variety of well-known assays, such as radioimmunoassays, enzyme immunoassays, e.g., ELISA, fluorescent immunoassays, and the like. (See U.S. Pat. Nos. 3,766,162; 3,791,932; 3,817,837; and 4,233,402 for example).

An antibody according to the invention may be conjugated to a therapeutic moiety such as a cytotoxin, a therapeutic agent, or a radioactive metal ion or radioisotope. Examples of radioisotopes include, but are not limited to, 1-131, 1-123, 1-125, Y-90, Re-188, Re-186, At-211, Cu-67, Bi-212, Bi-213, Pd-109, Tc-99, In-111, and the like. Such antibody conjugates can be used for modifying a given biological response; the drug moiety is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or diphtheria toxin.

Techniques for conjugating such therapeutic moiety to antibodies are well known. See, for example, Arnon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-256; ed. Hellstrom et al. (1987) "Antibodies for Drug Delivery," in Controlled Drug Delivery, ed. Robinson et al. (2d ed; Marcel Dekker, Inc.), pp. 623-653; Thorpe (1985) "Antibody Carriers of Cytotoxic Agents in Cancer Therapy: A Review," in Monoclonal Antibodies '84: Biological and Clinical Applications, ed. Pinchera et al. pp. 475-506 (Editrice Kurtis, Milano, Italy, 1985); "Analysis, Results, and Future Prospective of the Therapeutic Use of Radiolabeled Antibody in Cancer Therapy," in Monoclonal Antibodies for Cancer Detection and Therapy, ed. Baldwin et al. (Academic Press, New York, 1985), pp. 303-316; and Thorpe et al. (1982) Immunol. Rev. 62:119-158.

Alternatively, an antibody, or antibody fragment thereof, can be conjugated to a second antibody, or antibody fragment thereof, to form an antibody heteroconjugate as described in U.S. Pat. No. 4,676,980. In addition, linkers may be used between the labels and the antibodies of the invention (e.g., U.S. Pat. No. 4,831,175). Antibodies or, antigen-binding fragments thereof may be directly labeled with radioactive iodine, indium, yttrium, or other radioactive particle known in the art (e.g., U.S. Pat. No. 5,595,721). Treatment may consist of a combination of treatment with conjugated and non-conjugated antibodies administered simultaneously or subsequently (e.g., WO00/52031; WO00/52473).

Antibodies of the invention may also be attached to a solid support. Additionally, antibodies of the invention, or functional antibody fragments thereof, can be chemically modified by covalent conjugation to a polymer to, for example, increase their circulating half-life. Examples of polymers, and methods to attach them to peptides, are shown in U.S. Pat. Nos. 4,766,106; 4,179,337; 4,495,285 and 4,609,546. In some embodiments the polymers may be selected from polyoxyethylated polyols and polyethylene glycol (PEG). PEG is soluble in water at room temperature and has the general formula: $R(O-CH_2-CH_2)_n O-R$ where R can be hydrogen, or a protective group such as an alkyl or alkanol group. Preferably, the protective group may have between 1 and 8 carbons. For example, the protective group is methyl. The symbol n is a positive integer. In one embodiment n is between 1 and 1,000. In another embodiment n is between 2 and 500. Preferably, the PEG has an average molecular weight between 1,000 and 40,000, more preferably the PEG has a molecular weight between 2,000 and 20,000, even more preferably the PEG has a molecular weight between 3,000 and 12,000. Furthermore, PEG may have at least one hydroxy group, for example the PEG may have a terminal hydroxy group. For example, it is the terminal hydroxy group which is activated to react with a free amino group on the inhibitor. However, it will be understood that the type and amount of the reactive groups may be varied to achieve a covalently conjugated PEG/antibody of the present invention.

Water-soluble polyoxyethylated polyols are also useful in the present invention. They include polyoxyethylated sorbitol, polyoxyethylated glucose, polyoxyethylated glycerol (POG), and the like. In one embodiment, POG is used. Without being bound by any theory, because the glycerol backbone of polyoxyethylated glycerol is the same backbone occurring naturally in, for example, animals and humans in mono-, di-, triglycerides, this branching would not necessarily be seen as a foreign agent in the body. POG may have a molecular weight in the same range as PEG. Another drug delivery system that can be used for increasing circulatory half-life is the liposome. Methods of preparing liposome delivery systems are known to one of skill in the art. Other drug delivery systems are known in the art and are described in, for example, referenced in Poznansky et al. (1980) and Poznansky (1984).

Antibodies of the invention may be provided in purified form. Typically, the antibody will be present in a composition that is substantially free of other polypeptides e.g., where less than 90% (by weight), usually less than 60% and more usually less than 50% of the composition is made up of other polypeptides.

Antibodies of the invention may be immunogenic in non-human (or heterologous) hosts e.g., in mice. In particular, the antibodies may have an idiotope that is immunogenic in non-human hosts, but not in a human host. Antibodies of the invention for human use include those that cannot be easily isolated from hosts such as mice, goats, rabbits, rats, non-primate mammals, etc. and cannot generally be obtained by humanization or from xeno-mice.

Antibodies of the invention can be of any isotype (e.g., IgA, IgG, IgM i.e. an a, y or µ heavy chain), but will preferably be IgG. Within the IgG isotype, antibodies may be IgG1, IgG2, IgG3 or IgG4 subclass, whereby IgG1 is preferred. Antibodies of the invention may have a K or a light chain.

Production of Antibodies

Antibodies according to the invention can be made by any method known in the art. For example, the general methodology for making monoclonal antibodies using hybridoma technology is well known (Kohler, G. and Milstein, C., 1975; Kozbar et al. 1983). In one embodiment, the alternative EBV immortalization method described in WO2004/076677 is used.

Using the method described in WO 2004/076677, B cells producing the antibody of the invention can be transformed with EBV and a polyclonal B cell activator. Additional stimulants of cellular growth and differentiation may optionally be added during the transformation step to further enhance the efficiency. These stimulants may be cytokines such as IL-2 and IL-15. In one aspect, IL-2 is added during the immortalization step to further improve the efficiency of immortalization, but its use is not essential. The immortalized B cells produced using these methods can then be cultured using methods known in the art and antibodies isolated therefrom.

Using the method described in WO 2010/046775, plasma cells can be cultured in limited numbers, or as single plasma cells in microwell culture plates. Antibodies can be isolated from the plasma cell cultures. Further, from the plasma cell cultures, RNA can be extracted and PCR can be performed using methods known in the art. The VH and VL regions of the antibodies can be amplified by RT-PCR (reverse transcriptase PCR), sequenced and cloned into an expression vector that is then transfected into HEK293T cells or other host cells. The cloning of nucleic acid in expression vectors, the transfection of host cells, the culture of the transfected host cells and the isolation of the produced antibody can be done using any methods known to one of skill in the art.

The antibodies may be further purified, if desired, using filtration, centrifugation and various chromatographic methods such as HPLC or affinity chromatography. Techniques for purification of antibodies, e.g., monoclonal antibodies, including techniques for producing pharmaceutical-grade antibodies, are well known in the art.

Fragments of the antibodies of the invention can be obtained from the antibodies by methods that include digestion with enzymes, such as pepsin or papain, and/or by cleavage of disulfide bonds by chemical reduction. Alternatively, fragments of the antibodies can be obtained by cloning and expression of part of the sequences of the heavy or light chains. Antibody "fragments" include Fab, Fab', F(ab')2 and Fv fragments. The invention also encompasses single-chain Fv fragments (scFv) derived from the heavy and light chains of an antibody of the invention. For example, the invention includes a scFv comprising the CDRs from an antibody of the invention. Also included are heavy or light chain monomers and dimers, single domain heavy chain antibodies, single domain light chain antibodies, as well as single chain antibodies, e.g., single chain Fv in which the heavy and light chain variable domains are joined by a peptide linker.

Antibody fragments of the invention may impart monovalent or multivalent interactions and be contained in a variety of structures as described above. For instance, scFv molecules may be synthesized to create a trivalent "triabody" or a tetravalent "tetrabody." The scFv molecules may include a domain of the Fc region resulting in bivalent minibodies. In addition, the sequences of the invention may be a component of multispecific molecules in which the sequences of the invention target the epitopes of the invention and other regions of the molecule bind to other targets. Exemplary molecules include, but are not limited to, bispecific Fab2, trispecific Fab3, bispecific scFv, and diabodies (Holliger and Hudson, 2005, *Nature Biotechnology* 9: 1126-1136).

Standard techniques of molecular biology may be used to prepare DNA sequences encoding the antibodies or antibody fragments of the present invention. Desired DNA sequences may be synthesized completely or in part using oligonucleotide synthesis techniques. Site-directed mutagenesis and polymerase chain reaction (PCR) techniques may be used as appropriate.

Any suitable host cell/vector system may be used for expression of the DNA sequences encoding the antibody molecules of the present invention or fragments thereof. Bacterial, for example *E. coli*, and other microbial systems may be used, in part, for expression of antibody fragments such as Fab and F(ab')2 fragments, and especially Fv fragments and single chain antibody fragments, for example, single chain Fvs. Eukaryotic, e.g., mammalian, host cell expression systems may be used for production of larger antibody molecules, including complete antibody molecules. Suitable mammalian host cells include, but are not limited to, CHO, HEK293T, PER.C6, NS0, myeloma or hybridoma cells.

The present invention also provides a process for the production of an antibody molecule according to the present invention comprising culturing a host cell comprising a vector encoding a nucleic acid of the present invention under conditions suitable for expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

Alternatively, antibodies according to the invention may be produced by (i) expressing a nucleic acid sequence according to the invention in a host cell, and (ii) isolating the expressed antibody product. Additionally, the method may include (iii) purifying the isolated antibody. Transformed B cells and cultured plasma cells may be screened for those producing antibodies of the desired specificity or function.

The screening step may be carried out by any immunoassay, e.g., ELISA, by staining of tissues or cells (including transfected cells), by neutralization assay or by one of a number of other methods known in the art for identifying desired specificity or function. The assay may select on the basis of simple recognition of one or more antigens, or may select on the additional basis of a desired function e.g., to select neutralizing antibodies rather than just antigen-binding antibodies, to select antibodies that can change characteristics of targeted cells, such as their signaling cascades, their shape, their growth rate, their capability of influencing other cells, their response to the influence by other cells or by other reagents or by a change in conditions, their differentiation status, etc.

Individual transformed B cell clones may then be produced from the positive transformed B cell culture. The cloning step for separating individual clones from the mixture of positive cells may be carried out using limiting dilution, micromanipulation, single cell deposition by cell sorting or another method known in the art.

Nucleic acid from the cultured plasma cells can be isolated, cloned and expressed in HEK293T cells or other known host cells using methods known in the art.

The immortalized B cell clones or the transfected host-cells of the invention can be used in various ways e.g., as a source of monoclonal antibodies, as a source of nucleic acid (DNA or mRNA) encoding a monoclonal antibody of interest, for research, etc.

The invention also provides a composition comprising immortalized B memory cells or transfected host cells that produce antibodies according to the present invention.

The immortalized B cell clone or the cultured plasma cells of the invention may also be used as a source of nucleic acid for the cloning of antibody genes for subsequent recombinant expression. Expression from recombinant sources is more common for pharmaceutical purposes than expression from B cells or hybridomas e.g., for reasons of stability, reproducibility, culture ease, etc.

Thus the invention also provides a method for preparing a recombinant cell, comprising the steps of: (i) obtaining one or more nucleic acids (e.g., heavy and/or light chain mRNAs) from the B cell clone or the cultured plasma cells that encodes the antibody of interest; (ii) inserting the nucleic acid into an expression vector and (iii) transfecting the vector into a host cell in order to permit expression of the antibody of interest in that host cell.

Similarly, the invention provides a method for preparing a recombinant cell, comprising the steps of: (i) sequencing nucleic acid(s) from the B cell clone or the cultured plasma cells that encodes the antibody of interest; and (ii) using the sequence information from step (i) to prepare nucleic acid(s) for insertion into a host cell in order to permit expression of the antibody of interest in that host cell. The nucleic acid may, but need not, be manipulated between steps (i) and (ii) to introduce restriction sites, to change codon usage, and/or to optimize transcription and/or translation regulatory sequences.

Furthermore, the invention also provides a method of preparing a transfected host cell, comprising the step of transfecting a host cell with one or more nucleic acids that encode an antibody of interest, wherein the nucleic acids are nucleic acids that were derived from an immortalized B cell clone or a cultured plasma cell of the invention. Thus the procedures for first preparing the nucleic acid(s) and then using it to transfect a host cell can be performed at different times by different people in different places (e.g., indifferent countries).

These recombinant cells of the invention can then be used for expression and culture purposes. They are particularly useful for expression of antibodies for large-scale pharmaceutical production. They can also be used as the active ingredient of a pharmaceutical composition. Any suitable culture technique can be used, including but not limited to static culture, roller bottle culture, ascites fluid, hollow-fiber type bioreactor cartridge, modular minifermenter, stirred tank, microcarrier culture, ceramic core perfusion, etc.

Methods for obtaining and sequencing immunoglobulin-genes from B cells or plasma cells are well known in the art (e.g., see Chapter 4 of Kuby Immunology, 4th edition, 2000).

The transfected host cell may be a eukaryotic cell, including yeast and animal cells, particularly mammalian cells (e.g., CHO cells, NS0 cells, human cells such as PER.C6 or HKB-11 cells, myeloma cells), as well as plant cells. Preferred expression hosts can glycosylate the antibody of the invention, particularly with carbohydrate structures that are not themselves immunogenic in humans. In one embodiment the transfected host cell may be able to grow in serum-free media. In a further embodiment the transfected host cell may be able to grow in culture without the presence of animal-derived products. The transfected host cell may also be cultured to give a cell line.

The invention also provides a method for preparing one or more nucleic acid molecules (e.g., heavy and light chain genes) that encode an antibody of interest, comprising the steps of: (i) preparing an immortalized B cell clone or culturing plasma cells according to the invention; (ii) obtaining from the B cell clone or the cultured plasma cells nucleic acid that encodes the antibody of interest. Further, the invention provides a method for obtaining a nucleic acid sequence that encodes an antibody of interest, comprising the steps of: (i) preparing an immortalized B cell clone or culturing plasma cells according to the invention; (ii) sequencing nucleic acid from the B cell clone or the cultured plasma cells that encodes the antibody of interest.

The invention further provides a method of preparing nucleic acid molecule(s) that encode an antibody of interest, comprising the step of obtaining the nucleic acid that was obtained from a transformed B cell clone or cultured plasma cells of the invention. Thus the procedures for first obtaining the B cell clone or the cultured plasma cell, and then obtaining nucleic acid(s) from the B cell clone or the cultured plasma cells can be performed at different times by different people in different places (e.g., in different countries).

The invention also comprises a method for preparing an antibody (e.g., for pharmaceutical use) according to the present invention, comprising the steps of: (i) obtaining and/or sequencing one or more nucleic acids (e.g., heavy and light chain genes) from the selected B cell clone or the cultured plasma cells expressing the antibody of interest; (ii) inserting the nucleic acid(s) into or using the nucleic acid(s) sequence(s) to prepare an expression vector; (iii) transfecting a host cell that can express the antibody of interest; (iv) culturing or sub-culturing the transfected host cells under conditions where the antibody of interest is expressed; and, optionally, (v) purifying the antibody of interest.

The invention also provides a method of preparing an antibody comprising the steps of culturing or sub-culturing a transfected host cell population under conditions where the antibody of interest is expressed and, optionally, purifying the antibody of interest, wherein said transfected host cell population has been prepared by (i) providing nucleic acid(s) encoding a selected antibody of interest that is produced by a B cell clone or cultured plasma cells prepared as described above, (ii) inserting the nucleic acid(s) into an expression vector, (iii) transfecting the vector in a host cell that can express the antibody of interest, and (iv) culturing or sub-culturing the transfected host cell comprising the inserted nucleic acids to produce the antibody of interest.

Thus the procedures for first preparing the recombinant host cell and then culturing it to express antibody can be performed at very different times by different people in different places (e.g., in different countries).

Epitopes

As mentioned above, the antibodies of the invention can be used to map the epitopes to which they bind. The invention provides antibodies, which bind to known epitopes and antibodies, which bind to novel epitopes on the RABV G protein (glycoprotein G). These epitopes of the RABV G Protein and examples of antibodies, which bind to each of the epitopes, are described in detail in Examples 3 and 5, and more specifically concerning the conservation of antigenic sites I and III on the RABV G protein in Example 6.

In general, the epitopes to which the antibodies of the invention bind may be linear (continuous) or conformational (discontinuous). In one preferred embodiment, the antibodies and antibody fragments of the invention bind a conformational epitope. It is also preferred, that the conformational epitope is present only under non-reducing conditions.

Namely, the two reference antibodies CR57 and CR4098 were previously shown to recognize RABV G protein antigenic sites I and III (Bakker, A. B. H. et al., J Virol 79, 9062-9068, 2005), respectively. The exemplary antibodies according to the present invention can be clustered into 6 groups. RVA125, RVC3, RVC20 and RVD74 bind to the antigenic site I group. Of note, the binding of antigenic site I antibodies to G protein is enhanced by a subgroup of non-antigenic site-I antibodies. RVA22, RVA44, RVB492, RVC4, RVC69, RVC38 and RVC58 bind to the antigenic site III, whereby the RVC58 epitope might only partially overlap with antigenic site III. A third cluster composed by antibodies RVB181, RVC56, RVB185, RVC21, RVB161 and RVC111 binds to antigenic site 111.2, which is likely proximal to antigenic site III on the G protein. Three additional sites were defined named A, B and C. The site A is defined by the unique antibody RVB686, whereby RVB686 binding might induce an allosteric effect on the G protein that compromises the binding of most other antibodies. Site B is defined by antibody RVC44. Similarly, site C is defined by antibodies RVB143 and RVC68, which also recognize a unique and distinct epitope as compared to all the other antibodies. Of note, RVC44, RVB143 and RVC68 are the only antibodies of this panel capable of binding to G protein under reducing conditions, suggesting that they recognize a linear epitope on RABV G protein.

The polypeptides that bind to the antibodies of the present invention may have a number of uses. The polypeptides and polypeptide variants thereof in purified or synthetic form can be used to raise immune responses (i.e., as a vaccine, or for the production of antibodies for other uses) or for screening sera for antibodies that immunoreact with the epitope or mimotopes thereof. In one embodiment such polypeptides or polypeptide variants, or antigen comprising such polypeptides or polypeptide variants may be used as a vaccine for raising an immune response that comprises antibodies of the same quality as those described in the present invention.

Furthermore, the present invention also relates to the use of the antibody, or the antigen binding fragment thereof, according to the present invention, for monitoring the quality of anti-RABV and/or anti-non-RABV lyssavirus vaccines by checking that the antigen of said vaccine contains the specific epitope in the correct conformation.

The antibodies and antibody fragments of the invention can also be used in a method of monitoring the quality of vaccines. In particular the antibodies can be used to check that the antigen in a vaccine contains the correct immunogenic epitope in the correct conformation. The use of an antibody of the invention, or an antigen binding fragment thereof, for monitoring the quality of a vaccine against RABV and/or non-RABV lyssavirus by, for example, checking that the antigen of said vaccine contains the specific epitope in the correct conformation is also contemplated to be within the scope of the invention.

The polypeptides that bind to the antibodies of the present invention may also be useful in screening for ligands that bind to said polypeptides. Such ligands, include but are not limited to antibodies; including those from camels, sharks and other species, fragments of antibodies, peptides, phage display technology products, aptamers, adnectins or fragments of other viral or cellular proteins, may block the epitope and so prevent infection. Such ligands are encompassed within the scope of the invention.

Pharmaceutical Compositions

The invention provides a pharmaceutical composition comprising one or more of: the antibodies or antibody fragments of the invention; the nucleic acid encoding such antibodies or fragments; the vector encoding the nucleic acids; the cell expressing the antibody or comprising the vector; or the immunogenic polypeptide recognized by the antibodies or antigen binding fragment of the invention. The pharmaceutical composition may also contain a pharmaceutically acceptable carrier or excipient. Preferably, the pharmaceutical composition comprises the antibody, or the antigen binding fragment thereof, according to the present invention, the nucleic acid according to the present invention, the vector according to the present invention, the cell according to the present invention, or the immunogenic polypeptide according to the present invention, and a pharmaceutically acceptable excipient, diluent or carrier.

Although the carrier or excipient may facilitate administration, it should not itself induce the production of antibodies harmful to the individual receiving the composition. Nor should it be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the subject.

Compositions of the invention may be prepared in various forms. For example, the compositions may be prepared as injectables, either as liquid solutions or suspensions. Solid forms suitable for solution in, or suspension in, liquid vehicles prior to injection can also be prepared (e.g., a lyophilized composition, like Synagis™ and Herceptin™, for reconstitution with sterile water containing a preservative). The composition may be prepared for topical administration e.g., as an ointment, cream or powder. The composition may be prepared for oral administration e.g., as a tablet or capsule, as a spray, or as a syrup (optionally flavored). The composition may be prepared for pulmonary administration e.g., as an inhaler, using a fine powder or a spray. The composition may be prepared as a suppository or pessary. The composition may be prepared for nasal, aural or ocular administration e.g., as drops. The composition may be in kit form, designed such that a combined composition is reconstituted just prior to administration to a subject. For example, a lyophilized antibody can be provided in kit form with sterile water or a sterile buffer.

It will be appreciated that the active ingredient in the composition will be an antibody molecule, an antibody fragment or variants and derivatives thereof. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Gennaro (2000) Remington: The Science and Practice of Pharmacy, 20th edition, ISBN: 0683306472.

Pharmaceutical compositions of the invention generally have a pH between 5.5 and 8.5, in some embodiments this may be between 6 and 8, and in other embodiments about 7. The pH may be maintained by the use of a buffer. The composition may be sterile and/or pyrogen free. The composition may be isotonic with respect to humans. In one embodiment pharmaceutical compositions of the invention are supplied in hermetically-sealed containers.

Within the scope of the invention are compositions present in several forms of administration; the forms include, but are not limited to, those forms suitable for parenteral administration, e.g., by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilizing and/or dispersing agents. Alternatively, the antibody molecule may be in dry form, for reconstitution before use with an appropriate sterile liquid. A vehicle is typically understood to be a material that is suitable for storing, transporting, and/or administering a compound, such as a pharmaceutically active compound, in particular the antibodies according to the present invention. For example, the vehicle may be a physiologically acceptable liquid, which is suitable for storing, transporting, and/or administering a pharmaceutically active compound, in particular the antibodies according to the present invention. Once formulated, the compositions of the invention can be administered directly to the subject. In one embodiment the compositions are adapted for administration to mammalian, e.g., human subjects.

The pharmaceutical compositions of this invention may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue, whereby intravenously or intramuscularly injection are preferred and intramuscularly injection is more preferred. The compositions can also be administered into a lesion. Particularly preferably, the composition according to the present invention is administered similarly to known rabies immunoglobulins (RIGs) in post-exposure prophylaxis. For example, the WHO recommends to administer all of the RIG, or as much as anatomically possible to avoid possible compartment syndrome, into or around the wound site or sites (e.g., the bite site). The remaining immunoglobulin, if any, should be injected intramuscularly at a site distant from the site of vaccine administration (cf. who.int/rabies/human/WHO_strategy_prepost_exposure/en/indexi.html #, retrieved at Nov. 12, 2014). Accordingly, this administration method is also particularly preferred for the antibody and the pharmaceutical composition according to the present invention, at least in post-exposure prophylaxis and possibly also in treatment or other applications.

Dosage treatment may be a single dose schedule or a multiple dose schedule. Known antibody-based pharmaceuticals provide guidance relating to frequency of administration e.g., whether a pharmaceutical should be delivered daily, weekly, monthly, etc. Frequency and dosage may also depend on the severity of symptoms. In particular, the treatment schedule for rabies immunoglobulins provide guidance relating to frequency of administration. For RIGs it is recommended in post-exposure prophylaxis to administer the RIG for passive immunization only once, preferably at, or as soon as possible after, the initiation of post-exposure vaccination. Accordingly, this treatment schedule is also particularly preferred for the antibody and the pharmaceutical composition according to the present invention, at least in post-exposure prophylaxis. In more general, i.e. for all applications, it is preferred that the antibody or the pharmaceutical composition according to the present invention is administered in a single dose schedule, i.e. only one single dose. Accordingly, the pharmaceutical composition is preferably provided as single-dose product, i.e. as a product which comprises only one single dose. However, since the dose may depend on the bodyweight, in such cases a dose corresponding to a maximal bodyweight is considered as "single dose".

In particular, it is preferred that the amount of the antibody, or the antigen binding fragment thereof, in the pharmaceutical composition according to the present invention, does not exceed 100 mg, preferably does not exceed 50 mg, more preferably does not exceed 20 mg, even more preferably does not exceed 10 mg, and particularly preferably does not exceed 5 mg. This amount of antibody preferably refers to a single dose as described above. The dose of the antibody according the present invention, which is effective e.g. in post-exposure prophylaxis, is thus very low, whereas the recommended amount of HRIG is 20 IU/kg bodyweight, for ERIG and F(ab')2 it is even 40 IU/kg bodyweight. Such a low amount of the antibody according to the present invention could be produced and formulated in a stable form (i.e. lyophilized formulation, where for instance previous studies have shown that monoclonal antibodies preserved by lyophilization are stable for 33 months at 40° C. and 5 months at 50° C.) and at an affordable cost also for developing countries.

However, the antibody or the pharmaceutical composition according to the present invention may also be administered in more than one dose, e.g. in severe cases, for example in treatment protocols.

Preferably, the composition according to the invention is administered to a subject after an infection with a RABV and/or a non-RABV lyssavirus has taken place.

Pharmaceutical compositions will include an effective amount of one or more antibodies of the invention and/or a polypeptide comprising an epitope that binds an antibody of the invention i.e., an amount that is sufficient to treat, ameliorate, attenuate or prevent a desired disease or condition, or to exhibit a detectable therapeutic effect. Therapeutic effects also include reduction or attenuation in pathogenic potency or physical symptoms. The precise effective amount for any particular subject will depend upon their size, weight, and health, the nature and extent of the condition, and the therapeutics or combination of therapeutics selected for administration. The effective amount for a given situation is determined by routine experimentation and is within the judgment of a clinician. For purposes of the present invention, an effective dose will generally be from about 0.005 to about 100 mg/kg, preferably from about 0.0075 to about 75 mg/kg, more preferably from about 0.01 to about 60 mg/kg, even more preferably from about 0.03 to about 50 mg/kg of the antibody of the present invention in the individual to which it is administered.

Preferably, the pharmaceutical composition according to the present invention comprises at least two antibodies or antigen binding fragments thereof, according to the present invention, wherein the two antibodies, or the antigen binding fragments thereof, specifically bind to different epitopes on the glycoprotein G of RABV. For example, the pharmaceutical composition according to the present invention comprises a first antibody or an antigen binding fragment thereof, according to the present invention, and a second antibody, or an antigen binding fragment thereof, according to the present invention, wherein the first antibody, or the antigen binding fragment thereof, specifically binds to another epitope on the glycoprotein G of RABV than the second antibody or the second antigen binding fragment thereof.

I.e., the two antibodies according to the present invention bind specifically to the RABV G protein, but to different epitopes on the RABV G protein. For example, one antibody may specifically bind to antigenic site I on the RABV G protein and a further antibody may specifically bind to an epitope on the glycoprotein G of RABV, which at least partially overlaps with antigenic site III on the glycoprotein G of RABV. The antigenic sites of the exemplary antibodies according to the present invention are outlined in Example 3. Moreover, whether two antibodies bind to the same or different epitopes on the RABV G protein may be easily determined by the person skilled in the art, for example by use of any competition study, whereby an example of a competition study is shown in Example 3.

Preferably, one antibody of the at least two antibodies comprised by such a pharmaceutical composition according to the present invention binds (specifically) to antigenic site I on the glycoprotein G of RABV and another antibody of the at least two antibodies comprised by such a pharmaceutical composition according to the present invention binds (specifically) to antigenic site III on the glycoprotein G of RABV.

More preferably, at least one of the at least two antibodies or antigen binding fragments thereof comprised by such a pharmaceutical composition according to the present invention comprises a heavy chain CDRH3 comprising an amino acid sequence that is at least 80%, preferably at least 90%, identical to SEQ ID NO: 95 or to SEQ ID NO: 167.

In a preferred a pharmaceutical composition according to the present invention one of the at least two antibodies or antigen binding fragments thereof comprises (i) heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 93-97 and 99 or to the amino acid sequences of SEQ ID NOs: 93-96 and 98-99, respectively or (ii) heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 165-169 and 171 or to the amino acid sequences of SEQ ID NOs: 165-168 and 170-171, respectively. More preferably, one of the at least two antibodies or antigen binding fragments thereof comprises a heavy chain variable region having at least 80%, preferably at least 90%, sequence identity to the amino acid sequence of SEQ ID NO: 107 or of SEQ ID NO: 179.

In a particularly preferred pharmaceutical composition according to the present invention comprising at least two antibodies according to the present invention as described herein one of the at least two antibodies or antigen binding fragments thereof comprises a heavy chain CDRH3 comprising an amino acid sequence that is at least 80%, preferably at least 90%, identical to SEQ ID NO: 95 and wherein another of the at least two antibodies comprises a heavy chain CDRH3 comprising an amino acid sequence that is at least 80%, preferably at least 90%, identical to SEQ ID NO: 167. Preferably, one of the at least two antibodies or antigen binding fragments thereof comprises heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 93-97 and 99 or to the amino acid sequences of SEQ ID NOs: 93-96 and 98-99, respectively, and another of the at least two antibodies comprises heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 165-169 and 171 or to the amino acid sequences of SEQ ID NOs: 165-168 and 170-171, respectively. More preferably, one of the at least two antibodies or antigen binding fragments thereof is according to gRVC20 and wherein another of the at least two antibodies is according to gRVC58.

A particularly preferred example of two antibodies according to the present invention, which specifically bind to different epitopes on the glycoprotein G of RABV, is RVC20 and RVC58.

Moreover, the pharmaceutical composition may also contain more than two, e.g. 3, 4, 5, 6, etc., antibodies according to the present invention, whereby at least two, preferably more than two, more preferably all antibodies contained, bind to different epitopes on the RABV G protein.

Preferably, the (at least) two antibodies according to the present invention are present in the pharmaceutical composition at equimolar amounts, preferably as an equimolar mixture.

The combination of two such antibodies according to the present invention, which bind to different epitopes of the RABV G protein represents a treatment with an unprecedented breadth of reactivity and with reduced risk of escape mutant selection. In particular, a combination of two or more monoclonal antibodies according to the present invention, whereby the antibodies bind to a different epitopes or sites on the RABV G protein, increases the protective effect and prevents the escape of resistant variants of the virus.

Preferably, compositions can include two or more (e.g., 2, 3, 4, 5 etc.) antibodies of the invention to provide an additive or synergistic therapeutic effect. The term "synergy" is used to describe a combined effect of two or more active agents that is greater than the sum of the individual effects of each respective active agent. Thus, where the combined effect of two or more agents results in "synergistic inhibition" of an activity or process, it is intended that the inhibition of the activity or process is greater than the sum of the inhibitory effects of each respective active agent. The term "synergistic therapeutic effect" refers to a therapeutic effect observed with a combination of two or more therapies wherein the therapeutic effect (as measured by any of a number of parameters) is greater than the sum of the individual therapeutic effects observed with the respective individual therapies.

In another embodiment, the composition may comprise one or more (e.g., 2, 3, etc.) antibodies of the invention and one or more (e.g., 2, 3, etc.) additional antibodies against a RABV and/or a non-RABV lyssavirus. Further, the administration of antibodies of the invention together with antibodies specific to other pathogens are within the scope of the invention. The antibodies of the invention can be administered either combined/simultaneously or at separate times from antibodies of specific to pathogens other than a RABV and/or a non-RABV lyssavirus.

In another embodiment, the invention provides a pharmaceutical composition comprising two or more antibodies, wherein the first antibody is an antibody of the invention as described herein and the second antibody is specific for a different pathogen that may have co-infected the subject to whom the pharmaceutical composition is being administered.

In a particularly preferred embodiment, the pharmaceutical composition according to the present invention is administered in combination with a rabies vaccine (active immunization), in particular in post-exposure prophylaxis. Currently available rabies vaccines include the most widely used but highly risk-prone nerve tissue vaccines, or the safer but more costly cell culture and embryonated egg vaccines (CCEEVs). In Germany e.g. only two anti-rabies vaccines are on the market, Rabipur® and "Tollwut-Impfstoff (human diploid cell [H-IDC]) inaktiviert". These vaccines contain inactivated rabies virus. Both vaccines are recommended for pre- and postexposure use. Another example of a rabies vaccine is Imovax (Sanofi-Pasteur), which is a commercial inactivated human diploid cell vaccine. Rabies vaccines are in general administered according to the information of the manufacturer, whereby a typical post-exposure prophylaxis protocol includes administration of the vaccine at days 0, 3, 7, 14 and 28 after infection. The pharmaceutical composition according to the invention (passive immunization) is preferably administered only once, preferably simultaneously or as soon as possible after start of the vaccination. Preferably, the pharmaceutical composition according to the invention is administered at a site distant from the vaccine.

Examples of antibodies of the invention specific for, and that neutralize RABV and/or non-RABV lyssaviruses include, but are not limited to, RVA22, RVA44, RVB185, RVB492, RVC3, RVC20, RVC21, RVC38, RVC44, RVC58, RVC68, and RVC111.

The combination, in particular an equimolar combination, of antibodies according to gRVC20 and gRVC58, more preferably the antibodies RVC20 and RVC58, is particularly preferred. RVC20 binds to antigenic site I of RABV G protein and RVC58 binds to an epitope on the glycoprotein G of RABV, which at least partially overlaps with antigenic site III on the glycoprotein G of RABV. Thus, a pharmaceutical composition comprising the antibodies RVC58 and RVC20 or an antigen binding fragment thereof, preferably in equimolar amounts, and a pharmaceutically acceptable carrier is preferred.

Moreover, a pharmaceutical composition comprising the antibody according to gRVA122 or an antigen binding fragment thereof, and a pharmaceutically acceptable carrier is also preferred. A pharmaceutical composition comprising the antibody according to gRVA144 or an antigen binding fragment thereof, and a pharmaceutically acceptable carrier is also preferred. A pharmaceutical composition comprising the antibody according to gRVB185 or an antigen binding fragment thereof, and a pharmaceutically acceptable carrier is also preferred. A pharmaceutical composition comprising the antibody according to gRVB492 or an antigen binding fragment thereof, and a pharmaceutically acceptable carrier is also preferred. A pharmaceutical composition comprising the antibody according to gRVC3 or an antigen binding fragment thereof, and a pharmaceutically acceptable carrier is also preferred. A pharmaceutical composition comprising the antibody according to gRVC20 or an antigen binding fragment thereof, and a pharmaceutically acceptable carrier is also preferred. A pharmaceutical composition comprising the antibody according to gRVC21 or an antigen binding fragment thereof, and a pharmaceutically acceptable carrier is also preferred. A pharmaceutical composition comprising the antibody according to gRVC38 or an antigen binding fragment thereof, and a pharmaceutically acceptable carrier is also preferred. A pharmaceutical composition comprising the antibody according to gRVC44 or an antigen binding fragment thereof, and a pharmaceutically acceptable carrier is also preferred. A pharmaceutical composition comprising the antibody according to gRVC58 or an antigen binding fragment thereof, and a pharmaceutically acceptable carrier is also preferred. A pharmaceutical composition comprising the antibody according to gRVC68 or an antigen binding fragment thereof, and a pharmaceutically acceptable carrier is also preferred. A pharmaceutical composition comprising the antibody according to gRVC111 or an antigen binding fragment thereof, and a pharmaceutically acceptable carrier is also preferred.

In addition, a pharmaceutical composition comprising the antibody RVA122 or an antigen binding fragment thereof, and a pharmaceutically acceptable carrier is also preferred. A pharmaceutical composition comprising the antibody RVA144 or an antigen binding fragment thereof, and a pharmaceutically acceptable carrier is also preferred. A pharmaceutical composition comprising the antibody RVB185 or an antigen binding fragment thereof, and a pharmaceutically acceptable carrier is also preferred. A pharmaceutical composition comprising the antibody RVB492 or an antigen binding fragment thereof, and a pharmaceutically acceptable carrier is also preferred. A pharmaceutical composition comprising the antibody RVC3 or an antigen binding fragment thereof, and a pharmaceutically acceptable carrier is also preferred. A pharmaceutical composition comprising the antibody RVC20 or an antigen binding fragment thereof, and a pharmaceutically acceptable carrier is also preferred. A pharmaceutical composition comprising the antibody RVC21 or an antigen binding fragment thereof, and a pharmaceutically acceptable carrier is also preferred. A pharmaceutical composition comprising the antibody RVC38 or an antigen binding fragment thereof, and a pharmaceutically acceptable carrier is also preferred.

A pharmaceutical composition comprising the antibody RVC44 or an antigen binding fragment thereof, and a pharmaceutically acceptable carrier is also preferred. A pharmaceutical composition comprising the antibody RVC58 or an antigen binding fragment thereof, and a pharmaceutically acceptable carrier is also preferred. A pharmaceutical composition comprising the antibody RVC68 or an antigen binding fragment thereof, and a pharmaceutically acceptable carrier is also preferred. A pharmaceutical composition comprising the antibody RVC111 variant 3 or an antigen binding fragment thereof, and a pharmaceutically acceptable carrier is also preferred.

Antibodies may be administered to those subjects who have previously shown no response, i.e., have been shown to be refractive to treatment for RABV and/or non-RABV lyssavirus infection. Such treatment may include previous treatment with an anti-viral agent. This may be due to, for example, infection with an anti-viral resistant strain of RABV and/or non-RABV lyssaviruses.

In one embodiment, a composition of the invention may include antibodies of the invention, wherein the antibodies may make up at least 50% by weight (e.g., 60%, 70%, 75%, 80%, 85%, 90%, 95%, 97%, 98%, 99% or more) of the total protein in the composition. In such a composition, the antibodies are in purified form.

The invention provides a method of preparing a pharmaceutical composition comprising the steps of: (i) preparing an antibody of the invention; and (ii) admixing the purified antibody with one or more pharmaceutically-acceptable carriers.

In another embodiment, a method of preparing a pharmaceutical composition comprises the step of: admixing an antibody with one or more pharmaceutically-acceptable carriers, wherein the antibody is a monoclonal antibody that was obtained from a transformed B cell or a cultured plasma cell of the invention. Thus the procedures for first obtaining the monoclonal antibody and then preparing the pharmaceutical can be performed at very different times by different people in different places (e.g., in different countries).

As an alternative to delivering antibodies or B cells for therapeutic purposes, it is possible to deliver nucleic acid (typically DNA) that encodes the monoclonal antibody (or active fragment thereof) of interest derived from the B cell or the cultured plasma cells to a subject, such that the nucleic acid can be expressed in the subject in situ to provide a desired therapeutic effect. Suitable gene therapy and nucleic acid delivery vectors are known in the art.

Compositions of the invention may be immunogenic compositions, and in some embodiments may be vaccine compositions comprising an antigen comprising an epitope recognized by an antibody of the invention or an antigen binding fragment thereof, in particular pharmaceutical compositions of the invention, which comprise an immunogenic polypeptide according to the invention. Such "vaccines" according to the invention may either be prophylactic (i.e., prevent infection) or therapeutic (i.e., treat or ameliorate infection). Such vaccine compositions of the invention may elicit both a cell mediated immune response as well as a humoral immune response in order to effectively address RABV and non-RABV lyssavirus infection. This immune response may induce long lasting (e.g., neutralizing) antibodies and a cell mediated immunity that can quickly respond upon exposure to RABV and/or non-RABV lyssavirus.

Compositions may include an antimicrobial, particularly if packaged in a multiple dose format. They may comprise detergent e.g., a Tween (polysorbate), such as Tween 80. Detergents are generally present at low levels e.g., less than 0.01%. Compositions may also include sodium salts (e.g., sodium chloride) to give tonicity. A concentration of 10±2 mg/ml NaCl is typical.

Further, compositions may comprise a sugar alcohol (e.g., mannitol) or a disaccharide (e.g., sucrose or trehalose) e.g., at around 15-30 mg/ml (e.g., 25 mg/ml), particularly if they are to be lyophilized or if they include material which has been reconstituted from lyophilized material. The pH of a composition for lyophilisation may be adjusted to between 5 and 8, or between 5.5 and 7, or around 6.1 prior to lyophilisation.

The compositions of the invention may also comprise one or more immunoregulatory agents. In one embodiment, one or more of the immunoregulatory agents include(s) an adjuvant.

Kit of Parts

In a further aspect, the present invention provides a kit of parts comprising at least one antibody, or antigen binding fragment thereof, according to the present invention as described herein, at least one nucleic acid according to the present invention as described herein, at least one vector according to the present invention as described herein, at least one cell according to the present invention as described herein, at least one immunogenic polypeptide according to the present invention as described herein, and/or at least one pharmaceutical composition according to the present invention as described herein.

Preferably, such a kit of parts comprises at least two different antibodies, or antigen binding fragments thereof, according to the present invention as described herein, wherein the antibodies, or the antigen binding fragments thereof, specifically bind to different epitopes on the glycoprotein G of RABV. Such a kit of parts is particularly useful for the combination of two antibodies according to the present invention as described herein. The at least two antibodies may be present in the kit of parts as separate entities or combined, e.g. as a mixture, for example if both antibodies are contained in the same pharmaceutical composition. Preferably, the at least two different antibodies are separate entities in the kit of parts, which may be mixed by the user if needed. It is also preferred that the at least two different antibodies are combined, e.g. as a mixture, for example if both antibodies are contained in the same pharmaceutical composition.

Preferably, in such a kit of parts one antibody of the at least two antibodies binds to antigenic site I on the glycoprotein G of RABV and another antibody of the at least two antibodies binds to antigenic site III on the glycoprotein G of RABV.

It is also preferred in such a kit of parts that at least one of the at least two antibodies or antigen binding fragments thereof comprises a heavy chain CDRH3 comprising an amino acid sequence that is at least 80%, preferably at least 90%, identical to SEQ ID NO: 95 or to SEQ ID NO: 167. More preferably, in such a kit of parts at least one of the at least two antibodies or antigen binding fragments thereof comprises (i) heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 93-97 and 99 or to the amino acid sequences of SEQ ID NOs: 93-96 and 98-99, respectively or (ii) heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs:

165-169 and 171 or to the amino acid sequences of SEQ ID NOs: 165-168 and 170-171, respectively. Even more preferably, in such a kit of parts one of the at least two antibodies or antigen binding fragments thereof comprises a heavy chain variable region having at least 80%, preferably at least 90%, sequence identity to the amino acid sequence of SEQ ID NO: 107 or of SEQ ID NO: 179.

Preferably, one of the at least two antibodies or antigen binding fragments thereof comprises a heavy chain CDRH3 comprising an amino acid sequence that is at least 80%, preferably at least 90%, identical to SEQ ID NO: 95 and another of the at least two antibodies comprises a heavy chain CDRH3 comprising an amino acid sequence that is at least 80%, preferably at least 90%, identical to SEQ ID NO: 167. More preferably, in such a kit of parts one of the at least two antibodies or antigen binding fragments thereof comprises heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 93-97 and 99 or to the amino acid sequences of SEQ ID NOs: 93-96 and 98-99, respectively, and another of the at least two antibodies comprises heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 165-169 and 171 or to the amino acid sequences of SEQ ID NOs: 165-168 and 170-171, respectively. Even more preferably, in such a kit of parts one of the at least two antibodies or antigen binding fragments thereof is according to gRVC20 and wherein another of the at least two antibodies is according to gRVC58.

Medical Treatments and Uses

In a further aspect, the present invention provides the use of an antibody, or an antigen binding fragment thereof, according to the present invention, the nucleic acid according to the present invention, the vector according to the present invention, the cell according to the present invention, the immunogenic polypeptide according to the present invention, or the pharmaceutical composition according to the present invention in (i) prophylaxis, in particular post-exposure prophylaxis, treatment or attenuation of RABV and/or non-RABV lyssavirus infection; in (ii) vaccination against RABV and/or non-RABV lyssavirus infection; or in (iii) diagnosis of RABV and/or other lyssavirus infection.

Preferably, the antibodies and antibody fragments of the invention or derivatives and variants thereof may be used for the post-exposure prophylaxis and the treatment or attenuation of RABV and/or non-RABV lyssavirus infection, i.e., RABV infection or non-RABV lyssavirus infection or co-infection with both RABV and non-RABV lyssavirus; for the prevention of infection of RABV and/or non-RABV lyssavirus; or for the diagnosis of RABV and/or non-RABV lyssavirus infection. Preferably, the antibody, or the antigen binding fragment thereof, according to the present invention may be used in the post-exposure prophylaxis, treatment or attenuation of infection of RABV and/or non-RABV lyssavirus.

A combination of two or more antibodies according to the present invention, e.g. a combination of 2, 3, 4, 5, 6, 7 etc. antibodies according to the present invention, is particularly preferred for the use in (i) prophylaxis, in particular post-exposure prophylaxis, treatment or attenuation of RABV and/or non-RABV lyssavirus infection; and in (ii) vaccination against RABV and/or non-RABV lyssavirus infection. Such a combination may be for example a combination therapy as described below. Moreover, administration of the two or more antibodies in equimolar amounts is preferred. In particular a combination of two antibodies comprising the six CDR regions according to RVC20 and RVC58, respectively, is preferred, a combination of two antibodies according to gRVC20 and gRVC58 is more preferred, and a combination of the antibodies RVC20 and RVC58 is particularly preferred.

Moreover, in such a combination of two or more antibodies it is preferred that at least two, preferably more than two, more preferably all antibodies combined, bind to different epitopes on the RABV G protein as described above. For example, a first antibody in the combination may specifically bind to antigenic site I on the RABV G protein and a second antibody may specifically bind to an epitope on the glycoprotein G of RABV, which at least partially overlaps with antigenic site III on the glycoprotein G of RABV. The antigenic sites of the exemplary antibodies according to the present invention are outlined in Example 3. Moreover, whether two or more antibodies bind to the same or different epitopes on the RABV G protein may be easily determined by the person skilled in the art, for example by use of any competition study, whereby an example of a competition study is shown in Example 3. A particularly preferred example of a combination of two or more antibodies according to the present invention is a combination of antibodies according to gRVC20 and gRVC58, preferably RVC20 and RVC58. Moreover, a combination of two or more antibodies according to the present invention may for example include any combination of two or more antibodies according to gRVA122, gRVA144, gRVB185, gRVB492, gRVC3, gRVC20, gRVC21, gRVC38, gRVC44, gRVC58, gRVC68, and gRVC111, preferably any combination of two or more of RVA122, RVA144, RVB185, RVB492, RVC3, RVC20, RVC21, RVC38, RVC44, RVC58, RVC68, and RVC111.

Preferably, the two or more antibodies according to the present invention are administered in combination at equimolar amounts.

A "combination of (two or more) antibodies" as used herein refers to any combination, for example the two or more antibodies may be contained in one pharmaceutical composition, or, preferably, the two or more antibodies are administered as combination therapy, in particular they may be administered separately from each other, e.g. in separate antibody preparations, for example in separate pharmaceutical compositions. This means, that in the combination preferably at least one of the combined antibodies, more preferably 2, 3, 4, 5, or 6 of the combined antibodies, more preferably every of the combined antibodies is/are administered separately. In the combination therapy, the antibodies of the invention can be administered either combined/simultaneously ed/simultaneously or consecutively, i.e. one antibody after the other.

In another embodiment, the combination may comprise one or more (e.g., 2, 3, etc.) antibodies of the invention and one or more (e.g., 2, 3, etc.) additional antibodies against a RABV and/or a non-RABV lyssavirus. Further, the administration of antibodies of the invention together with antibodies specific to other pathogens are within the scope of the invention.

The antibody, or the antigen binding fragment thereof, the nucleic acid, the vector, the cell, the immunogenic polypeptide, or the pharmaceutical composition according to the present invention may be provided for use as a medicament for (i) prophylaxis, in particular post-exposure prophylaxis, treatment or attenuation of RABV and/or non-RABV lyssavirus infection; (ii) vaccination against RABV and/or non-RABV lyssavirus infection; or (iii) diagnosis of RABV and/or other lyssavirus infection.

Within the scope of the invention are several forms and routes of administration of the antibody, or the antigen binding fragment thereof, the nucleic acid, the vector, the cell, the immunogenic polypeptide, or the pharmaceutical composition, as described above, in respect to the pharmaceutical composition. This applies also in the context of the use of the antibody, or the antigen binding fragment thereof, the nucleic acid, the vector, the cell, the immunogenic polypeptide as described herein, in particular regarding preferred forms and routes of administration.

Methods of diagnosis may include contacting an antibody or an antibody fragment with a sample. Such samples may be tissue samples taken from, for example, nasal passages, sinus cavities, salivary glands, lung, liver, pancreas, kidney, ear, eye, placenta, alimentary tract, heart, ovaries, pituitary, adrenals, thyroid, brain or skin. The methods of diagnosis may also include the detection of an antigen/antibody complex.

The invention therefore provides (i) an antibody, an antibody fragment, or variants and derivatives thereof according to the invention, (ii) an immortalized B cell clone according to the invention, (iii) an epitope capable of binding an antibody of the invention or (iv) a ligand, preferably an antibody, capable of binding an epitope that binds an antibody of the invention for use in therapy.

Preferably, the antibody, or the antigen binding fragment thereof, according to the present invention, the nucleic acid according to the present invention, the vector according to the present invention, the cell according to the present invention, the immunogenic polypeptide according to the present invention, or the pharmaceutical composition according to the present invention are used in post-exposure prophylaxis, treatment or attenuation of RABV and/or non-RABV lyssavirus infection, wherein the antibody, or the antigen binding fragment thereof, the nucleic acid, the vector, the cell, or the pharmaceutical composition is administered up to seven days, preferably up to five days, after infection.

The term "post-exposure prophylaxis" as used herein refers to a treatment protocol, which starts after exposure to the virus and before the first symptoms of rabies are detectable. However, since there is currently no real treatment, i.e. after start of the symptoms, for rabies, post-exposure prophylaxis may also be applied after the first symptoms of rabies are detectable, however, conventional post-exposure prophylaxis is known to be almost not effective at such a late time point.

In general, post-exposure prophylaxis is started as soon as possible after exposure or suspected exposure to the virus, preferably within a few hours until up to 24 hours or up to 48 hours after exposure. In this limited time window, post-exposure prophylaxis is known to be most effective.

However, the antibodies according to the present invention are also effective when administered at a later time point, presumably even after start of the first symptoms. Therefore, the antibodies according to the present invention considerably enlarge the time window for starting the post-exposure prophylaxis, treatment or attenuation of RABV and/or non-RABV lyssavirus infection. Preferably, the antibody, or the antigen binding fragment thereof, the nucleic acid, the vector, the cell, or the pharmaceutical composition according to the present invention is administered at least up to seven days, preferably at least up to five days, after infection.

It is also preferred that the antibody, or the antigen binding fragment thereof, according to the present invention, the nucleic acid according to the present invention, the vector according to the present invention, the cell according to the present invention, the immunogenic polypeptide according to the present invention, or the pharmaceutical composition according to the present invention is used in post-exposure prophylaxis, treatment or attenuation of RABV and/or non-RABV lyssavirus infection, wherein the antibody, or the antigen binding fragment thereof, the nucleic acid, the vector, the cell, or the pharmaceutical composition is administered in combination with a vaccine, preferably a rabies vaccine, an antiviral, preferably ribavirin, interferon-alpha and/or ketamine.

As described above, currently available rabies vaccines include the most widely used but highly risk-prone nerve tissue vaccines, or the safer but more costly cell culture and embryonated egg vaccines (CCEEVs). In Germany e.g. only two anti-rabies vaccines are on the market, Rabipur® and "Tollwut-Impfstoff (human diploid cell [HDC]) inaktiviert". These vaccines contain inactivated rabies virus. Both vaccines are recommended for pre- and postexposure use. Another example of a rabies vaccine is Imovax (Sanofi-Pasteur), which is a commercial inactivated human diploid cell vaccine. Rabies vaccines are in general administered according to the information of the manufacturer, whereby a typical post-exposure prophylaxis protocol includes administration of the vaccine at days 0, 3, 7, 14 and 28 after infection.

An antiviral refers to a class of medication used specifically for treating viral infections. Like antibiotics for bacteria, specific antivirals are used for specific viruses. Unlike most antibiotics, antiviral drugs do not destroy their target pathogen; instead they inhibit their development. Particularly preferred is the antiviral ribavirin.

In a preferred embodiment, the antibody, or the antigen binding fragment thereof, according to the present invention, the nucleic acid according to the present invention, the vector according to the present invention, the cell according to the present invention, the immunogenic polypeptide according to the present invention, or the pharmaceutical composition according to the present invention are used in post-exposure prophylaxis, treatment or attenuation of RABV and/or non-RABV lyssavirus infection, wherein the antibody, or the antigen binding fragment thereof, the nucleic acid, the vector, the cell, or the pharmaceutical composition is administered in a standard PEP scheme, preferably in combination with a vaccine, preferably in the first treatment of the standard PEP scheme only.

A "standard PEP scheme" typically refers to the post-exposure prophylaxis scheme as recommended by the WHO (cf. who.int/rabies/human/WHO_strategy_prepost_exposure/en/index1.html #, retrieved at Nov. 12, 2014), whereby the antibodies according to the invention replace the RIGs, i.e. HRIG or ERIG. Namely, a post-exposure vaccination is started as soon as possible after exposure with a rabies vaccine as described herein, which follows the protocol of the manufacturer, typically at least two injections. For example, a standard protocol includes injections of the vaccine at days 0, 3, 7, 14, and 28 after exposure. Concomitantly to the first injection, or as soon as possible afterwards, the only and single dose of the antibody is administered.

When used in in post-exposure prophylaxis, treatment or attenuation of RABV and/or non-RABV lyssavirus infection, preferably the antibody, or the antigen binding fragment thereof, according to the present invention is preferably administered at a dose of 0.005 to 100 mg/kg, preferably at a dose of 0.0075 to 50 mg/kg, more preferably at a dose of 0.01 to 10 mg/kg, even more preferably at a dose of 0.01 to 1 mg/kg, and particularly preferably at a dose of 0.01 to 0.1 mg/kg. Such a dose is particularly preferred in a standard PEP scheme as described above.

It is also preferred that the antibody, or the antigen binding fragment thereof, according to the present invention, the nucleic acid according to the present invention, the vector according to the present invention, the cell according to the present invention, the immunogenic polypeptide according to the present invention, or the pharmaceutical composition according to the present invention for use in post-exposure prophylaxis, treatment or attenuation of RABV and/or non-RABV lyssavirus infection, is administered from 1 to 6 days, preferably from 2 to 5 days, after infection.

In another preferred embodiment, which does not refer to the standard PEP scheme, the antibody, or the antigen binding fragment thereof, according to the present invention, for use in post-exposure prophylaxis, treatment or attenuation of RABV and/or non-RABV lyssavirus infection, is administered without concomitant and/or subsequent administration of a vaccine.

In addition to administration in combination with a vaccine, e.g. in a standard PEP scheme, the antibodies according to the present invention are also effective when administered without a vaccine, for example as treatment of rabies, e.g. if administered more than one or two days after exposure.

Moreover, it is preferred that in the antibody, or the antigen binding fragment thereof, according to the present invention or in the pharmaceutical composition according to any of claims 21 to 24 for use in post-exposure prophylaxis, treatment or attenuation of RABV and/or non-RABV lyssavirus infection, that the antibody, or the antigen binding fragment thereof, is administered at a dose of 0.01 to 100 mg/kg, preferably at a dose of 0.1 to 75 mg/kg, more preferably at a dose of 1 to 60 mg/kg, and even more preferably at a dose of 10 to 50 mg/kg. Such "higher" doses are in particular preferred if the exposure was severe and/or if treatment is initiated later than one or two days after exposure.

The invention also provides a method of treating a subject comprising administering to the subject an antibody, an antibody fragment, or variants and derivatives thereof according to the invention, or, a ligand, preferably an antibody, capable of binding an epitope that binds an antibody of the invention. In one embodiment, the method results in reduced RABV and/or non-RABV lyssavirus infection in the subject. In another embodiment, the method prevents, reduces the risk or delays RABV and/or non-RABV lyssavirus infection in the subject.

In particular, the present invention provides a method of preventing and/or treating a RABV and/or non-RABV lyssavirus infection in a subject, wherein the method comprises administering to a subject in need thereof the antibody, or the antigen binding fragment thereof, according to the present invention as described herein, the nucleic acid according to according to the present invention as described herein, the vector according to according to the present invention as described herein, the cell according to according to the present invention as described herein, the immunogenic polypeptide according to according to the present invention as described herein, and/or the pharmaceutical composition according to according to the present invention as described herein. Such a method preferably comprises post-exposure prophylaxis as described herein. It is also preferred that such a method comprises vaccination against RABV and/or non-RABV lyssavirus infection.

The present invention also provides a method of diagnosing a RABV and/or non-RABV lyssavirus infection in a subject, wherein the method comprises administering to a subject in need thereof the antibody, or the antigen binding fragment thereof, according to the present invention as described herein, the nucleic acid according to the present invention as described herein, the vector according to the present invention as described herein, the cell according to the present invention as described herein, the immunogenic polypeptide according to the present invention as described herein, and/or the pharmaceutical composition according to the present invention as described herein.

Preferably, in the above described methods according to the present invention at least two antibodies, or antigen binding fragments thereof, according to the present invention as described herein are administered to the subject, which antibodies, or antigen binding fragments thereof, specifically bind to different epitopes on the glycoprotein G of RABV. Preferably one antibody of the at least two antibodies binds to antigenic site I on the glycoprotein G of RABV and another antibody of the at least two antibodies binds to antigenic site III on the glycoprotein G of RABV. Preferably at least one of the at least two antibodies or antigen binding fragments thereof comprises a heavy chain CDRH3 comprising an amino acid sequence that is at least 80%, preferably at least 90%, identical to SEQ ID NO: 95 or to SEQ ID NO: 167. More preferably, at least one of the at least two antibodies or antigen binding fragments thereof comprises (i) heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 93-97 and 99 or to the amino acid sequences of SEQ ID NOs: 93-96 and 98-99, respectively or (ii) heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 165-169 and 171 or to the amino acid sequences of SEQ ID NOs: 165-168 and 170-171, respectively. Even more preferably, one of the at least two antibodies or antigen binding fragments thereof comprises a heavy chain CDRH3 comprising an amino acid sequence that is at least 80%, preferably at least 90%, identical to SEQ ID NO: 95 and another of the at least two antibodies comprises a heavy chain CDRH3 comprising an amino acid sequence that is at least 80%, preferably at least 90%, identical to SEQ ID NO: 167. Particularly preferably, one of the at least two antibodies or antigen binding fragments thereof comprises heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 93-97 and 99 or to the amino acid sequences of SEQ ID NOs: 93-96 and 98-99, respectively, and another of the at least two antibodies comprises heavy chain CDRH1, CDRH2, and CDRH3 amino acid sequences and light chain CDRL1, CDRL2, and CDRL3 amino acid sequences that are at least 80%, preferably at least 90%, identical to the amino acid sequences of SEQ ID NOs: 165-169 and 171 or to the amino acid sequences of SEQ ID NOs: 165-168 and 170-171, respectively.

The invention also provides the use of (i) an antibody, an antibody fragment, or variants and derivatives thereof according to the invention, (ii) an immortalized B cell clone according to the invention, (iii) an epitope capable of binding an antibody of the invention, (iv) a ligand, preferably an antibody, that binds to an epitope capable of binding an antibody of the invention, or (v) a pharmaceutical composition of the invention in (i) the manufacture of a medicament for the treatment or attenuation of infection by RABV and/or non-RABV lyssavirus (ii) a vaccine, or (iii) diagnosis of RABV and/or non-RABV lyssavirus infection.

The invention provides a composition of the invention for use as a medicament for the prevention or treatment of RABV and/or non-RABV lyssavirus infection. It also provides the use of an antibody of the invention and/or a protein comprising an epitope to which such an antibody binds in the manufacture of a medicament for treatment of a subject and/or diagnosis in a subject. It also provides a method for treating a subject, comprising the step of administering to the subject a composition of the invention. In some embodiments the subject may be a human. One way of checking efficacy of therapeutic treatment involves monitoring disease symptoms after administration of the composition of the invention. Treatment can be a single dose schedule or a multiple dose schedule.

In one embodiment, an antibody, antibody fragment, immortalized B cell clone, epitope or composition according to the invention is administered to a subject in need of such treatment. Such a subject includes, but is not limited to, one who is particularly at risk of or susceptible to RABV and/or non-RABV lyssavirus infection.

Antibodies and fragments thereof as described in the present invention may also be used in a kit for the diagnosis of RABV and/or non-RABV lyssavirus infection. Further, epitopes capable of binding an antibody of the invention may be used in a kit for monitoring the efficacy of vaccination procedures by detecting the presence of protective anti-RABV or anti-non-RABV lyssavirus antibodies. Antibodies, antibody fragment, or variants and derivatives thereof, as described in the present invention may also be used in a kit for monitoring vaccine manufacture with the desired immunogenicity.

Antibodies and fragments thereof as described in the present invention may also be used for monitoring the quality of anti-RABV or anti-non-RABV lyssavirus vaccines by checking that the antigen of said vaccine contains the specific epitope in the correct conformation.

The invention also provides an epitope that specifically binds to an antibody of the invention or an antigen binding fragment thereof, for use (i) in therapy, (ii) in the manufacture of a medicament for the treatment or attenuation of RABV and/or non-RABV lyssavirus infection, (iii) as a vaccine, or (iv) in screening for ligands able to neutralize RABV and/or non-RABV lyssavirus infection.

The invention also provides a method of preparing a pharmaceutical, comprising the step of admixing a monoclonal antibody with one or more pharmaceutically-acceptable carriers, wherein the monoclonal antibody is a monoclonal antibody that was obtained from a transfected host cell of the invention. Thus the procedures for first obtaining the monoclonal antibody (e.g., expressing it and/or purifying it) and then admixing it with the pharmaceutical carrier(s) can be performed at very different times by different people in different places (e.g., in different countries).

Starting with a transformed B cell or a cultured plasma cell of the invention, various steps of culturing, sub-culturing, cloning, sub-cloning, sequencing, nucleic acid preparation etc. can be performed in order to perpetuate the antibody expressed by the transformed B cell or the cultured plasma cell, with optional optimization at each step. In one embodiment, the above methods further comprise techniques of optimization (e.g., affinity maturation or optimization) applied to the nucleic acids encoding the antibody. The invention encompasses all cells, nucleic acids, vectors, sequences, antibodies etc. used and prepared during such steps.

In all these methods, the nucleic acid used in the expression host may be manipulated to insert, delete or alter certain nucleic acid sequences. Changes from such manipulation include, but are not limited to, changes to introduce restriction sites, to amend codon usage, to add or optimize transcription and/or translation regulatory sequences, etc. It is also possible to change the nucleic acid to alter the encoded amino acids. For example, it may be useful to introduce one or more (e.g., 1, 2, 3, 4, 5, 6, 7, 8, 9, 10, etc.) amino acid substitutions, deletions and/or insertions into the antibody's amino acid sequence. Such point mutations can modify effector functions, antigen-binding affinity, post-translational modifications, immunogenicity, etc., can introduce amino acids for the attachment of covalent groups (e.g., labels) or can introduce tags (e.g., for purification purposes). Mutations can be introduced in specific sites or can be introduced at random, followed by selection (e.g., molecular evolution). For instance, one or more nucleic acids encoding any of the CDR regions, heavy chain variable regions or light chain variable regions of antibodies of the invention can be randomly or directionally mutated to introduce different properties in the encoded amino acids. Such changes can be the result of an iterative process wherein initial changes are retained and new changes at other nucleotide positions are introduced. Further, changes achieved in independent steps may be combined. Different properties introduced into the encoded amino acids may include, but are not limited to, enhanced affinity.

The following Figures, Sequences and Examples are intended to illustrate the invention further. They are not intended to limit the subject matter of the invention thereto.

DESCRIPTION OF FIGURES

FIG. 1 shows a summary of the characteristics of the RABV and non-RABV lyssavirus isolates referred to herein. This includes isolate name, viral species and phylogroup (as shown in Table 1 for the non-RABV lyssavirus isolates) as well as host species, country and year of origin, lineage and the GenBank accession number of the amino acid and/or nucleotide sequence of the glycoprotein G of that isolate, if available.

FIG. 2 shows the results of RABV G-protein binding (A) and neutralization (B) by a panel of 90 and 29 plasma samples from RABV vaccinees, respectively. Black symbols indicate HRIG (Berirab®), grey symbols indicate the 4 donors selected for the memory B cell interrogation.

FIG. 3 shows a summary of all the genetic and functional characteristics of the panel of 21 isolated human RABV neutralizing antibodies. Shown are VH, VL and VK usage, the percentage of nucleotide identity to the corresponding germline gene, the neutralization potency on CVS-11 RABV pseudoviruses (pp) expressed as the concentration of IgG in ng/ml able to neutralize 90% of viral infectivity ($IC_{90}$) and the reactivity of the antibodies in western blot (WB) under non-reducing or reducing conditions.

FIG. 4 shows the results of a monoclonal antibody cross-competition matrix performed by ELISA on the 21 isolated antibodies and two reference antibodies of known epitope specificity (CR57 and CR4098). Shown is the percentage of inhibition of binding of the biotinylated antibodies shown in the upper row by the antibodies listed in the left column.

FIG. 5 shows the results of neutralization of 13 different lyssavirus species (22 viral isolates) tested as pseudoviruses by a selection of 12 human monoclonal antibodies from the isolated panel as compared to the three reference antibodies RAM, CR57 and CR4098 and the polyclonal human immunoglobulins (HRIG, Berirab®). Shown is the $IC_{90}$ value in ng/ml, whereby $IC_{90}$>10'000 ng/ml were scored as negative (values for Berirab® neutralization are scored as negative if $IC_{90}$>50'000 ng/ml).

FIG. 6 shows the results of neutralization of 8 different lyssavirus species (16 viral isolates) tested as infectious viruses by a selection of 12 human monoclonal antibodies from the isolated panel as compared to the three reference antibodies RAM, CR57 and CR4098 and the polyclonal human immunoglobulins (HRIG, Berirab®). Shown is the $IC_{50}$ value in ng/ml, whereby $IC_{50}$>10'000 ng/ml were scored as negative (values for Berirab® neutralization are scored as negative if $IC_{50}$>50'000 ng/ml).

FIG. 7 shows the results of neutralization of 13 different lyssavirus species tested as pseudoviruses (A, 22 viral isolates) or viruses (B, 16 viral isolates) by a selection of 12 monoclonal antibodies from the isolated panel as compared to the two reference CR57 and CR4098 antibodies and the polyclonal human immunoglobulins (HRIG, Berirab®).

FIG. 8 shows a summary of the percentage of non-RABV lyssavirus isolates (n=32) (A) and phylogroup I non-RABV lyssavirus isolates (n=22) (B) neutralized with $IC_{50}$ (for viruses) or $IC_{90}$ (for pseudoviruses) below 10000 ng/ml by RVC20, RVC58, RAB1, CR57, CR4098 monoclonal antibodies, or a combination of RVC20 with RVC58 or CR57 with CR4098. The list of the isolates (and their phylogroup) used for this analysis is shown in FIGS. 5 and 6. N, number of isolates used in the calculation of the neutralized isolates. *, HRIG was scored as negative when $IC_{50}$ or $IC_{90}$ was >50'000 ng/ml; **, RAM was tested against 26 non RABV-isolates and 16 non-RABV phylogroup I isolates, respectively.

FIG. 10 shows that RVC20 and RVC58 potently neutralize multi-lineage RABV isolates. (A) Neutralization of RABV isolates tested as for pseudotyped viruses (filled circles, n=8; shown are $IC_{90}$ values) or live viruses (empty circles, n=27; shown are the $IC_{50}$ values) by the selected RVC20 and RVC58 antibodies from our panel, the reference CR57, CR4098 and RAB1 antibodies and HRIG. CVS-11 strain neutralization is shown using live viruses (RFFIT assay, see FIG. 11). Dotted line indicate a threshold for neutralization above 1'000 ng/ml. Shown is the geometric mean value for each data set. The P value of a Wilcoxon matched-pairs signed rank test (**P<0.0001; *P<0.001) is shown. (B) Phylogenetic tree of 2215 G protein sequences retrieved from public databases. Highlighted with dots are the sequences of the RABV isolates tested in this work (two G protein sequences, i.e. CV9.13 and Mauritania/dog/2019-2006/V6235-2007, were not available and were therefore not included in the tree) including those that were tested by FACS for binding (cf. FIG. 11).

FIG. 11 shows a summary of the 43 RABV isolates tested. Neutralization activity ($IC_{50}$ for viruses and $IC_{90}$ for pseudoviruses in ng/ml) of RVC20, RVC58, CR57, CR4098 and RAB1 monoclonal antibodies and HRIG as illustrated in FIG. 10. RFFIT, rapid fluorescent focus inhibition test; FAVN, fluorescent-antibody virus neutralization test; PV, pseudovirus-based neutralization assay. *, viruses tested by FACS for binding to G protein transfectants.

FIG. 12 shows the characteristics of 26 selected RABV isolates tested as viruses or pseudoviruses as well as the neutralization activity in ng/ml of RVC20, RVC58, CR57, CR4098 monoclonal antibodies and HRIG as illustrated in FIGS. 9 and 10. RFFIT, rapid fluorescent focus inhibition test; FAVN, fluorescent-antibody virus neutralization test; PV, pseudovirus-based neutralization assay. Shown are $IC_{50}$ for the FAVN and RFFIT results and $IC_{90}$ for the PV results.

FIG. 13 shows the characteristics of 28 selected non-RABV lyssavirus isolates tested as viruses or pseudoviruses as well as the neutralization activity in ng/ml of RVC20, RVC58, CR57, CR4098 monoclonal antibodies and HRIG as illustrated in FIGS. 5, 6 and 7. RFFIT, rapid fluorescent focus inhibition test; FAVN, fluorescent-antibody virus neutralization test; PV, pseudovirus-based neutralization assay. Shown are $IC_{50}$ for the FAVN and RFFIT results and $IC_{90}$ for the PV results.

FIG. 14 shows the results of neutralization of CVS-11 and different CVS-11 mutants by the panel of 12 selected monoclonal antibodies according to the invention and the reference antibodies RAB1, CR57 and CR4098. Black cells indicate full neutralization, grey cells partial neutralization and white cells no neutralization. Nd, not tested.

FIG. 16 shows an alignment of antigenic site sequences of the G protein from all the tested and sequenced lyssaviruses. Shown are phylogroup I non-RABV and phylogroup II-IV non-RABV lyssaviruses, respectively. Nd, not tested. (A) Antigenic site I with arrows in the first column indicating a lack of neutralization by CR57 and arrows in the second column (most right column of panel A) indicating a lack of neutralization by RVC20. (B) Antigenic site III with arrows in the first column indicating a lack of neutralization by CR4098, arrows in the second column indicating a lack of neutralization by RAB1 and arrows in the third column (most right column of panel B) indicating a lack of neutralization by RVC58. Dotted arrows indicate weak or partial neutralization.

FIG. 20 shows the RABV NP mRNA amounts as measured by RT-PCR on post-mortem CNS samples (A) and the levels of hamster IgG antibodies binding to G protein as measured by ELISA (B) from the experiment shown in FIG. 18. Asterisks indicate animals succumbing the infection, diamonds animals showing a permanent paralysis of the back leg that was site of the viral challenge and open circles asymptomatic animals.

FIG. 22 shows the amino acid sequences for the heavy and light chains of antibody RVA122 as well as the nucleic acid sequences that encode them. The sequences highlighted in bold are CDR regions (nucleotide or aa) and the underlined residues are mutated residues as compared to the "germline" sequence.

FIG. 23 shows the amino acid sequences for the heavy and light chains of antibody RVA144 as well as the nucleic acid sequences that encode them. The sequences highlighted in bold are CDR regions (nucleotide or aa) and the underlined residues are mutated residues as compared to the "germline" sequence.

FIG. 24 shows the amino acid sequences for the heavy and light chains of antibody RVB185 as well as the nucleic acid sequences that encode them. The sequences highlighted in bold are CDR regions (nucleotide or aa) and the underlined residues are mutated residues as compared to the "germline" sequence.

FIG. 25 shows the amino acid sequences for the heavy and light chains of antibody RVB492 as well as the nucleic acid sequences that encode them. The sequences highlighted in bold are CDR regions (nucleotide or aa) and the underlined residues are mutated residues as compared to the "germline" sequence.

FIG. 26 shows the amino acid sequences for the heavy and light chains of antibody RVC3 as well as the nucleic acid sequences that encode them. The sequences highlighted in bold are CDR regions (nucleotide or aa) and the underlined residues are mutated residues as compared to the "germline" sequence.

FIG. 27 shows the amino acid sequences for the heavy and light chains of antibody RVC20 as well as the nucleic acid sequences that encode them. The sequences highlighted in bold are CDR regions (nucleotide or aa) and the underlined residues are mutated residues as compared to the "germline" sequence.

FIG. 28 shows the amino acid sequences for the heavy and light chains of antibody RVC21 as well as the nucleic acid sequences that encode them. The sequences highlighted in bold are CDR regions (nucleotide or aa) and the underlined residues are mutated residues as compared to the "germline" sequence.

FIG. 29 shows the amino acid sequences for the heavy and light chains of antibody RVC38 as well as the nucleic acid sequences that encode them. The sequences highlighted in bold are CDR regions (nucleotide or aa) and the underlined residues are mutated residues as compared to the "germline" sequence.

FIG. 30 shows the amino acid sequences for the heavy and light chains of antibody RVC44 as well as the nucleic acid sequences that encode them. The sequences highlighted in bold are CDR regions (nucleotide or aa) and the underlined residues are mutated residues as compared to the "germline" sequence.

FIG. 31 shows the amino acid sequences for the heavy and light chains of antibody RVC58 as well as the nucleic acid sequences that encode them. The sequences highlighted in bold are CDR regions (nucleotide or aa) and the underlined residues are mutated residues as compared to the "germline" sequence.

FIG. 32 shows the amino acid sequences for the heavy and light chains of antibody RVC6S as well as the nucleic acid sequences that encode them. The sequences highlighted in bold are CDR regions (nucleotide or aa) and the underlined residues are mutated residues as compared to the "germline" sequence.

FIG. 33 shows the amino acid sequences for the heavy and light chains of antibody RVC111 as well as the nucleic acid sequences that encode them. The sequences highlighted in bold are CDR regions (nucleotide or aa) and the underlined residues are mutated residues as compared to the "germline" sequence.

EXAMPLES

Figure 9:
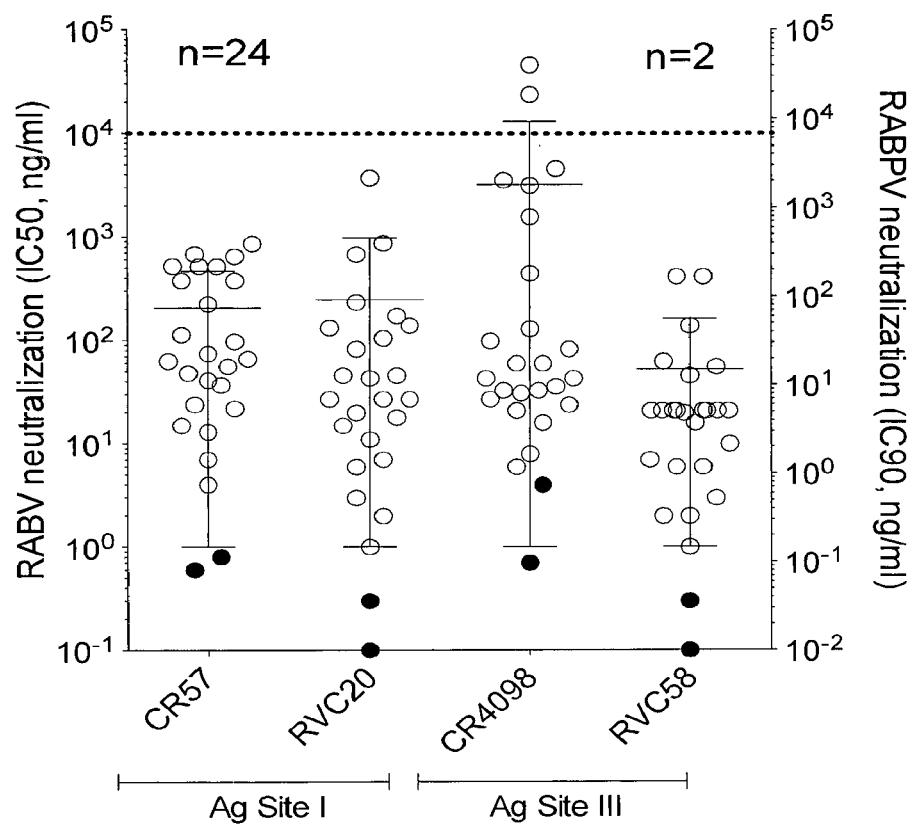
FIG. 9 shows the results of neutralization of RABV isolates tested as pseudoviruses (filled circles, n=2) or viruses (empty circles, n=24) by the selected RVC20 and RVC58 antibodies from our panel and the two reference CR57 and CR4098 antibodies.

Exemplary embodiments of the present invention are provided in the following examples. The following examples are presented only by way of illustration and to assist one of ordinary skill in using the invention. The examples are not intended in any way to otherwise limit the scope of the invention.

Example 1

Figure 2:
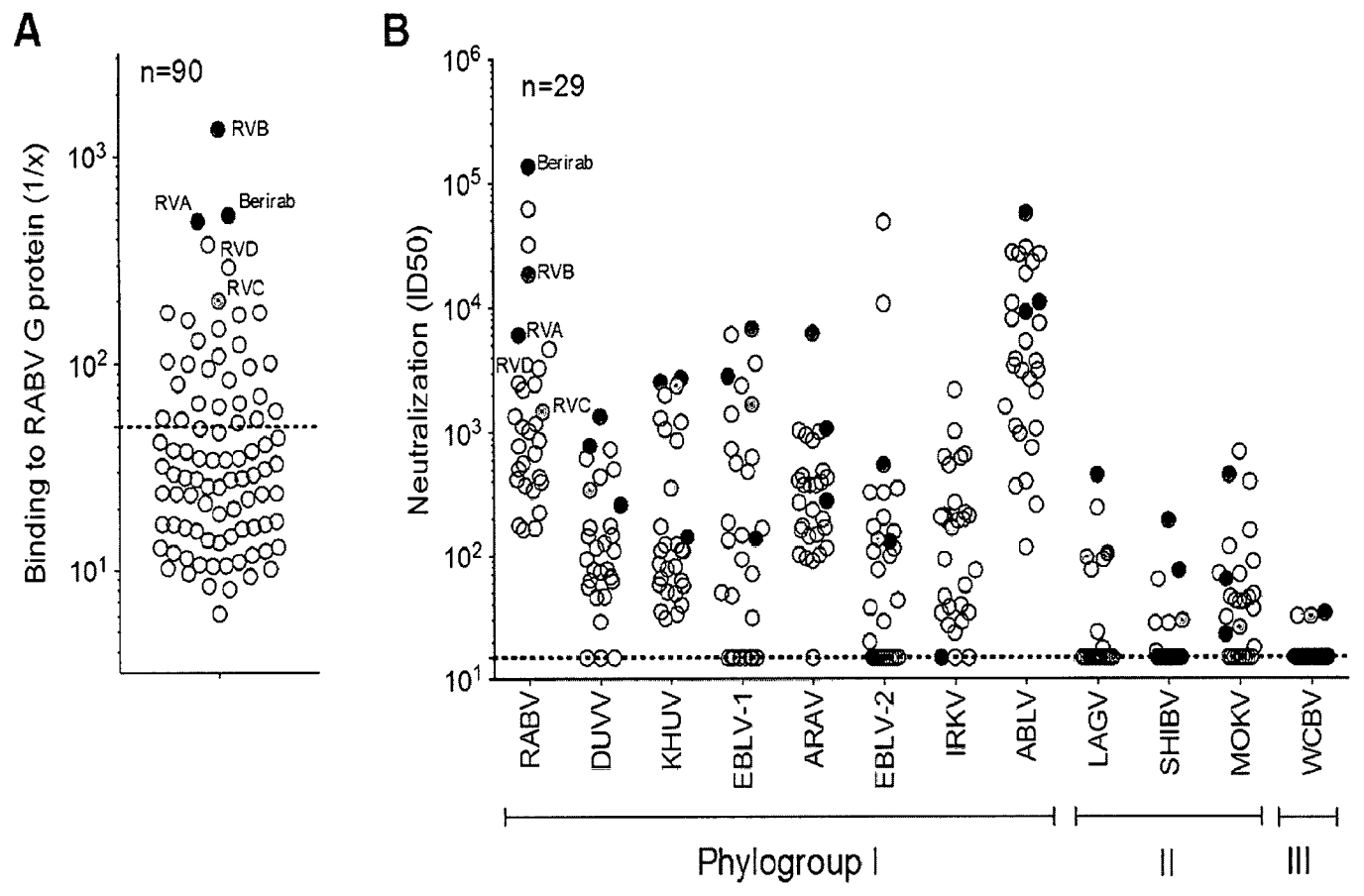

Selection of Rabies Vaccinees for the Isolation of Broadly Neutralizing Antibodies In order to isolate broadly neutralizing antibodies capable to neutralize RABV isolates but also non-RABV lyssaviruses, 90 plasma samples from vaccinees were screened for the presence of high titers of antibodies binding to RABV G protein (CVS-11 strain) by ELISA (FIG. 2A) and selected 29 samples with the highest binding titers ($EC_{50}$>50) for further analysis. In particular the selected 29 plasma samples were tested for their ability to neutralize on a panel of 12 pseudotyped lyssaviruses including phylogroup I viruses RABV, DUVV, KHUV, EBLV1, ARAV, EBLV2, IRKV, ABLV, phylogroup II viruses LABV, SHIBV, MOKV and phylogroup III WCBV (FIG. 2B). Human rabies immunoglobulin (HRIG) Berirab® (Zydus Cadila) was included as a reference. As expected all samples neutralized, albeit with variable titers, the homologous RABV CVS-11 isolate. The neutralization profile of the other lyssavirus species varied considerably in all donors tested where in a few cases all species were neutralized. Of note, HRIG (Berirab®) showed only modest activity against non-RABV phylogroup I species, and no-crossreactivity with phylogroup II and III viruses. This analysis allowed to select four vaccinees as blood donors for the subsequent isolation and characterization of potent broadly neutralizing antibodies.

Example 2

Isolation and Characterization of Rabies Broadly Neutralizing Antibodies

IgG+ memory B cells were isolated from cryopreserved PBMCs of the four selected vaccinees using CD22 microbeads (Miltenyi Biotec), followed by depletion of cells carrying IgM, IgD and IgA by cell sorting. Memory B cells from the four selected vaccinees were then immortalized with EBV (Epstein Barr Virus) and CpG (CpG oligodeoxynucleotide 2006) in multiple replicate wells as previously described (Traggiai, E. et al., Nat. Med. 10, 871-875, 2004) and culture supernatants were then tested in a primary screening using a 384-well based CSV-11 RABV pseudotyped neutralization assay (CVS-11 reference isolate, vaccine strain). Human embryonic kidney 293T cells were used for production of the lentiviral pseudotypes (lyssavirus surrogates). Neutralisation assays were undertaken on baby hamster kidney 21 cells clone 13 (BHK). In a 384-well plate, CVS-11 pseudovirus that resulted in an output of 50-100×$10^4$ relative light units (RLU) was incubated with doubling dilutions of sera for 1 h at 37% (5% CO2) before the addition of 3'000 BHK-21 cells. These were incubated for a further 48 h, after which supernatant was removed and 15 μl Steadylite reagent (Perkin Elmer) was added. Luciferase activity was detected 5 min later by reading the plates on a Synergy microplate luminometer (BioTek) (Wright, E. et al., J Gen. Virol 89, 2204-2213, 2008). Positive cultures were collected and expanded. From positive cultures the VH and VL sequences were retrieved by RT-PCR. RVC20 and RVC58 antibodies were cloned into human IgG1 and Ig kappa or Ig lambda expression vectors (kindly provided by Michel Nussenzweig, Rockefeller University, New York, US) essentially as described (Tiller T, Meffre E, Yurasov S, Tsuiji M, Nussenzweig M C, Wardemann H (2008) Efficient generation of monoclonal antibodies from single human B cells by single cell RT-PCR and expression vector cloning. J Immunol Methods 329: 112-124). Monoclonal antibodies were produced from EBV-immortalized B cells or by transient transfection of 293 Freestyle cells (Invitrogen). Supernatants from B cells or transfected cells were collected and IgG were affinity purified by Protein A or Protein G chromatography (GE Healthcare) and desalted against PBS.

Five hundred human monoclonal antibodies were isolated for their ability to neutralize RABV. Twenty-one human monoclonal antibodies were selected for their high neutralizing potency against CVS-11 RABV, with $IC_{90}$ (concentration of antibody neutralizing 90% of viral infectivity) ranging from 0.01 to 317 ng/ml (FIG. 3), produced by EBV-immortalized B cells and affinity purified by Protein A or Protein G (in the case of IgG3) chromatography. As a reference HRIG and two other human monoclonal antibodies (CR57 and CR4098) that were developed up to Phase III to replace RIGs (but recently failed due to the lack of neutralizing activity against some circulating field RABV isolates) were also tested. In addition, all antibodies were then shown to bind to RABV G protein by ELISA (CVS-11). To this end, a standard ELISA was used. Briefly, ELISA plates were coated with RABV G protein at 5 μg/ml, blocked with 10% FCS in PBS, incubated with sera or human antibodies and washed. Bound antibodies were detected by incubation with AP-conjugated goat anti-human IgG (Southern Biotech). Plates were then washed, substrate (p-NPP, Sigma) was added and plates were read at 405 nm. The relative affinities of sera binding or monoclonal antibody binding were determined by measuring the dilution of sera (ED50) or the concentration of antibody (EC50) required to achieve 50% maximal binding at saturation.

In order to understand whether the cognate epitope is conformational or not the RABV G protein was run on a SDS-PAGE gel under reducing (RED) or non-reducing (NR) conditions and probed by Western blot with all the isolated human monoclonal antibodies. With a few exceptions (RVB143, RVC44 and RVC68) all antibodies did not bind to RABV G protein under reducing conditions, thus suggesting that the epitope recognized is conformational (FIG. 3).

Example 3

Antibody Competition Studies: Determination of Antigenic Sites on RABV G Protein Competition studies were then performed to determine the spatial proximity of each of the conformational epitopes recognized by the all antibodies of the panel. The two reference antibodies CR57 and CR4098 were previously shown to recognize G protein antigenic sites I and III (Bakker, A. B. H. et al., J Virol 79, 9062-9068, 2005; de Kruif, J. et al., Annu Rev Med 58, 359-368, 2007), respectively, and were therefore used in this assay as probes to map the specificity of each antibody of our panel. In particular, CR57, CR4098 and all 21 antibodies selected were purified and labeled with biotin and then tested by ELISA in a full matrix competition assay, in which unlabeled antibodies were incubated first at a concentration of 10 μg/ml on RABV G protein coated plates, followed by the addition of biotinylated antibodies at a concentration of 100 ng/ml (i.e. 100 fold less than the unlabeled antibody), whose binding was revealed with alkaline-phosphatase conjugated streptavidin. Results shown in FIG. 4 and indicate the percentage of blocking of binding of the labeled antibodies in all possible combinations (i.e. 21×21) and were used to cluster antibodies into 6 groups. When interpreting competition results, it should be taken into account that if two epitopes overlap, or the areas covered by the arms of the two antibodies overlap, competition should be almost complete. Weak inhibitory or enhancing effects may reflect a decrease in affinity owing to steric or allosteric effects.

RVA125, RVC3, RVC20 and RVD74 were assigned to the antigenic site I group according to the competition with CR57 and to their reciprocal competitions. Of note, the binding of antigenic site I antibodies to G protein is enhanced by a subgroup of non-antigenic site-I antibodies. RVA122, RVA144, RVB492, RVC4, RVC69, RVC38 and RVC58 were assigned to the antigenic site III according to the competition with CR4098 and to their reciprocal competitions. RVC58 showed only a partial competition with CR4098 (i.e. 64%) as well as competition with non-antigenic site I and III antibodies, thus suggesting that the RVC58 epitope might only partially overlap with antigenic site III. A third cluster composed by antibodies RVB181, RVC56, RVB185, RVC21, RVB161 and RVC111 was named 111.2 since the binding of all these biotinylated antibodies was blocked by all antigenic site III antibodies but reciprocally all these antibodies were not able to block the binding of several antigenic site III antibodies like CR4098, RVC4 and RVC69. In interpreting competition results, it should be taken into account that when two epitopes overlap, or when the areas covered by the arms of the two antibodies overlap, competition should be almost complete. Weak inhibitory or enhancing effects may simply reflect a decrease in affinity owing to steric or allosteric effects. For this reason here we have defined a novel site called 111.2, which is likely proximal to antigenic site III on the G protein. Following the same criteria three additional sites were defined named A, B and C. The site A is defined by the unique antibody RVB686, whose binding compromises the binding of the majority of the labeled antibodies of the panel, but reciprocally the binding of the labeled RBV686 is not blocked by any antibody of the panel. These results might suggest that RVB686 binding induces an allosteric effect on the G protein that compromises the binding of most other antibodies. Site B is defined by antibody RVC44, whose binding is not blocked by any other antibody of the panel. Similarly, site C is defined by antibodies RVB143 and RVC68, which also recognize a unique and distinct epitope as compared to all the other antibodies. Of note, RVC44, RVB143 and RVC68 are the only antibodies of this panel capable of binding by western blot to G protein under reducing conditions, suggesting that they recognize a linear epitope on RABV G protein.

Example 4

Figure 7:
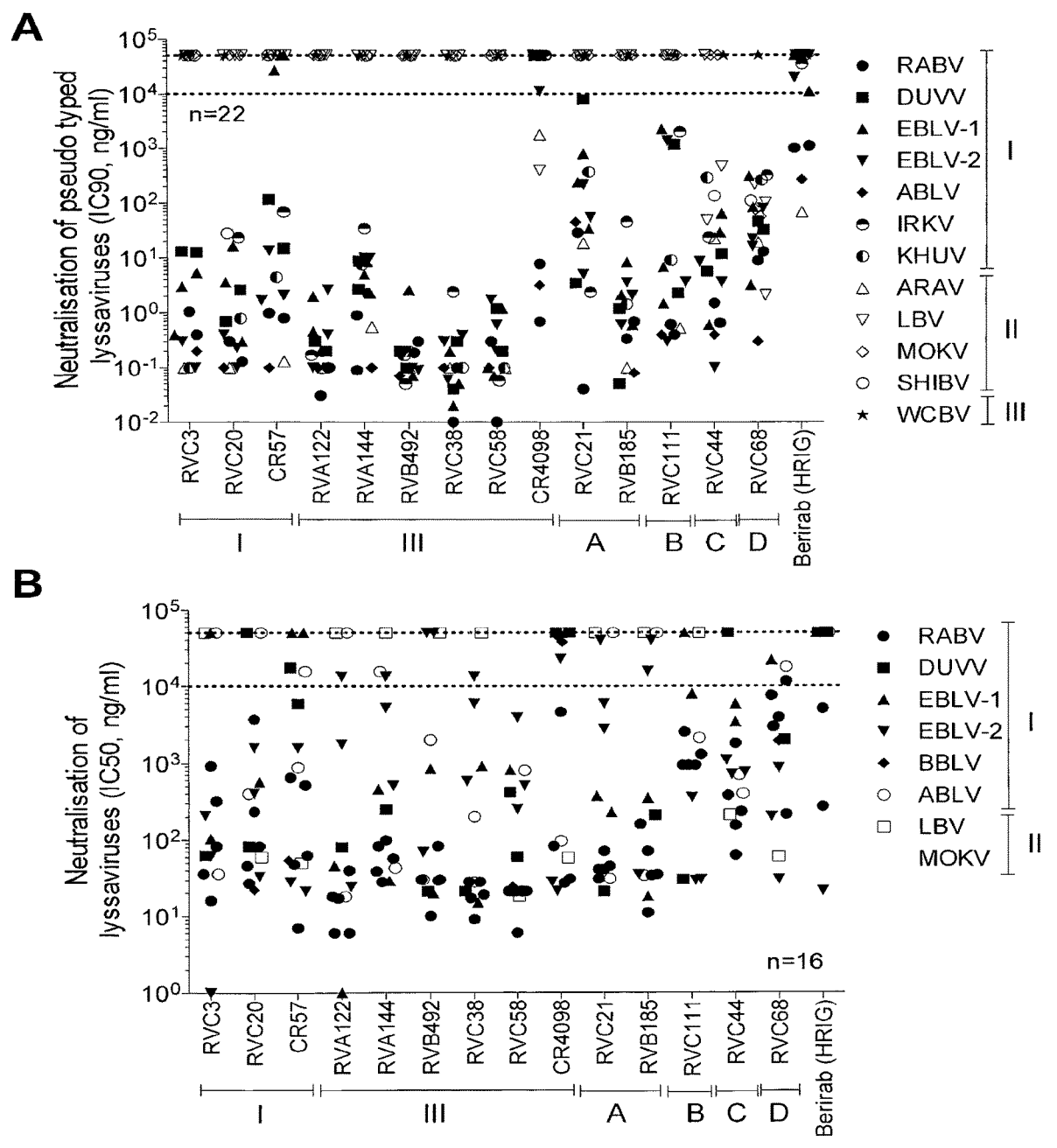

The Antibodies According to the Present Invention Potently Neutralize RABV and Non-RABV Lyssaviruses Twelve of the 22 antibodies were selected for their potency and for the recognition of distinct sites on the RABV G protein for being tested, along with the reference antibodies CR57, CR4098, RAM and Berirab® (HRIG), against a large panel of lyssaviruses using pseudotyped (22 isolates, as shown in FIG. 5) and infectious viruses (16 isolates, as shown in FIG. 6) covering RABV, DUVV, EBLV-1, EBLV-2, ABLV, IRKV, KHUV, ARAV, LBV, MOK, SHIBV, BBLV, WCBV and IKOV species (FIGS. 5, 6 and 7).

Production of Pseudotyped Viruses and Neutralization Assay.

Human embryonic kidney 293T clone 17 cells (HEK 293T/17; ATCC CRL-11268) were used for production of the lentiviral pseudotypes. Neutralisation assays were undertaken on BHK-21 cells clone 13 (ATCC CCL-10). In a 384-well plate, pseudotyped virus that resulted in an output of 50-100×10$^4$ relative light units (RLU) was incubated with doubling dilutions of sera or antibodies for 1 h at 37% (5% CO2) before the addition of 3'000 BHK-21 cells. These were incubated for a further 48 hours, after which supernatant was removed and 15 µl Steadylite reagent (Perkin Elmer) was added. Luciferase activity was detected 5 min later by reading the plates on a Synergy microplate luminometer (BioTek) (Wright et al. 2008). The reduction of infectivity was determined by comparing the RLU in the presence and absence of antibodies and expressed as percentage of neutralization. The neutralization potency for the monoclonal antibodies is here measured as $IC_{90}$, which was defined as the antibody concentration at which RLU were reduced 90% compared with virus control wells after subtraction of background RLU in cell control wells (ID50 for the sera, i.e. the dilution of sera at which RLU were reduced 50%). $ID_{50}$ values for the sera correspond to the dilution at which RLU were reduced 50%.

Lyssavirus Cell-Adaptation and In Vitro Neutralization Assays.

Selected RABVs and non-RABV lyssaviruses were isolated on Neuro-2A (ATCC cat n. CCL-131), further cell adapted and working stocks produced and titrated on BSR cells (a clone of BHK-21). Two protocols slightly modified from Fluorescent Antibody Virus Neutralization (mFAVN) and from Rapid Fluorescent Foci Inhibition (mRFFIT) test (FAVN: Cliquet, F., et al., J. Immunol Methods 212, 79-87, 1998; RFFIT: Smith, J. S., et al., Bull. World Health Organ. 48, 535-541, 1973, Warrell M J, Riddell A, Yu L M, Phipps J, Diggle L, Bourhy H, Deeks J J, Fooks A R, Audry L, Brookes S M, et al (2008) A simplified 4-site economical intradermal post-exposure rabies vaccine regimen: a randomised controlled comparison with standard methods. PLoS Negl Trop Dis 2: e224), respectively, were applied to test the potency of antibodies under study. CVS-11 working stock was amplified and titrated on either BSR or BHK-21, according to the neutralization test adopted, RFFIT or FAVN, respectively. As well, standard FAVN and RFFIT assays were undertaken to assess the potency of tested antibodies against CVS-11. Briefly, mFAVN assays were based on standard FAVN but were undertaken on BSR cells.

The cut-off for neutralization was an $IC_{go}$ (pseudotyped viruses) or an $IC_{50}$ (infectious viruses) above 10000 ng/ml. In other words, if an $IC_{go}$ (pseudotyped viruses) or an $IC_{50}$ (infectious viruses) above 10000 ng/ml was achieved with an antibody, the respective antibody was considered as "not neutralizing".

Amongst the antigenic site I antibodies tested in the pseudotyped neutralization assay (Wright, E. et al., J Gen. Virol 89, 2204-2213, 2008; Wright, E. et al., Vaccine 27, 7178-7186; 2009), RVC20 showed the best breadth of reactivity being able to neutralize RABV, DUVV, EBLV-1, EBLV-2, ABLV, IRKV, KHUV, ARAV phylogroup I viruses as well as SHIBV from phylogroup II and IKOV from putative phylogroup IV (FIG. 5). A full description of the pseudovirus isolates used can be retrieved from FIG. 1. As a comparison, the antigenic site I antibody CR57 was clearly inferior to RVC20, since it was not able to neutralize EBLV-1, SHIBV and IKOV isolates (cf. FIG. 5).

When tested on infectious viruses using either the FAVN (Cliquet, F., et al., J. Immunol Methods 212, 79-87, 1998) or the RFFIT (Smith, J. S., et al., Bull. World Health Organ. 48, 535-541, 1973) assays, RVC20 was also superior in its breadth being able to neutralize RABV, DUVV, EBLV-1, EBLV-2, ABLV, BBLV as well as the phylogroup II MOKV (cf. FIG. 6; the only species which was not neutralized is LBV). A full description of the infectious virus isolates used can be retrieved from FIG. 1. In the same analysis, CR57 did not neutralize EBLV-1 isolates (as observed with pseudoviruses), LBV isolates and MOKV isolates (cf. FIG. 6).

Amongst the antigenic site III antibodies tested in the pseudotyped neutralization assay, RVC58 potently neutralized with $IC_{90}$<10 ng/ml all phylogroup I viruses (i.e. RABV, DUVV, EBLV-1, EBLV-2, ABLV, IRKV, KHUV, ARAV, cf. FIG. 5). As a comparison the antigenic site III antibody CR4098 was far inferior to RVC58, since it was not able to neutralize DUVV, EBLV-1, EBLV-2, IRKV and KHUV isolates and poorly neutralized ARAV (cf. FIG. 5).

When tested on infectious viruses, of all antigenic site III antibodies tested RVC58 was also superior in its breadth, since it was able to potently neutralize RABV, DUVV, EBLV-1, EBLV-2, ABLV, BBLV (cf. FIG. 6; the only species which were not neutralized are MOKV and LBV). In the same analysis CR4098 did not neutralize EBLV-1, DUVV, BBLV, one of the four RABV isolates tested, one of the three EBLV-2 isolates tested and one of the two ABLV isolates tested (cf. FIG. 6).

Of note, antigenic site C antibody RVC68 neutralized all phylogroup I and II pseudoviruses tested (only WCBV was not neutralized), although with $IC_{90}$ values 10-100 fold higher as compared to RVC20 and RVC58 (FIGS. 5 and 7). When tested on infectious viruses, antibody RVC68 was, however, not able to neutralize EBLV, ABLV, MOKV as well as one of the four RABV isolates tested (FIGS. 6 and 7).

If the analysis of the antibody breadth is limited to non-RABV lyssaviruses (scoring as positives all viruses neutralized with $IC_{50}$<10000 ng/ml), RVC58 (antigenic site III) is able to neutralize 69% of all non-RABV lyssaviruses tested and, remarkably, all the phylogroup I lyssaviruses tested. In comparison antibody CR4098 and RAB1 neutralized only 19% and 27%, respectively, of the non-RABV lyssaviruses and 23% and 25%, respectively, of the phylogroup I non-RABV lyssaviruses. In parallel, RVC20 (antigenic site I) is able to neutralize 72% and 91% of the non-RABV lyssaviruses and phylogroup I non-RABV lyssaviruses, respectively. In comparison antibody CR57 neutralized 47% and 68% of the non-RABV lyssaviruses and phylogroup I non-RABV lyssaviruses, respectively.

When combined, RVC58 and RVC20 covered 78% and 100% of the non-RABV lyssaviruses and phylogroup I non-RABV lyssaviruses, respectively, while CR57 and CR4098 covered only 50% and 68% of the non-RABV lyssaviruses and phylogroup I non-RABV lyssaviruses, respectively (FIG. 8A-B). HRIGs were also tested against the panel of pseudoviruses and viruses and even if it is a mixture of polyclonal anti-G protein antibodies covered only 25% of the non-RABV lyssaviruses and 36% of the phylogroup I non-RABV lyssaviruses (cf. FIG. 8).

To investigate the ability of the antibodies according to the present invention to neutralize different RABV isolates in more detail, the analysis of the neutralizing activity of the antibodies according to the present invention RVC20 and RVC58, and of the reference antibodies CR57 and CR4098 was then extended to a very large panel of RABV isolates (n=26, 24 viruses and 2 pseudoviruses), which are representative of all circulating lineages (i.e. American, Asian, Cosmopolitan, Africa 2, Africa 3 and Arctic/Arctic-like lineages) (FIG. 9). All 26 RABV isolates were effectively neutralized by RVC20 and RVC58 antibodies with $IC_{50}$ and $IC_{90}$ geometric means of 26 and 12 ng/ml, respectively. As a comparison CR57 and CR4098 also neutralized all the RABV tested but with higher $IC_{50}$ and $IC_{90}$ values of 61 and 100 ng/ml, respectively. Of note, CR4098 neutralized two RABV isolates with $IC_{50}$>10000 ng/ml, a concentration which is likely not to be effective in vivo.

In a further step, the analysis of the RABV neutralizing activity of the antibodies was further extended, including the further reference antibody RAB1 and an even larger panel of RABV isolates (n=35, 27 viruses and 8 pseudoviruses; CVS-11 was tested as infectious virus and as pseudovirus with FIG. 10 including CVS-11 tested as infectious virus and FIG. 11 showing the results for all three neutralization assays performed with CVS-11, namely pseudovirus (PV), FAVN and RFFIT), which are representative of all circulating lineages (i.e. American, Asian, Cosmopolitan, Africa 2, Africa 3 and Arctic/Arctic-like lineages) (FIG. 10B). The full description of the isolates can be retrieved from FIG. 1. As shown in FIG. 10A, all 35 RABV isolates were effectively neutralized by RVC20 and RVC58 antibodies with $IC_{50}$ values (for infectious viruses) or $IC_{90}$ values (for pseudoviruses) ranging from 0.1 to 140 ng/ml. As a comparison, reference antibodies CR57, CR4098 and RAB1 neutralized all the RABV tested, but with significantly lower potency than RVC20 and RVC58 and with a broader range of $IC_{50}$ or $IC_{90}$ values (i.e. 0.6-969 ng/ml, 0.7-23600 ng/ml, 1-4153 ng/ml, respectively, cf FIG. 10A). Similarly to RVC20 and RVC58, HRIG neutralized the large majority of the RABV strains tested with a narrow range of $IC_{50}$ values.

Importantly, CR4098 and RAB1 neutralized six and three RABV isolates, respectively, with an $IC_{50}$>1000 ng/ml (cf. FIG. 10A), a concentration which is likely not to be effective in post-exposure prophylaxis.

This analysis was extended to additional 8 RABV isolates for which the ability of the antibodies to bind to G-protein transfectant cells was tested by flow-cytometry (FIG. 11) The full length G genes of RABV strains were codon optimized for eukaryotic cell expression and cloned into the phCMV1 vector (Genlantis). G protein expressing plasmids were used to transfect 293F-Expi cells. Three days after transfection, cells were collected, fixed and permeabilized with saponin for immunostaining all test antibodies. Binding of antibodies to transfected cells was analysed using a Becton Dickinson FACSCanto2 (BD Biosciences) with FlowJo software (TreeStar). As shown in FIG. 11, all these RABV strains were recognized by RVC20 and RVC58, whereas RAB1 did not bind to the 91001USA strain and CR57 did not bind to RV/R.3PHL/2008/TRa-065 and 09029NEP strains. These findings extend the number of RABV isolates recognized by RVC20 and RVC58 to 43.

FIG. 10B shows the phylogenetic tree of 2215 RABV G protein sequences retrieved from public databases. Highlighted with black dots are the sequences of the RABV viruses tested (two G protein sequences, i.e. CV9.13, Mauritania/dog/2019-2006/V6235-2007 were not available and were therefore not included in the tree). This shows that RABV viruses tested (black dots) are representative of all circulating lineages (i.e. American, Asian, Cosmopolitan, Africa 2, Africa 3 and Arctic/Arctic-like lineages).

A selection of neutralization results using RABV pseudoviruses (PV, the PV neutralization assay was performed according to Wright, E. et al., J Gen. Virol 89, 2204-2213, 2008 and Wright, E. et al., Vaccine 27, 7178-7186, 2009, which is incorporated by reference herein) or infectious viruses (as measured by either the fluorescent-antibody virus neutralization test, FAVN, according to Cliquet, F., et al., J. Immunol Methods 212, 79-87, 1998, which is incorporated by reference herein, or the rapid fluorescent focus inhibition test, RFFIT, according to Smith, J. S., et al., Bull. World Health Organ. 48, 535-541, 1973, which is incorporated by reference herein) and the characteristics of selected RABV and non-RABV isolates are shown in FIGS. 12 and 13, respectively.

Example 5

Epitope Mapping Using Mutant Pseudoviruses.

In order to better refine the epitope specificity of the 12 selected human monoclonal antibodies, they were tested against engineered RABV pseudotypes. In particular, the amino acid changes K226E, K226N, G229E, N336D and N336S found in CR57 and CR4098 viral escape mutants described in Bakker, A. B. H. et al., J Virol 79, 9062-9068, 2005 and in Marissen, W. et al., J Virol 79, 4672-4678, 2005, were introduced into CVS-11 G gene and the corresponding mutant pseudoviruses were produced.

The panel of 12 selected antibodies as well as reference antibodies CR57 and CR4098 were tested at 15 μg/ml for their ability to neutralize the 5 mutant pseudoviruses (K226E, K226N, G229E,N336D and N336S) and compared with the corresponding parental CVS-11 strain. The results of this analysis are summarized in FIG. 14. CR57 and RVC20, but not RVC3, antibodies were not able to neutralize the CR57 CVS-11 escape mutants K226E, K226N and G229E. These results indicate that RVC3 recognizes an epitope in the antigenic site I which is distinct from that recognized by CR57, and that RVC20 recognize an epitope similar to that recognized by CR57. However, the finding that RVC20 is characterized by a broader reactivity against non-RABV lyssaviruses (FIG. 8) as compared to CR57 indicates that RVC20 antibody mode of recognition of its cognate epitope in the antigenic site I is distinct to that of CR57, being able to tolerate a larger number of amino acid changes in the binding site and in the surroundings residues.

All antibodies, including CR4098, with the exception of RAM (data not shown), were able to neutralize the CR4098 CVS-11 escape mutants N336D, thus indicating that this mutation does not have a significant impact on the binding to their cognate epitopes in the context of the CSV-11 G protein. In addition, all the inventive antigenic site III antibodies, RVC58 in particular, showed a greater breadth of reactivity with non-RABV lyssaviruses as compared to CR4098 (FIG. 7).

Example 6

Analysis of the Conservation of RVC20 and RVC58 Epitopes within RABV Isolates.

The antigenic site I recognized by the antibody CR57 was defined by peptide scanning analysis and by the isolation of viral escape mutants K226E, K226N, and G229E and found to locate to the minimal binding region composed by residues KLCGVL (consensus sequence and positions 226-231 of the RABV G protein; Marissen, W. et al., J. Virol 79, 4672-4678, 2005). The competition results shown in FIG. 4 and the results of the mutant pseudovirus test shown in FIG. 14 indicate that RVC20 binds to the antigenic site I. The present inventors therefore analyzed the degree of conservation of the antigenic site I amino acid residues in a panel of 2566 sequences from independent RABV isolates retrieved from multiple public databases representative of the global RABV diversity.

Figure 15:
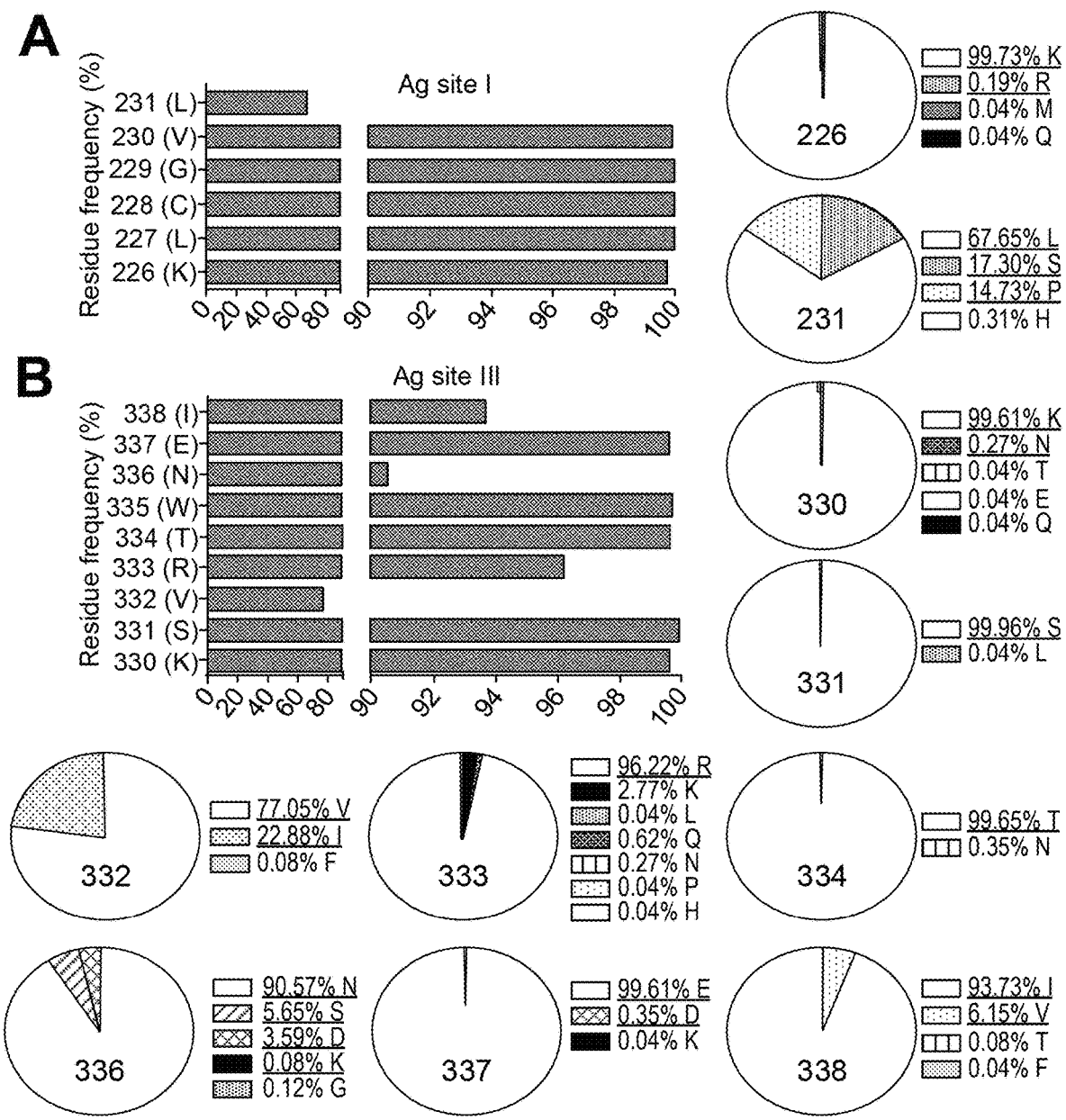
FIG. 15 shows that RVC20 and RVC58 target highly conserved epitopes in antigenic sites I and III. Level of amino acid residue conservation in antigenic sites I and III as calculated by the analysis of the G-protein sequences from 2566 RABVs. Pie charts shows the detailed distribution of amino acid usage at each position. Underlined residues indicate that viruses carrying the corresponding residue in that position are neutralized by either RVC20 or RVC58. (A) Frequency of amino acid residues in antigenic site I; (B) Frequency of amino acid residues in antigenic site III.
Figure 16:
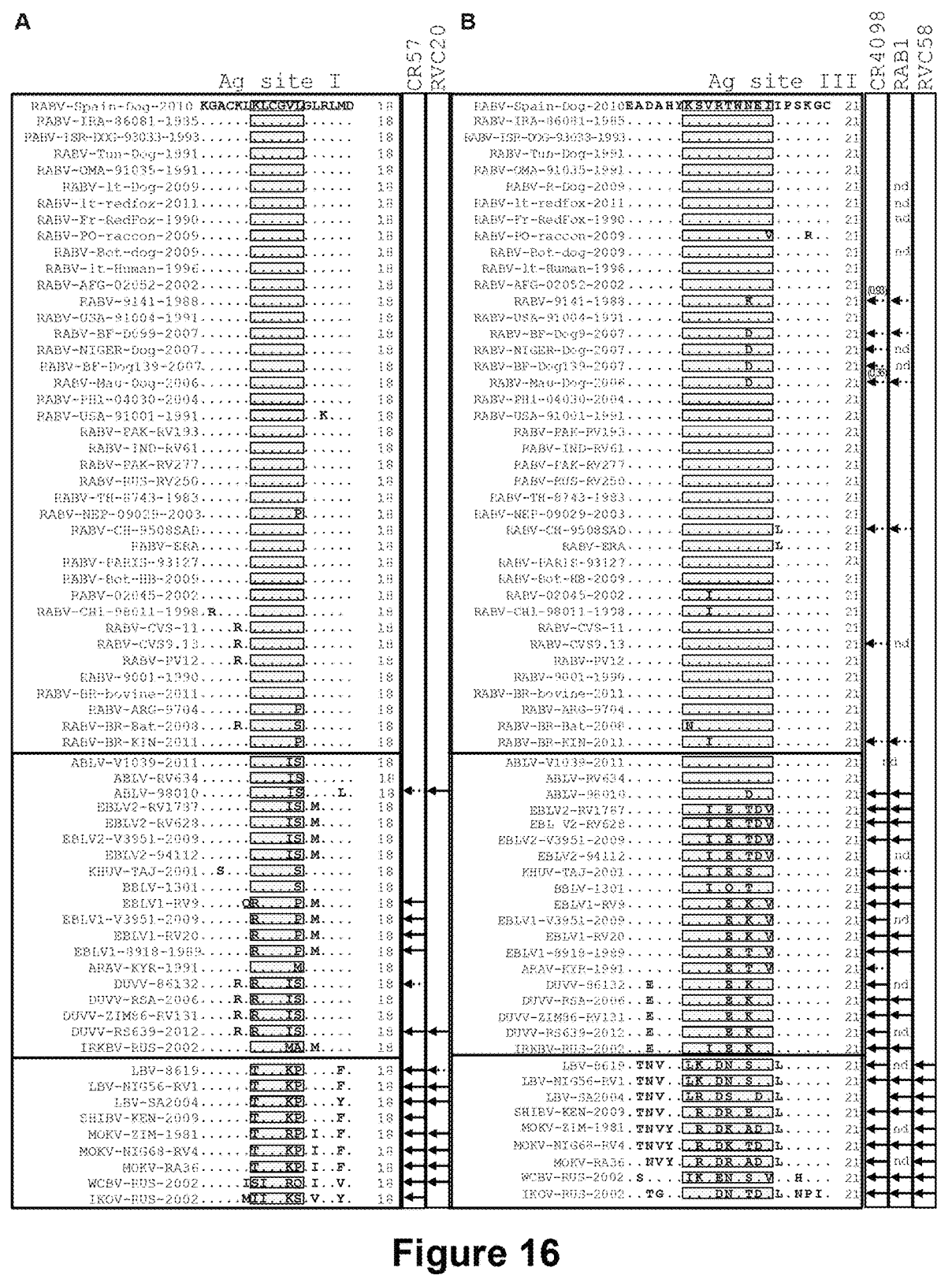

Thereby, it was found that position 226 is a K in 99.73% and R in 0.19% of the sequences analyzed (R or K in 99.92% of the isolates) (FIG. 15A). RVC20, but not CR57, neutralizes viruses carrying both K and R at position 226 (FIG. 16). The other polymorphic position in the antigenic site I is residue 231, which is L in 67.65%, S in 17.30% and P in 14.73% of the RABV isolates analyzed (L, S or P are present in 99.69% of the sequences, FIG. 15A). RVC20 and CR57 were tested and neutralized lyssaviruses carrying leucine, serine or proline residues at position 231 (FIG. 16). This analysis confirmed our previous neutralization results and indicated that RVC20 antibody epitope is highly conserved in RABV. Importantly, all three CR57 and RVC20 CVS-11 escape mutants at position 226 are efficiently neutralized by RVC58.

A similar analysis was performed for the antigenic site III antibody RVC58. Antigenic site III is primarily formed by residues KSVRTWNEI (consensus sequence and positions 330-338 of the RABV G protein; (Walker, P. J. et al., J. Gen. Virol 80, 1211-1220, 1999; Bakker, A. B. H. et al; J Virol 79, 9062-9068, 2005). The competition results shown in FIG. 4 and the results of the mutant pseudovirus test shown in FIG. 14 indicate that RVC58 recognizes residues within the antigenic site III. The present inventors therefore analyzed, as described above for the antigenic site I, the degree of conservation of the antigenic site III amino acid residues in a panel of 2566 sequences from independent RABV isolates retrieved from multiple public databases representative of the global RABV diversity (as for antigenic site I above).

Thereby, it was found that positions 330, 331, 334, 335 and 337 are highly conserved (>99.61%), while residues 332, 333, 336 and 338 are polymorphic (FIG. 15B). Position 330 is a K in 99.61% and N in 0.27% of the sequences analyzed (K or N are present in 99.88% of the sequences). RVC58 was shown to neutralize viruses carrying either K or N at position 330 (FIG. 16). Position 331 is highly conserved being encoded by S in 99.96% of the isolates. Position 332 is a V in 77.05% and I in 22.88% of the sequences (V or I are present in 99.93% of the isolates). RVC58 was shown to neutralize lyssaviruses carrying either V or I at position 332. Position 333 is R in 96.22% of the isolates. Several other residues, but not D, are found at position 333 in RABV isolates. In contrast, phylogroup II lyssaviruses carry a D in that position and these viruses are not neutralized by RVC58, thus suggesting that a D in position 333 might compromise RVC58 binding, but this residue is not found in natural RABV isolates. Position 334 is a T in 99.65% of the isolates. Position 335 is W in 100% of the isolates. Position 336 is N in 90.57%, D in 3.59%, S in 5.65% and K in 0.08% of the RABV isolates analysed (N, D, S or K are present in 99.89% of the isolates). RVC58 was shown to neutralize lyssaviruses carrying either N, D, S or K at position 336. Of note, RABV carrying D at position 336 are not neutralized by CR4098 and RAB1, thus suggesting that potentially 4% of the circulating RABV are resistant to CR4098 neutralization and to RAB1 neutralization. Of note, the majority of the African RABV isolates analyzed here (59.1%) carry a D at position 336 represent. These isolates correspond to lineage Africa2. Position 337 is a E in 99.61% and D in 0.35% of the isolates (E or D are present in 99.96% of the isolates). RVC58 was shown to neutralize lyssaviruses carrying either E or D at position 337. Finally, position 338 is I in 93.73% and V in 6.16% of the isolates analyzed (I or V are present in 99.9% of the isolates). RVC58 was shown to neutralize lyssaviruses carrying either I or V at position 338.

Thus, RVC58 recognizes RABV and non-RABV isolates carrying multiple residues in the polymorphic positions that are representative of at least 99.80% of the RABV analyzed (FIG. 15B, FIG. 16). This analysis confirmed our previous neutralization results wherein RVC58 neutralized all phylogroup I lyssaviruses tested and indicated that RVC58 antibody epitope is highly conserved in RABV and non-RABV lyssaviruses.

In summary, the two antibodies RVC58 and RVC20 potently neutralized human and animal RABV isolates as well as most non-RABV lyssaviruses (including the new Eurasian bat viruses) by binding two distinct antigenic sites (site I and III) on the virus G protein. The combination of these two antibodies represents a treatment with an unprecedented breadth of reactivity and with reduced risk of escape mutant selection.

Example 7

RVC58 and RVC20 Antibodies Protect Syrian Hamsters from a Lethal RABV Infection.

Figure 17:
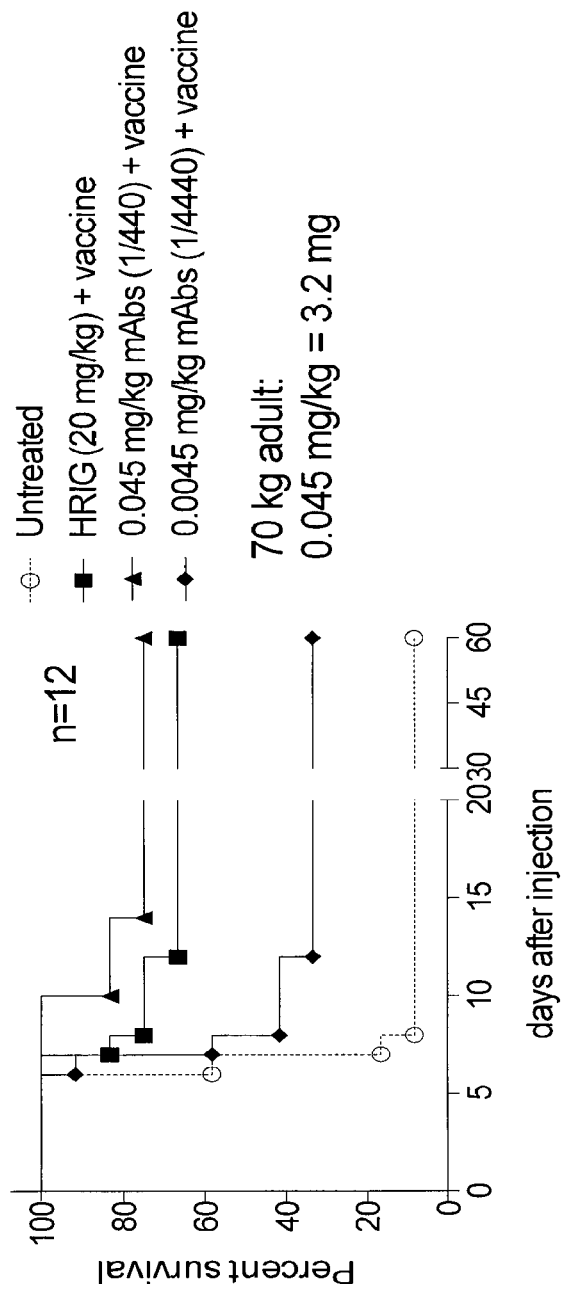
FIG. 17 shows the percent survival in Syrian hamsters infected with RABV CVS-11 isolate and then left untreated or treated with the standard PEP (HRIG and vaccination) or with two different doses of a cocktail of RVC20+RVC58 monoclonal antibodies (and vaccination). The RABV virus was administered intramuscularly (50 µl of $10^{5.7}$ TCID50/ml) in the gastrocnemius muscle of the hind left leg. The vaccine used is a commercial inactivated human diploid cell vaccine (Imovax; Sanofi-Pasteur) and was administered intramuscularly (0.05 ml) in the in the gastrocnemius muscle of the hind right leg.

To investigate whether the antibodies RVC58 and RVC20 display neutralizing activity against a lethal RABV infection in vivo, we performed a Syrian hamster (*Mesocricetus auratus*) study. At 6 h after administration of a lethal dose of RABV CVS-11 (50 µl of $10^{5.7}$ TCID50/ml in the gastrocnemius muscle of the hind left leg, hamsters (n=12 per group) were left untreated or prophylaxis was initiated with either vaccine (Imovax; Sanofi-Pasteur: a commercial inactivated human diploid cell vaccine, which was administered intramuscularly in a volume of 0.05 ml in the in the gastrocnemius muscle of the hind right leg, a dose that correspond to 0.125 international units of rabies antigen)

plus HRIG (Berirab®, 20 mg/kg, equivalent to 20 IU/kg and administered intramuscularly in a volume of 0.05 ml), or vaccine plus 0.045 mg/kg of an equimolar mixture of RVC20 and RVC58 antibodies or vaccine plus 0.0045 mg/kg of an equimolar mixture of RVC20 and RVC58 antibodies. Treated animals also received the rabies vaccine on days, 3, 7, 14 and 28. Animals were monitored during the course of the experiment and were euthanized when signs of clinical rabies occurred. Eleven out of 12 animals that were not treated after infection succumbed by day 8 (FIG. 17). The standard post-exposure prophylaxis (PEP) based on 20 mg/kg HRIG and vaccine was effective in reducing the overall mortality to 33% (8/12 animals survived; FIG. 17). Strikingly, the combination of RVC58+RVC20 at 0.045 mg/kg (which correspond to 1/440 of the administered HRIG) protected 75% of the animals (9/12), while a 10 times lower dose of RVC58 and RVC20 (0.0045 mg/kg) protected only 33% of the animals. This suggests that 0.045 mg/kg RVC58+RVC20 is superior to the 20 mg/kg HRIG dose. The protective dose of 0.045 mg/kg RVC58+RVC20 corresponds in humans to an average total dose to be administered during the PEP of only 3 mg of the RVC58+RVC20 mixture. This amount could be produced and formulated in a stable form (i.e. lyophilized formulation, where for instance previous studies have shown that monoclonal antibodies preserved by lyophilization are stable for 33 months at 40° C. and 5 months at 50° C.) and at an affordable cost for developing countries.

Example 8

RVC58 and RVC20 Antibodies do not Interfere with Vaccination.

During PEP, there is the possibility that the simultaneous administration of antibodies and vaccine decreases the ability of the vaccine to induce the threshold levels of neutralizing antibodies required for protection. Therefore, it is critical to evaluate the degree to which an antibody treatment interferes with vaccination. To determine the effect of the antibodies mixture on vaccine potency, an in vivo animal experiment was performed in the absence of RABV challenge. In particular, all animals (n=12 per group) were vaccinated with rabies vaccine on day 0, 3, 7, 14 and 28 (Imovax, Sanofi-Pasteur, administered intramuscularly in a volume of 0.05 ml in the in the gastrocnemius muscle of the hind right leg, a dose that correspond to 0.125 international units of rabies antigen) and concomitantly administered on day 0 with HRIG (Berirab®, 20 mg/kg) or an equimolar mixture of RVC58+RVC20 at 0.045 mg/kg or 40 mg/kg (888 times higher dose) that were injected intramuscularly in the in the gastrocnemius muscle of the hind left leg. Serum binding titers (measured in ELISA on RABV G-protein coated plates by detecting the G-protein-bound hamster antibodies with alkaline-phosphatase-conjugated anti-hamster polyclonal antibodies), serum neutralizing titers (neutralization FAVN assay on CVS-11; according to Cliquet, F., et al., J. Immunol Methods 212, 79-87, 1998) and levels of residual human IgG antibodies were determined on day 42. HRIG and 0.045 mg/kg of RVC58+RVC20 did not reduce the endogenous hamster IgG binding antibody response to the RABV G protein (FIG. 18A) as compared to animals receiving vaccine alone. Of note, the level of neutralizing antibodies in animals treated with both the 0.045 and the 40 mg/kg doses is comparable to that elicited by the vaccine alone or by the vaccine and HRIG treated animals and in most animals the neutralizing titer is above 10 IU/ml (FIG. 18B). Finally, while still high levels of human antibodies (above 10 µg/ml) are found on day 42 in animals treated with 20 mg/kg of HRIG or 40 mg/kg of RVC58+RVC20, undetectable to low levels of human IgG were found in the sera of animals treated with 0.045 mg/kg of RVC58+RVC20 (FIG. 18C). These results suggest that a dose of 0.045 mg/kg RVC58+RVC20, which was shown to be protective, does not compromise the production of virus neutralizing antibodies elicited in animals upon RABV vaccination.

Example 9

RVC58 and RVC20 Antibodies Act Therapeutically in Syrian Hamsters Lethally Infected with RABV.

Currently, there is no treatment for rabies. The development of a treatment would be of benefit for at least two classes of patients: those with known exposure to RABV but who have failed to receive prompt post-exposure prophylaxis due to circumstances and who are at increased risk of developing RABV infection, and those who did not recognize contact with the virus and present signs (of different severity) of the disease (e.g. individuals infected by unnoticed contacts with infected bats; RABV of bat origin where dog rabies is controlled has become the leading cause of human rabies). Single or multiple i.v. injections with the RVC58 and RVC20 cocktail (i.e. an equimolar mixture of RVC58 and RVC20 antibodies) would provide high titres of systemic neutralising antibodies (including in the CNS) and block viral replication and disease progression. The development of a cocktail of potent and broadly neutralizing antibodies may help to expand the post-exposure treatment window for human RABV infection, that is currently limited to the first days after infection. In these individuals the RV might has already reached the CNS tissues and early or late signs of the disease might have also appeared. These patients could benefit from a treatment with highly potent neutralizing antibodies that can leak across the blood brain barrier (or administered directly in the CSN) delivering a sufficient amount of antibodies capable of effectively neutralizing the virus replication in the CNS tissue.

Figure 19:
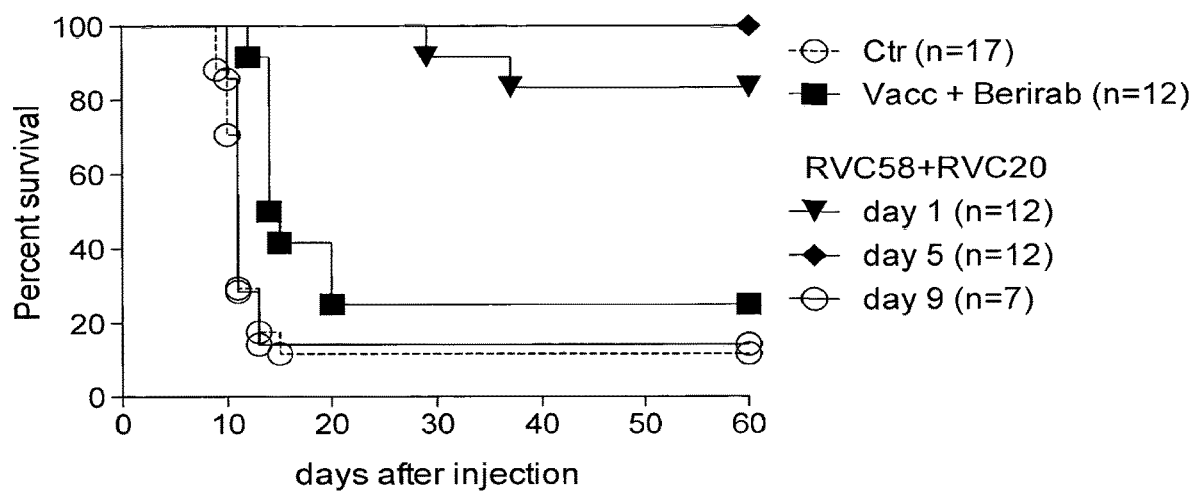
FIG. 19 shows the percent survival in Syrian hamsters infected with a field RABV virus isolated from the salivary glands of an infected fox (Italy/red fox/673/2011) and then left untreated, treated on day 1 with the standard PEP (i.e. HRIG and vaccination) or treated either on day 1, 5 or 9 after infection with a single dose of RVC58±RVC20 at 40 mg/kg.

The therapeutic potential of RVC58+RVC20 antibodies was evaluated in Syrian hamsters lethally challenged with a field RABV isolate. In particular, RVC58+RVC20 were tested in Syrian hamsters challenged in the gastrocnemius muscle of a back leg with a lethal dose of a field virus isolated from the salivary glands of an infected fox (Italy/red fox/673/2011). In infected animals, RABV was detectable in the CNS (central nervous system) on day 5 after challenge. Animals were treated with a single injection of 40 mg/kg of RVC58+RVC20 given either on day 1 (n=12), on day 5 (n=12) or on day 9 (11=7) after infection without a concomitant administration of the vaccine. Control groups received either phosphate-buffered saline (n=17) or the standard PEP (20 mg/kg HRIG and vaccine; n=12). Animals were monitored twice daily and euthanized when clinical signs of rabies appeared. Strikingly, RVC58+RVC20 protected animals from lethal infection when administered up to 5 days after infection (FIG. 19). Of note, 3 out of the 12 treated animals showed clinical signs of the disease (paralysis of back leg site of challenge), which however did not develop further. In this model the classical PEP conferred only a modest protection as compared to untreated animals (FIG. 19). No signs of disease were detected in surviving animals up to 60 days after infection.

In all succumbed animals and in all survivors (which were sacrificed on day 60) the presence of RABV was revealed by quantifying the genomic RNA and viral mRNA encoding for the N protein in spinal cord, medulla oblongata/cerebellum and brain quantified using quantitative real-time PCR. Of note, detectable levels of viral RNA were measured in the CNS of asymptomatic animals treated with RVC58+RVC20 on day 1 or 5 after infection (albeit at levels 100-1000 lower than those measured in succumbing animals) (FIG. 20A), thus indicating that the initial RABV infection was not abortive but kept under control within the CNS by the administered highly potent neutralizing antibodies and most likely by a concomitant endogenous immune response to the virus.

Figure 18:
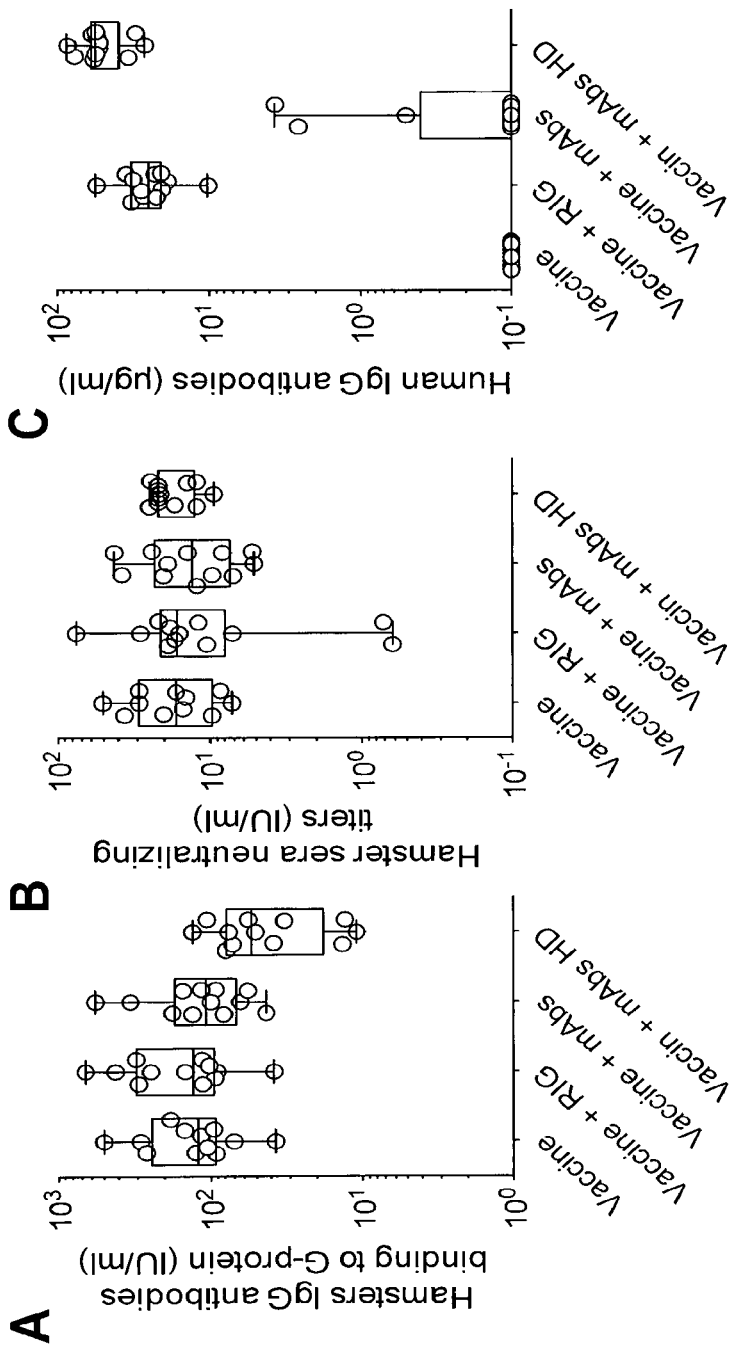
FIG. 18 shows the level of hamster IgG antibodies binding to G protein as measured by ELISA (A), the level of hamsters sera neutralizing antibodies (B) and the levels of residuals human IgG antibodies (C) as measured on sera collected 42 days after immunization with RABV vaccine in unchallenged Syrian hamsters.
Figure 20:
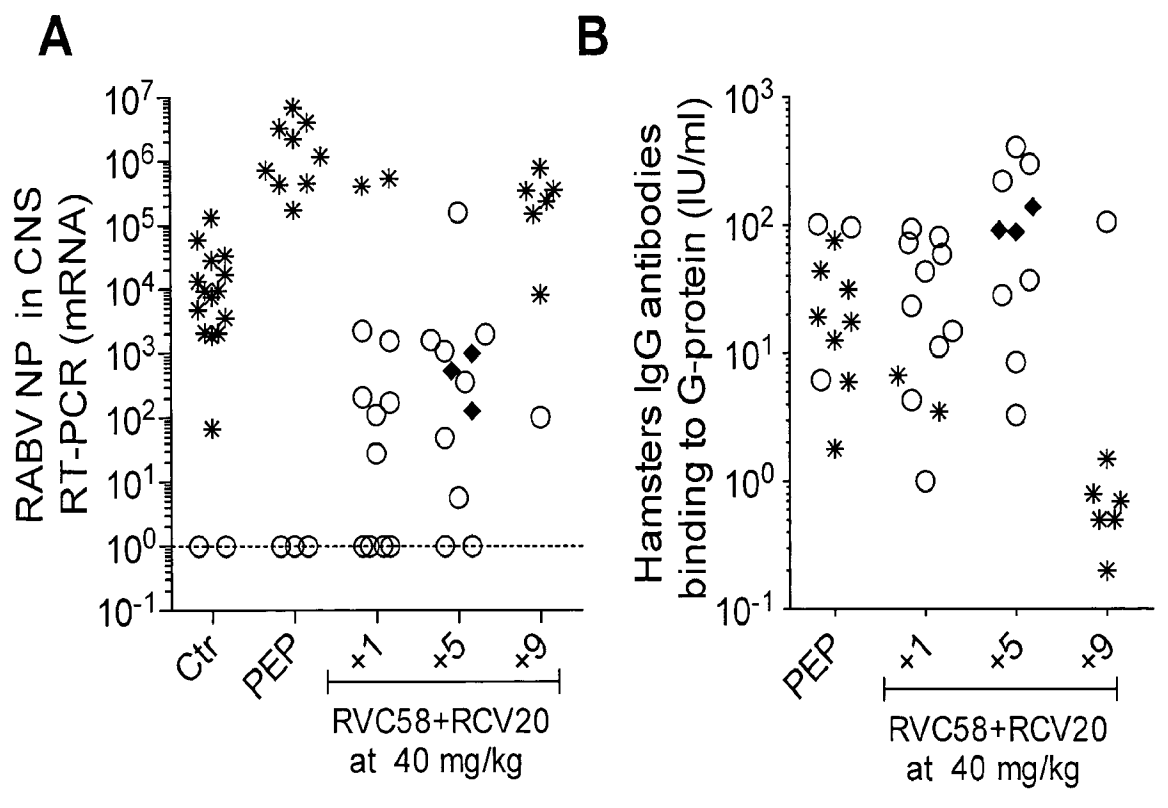

The development of a robust endogenous immune response was also confirmed by the measurement of RABV G-protein-specific hamster IgG antibody titers in the sera of all animals (FIG. 20B). Of note, animals receiving RVC58+ RVC20 on day 5 (all survived the lethal infection) developed high levels of G-protein-specific IgG antibodies at levels comparable, or higher, than those elicited in surviving animals by the vaccine in the PEP group. The level of these antibodies was also comparable or higher than those elicited in unchallenged animals receiving the standard PEP (see FIG. 18). Finally, the high dose of RVC58+RVC20 might also be compatible with the concomitant vaccination as shown by the finding that the use of a high dose of these antibodies do not compromise the immune response to the vaccine (FIG. 18A-B).

Figure 21:
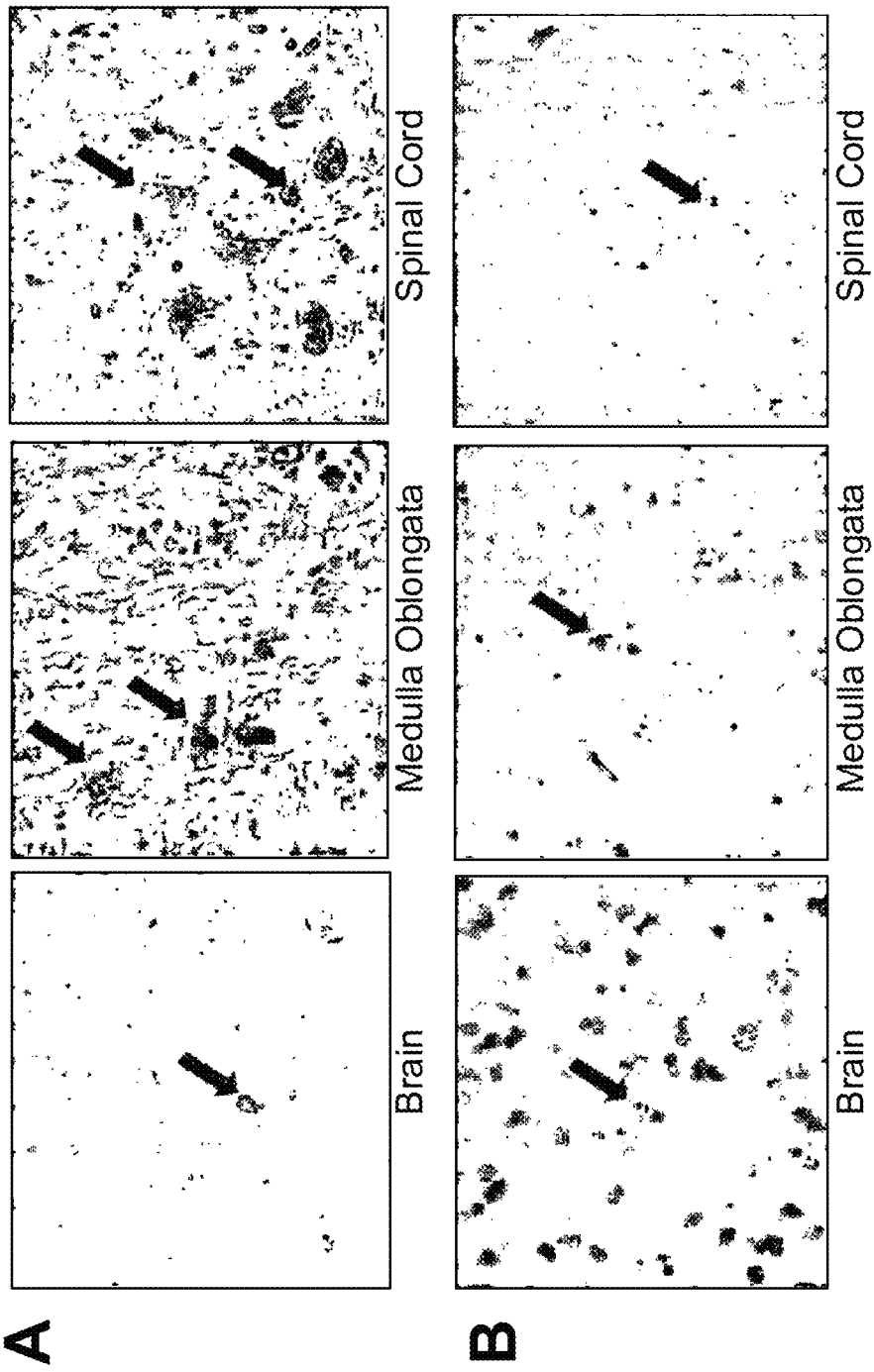
FIG. 21 shows the histologic analysis of brain, medulla oblongata and spinal cord tissues from two representative animals treated with RVC58 and RVC20 on day 5 after infection (A) or left treated (B). In particular, the immunohistochemistry analysis was aimed to reveal the presence of RABV N antigen to identify the pathognomonic inclusion bodies (Negri bodies).

Tissue samples from the brain, medulla oblongata and spinal cord of symptomatic control animals or animals receiving RVC58+RVC20 on day 5 (and sacrificed on day 60) were analyzed for the presence of RABV N antigen by immunohistochemistry (IHC). In particular, the IHC analysis was focused on the identification of Negri bodies, which are eosinophilic, sharply outlined, pathognomonic inclusion bodies (2-10 μm in diameter) made by aggregates of nucleocapsids and found in the cytoplasm of neurons containing the rabies virus. While numerous Negri bodies were found in CNS tissues from positive control animals, only very few bodies were identified in animals treated with antibodies on day 5 (FIG. 21). These results confirm that RABV has reached the CNS, and even the brain, in animals treated with the high dose of RVC58+RVC20 without causing symptoms.

The presence of RABV neutralizing antibodies early in patients clinical course is considered an important factor contributing to a favorable outcome. This probably occurs in less than 20% of all patients with rabies. The presence of RABV neutralizing antibodies is a marker of an active adaptive immune response that is essential for viral clearance (Lafon, M., in "Rabies", A. C. Jackson and W. H. Wunner, 3rd eds., pp. 489-504, Elsevier Academic Press, London, 2013). There have been six survivors of rabies who received rabies vaccine prior to the onset of their disease (and only one who did not receive vaccine). This supports the notion that an early immune response is associated with a positive outcome. Finally, most survivors of rabies have shown RABV neutralizing antibodies in sera and cerebrospinal fluid. The potent and broad human RABV neutralizing antibodies according to the present invention, for example RVC20 and RVC58, offer the opportunity to confer an immediate and robust passive immunity, which might represent (i) a potent agent for post-exposure therapy, which is effective at much lower concentrations compared to HRIG and (ii) a valid therapeutic agent for the treatment of patients with an early clinical diagnosis of rabies. In this regard it is conceivable that a prompt initiation of therapy might offer the best opportunity for a favorable outcome. The antibodies according to the present invention, for example the human monoclonal antibodies RVC58 and RVC20, can therefore represent an effective therapy alone or in combination with other therapies including rabies vaccination, ribavirin (or other antivirals), interferon-alpha and ketamine.

Table of Sequences and SEQ ID Numbers

| SEQ ID NO | Description | | Sequence* |
|---|---|---|---|
| | | | RVA122 ANTIBODY |
| 1 | CDRH1 | aa | GDSMNNFY |
| 2 | CDRH2 | aa | IYYSGTT |
| 3 | CDRH3 | aa | ARDSGDYVSYYYYGMDV |
| 4 | CDRL1 | aa | SSNIGSNY |
| 5 | CDRL2 | aa | KSD |
| 6 | CDRL2 long | aa | LIYKSDKRP |
| 7 | CDRL3 | aa | AAWDNRLSGWL |
| 8 | CDRH1 | nuc | GGTGACTCCATGAATAATTTCTAC |
| 9 | CDRH2 | nuc | ATCTATTACAGTGGGACCACC |
| 10 | CDRH3 | nuc | GCGAGAGACTCCGGTGACTACGTCAGCTACTACTATTATGGTATGGACGTC |
| 11 | CDRL1 | nuc | AGCTCCAACATCGGAAGTAATTAT |
| 12 | CDRL2 | nuc | AAGAGTGAT |
| 13 | CDRL2 long | nuc | cttatttacAAGAGTGATaagcggccc |
| 14 | CDRL3 | nuc | GCAGCATGGGATAACAGGCTGAGTGGTTGGCTC |

Table of Sequences and SEQ ID Numbers

| SEQ ID NO | Description | Sequence* |
|---|---|---|
| 15 | heavy chain aa | QVHLQESGPGLVKPSETLSLTCTVSGDSMNNFYWGWIRQP AGKGLEWIGYIYYSGTTNYNPSLKSRVTISIDTSKNQFSL KVNSVTAADTAVYYCARDSGDYVSYYYYGMDVWGPGTTVT VSS |
| 16 | light chain aa | QSVLTQSPSASDTPGQRVTISCSGSSSNIGSNYVYWYQQF PGTAPKLLIYKSDKRPSGVPDRFSGSTSGTSASLAISGLR SEDEADYYCAAWDNRLSGWLFGGGTKLTVL |
| 17 | heavy chain nuc | caggtgcacctgcaggagtcgggcccaggactggtgaagc cttcggagaccctgtccctcacctgcactgtctctGGTGA CTCCATGAATAATTTCTACtggggctggatccggcagccc gcagggaagggactggagtggattggatatATCTATTACA GTGGGACCACCaactacaacccctccctcaagagtcgagt caccatatcaatagacacgtccaagaaccaattctccctg aaggtgaactctgtgaccgctgcggacacggccgtgtatt attgtGCGAGAGACTCCGGTGACTACGTCAGCTACTACTA TTATGGTATGGACGTCtggggcccagggaccacggtcacc gtctcctcag |
| 18 | light chain nuc | cagtctgtgctgactcagtcaccctcagcgtctgatacccc cgggcagagggtcaccatctcttgttctggaagcAGCTC CAACATCGGAAGTAATTATgtgtattggtaccagcagttc ccaggaacggccccaaactcctatttacAAGAGTGATa agcgggccctcagggtccctgaccgattctctggctccac gtctggcacctcagcctccctggccatcagtgggctccgg tccgaagatgaggctgattattactgtGCAGCATGGGATA ACAGGCTGAGTGGTTGGCTcttcggcggagggacgaagct gaccgtcctag |

RVA144 ANTIBODY

| SEQ ID NO | Description | Sequence* |
|---|---|---|
| 19 | CDRH1 aa | GGSISSTIFY |
| 20 | CDRH2 aa | VYYNGHT |
| 21 | CDRH3 aa | ARPSTYDYSIGR |
| 22 | CDRL1 aa | SSNIGAGYD |
| 23 | CDRL2 aa | GNT |
| 24 | CDRL2 long aa | LIYGNTKRP |
| 25 | CDRL3 aa | QSFDSSLSAWV |
| 26 | CDRH1 nuc | GGTGGTTCCATCAGCAGTACTATTTTCTAC |
| 27 | CDRH2 nuc | GTCTATTATAATGGACACACC |
| 28 | CDRH3 nuc | GCGAGACCCTCAACATATGACTACAGTATTGGGCGC |
| 29 | CDRL1 nuc | AGCTCCAACATCGGGGCAGGTTATGAT |
| 30 | CDRL2 nuc | GGTAACACC |
| 31 | CDRL2 long nuc | ctcatctatGGTAACACCaagcggccc |
| 32 | CDRL3 nuc | CAGTCCTTTGACAGCAGCCTGAGTGCTTGGGTA |
| 33 | heavy chain aa | QLQLQESGPGLVKPSETLSLTCTVSGGSISSTIFYWGWIR QPPGKGLEWIGSVYYNGHTYYNPSLKSRVAISIDKSKNQF SLRLNSVTAADTAVYYCARPSTYDYSIGRWGQGTLVTVSS |
| 34 | light chain aa | QSVLTQPPSVSRAPGQRVTISCTGSSSNIGAGYDVHWYQQ LPGTAPKLLIYGNTKRPSGVPDRFSGSKSGTSASLAITGL LTEDEADYYCQSFDSSLSAWVFGGGTKLTVL |
| 35 | heavy chain nuc | cagctgcagctgcaggagtcgggcccaggactggtgaagc cctcggagaccctgtccctcacttgcactgtctctGGTGG TTCCATCAGCAGTACTATTTTCTACtggggctggatccgc cagcccccagggaagggactggagtggattgggagt**GTCT |

Table of Sequences and SEQ ID Numbers

| SEQ ID NO | Description | Sequence* |
|---|---|---|
| | | ATTATAATGGACACACCtactacaatccgtccctcaagagtcgagtcgccatatccattgacaagtccaagaaccagttctccctgaggcttaactctgtgaccgccgcggacacggctgtatattactgtGCGAGACCCTCAACATATGACTACAGTATTGGGCGCtggggccagggaaccctggtcaccgtctcctcag |
| 36 | light chain nuc | cagtccgtgctgacgcagccgccctcagtgtctcgggcccagggcagagggtcaccatctcctgcactgggagcAGCTCCAACATCGGGGCAGGTTATGATgtccactggtaccagcaacttccaggaacagcccccaaactcctcatctatGGTAACACCagcggccctcaggggtccctgaccgattctctggctccaagtctggcacctcagcctccctggccatcactgggctctgactgaggatgaggctgattattactgccAGTCCTTTGACAGCAGCCTGAGTGCTTGGGTAttcggcggagggaccaaactgaccgtcctgg |

RVB185 ANTIBODY

| | | |
|---|---|---|
| 37 | CDRH1 aa | GAPVSGVNSY |
| 38 | CDRH2 aa | IKYSGST |
| 39 | CDRH3 aa | ARQSTMTGRDY |
| 40 | CDRL1 aa | RSNIGSHP |
| 41 | CDRL2 aa | GDS |
| 42 | CDRL2 long aa | LIYGDSQRP |
| 43 | CDRL3 aa | AAWDDSLSGLWV |
| 44 | CDRH1 nuc | GGTGCCCCCGTCAGTGGTGTTAACTCCTAC |
| 45 | CDRH2 nuc | ATCAAGTACAGTGGGAGCACC |
| 46 | CDRH3 nuc | GCCAGACAAAGTACTATGACGGGCCGGGACTAC |
| 47 | CDRL1 nuc | AGATCCAACATCGGAAGCCATCCT |
| 48 | CDRL2 nuc | GGTGATAGT |
| 49 | CDRL2 long nuc | ctcatctatGGTGATAGTcagcgaccc |
| 50 | CDRL3 nuc | GCAGCATGGGATGACAGCCTGAGTGGCCTTTGGGTG |
| 51 | heavy chain aa | QVQLQESGPGLVKPSETLSLTCSVSGAPVSGVNSYWVWIRQPPGKGLEWIATIKYSGSTHRSPSLRSRVTISVDTSKNQFSLELSSVTAADTAVYYCARQSTMTGRDYWGQGTLVTVSS |
| 52 | light chain aa | QSVLTQPPSASGTPGQRVTISCSGSRSNIGSHPVNWYQQLPGAAPKLLIYGDSQRPSGVPDRFSGSKSGPSASLAISGLQSEDEADYYCAAWDDSLSGLWVFGGGTKLTVL |
| 53 | heavy chain nuc | caggtgcagctgcaggagtcgggcccaggactggtgaagccttcggagaccctgtccctcacctgcagtgtctccGGTGCCCCCGTCAGTGGTGTTAACTCCTACtgggtgtggatccgcagccccccgggaaggggctggagtggattgcgactATCAAGTACAGTGGGAGCACCcaccgtagcccgtcgctcaggagtcgagtcaccatatccgtagacacgtccaagaatcagttctccctggagctgagctctgtgaccgccgctgacacggctgtatattactgtGCCAGACAAAGTACTATGACGGGCCGGGACTACtgggccagggaaccctggtcaccgtctcctcag |

Table of Sequences and SEQ ID Numbers

| SEQ ID NO | Description | Sequence* |
|---|---|---|
| 54 | light chain nuc | cagtctgtgctgactcagccaccctcagcgtctgggaccc ccgggcagagggtcaccatctcttgttctggaagcAGATC CAACATCGGAAGCCATCCTgtaaactggtaccagcagctc ccggggagcggccccccaagctcctcatctatGGTGATAGTc agcgaccctcagggtccctgaccgattctctggctccaa gtctggccctcagcctccctggccatcagtggactccag tctgaagatgaggctgattattactgtGCAGCATGGGATG ACAGCCTGAGTGGCCTTTGGGTGttcggcggagggaccaa gctgaccgtcctaa |

RVB492 ANTIBODY

| SEQ ID NO | Description | Sequence* |
|---|---|---|
| 55 | CDRH1 aa | GFSFSSYA |
| 56 | CDRH2 aa | LNSIDHRT |
| 57 | CDRH3 aa | ARGVGLWFGELSWNYFDY |
| 58 | CDRL1 aa | SNDIGGYNY |
| 59 | CDRL2 aa | YVN |
| 60 | CDRL2 long aa | MIFYVNKRP |
| 61 | CDRL3 aa | CSFAGSYSL |
| 62 | CDRH1 nuc | GGATTCAGCTTTAGCAGCTATGCC |
| 63 | CDRH2 nuc | CTTAATTCTATTGATCATAGAACA |
| 64 | CDRH3 nuc | GCTCGGGGGGTGGGACTATGGTTCGGTGAATTATCCTGGA ATTACTTTGACTAC |
| 65 | CDRL1 nuc | AGCAATGATATTGGTGGTTATAACTAT |
| 66 | CDRL2 nuc | TATGTCAAT |
| 67 | CDRL2 long nuc | atgatttttTATGTCAATaagcggccc |
| 68 | CDRL3 nuc | TGCTCATTTGCAGGCAGTTACTCCTTA |
| 69 | heavy chain variant 1 aa | EVQLMESGGGLVQPGGSMRLYCAASGFSFSSYAMSWVRQA PGKGLEWVSSLNSIDHRTDYADSVKGRFTISRDNSKNTLY LQMDSLRVEDSAMYYCARGVGLWFGELSWNYFDY**WGQGTL VTVSS |
| 70 | heavy chain variant 2 aa | EVQLVQSGGGLVQPGGSMRLYCAASGFSFSSYAMSWVRQA PGKGLEWVSSLNSIDHRTDYADSVKGRFTISRDNSKNTLY LQMDSLRVEDSAMYYCARGVGLWFGELSWNYFDY**WGQGTL VTVSS |
| 71 | light chain aa | QSALTQPRSVSGSPGQSVTISCTGTSNDIGGYNYVSWYQQ HPGKAPKLMIFYVNKRPSGVPDRFSGSKSGNTASLTISGL QAEDEADYYCCSFAGSYSLFGRGTKLTVL |
| 72 | heavy chain variant 1 nuc | gaggtgcagctgatggagtctggggggaggcctggtacagc cggggggtccatgagactctactgtgcagcctctGGATT CAGCTTTAGCAGCTATGCCatgagctgggtccgccaggct ccagggaaggggctcgagtgggtctcaagtCTTAATTCTA TTGATCATAGAACAgactatgcagactccgtgaagggccg gttcaccatctccagagacaattccaagaacaccctgtat ttacaaatggacagcctgagagtcgaggactcggccatgt attactgtGCTCGGGGGGTGGGACTATGGTTCGGTGAATT ATCCTGGAATTACTTTGACTACtggggccagggaaccctg gtcaccgtctcctcag |
| 73 | heavy chain variant 2 nuc | gaggtgcagctggtgcagtctggggggaggcctggtacagc cggggggtccatgagactctactgtgcagcctctGGATT CAGCTTTAGCAGCTATGCCatgagctgggtccgccaggct ccagggaaggggctcgagtgggtctcaagtCTTAATTCTA TTGATCATAGAACAgactatgcagactccgtgaagggccg gttcaccatctccagagacaattccaagaacaccctgtat ttacaaatggacagcctgagagtcgaggactcggccatgt |

-continued

Table of Sequences and SEQ ID Numbers

| SEQ ID NO | Description | Sequence* |
|---|---|---|
| | | attactgtGCTCGGGGGGTGGGACTATGGTTCGGTGAATT ATCCTGGAATTACTTTGACTACtggggccagggaaccctg gtcaccgtctcctcag |
| 74 | light chain nuc | cagtctgccctgactcagcctcgctcagtgtccgggtctc ctggacagtcagtcaccatctcctgcactggaaccAGCAA TGATATTGGTGGTTATAACTATgtctcctggtaccaacaa cacccaggcaaagcccccaaactcatgatttttTATGTCA ATaagcggccctcaggggtccctgatcgcttctctggctc caagtctggcaacacggcctccctgaccatctctgggctc caggctgaggatgaagctgattattactgcTGCTCATTTG CAGGCAGTTACTCCTTAttcggcagagggaccaagctgac cgtcctag |

RVC3 ANTIBODY

| 75 | CDRH1 aa | TFTF<u>R</u>NYA |
| 76 | CDRH2 aa | IS<u>A</u>SG<u>S</u>ST |
| 77 | CDRH3 aa | AKFANDFWSGYSYFD<u>S</u> |
| 78 | CDRL1 aa | QSV<u>N</u>SN |
| 79 | CDRL2 aa | GAS |
| 80 | CDRL2 long aa | LIYGASTRA |
| 81 | CDRL3 aa | QQYNNWVSIT |
| 82 | CDRH1 nuc | ACATTCACGTTTAGAAACTATGCC |
| 83 | CDRH2 nuc | ATTAGTGCTAGTGGTAGTAGCACG |
| 84 | CDRH3 nuc | GCGAAATTTGCTCACGATTTTTGGAGTGGTTATTCTTACT TTGACTCC |
| 85 | CDRL1 nuc | CAGAGTGTTAACAGCAAC |
| 86 | CDRL2 nuc | GGTGCATCC |
| 87 | CDRL2 long nuc | ctcatctatGGTGCATCCaccagggcc |
| 88 | CDRL3 nuc | CAGCAGTATAATAATTGGGTTTCGATCACC |
| 89 | heavy chain aa | EVQLLESGGGLVQPGGSLRLSCAASTFTF<u>R</u>NYAMSWVRQA PGKGL<u>D</u>WVSGIS<u>A</u>SG<u>S</u>STNYA<u>A</u>SLKGRFTISRDNSKNTLY LQMNSLRAEDTAVYYCAKFANDFWSGYSYFD<u>S</u>WGQGTLVT VSS |
| 90 | light chain aa | EIVMTQSPATLSVSPGERATLSCRAGQSV<u>N</u>SNLAWYQQKP GQAPRLLIYGASTRATGIPARFSGSGSGTEFTLTISSLQS EDFAVYYCQQYNNWVSITFGQGTRLEIK |
| 91 | heavy chain nuc | gaggtgcagctgttggagtctgggggaggcctggtgcagc cggggggtccctgagactctcctgtgcagcctctACATT CACGTTTAGAAACTATGCCatgtcctgggtccgccaggct ccagggaaggggctggactgggtctcagggATTAGTGCTA GTGGTAGTAGCACGaattatgcagcctccctgaagggccg atttaccatctccagagacaattccaagaacacattgtat ctgcaaatgaacagcctgagagccgaggacacggccgtct attactgtGCGAAATTTGCTCACGATTTTTGGAGTGGTTA TTCTTACTTTGACTCCtggggccagggaaccctggtcacc gtctcctcag |

Table of Sequences and SEQ ID Numbers

| SEQ ID NO | Description | Sequence* |
|---|---|---|
| 92 | light chain nuc | gaaatagtgatgacgcagtctccagccaccctgtctgtgt ctccaggggaaagagccaccctctcctgcagggccggtCA GAGTGTTAACAGCAACttagcctggtaccagcagaaacct gggcaggctcccagactcctcatctatGGTGCATCCacca gggccactggtatcccagccaggttcagtggcagtgggtc tgggacagagttcactctcaccatcagcagcctgcagtct gaagattttgcagtttattactgtCAGCAGTATAATAATT GGGTTTCGATCACCttcggccaagggacacgactggagat taaac |

RVC20 ANTIBODY

| SEQ ID NO | Description | Sequence* |
|---|---|---|
| 93 | CDRH1 aa | GGSFSSGSYS |
| 94 | CDRH2 aa | IYYSGST |
| 95 | CDRH3 aa | ARGTYSDFWGSPLDY |
| 96 | CDRL1 aa | QGISNY |
| 97 | CDRL2 aa | AAS |
| 98 | CDRL2 long aa | LIYAASSLQ |
| 99 | CDRL3 aa | QQYDTYPLT |
| 100 | CDRH1 nuc | GGTGGCTCCTTCAGCAGTGGAAGTTACTCC |
| 101 | CDRH2 nuc | ATCTATTACAGTGGGAGCACT |
| 102 | CDRH3 nuc | GCGAGAGGCACGTATTCCGATTTTTGGAGTGGTTCCCCTT TAGACTAC |
| 103 | CDRL1 nuc | CAGGGCATTAGCAATTAT |
| 104 | CDRL2 nuc | GCTGCATCC |
| 105 | CDRL2 long nuc | ctgatctatGCTGCATCCagtttgcaa |
| 106 | CDRL3 nuc | CAACAGTATGATACTTACCCTCTCACT |
| 107 | heavy chain aa | QVQLQESGPGLVKPSQTLSLTCTVSGGSFSSGSYSWNWIR QHPGKGLEWIGYIYYSGSTYYNPSLKSRVTMSVHTSKNQF SLKLNSITAADTAVYYCARGTYSDFWGSPLDY**WGQGTLV TVSS |
| 108 | light chain aa | DIQMTQSPSSLSASVGDRVTITCRASQGISNYLAWFQQKP GKAPKSLIYAASSLQSGVPSRFSGSGSGTDFTLTINSLQP EDFVTYFCQQYDTYPLTFGGGTKVEIK |
| 109 | heavy chain nuc | caggtgcagctgcaggagtcgggcccaggactggtgaagc cttcacagaccctgtccctcacctgcactgtctccGGTGG CTCCTTCAGCAGTGGAAGTTACTCCtggaactggatccgc cagcacccagggaagggcctggagtggattgggtacATCT ATTACAGTGGGAGCACTtattacaaccgtccctcaagag tcgagttaccatgtcagtacacacgtctaagaaccagttc tccctgaagctgaactctataactgccgcggacacggccg tgtattactgtGCGAGAGGCACGTATTCCGATTTTTGGAG TGGTTCCCCTTTAGACTACtggggccagggaaccctggtc accgtctcctcag |
| 110 | light chain nuc | gacatccagatgacccagtctccatcctcactgtctgcat ctgtaggagacagagtcaccatcacttgtcgggcgagtCA GGGCATTAGCAATTATttagcctggtttcagcagaaacca gggaaagcccctaagtccctgatctatGCTGCATCCagtt tgcaaagtggggtcccatcaaggttcagcggcagtggatc tgggacagatttcactctcaccatcaacagcctgcagcct gaagattttgtaacttattctgcCAACAGTATGATACTT ACCCTCTCACTttcggcggagggaccaaggtggagatcaa ac |

Table of Sequences and SEQ ID Numbers

| SEQ ID NO | Description | Sequence* |
|---|---|---|
| | RVC21 ANTIBODY | |
| 111 | CDRH1 aa | GGSISNPNYY |
| 112 | CDRH2 aa | IYNGYT |
| 113 | CDRH3 aa | ATQSTMTTIAGHY |
| 114 | CDRL1 aa | TSNIGNSY |
| 115 | CDRL2 aa | DNN |
| 116 | CDRL2 long aa | LIYDNNKRP |
| 117 | CDRL3 aa | GTWDSSLNAYV |
| 118 | CDRH1 nuc | GGTGGCTCCATCAGCAACCCTAACTACTAC |
| 119 | CDRH2 nuc | ATCTATTATAATGGGTACACC |
| 120 | CDRH3 nuc | GCGACGCAATCTACGATGACTACCATAGCGGGCCACTAC |
| 121 | CDRL1 nuc | ACATCCAACATTGGGAATTCTTAT |
| 122 | CDRL2 nuc | GACAATAAT |
| 123 | CDRL2 long nuc | ctcatttatGACAATAATaagcgaccc |
| 124 | CDRL3 nuc | GGAACATGGGACAGCAGCCTGAATGCTTATGTC |
| 125 | heavy chain aa | QLQLQESGPGLVKPSETLSLTCTVSGGSISNPNYYWGWIR QPPGKGLEWIGSIYYNGYTYYNPSLKSRVTISVDKSKDQF FLKMTSLTAADTAVYYCATQSTMTTIAGHYWGQGTLVTVS S |
| 126 | light chain aa | QSVLTQAPSVSAAPGLKVTISCSGSTSNIGNSYVSWYQQL PGTAPKLLIYDNNKRPSGIPDRFSGSKSDTSATLGITGLQ TGDEADYYCGTWDSSLNAYVFGTGTKVTVL |
| 127 | heavy chain nuc | cagctgcagctgcaggagtcgggcccaggactggtgaagc cttcggagaccctgtccctcacgtgcactgtctctGGTGG CTCCATCAGCAACCCTAACTACTACtggggctggatccgc cagcccccagggaagggtctggaatggattgggagtATCT ATTATAATGGGTACACCtactacaacccgtccctcaagag tcgagttaccatatccgtggacaagtccaaggaccagttc tttctgaagatgacctctctgaccgccgcagacacggctg tgtattactgtGCGACGCAATCTACGATGACTACCATAGC GGGCCACTACtggggcagggaaccctggtcaccgtctcc tcag |
| 128 | light chain nuc | cagtctgtattgacgcaggcgccctcagtgtctgcggccc caggactaaaggtcaccatctcctgctctggaagcACATC CAACATTGGGAATTCTTATgtatcctggtaccagcagctc ccaggaacagcccccaaactcctcatttatGACAATAATa agcgaccctcagggattcctgaccgattctctggctccaa gtctgacacgtcagccaccctgggcatcaccggactccag actggggacgaggccgattattactgcGGAACATGGGACA GCAGCCTGAATGCTTATGTCttcggaactgggaccaaggt caccgtcctag |
| | RVC38 ANTIBODY | |
| 129 | CDRH1 aa | GGTFSSYA |
| 130 | CDRH2 aa | IMPMFVAA |
| 131 | CDRH3 aa | ARGDGYNYKWYFDL |
| 132 | CDRL1 aa | QDISNY |
| 133 | CDRL2 aa | AAS |
| 134 | CDRL2 long aa | LIYAASTLQ |

Table of Sequences and SEQ ID Numbers

| SEQ ID NO | Description | Sequence* |
|---|---|---|
| 135 | CDRL3 aa | QQLDTYVALT |
| 136 | CDRH1 nuc | ggaggcaccttcagcagctatgcc |
| 137 | CDRH2 nuc | atcatgcctatgtttgtggcggca |
| 138 | CDRH3 nuc | gcgagaggggatggctacaattacaagtggtattttgacctt |
| 139 | CDRL1 nuc | caggacattagtaattat |
| 140 | CDRL2 nuc | gctgcatcc |
| 141 | CDRL2 long nuc | ctgatctatgctgcatccactttgcaa |
| 142 | CDRL3 nuc | caacagcttgatacttacgtcgcgctcact |
| 143 | heavy chain aa | EVQLVQSGAEVKKPGSSVRVSCKASGGTFSSYAISWVRQAPGLGLEWMGGIMPMFVAANYAQNFQGRVTVSVDKSTNTAYMEMHNLRSDDTAMYYCARGDGYNYKWYFDLWGQGTLTVSS |
| 144 | light chain aa | DIQLTQSPSFLSASVGDRVTITCRASQDISNYLAWYQQKPGKPPKLLIYAASTLQRGVPSRFSGSGSGSEFTLTISSLQPEDFATYYCQQLDTYVALTFGGGTKVEIK |
| 145 | heavy chain nuc | gaggtgcagctggtgcagtctggggctgaggtgaagaagcctgggtcctcggtgagggtctcctgcaaggcttctggaggcaccttcagcagctatgccatcagctgggtgcgacaggcccctgggctagggcttgagtggatgggagggatcatgcctatgtttgtggcggcaaactacgcacagaacttccagggcagagtcacggtttctgtggacaaatccacgaacaccgcctatatggagatgcacaacctgagatctgacgacacggccatgtattactgtgcgagaggggatggctacaattacaagtggtattttgacctttggggccagggaaccctagtcaccgtctcctcag |
| 146 | light chain nuc | gacatccagttgacccagtctccatccttcctgtctgcatctgtaggagacagagtcaccatcacttgccgggccagtcaggacattagtaattatttagcctggtatcagcaaaaaccagggaagcccccctaaactcctgatctatgctgcatccactttgcaaggggggtcccatcaaggttcagtggcagtggatctgggtcagaattcactctcacaatcagcagcctgcagcctgaagattttgcaacttattactgtcaacagcttgatacttacgtcgcgctcactttcggcggagggaccaaggtggagatcaaac |

RVC44 ANTIBODY

| SEQ ID NO | Description | Sequence* |
|---|---|---|
| 147 | CDRH1 aa | GFTFSSYS |
| 148 | CDRH2 aa | ISTTGTYI |
| 149 | CDRH3 aa | ARRSAIALAGTQRAFDI |
| 150 | CDRL1 aa | QNINNY |
| 151 | CDRL2 aa | AAS |
| 152 | CDRL2 long aa | LIYAASSLH |
| 153 | CDRL3 aa | QQSYSNPWT |
| 154 | CDRH1 nuc | GGCTTCACCTTTAGTAGTTATAGT |
| 155 | CDRH2 nuc | ATCAGTACTACTGGTACTTACATA |
| 156 | CDRH3 nuc | GCGAGACGGTCGGCCATAGCACTGGCTGGTACGCAGCGTGCTTTTGATATC |
| 157 | CDRL1 nuc | CAGAACATTAACAACTAT |

Table of Sequences and SEQ ID Numbers

| SEQ ID NO | Description | Sequence* |
|---|---|---|
| 158 | CDRL2 nuc | GCTGCATCC |
| 159 | CDRL2 long nuc | ctgatctatGCTGCATCCagtttacat |
| 160 | CDRL3 nuc | caacagagttacagtaacccttggacg |
| 161 | heavy chain aa | EVQLVQSGGGLVKPGGSLRLSCAASGFTFSSYSMWVRQAPGKGLEWVSSISTTGTYIYYADSVEGRFSISRDSARSSLFLQMNSLRAEDTAVYYCARRSAIALAGTQRAFDIWGPGTNVIVSS |
| 162 | light chain aa | DIQMTQSPSSLSASVGDRVTITCRASQNINNYLNWYQQKLGKAPKLLIYAASSLHSGVPSRFSASGSGTDFILTISNLQPEDCATYYCQQSYSNPWTFGQGTKVEIK |
| 163 | heavy chain nuc | gaggtgcagctggtgcagtctggggggaggcctggtcaagcctggggggtccctgagactctcctgtgcagcctctGGCTTCACCTTTAGTAGTTATAGTatgagttgggtccgccaggctccagggaagggcctggagtgggtctcatccATCAGTACTACTGGTACTTACATAtactacgcagactcagtggagggccgattctccatttccagagacagcgccaggagctctctgtttctgcaaatgaacagcctgagagccgaggacacggctgtctattactgtGCGAGACGGTCGGCCATAGCACTGGCTGGTACGCAGCGTGCTTTTGATATCtggggcccagggacaaacgtcatcgtctcttcag |
| 164 | light chain nuc | gacatccagatgacccagtctccatcttccctgtctgcatctgtaggagacagagtcaccatcacttgccgggcaagtCAGAACATTAACAACTATttaaattggtatcagcagaaactagggaaagcccctaagctcctgatctatGCTGCATCCagtttacatagtggggtcccatcaaggttcagtgccagtggatctgggacagatttcattctgaccatcagtaatctgcaacctgaagattgtgcaacttactactgtcaacagagttacagtaacccttggacgttcggccaagggaccaaggtggaaatcaaac |

RVC58 ANTIBODY

| SEQ ID NO | Description | Sequence* |
|---|---|---|
| 165 | CDRH1 aa | GFTFSTYA |
| 166 | CDRH2 aa | ISDRGGSR |
| 167 | CDRH3 aa | ARDIAPPYNYYFYGMDV |
| 168 | CDRL1 aa | SSDIGAFNY |
| 169 | CDRL2 aa | EVS |
| 170 | CDRL2 long aa | IIYEVSNRP |
| 171 | CDRL3 aa | NSYTSSSTQL |
| 172 | CDRH1 nuc | GGATTCACCTTTAGCACCTATGCC |
| 173 | CDRH2 nuc | ATTAGTGATAGAGGTGGTAGTAGA |
| 174 | CDRH3 nuc | GCGAGAGATATTGCCCCCCCATATAACTACTACTTCTACGGTATGGACGTC |
| 175 | CDRL1 nuc | AGCAGTGACATTGGTGCTTTTAACTAT |
| 176 | CDRL2 nuc | GAGGTCAGT |
| 177 | CDRL2 long nuc | ataatttatGAGGTCAGTaatcggccc |
| 178 | CDRL3 nuc | AACTCATATACAAGCAGCAGCACTCAGTTA |
| 179 | heavy chain aa | EVQLVESGGGLVQPGGSLRLSCAASGFTFSTYAMNWVRQAPGKGLEWVSGISDRGGSRYYAGSVKGRFTISRDNSKNTLFLQMNSLRAEDTAVYYCARDIAPPYNYYFYGMDVWGRGTTVTVSS |

Table of Sequences and SEQ ID Numbers

| SEQ ID NO | Description | Sequence* |
|---|---|---|
| 180 | light chain aa | QSALTQPASVSGSPGQSITISCTGTSSDIGAFNYVSWYQQ HPGKAPKLIIYEVSNRPSGVSNRFSGSKSGNTASLTISGL QAEDEADYYCNSYTSSSTQLFGGGTKLTVL |
| 181 | heavy chain nuc | gaggtgcagctggtggagtctggggggaggcttggtacagc ctgggggggtccctgagactctcctgtgcggcctctGGATT CACCTTTAGCACCTATGCCatgaattgggtccgccaggct ccagggaaggggctggagtgggtctcaggtATTAGTGATA GAGGTGGTAGTAGAtactacgcaggctccgtgaagggccg gttcaccatctccagagacaattccaagaacacgctgttt ctgcaaatgaacagcctgagagccgaggacacggccgtat attactgtGCGAGAGATATTGCCCCCCCATATAACTACTA CTTCTACGGTATGGACGTCtggggccgagggaccacggtc accgtctcctcag |
| 182 | light chain nuc | cagtctgccctgactcagcctgcctccgtgtctgggtctc ctggacagtcgatcaccatctcctgcactggtaccAGCAG TGACATTGGTGCTTTTAACTATgtctcttggtaccaacag cacccaggcaaagcccccaaactcataatttatGAGGTCA GTaatcggccctcaggggtttctaatcgcttctctggctc caagtctggcaacacggcctccctgaccatctctgggctc caggctgaggacgaggctgattattactgcAACTCATATA CAAGCAGCAGCACTCAGTTAttcggcggagggaccaagct gaccgtcctag |

RVC68 ANTIBODY

| SEQ ID NO | Description | Sequence* |
|---|---|---|
| 183 | CDRH1 aa | GGSISEHH |
| 184 | CDRH2 aa | IFHSGST |
| 185 | CDRH3 aa | ARAVSTYYYYYIDV |
| 186 | CDRL1 aa | QDISNW |
| 187 | CDRL2 aa | AAS |
| 188 | CDRL2 long aa | LIYAASSLQ |
| 189 | CDRL3 aa | QQAKSFPLT |
| 190 | CDRH1 nuc | GGTGGCTCCATTAGTGAGCACCAC |
| 191 | CDRH2 nuc | ATCTTTCACAGTGGGAGTACC |
| 192 | CDRH3 nuc | GCGAGAGCGGTGTCTACTTACTACTACTATTACATAGACGTC |
| 193 | CDRL1 nuc | CAGGATATTAGCAACTGG |
| 194 | CDRL2 nuc | GCTGCGTCC |
| 195 | CDRL2 long nuc | ctgatctatGCTGCGTCCagtttgcaa |
| 196 | CDRL3 nuc | CAACAGGCTAAGAGTTTCCCTCTTACT |
| 197 | heavy chain aa | QVQLQESGPRLVKPSETLSLTCTFSGGSISEHHWSWLRQS PGKGLEWIGYIFHSGSTNYNPSLKSRVNISLDKSKNQFSL KLSSVTAADTAVYFCARAVSTYYYYIDVWGQGTTVTVSS |
| 198 | light chain aa | DIQMTQSPSSVSASVGDRVTITCRASQDISNWLAWYQQKP GKAPKLLIYAASSLQSGISSRFSGGGSGTDFTLTISSLQP EDFASYYCQQAKSFPLTFGQGTKLEIK |

Table of Sequences and SEQ ID Numbers

| SEQ ID NO | Description | Sequence* |
|---|---|---|
| 199 | heavy chain nuc | caggtgcagctacaggagtcgggcccaagactggtgaagc cctcggagaccctgtccctcacctgcactttctctGGTGG CTCCATTAGTGAGCACCACtggagctggctccggcagtcc ccagggaagggactggagtggattggatatATCTTTCACA GTGGGAGTACCaactacaaccccctccctcaagagtcgagt caacatatcattagacaagtccaagaaccagttctccctg aagctgagttctgtgaccgctgcggacacggccgtgtatt tctgtGCGAGAGCGGTGTCTACTTACTACTACTATTACAT AGACGTCtggggccaagggaccacggtcaccgtctcctca g |
| 200 | light chain nuc | gacatccagatgacccagtctccatcttccgtgtctgcat ctgtaggagacagagtcaccatcacttgtcgggcgagtCA GGATATTAGCAACTGGttagcctggtatcagcagaaacca gggaaagcccctaaactcctgatctatGCTGCGTCCagtt tgcaaagtgggatctcatctaggttcagcggcggtggctc tgggacagatttcactctcaccatcagcagcctgcagcct gaagattttgcaagttactactgtCAACAGGCTAAGAGTT TCCCTCTTACTtttggccaggggaccaagctggagatcaa ac |

RVC111 ANTIBODY

| SEQ ID NO | Description | Sequence* |
|---|---|---|
| 201 | CDRH1 aa | GFSFSSYV |
| 202 | CDRH2 aa | ISYDGSNK |
| 203 | CDRH3 aa | ARGSGTQTPLFDY |
| 204 | CDRL1 aa | QSITSW |
| 205 | CDRL2 aa | DDS |
| 206 | CDRL2 long aa | LIYDDSTLE |
| 207 | CDRL3 aa | QQYESYSGT |
| 208 | CDRH1 nuc | ggattctccttcagtagctatgtt |
| 209 | CDRH2 nuc | atatcatatgatggaagtaataaa |
| 210 | CDRH3 nuc | gcgagagggtccggaacccaaactcccctctttgactac |
| 211 | CDRL1 nuc | cagagtattactagctgg |
| 212 | CDRL2 nuc | gatgactcc |
| 213 | CDRL2 long nuc | ctgatctatgatgactccactttggaa |
| 214 | CDRL3 nuc | caacagtatgagagttattcagggacg |
| 215 | heavy chain aa | QVQLVESGGGVVQPGRSLRLSCAASGFSFSSYVMYWVRQA PGKGLEWVTIISYDGSNKYYADSVKGRFTISRDNSKNTLY LQMNSLRAEDTAVYYCARGSGTQTPLFDYWGQGTLVTVSS |
| 216 | light chain aa | DIQMTQSPSTLSASVGDRVTITCRANQSITSWVAWYQQMP GRAPKLLIYDDSTLESGVPSRFSGSGSGTEFTLTISSLQP DDFATYYCQQYESYSGTFGQGTKVEIK |
| 217 | heavy chain nuc | caggtgcaactggtggagtctgggggaggcgtggtccagc ctgggaggtccctgagactctcctgtgcagcctctggatt ctccttcagtagctatgttatgtactgggtccgccaggct ccaggcaaggggctggagtgggtgacaattatatcatatg atggaagtaataaatactacgcagactccgtgaagggccg attcaccatctccagagacaattccaagaacacgctgtat ctgcaaatgaacagcctgagagctgaggacacggctgtct attactgtgcgagagggtccggaacccaaactcccctctt tgactactggggccaggggaaccctggtcaccgtctcctca g |
| 218 | light chain nuc | gacatccagatgacccagtctccttccacccctgtctgcat ctgtgggagacagagtcaccatcacttgccgggccaatca gagtattactagctgggtggcctggtatcagcagatgcca |

Table of Sequences and SEQ ID Numbers

| SEQ ID NO | Description | Sequence* |
|---|---|---|
| | | gggagagcccctaaactcctgatctatgatgactccacttt<br>tggaaagtggggtcccatcaaggttcagcggcagtggatc<br>tgggacagaattcactctcaccatcagcagcctgcagcct<br>gatgattttgcaacttattactgccaacagtatgagagtt<br>attcagggacgttcggccaagggaccaaggtggaaatcaa<br>ac |

*the sequences highlighted in bold are CDR regions (nucleotide or aa) and the underlined residues are mutated residues as compared to the "germline" sequence.

---

The invention claimed is:

1. An isolated antibody, or an antigen binding fragment thereof, that neutralizes a lyssavirus infection, wherein the antibody, or the antigen binding fragment thereof, comprises heavy chain CDRH1, CDRH2, and CDRH3 amino acid sequences and light chain CDRL1, CDRL2, and CDRL3 amino acid sequences as set forth in SEQ ID NOs: 93-95, 96, 97, and 99, respectively, or in SEQ ID NOs: 93-95, 96, 98, and 99, respectively, and wherein the antibody comprises an amino acid sequence corresponding to a human IgG1, IgG2, or IgG4 isotype.

2. The antibody or antigen binding fragment according to claim 1, wherein the antibody or antigen binding fragment comprises a heavy chain variable region having at least 80% sequence identity to the amino acid sequence of SEQ ID NO:107 and a light chain variable region having at least 80% sequence identity to the amino acid sequence of SEQ ID NO: 108, provided that the antibody or antigen binding fragment comprises heavy chain CDRH1, CDRH2, and CDRH3 amino acid sequences and light chain CDRL1, CDRL2, and CDRL3 amino acid sequences as set forth in SEQ ID NOs: SEQ ID NOs: 93-95, 96, 97, and 99, respectively, or in SEQ ID NOs: 93-95, 96, 98, and 99, respectively.

3. The antibody or antigen binding fragment according to claim 1, wherein the antibody or antigen binding fragment comprises a heavy chain variable region having at least 90% sequence identity to the amino acid sequence of SEQ ID NO:107 and a light chain variable region having at least 90% sequence identity to the amino acid sequence of SEQ ID NO: 108, provided that the antibody or antigen binding fragment comprises heavy chain CDRH1, CDRH2, and CDRH3 amino acid sequences and light chain CDRL1, CDRL2, and CDRL3 amino acid sequences as set forth in SEQ ID NOs: SEQ ID NOs: 93-95, 96, 97, and 99, respectively, or in SEQ ID NOs: 93-95, 96, 98, and 99, respectively.

4. The antibody or antigen binding fragment thereof according to claim 1, wherein the antibody or antigen binding fragment comprises a heavy chain variable region having at least 95% sequence identity to the amino acid sequence of SEQ ID NO:107 and a light chain variable region having at least 95% sequence identity to the amino acid sequence of SEQ ID NO: 108, provided that the antibody or antigen binding fragment comprises heavy chain CDRH1, CDRH2, and CDRH3 amino acid sequences and light chain CDRL1, CDRL2, and CDRL3 amino acid sequences as set forth in SEQ ID NOs: SEQ ID NOs: 93-95, 96, 97, and 99, respectively, or in SEQ ID NOs: 93-95, 96, 98, and 99, respectively.

5. The antibody or antigen binding fragment according to claim 1, wherein the antibody or antigen binding fragment comprises a heavy chain variable region having at least 97% sequence identity to the amino acid sequence of SEQ ID NO:107 and a light chain variable region having at least 97% sequence identity to the amino acid sequence of SEQ ID NO: 108, provided that the antibody or antigen binding fragment comprises heavy chain CDRH1, CDRH2, and CDRH3 amino acid sequences and light chain CDRL1, CDRL2, and CDRL3 amino acid sequences as set forth in SEQ ID NOs: SEQ ID NOs: 93-95, 96, 97, and 99, respectively, or in SEQ ID NOs: 93-95, 96, 98, and 99, respectively.

6. The antibody or antigen binding fragment according to claim 1, wherein the antibody or antigen binding fragment comprises a heavy chain variable region having at least 99% sequence identity to the amino acid sequence of SEQ ID NO:107 and a light chain variable region having at least 99% sequence identity to the amino acid sequence of SEQ ID NO: 108, provided that the antibody or antigen binding fragment comprises heavy chain CDRH1, CDRH2, and CDRH3 amino acid sequences and light chain CDRL1, CDRL2, and CDRL3 amino acid sequences as set forth in SEQ ID NOs: SEQ ID NOs: 93-95, 96, 97, and 99, respectively, or in SEQ ID NOs: 93-95, 96, 98, and 99, respectively.

7. The antibody or antigen binding fragment according to claim 1, wherein the antibody or antigen binding fragment comprises a heavy chain variable region having the amino acid sequence of SEQ ID NO:107 and a light chain variable region having the amino acid sequence of SEQ ID NO: 108.

8. The antibody or antigen binding fragment according to claim 1, characterized in that the antibody or antigen binding fragment is a monoclonal antibody or an antigen binding fragment.

9. The antibody or antigen binding fragment according to claim 1, wherein the antibody or antigen binding fragment neutralizes infection by RABV CVS-11 with an $IC_{90}$ of 400 ng/ml or less.

10. The antibody or antigen binding fragment according to claim 1, wherein the antibody or antigen binding fragment is according to gRVC20.

11. The antibody or antigen binding fragment according to claim 1, wherein the antibody or antigen binding fragment is RVC20.

12. The antibody or antigen binding fragment according to claim 1, wherein the antibody or antigen binding fragment is a human antibody, a monoclonal antibody, a human monoclonal antibody, a purified antibody, a single chain antibody, Fab, Fab', F(ab')2, Fv or scFv.

13. The antibody or antigen binding fragment according to claim 1, wherein the antibody or antigen binding fragment neutralizes lyssavirus infection by (i) RABV and (ii) at least 50% of all isolates of non-RABV lyssaviruses selected from the group consisting of ABLV/Australia/bat/9810AUS-1998/V1039-2011/ABLV, 98010/ABLV, 1301 Bokeloh bat lyssavirus/BBLV, 86132SA/DUVV, DUVV/South Africa/human/96132SA-1971/RS639-2012/DUVV, EBLV1a/France/bat/122938-2002/V3951-2009/EBLV-1, EBLV1b/France/bat/8918-1989/EBLV-1, EBLV2/UK/bat/RV1332-2002/V3951-2009/EBLV-2, 94112/EBLV-2, 02053/EBLV-2, 8619/LBV, MOK/MOK, Shimoni bat Virus/SHIV, West Caucasian bat Virus/WCBV, Australian bat lyssavirus/RV634/ABLV, Aravan Virus/ARAV, Duvenhage Virus RSA2006/DUVV, Duvenhage Virus ZIM86-RV 131/DUVV, European bat lyssavirus 1.RV20/EBLV-1, European bat lyssavirus 1.RV9/EBLV-1, EBLV 1a/France/bat/122938-2002/V3951-2009/EBLV-1, EBLV2/UK/bat/RV1332-2002/V3951-2009/EBLV-2, European bat lyssavirus 2.RV1787/EBLV-2, European bat lyssavirus 2.RV628/EBLV-2, Irkut Virus/IRKV, Khujand Virus/KHUV, 8619/LBV, Lagos Bat Virus NIG56-RV1/LBV, Lagos Bat Virus SA2004/LBV, Mokola Virus NIG68.RV4/MOK, Mokola Virus 98/071 RA36/MOK and Ikoma lyssavirus/IKOV with an IC50 of less than 10000 ng/ml for ABLV/Australia/bat/9810AUS-1998/V1039-2011/ABLV, 98010/ABLV, 1301 Bokeloh bat lyssavirus/BBLV, 86132SA/DUVV, DUVV/SouthAfrica/human/96132SA-1971/ RS639-2012/DUVV, EBLV1a/France/bat/122938-2002/V3951-2009/EBLV-1, EBLV1b/France/bat/8918-1989/EBLV-1, EBLV2/UK/bat/RV1332-2002/V3951-2009/EBLV-2, 94112/EBLV-2, 02053/EBLV-2, 8619/LBV, MOK/MOK tested as infectious viruses and with an IC90 of less than 10000 ng/ml for Shimoni bat Virus/SHIV, West Caucasian bat Virus/WCBV, Australian bat lyssavirus/RV634/ABLV, Aravan Virus/ARAV, Duvenhage Virus RSA2006/DUVV, Duvenhage Virus ZIIIVI86-RV 131/DUVV, European bat lyssavirus 1.RV20/EBLV-1, European bat lyssavirus 1.RV9/EBLV-1, EBLV 1a/France/bat/122938-2002/V3951-2009/EBLV-1, EBLV2/UK/bat/RV1332-2002/V3951-2009/EBLV-2, European bat lyssavirus 2.RV1787/EBLV-2, European bat lyssavirus 2.RV628/EBLV-2, Irkut Virus/IRKV, Khujand Virus/KHUV, 8619/LBV, Lagos Bat Virus NIG56-RV1/LBV, Lagos Bat Virus SA2004/LBV, Mokola Virus NIG68.RV4/MOK, Mokola Virus 98/071 RA36/MOK and Ikoma lyssavirus /IKOV tested as pseudotyped viruses.

14. The antibody or antigen binding fragment according to claim 1, wherein the antibody or antigen binding fragment neutralizes lyssavirus infection by at least 70% of non-RABV phylogroup I lyssaviruses selected from the group consisting of DUVV, EBLV-1, EBLV-2, ABLV, IRKV, KHUV, and ARAV, with an IC50 of less than 10000 ng/ml.

15. The antibody or antigen binding fragment according to claim 1, wherein the antibody or antigen binding fragment neutralizes lyssavirus infection by at least 70% of the isolates of non-RABV phylogroup I lyssaviruses selected from the group consisting of ABLV/Australia/bat/9810AUS-1998/V1039-2011/ABLV, 98010/ABLV, 1301 Bokeloh bat lyssavirus/BBLV, 86132SA/DUVV, DUVV/SouthAfrica/human/96132SA-1971/RS639-2012/DUVV, EBLV1a/France/bat/122938-2002/V3951-2009/EBLV-1, EBLV1b/France/bat/8918-1989/EBLV-1, EBLV2/UK/bat/RV1332-2002/V3951-2009/EBLV-2, 94112/EBLV-2, 02053/EBLV-2, Australian batlyssavirus/RV634/ABLV, Aravan Virus/ARAV, Duvenhage Virus RSA2006/DUVV, Duvenhage Virus ZIIIVI86-RV 131/DUVV, European bat lyssavirus 1.RV20/EBLV-1, European bat lyssavirus 1.RV9/EBLV-1, EBLV 1a/France/bat/122938-2002/V3951-2009/EBLV-1, EBLV2/UK/bat/RV1332-2002/V3951-2009/EBLV-2, European bat lyssavirus 2.RV1787/EBLV-2 and European bat lyssavirus 2.RV628/EBLV-2, Irkut Virus/IRKV, Khujand Virus/KHUV, with an IC50 of less than 10000 ng/ml for ABLV/Australia/bat/9810AUS-1998/V1039-2011/ABLV, 98010/ABLV, 1301 Bokeloh bat lyssavirus/BBLV, 86132SA/DUVV, DUVV/SouthAfrica/human/96132SA-1971/ RS639-2012/DUVV, EBLV1a/France/bat/122938-2002/V3951-2009/EBLV-1, EBLV1b/France/bat/8918-1989/EBLV-1, EBLV2/UK/bat/RV1332-2002/V3951-2009/EBLV-2, 94112/EBLV-2 and 02053/EBLV-2, tested as infectious viruses and with an IC90 of less than 10000 ng/ml for Australian bat lyssavirus/RV634/ABLV, Aravan Virus/ARAV, Duvenhage Virus RSA2006/DUVV, Duvenhage Virus ZIIIVI86-RV 131/DUVV, European bat lyssavirus 1.RV20/EBLV-1, European bat lyssavirus 1.RV9/EBLV-1, EBLV 1a/France/bat/122938-2002/V3951-2009/EBLV-1, EBLV2/UK/bat/RV1332-2002/V3951-2009/EBLV-2, European bat lyssavirus 2.RV1787/EBLV-2, European bat lyssavirus 2.RV628/EBLV-2, Irkut Virus/IRKV and Khujand Virus/KHUV tested as pseudotyped viruses.

16. The antibody or antigen binding fragment according to claim 1, wherein the antibody or antigen binding fragment neutralizes infection by EBLV-1.

17. A pharmaceutical composition comprising the antibody or antigen binding fragment according to claim 1, and a pharmaceutically acceptable excipient, diluent or carrier.

18. The pharmaceutical composition of claim 17, comprising a further antibody or antigen binding fragment, wherein the further antibody or antigen binding fragment comprises heavy chain CDRH1, CDRH2, and CDRH3 amino acid sequences and light chain CDRL1, CDRL2, and CDRL3 amino acid sequences as set forth in SEQ ID NOs: 165-169 and 171, respectively, or in SEQ ID NOs: 165-168 and 170-171, respectively.

19. The pharmaceutical composition of claim 18, wherein the further antibody or antigen binding fragment comprises a heavy chain variable region having the amino acid sequence of SEQ ID NO: 179 and a light chain variable region having the amino acid sequence of SEQ ID NO: 180.

20. A method of preventing and/or treating a RABV and/or non-RABV lyssavirus infection in a subject, wherein the method comprises administering to a subject in need thereof the antibody or antigen binding fragment of claim 1.

* * * * *

SEQUENCE LISTING

<160> NUMBER OF SEQ ID NOS: 218

<210> SEQ ID NO 1
<211> LENGTH: 8
<212> TYPE: PRT
<213> ORGANISM: Artificial Sequence
<220> FEATURE:
<223> OTHER INFORMATION: RVA122 CDRH1 aa

<400> SEQUENCE: 1

Gly Asp Ser Met Asn Asn Phe Tyr
1               5

<210> SEQ ID NO 2
<211> LENGTH: 7
<212> TYPE: PRT
<213> ORGANISM: Artificial Sequence
<220> FEATURE:
<223> OTHER INFORMATION: RVA122 CDRH2 aa

<400> SEQUENCE: 2

Ile Tyr Tyr Ser Gly Thr Thr
1               5

<210> SEQ ID NO 3
<211> LENGTH: 17
<212> TYPE: PRT
<213> ORGANISM: Artificial Sequence
<220> FEATURE:
<223> OTHER INFORMATION: RVA122 CDRH3 aa

<400> SEQUENCE: 3

Ala Arg Asp Ser Gly Asp Tyr Val Ser Tyr Tyr Tyr Gly Met Asp
1               5                   10                  15

Val

<210> SEQ ID NO 4
<211> LENGTH: 8
<212> TYPE: PRT
<213> ORGANISM: Artificial Sequence
<220> FEATURE:
<223> OTHER INFORMATION: RVA122 CDRL1 aa

<400> SEQUENCE: 4

Ser Ser Asn Ile Gly Ser Asn Tyr
1               5

<210> SEQ ID NO 5

```
<400> SEQUENCE: 5

000

<210> SEQ ID NO 6
<211> LENGTH: 9
<212> TYPE: PRT
<213> ORGANISM: Artificial Sequence
<220> FEATURE:
<223> OTHER INFORMATION: RVA122 CDRL2 long aa

<400> SEQUENCE: 6

Leu Ile Tyr Lys Ser Asp Lys Arg Pro
1               5

<210> SEQ ID NO 7
<211> LENGTH: 11
<212> TYPE: PRT
<213> ORGANISM: Artificial Sequence
<220> FEATURE:
<223> OTHER INFORMATION: RVA122 CDRL3 aa

<400> SEQUENCE: 7

Ala Ala Trp Asp Asn Arg Leu Ser Gly Trp Leu
1               5                   10

<210> SEQ ID NO 8
<211> LENGTH: 24
<212> TYPE: DNA
<213> ORGANISM: Artificial Sequence
<220> FEATURE:
<223> OTHER INFORMATION: RVA122 CDRH1 nuc

<400> SEQUENCE: 8
ggtgactcca tgaataattt ctac                                            24

<210> SEQ ID NO 9
<211> LENGTH: 21
<212> TYPE: DNA
<213> ORGANISM: Artificial Sequence
<220> FEATURE:
<223> OTHER INFORMATION: RVA122 CDRH2 nuc

<400> SEQUENCE: 9
atctattaca gtgggaccac c                                               21

<210> SEQ ID NO 10
<211> LENGTH: 51
<212> TYPE: DNA
<213> ORGANISM: Artificial Sequence
<220> FEATURE:
<223> OTHER INFORMATION: RVA122 CDRH3 nuc

<400> SEQUENCE: 10
gcgagagact ccggtgacta cgtcagctac tactattatg gtatggacgt c              51

<210> SEQ ID NO 11
<211> LENGTH: 24
<212> TYPE: DNA
<213> ORGANISM: Artificial Sequence
<220> FEATURE:
<223> OTHER INFORMATION: RVA122 CDRL1 nuc

<400> SEQUENCE: 11
agctccaaca tcggaagtaa ttat                                            24
```

<210> SEQ ID NO 12
<400> SEQUENCE: 12

000

<210> SEQ ID NO 13
<211> LENGTH: 27
<212> TYPE: DNA
<213> ORGANISM: Artificial Sequence
<220> FEATURE:
<223> OTHER INFORMATION: RVA122 CDRL2 long nuc

<400> SEQUENCE: 13
cttatttaca agagtgataa gcggccc                                          27

<210> SEQ ID NO 14
<211> LENGTH: 33
<212> TYPE: DNA
<213> ORGANISM: Artificial Sequence
<220> FEATURE:
<223> OTHER INFORMATION: RVA122 CDRL3 nuc

<400> SEQUENCE: 14
gcagcatggg ataacaggct gagtggttgg ctc                                   33

<210> SEQ ID NO 15
<211> LENGTH: 123
<212> TYPE: PRT
<213> ORGANISM: Artificial Sequence
<220> FEATURE:
<223> OTHER INFORMATION: RVA122 heavy chain aa

<400> SEQUENCE: 15

Gln Val His Leu Gln Glu Ser Gly Pro Gly Leu Val Lys Pro Ser Glu
1               5                   10                  15

Thr Leu Ser Leu Thr Cys Thr Val Ser Gly Asp Ser Met Asn Asn Phe
            20                  25                  30

Tyr Trp Gly Trp Ile Arg Gln Pro Ala Gly Lys Gly Leu Glu Trp Ile
        35                  40                  45

Gly Tyr Ile Tyr Tyr Ser Gly Thr Thr Asn Tyr Asn Pro Ser Leu Lys
    50                  55                  60

Ser Arg Val Thr Ile Ser Ile Asp Thr Ser Lys Asn Gln Phe Ser Leu
65                  70                  75                  80

Lys Val Asn Ser Val Thr Ala Ala Asp Thr Ala Val Tyr Tyr Cys Ala
                85                  90                  95

Arg Asp Ser Gly Asp Tyr Val Ser Tyr Tyr Tyr Gly Met Asp Val
            100                 105                 110

Trp Gly Pro Gly Thr Thr Val Thr Val Ser Ser
        115                 120

<210> SEQ ID NO 16
<211> LENGTH: 110
<212> TYPE: PRT
<213> ORGANISM: Artificial Sequence
<220> FEATURE:
<223> OTHER INFORMATION: RVA122 light chain aa

<400> SEQUENCE: 16

Gln Ser Val Leu Thr Gln Ser Pro Ser Ala Ser Asp Thr Pro Gly Gln
1               5                   10                  15

Arg Val Thr Ile Ser Cys Ser Gly Ser Ser Ser Asn Ile Gly Ser Asn
            20                  25                  30

```
Tyr Val Tyr Trp Tyr Gln Gln Phe Pro Gly Thr Ala Pro Lys Leu Leu
             35                  40                  45

Ile Tyr Lys Ser Asp Lys Arg Pro Ser Gly Val Pro Asp Arg Phe Ser
     50                  55                  60

Gly Ser Thr Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asn Arg Leu
                 85                  90                  95

Ser Gly Trp Leu Phe Gly Gly Gly Thr Lys Leu Thr Val Leu
             100                 105                 110

<210> SEQ ID NO 17
<211> LENGTH: 370
<212> TYPE: DNA
<213> ORGANISM: Artificial Sequence
<220> FEATURE:
<223> OTHER INFORMATION: RVA122 heavy chain nuc

<400> SEQUENCE: 17
caggtgcacc tgcaggagtc gggcccagga ctggtgaagc cttcggagac cctgtccctc      60
acctgcactg tctctggtga ctccatgaat aatttctact ggggctggat ccggcagccc     120
gcagggaagg gactggagtg gattggatat atctattaca gtgggaccac caactacaac     180
ccctccctca gagtcgagt caccatatca atagacacgt ccaagaacca attctccctg      240
aaggtgaact ctgtgaccgc tgcggacacg gccgtgtatt attgtgcgag agactccggt     300
gactacgtca gctactacta ttatggtatg gacgtctggg gccagggac cacggtcacc     360 gtctcctcag                                                            370

<210> SEQ ID NO 18
<211> LENGTH: 331
<212> TYPE: DNA
<213> ORGANISM: Artificial Sequence
<220> FEATURE:
<223> OTHER INFORMATION: RVA122 light chain nuc

<400> SEQUENCE: 18
cagtctgtgc tgactcagtc accctcagcg tctgataccc ccgggcagag ggtcaccatc      60
tcttgttctg gaagcagctc caacatcgga agtaattatg tgtattggta ccagcagttc     120
ccaggaacgg cccccaaact ccttatttac aagagtgata gcggccctc aggggtccct      180 gaccgattct ctggctccac gtctggcacc tcagcctccc tggccatcag tgggctccgg     240
tccgaagatg aggctgatta ttactgtgca gcatgggata caggctgag tggttggctc     300 ttcggcggag ggacgaagct gaccgtccta g                                    331

<210> SEQ ID NO 19
<211> LENGTH: 10
<212> TYPE: PRT
<213> ORGANISM: Artificial Sequence
<220> FEATURE:
<223> OTHER INFORMATION: RVA144 CDRH1 aa

<400> SEQUENCE: 19

Gly Gly Ser Ile Ser Ser Thr Ile Phe Tyr
 1               5                  10

<210> SEQ ID NO 20
<211> LENGTH: 7
<212> TYPE: PRT
```

```
<213> ORGANISM: Artificial Sequence
<220> FEATURE:
<223> OTHER INFORMATION: RVA144 CDRH2 aa

<400> SEQUENCE: 20

Val Tyr Tyr Asn Gly His Thr
1               5

<210> SEQ ID NO 21
<211> LENGTH: 12
<212> TYPE: PRT
<213> ORGANISM: Artificial Sequence
<220> FEATURE:
<223> OTHER INFORMATION: RVA144 CDRH3 aa

<400> SEQUENCE: 21

Ala Arg Pro Ser Thr Tyr Asp Tyr Ser Ile Gly Arg
1               5                   10

<210> SEQ ID NO 22
<211> LENGTH: 9
<212> TYPE: PRT
<213> ORGANISM: Artificial Sequence
<220> FEATURE:
<223> OTHER INFORMATION: RVA144 CDRL1 aa

<400> SEQUENCE: 22

Ser Ser Asn Ile Gly Ala Gly Tyr Asp
1               5

<210> SEQ ID NO 23

<400> SEQUENCE: 23

000

<210> SEQ ID NO 24
<211> LENGTH: 9
<212> TYPE: PRT
<213> ORGANISM: Artificial Sequence
<220> FEATURE:
<223> OTHER INFORMATION: RVA144 CDRL2 long aa

<400> SEQUENCE: 24

Leu Ile Tyr Gly Asn Thr Lys Arg Pro
1               5

<210> SEQ ID NO 25
<211> LENGTH: 11
<212> TYPE: PRT
<213> ORGANISM: Artificial Sequence
<220> FEATURE:
<223> OTHER INFORMATION: RVA144 CDRL3 aa

<400> SEQUENCE: 25

Gln Ser Phe Asp Ser Ser Leu Ser Ala Trp Val
1               5                   10

<210> SEQ ID NO 26
<211> LENGTH: 30
<212> TYPE: DNA
<213> ORGANISM: Artificial Sequence
<220> FEATURE:
<223> OTHER INFORMATION: RVA144 CDRH1 nuc

<400> SEQUENCE: 26
ggtggttcca tcagcagtac tattttctac                                    30
```

<210> SEQ ID NO 27
<211> LENGTH: 21
<212> TYPE: DNA
<213> ORGANISM: Artificial Sequence
<220> FEATURE:
<223> OTHER INFORMATION: RVA144 CDRH2 nuc

<400> SEQUENCE: 27
gtctattata atggacacac c                                        21

<210> SEQ ID NO 28
<211> LENGTH: 36
<212> TYPE: DNA
<213> ORGANISM: Artificial Sequence
<220> FEATURE:
<223> OTHER INFORMATION: RVA144 CDRH3 nuc

<400> SEQUENCE: 28
gcgagaccct caacatatga ctacagtatt gggcgc                        36

<210> SEQ ID NO 29
<211> LENGTH: 27
<212> TYPE: DNA
<213> ORGANISM: Artificial Sequence
<220> FEATURE:
<223> OTHER INFORMATION: RVA144 CDRL1 nuc

<400> SEQUENCE: 29
agctccaaca tcggggcagg ttatgat                                  27

<210> SEQ ID NO 30

<400> SEQUENCE: 30

000

<210> SEQ ID NO 31
<211> LENGTH: 27
<212> TYPE: DNA
<213> ORGANISM: Artificial Sequence
<220> FEATURE:
<223> OTHER INFORMATION: RVA144 CDRL2 long nuc

<400> SEQUENCE: 31
ctcatctatg gtaacaccaa gcggccc                                  27

<210> SEQ ID NO 32
<211> LENGTH: 33
<212> TYPE: DNA
<213> ORGANISM: Artificial Sequence
<220> FEATURE:
<223> OTHER INFORMATION: RVA144 CDRL3 nuc

<400> SEQUENCE: 32
cagtcctttg acagcagcct gagtgcttgg gta                           33

<210> SEQ ID NO 33
<211> LENGTH: 120
<212> TYPE: PRT
<213> ORGANISM: Artificial Sequence
<220> FEATURE:
<223> OTHER INFORMATION: RVA144 heavy chain aa

<400> SEQUENCE: 33

Gln Leu Gln Leu Gln Glu Ser Gly Pro Gly Leu Val Lys Pro Ser Glu

```
                1               5                   10                  15
            Thr Leu Ser Leu Thr Cys Thr Val Ser Gly Gly Ser Ile Ser Ser Thr
                            20                  25                  30
            Ile Phe Tyr Trp Gly Trp Ile Arg Gln Pro Pro Gly Lys Gly Leu Glu
                        35                  40                  45
            Trp Ile Gly Ser Val Tyr Tyr Asn Gly His Thr Tyr Tyr Asn Pro Ser
                    50                  55                  60
            Leu Lys Ser Arg Val Ala Ile Ser Ile Asp Lys Ser Lys Asn Gln Phe
            65                  70                  75                  80
            Ser Leu Arg Leu Asn Ser Val Thr Ala Ala Asp Thr Ala Val Tyr Tyr
                            85                  90                  95
            Cys Ala Arg Pro Ser Thr Tyr Asp Tyr Ser Ile Gly Arg Trp Gly Gln
                            100                 105                 110
            Gly Thr Leu Val Thr Val Ser Ser
                        115                 120
```

<210> SEQ ID NO 34
<211> LENGTH: 111
<212> TYPE: PRT
<213> ORGANISM: Artificial Sequence
<220> FEATURE:
<223> OTHER INFORMATION: RVA144 light chain aa

<400> SEQUENCE: 34

```
                1               5                   10                  15
            Gln Ser Val Leu Thr Gln Pro Pro Ser Val Ser Arg Ala Pro Gly Gln
                            20                  25                  30
            Arg Val Thr Ile Ser Cys Thr Gly Ser Ser Ser Asn Ile Gly Ala Gly
                        35                  40                  45
            Tyr Asp Val His Trp Tyr Gln Gln Leu Pro Gly Thr Ala Pro Lys Leu
                    50                  55                  60
            Leu Ile Tyr Gly Asn Thr Lys Arg Pro Ser Gly Val Pro Asp Arg Phe
            65                  70                  75                  80
            Ser Gly Ser Lys Ser Gly Thr Ser Ala Ser Leu Ala Ile Thr Gly Leu
                            85                  90                  95
            Leu Thr Glu Asp Glu Ala Asp Tyr Tyr Cys Gln Ser Phe Asp Ser Ser
                            100                 105                 110
            Leu Ser Ala Trp Val Phe Gly Gly Gly Thr Lys Leu Thr Val Leu
```

<210> SEQ ID NO 35
<211> LENGTH: 361
<212> TYPE: DNA
<213> ORGANISM: Artificial Sequence
<220> FEATURE:
<223> OTHER INFORMATION: RVA144 heavy chain nuc

<400> SEQUENCE: 35

```
cagctgcagc tgcaggagtc gggcccagga ctggtgaagc cctcggagac cctgtccctc        60
acttgcactg tctctggtgg ttccatcagc agtactattt tctactgggg ctggatccgc       120 cagccccag  ggaagggact ggagtggatt gggagtgtct attataatgg acacacctac       180
tacaatccgt ccctcaagag tcgagtcgcc atatccattg acaagtccaa gaaccagttc       240
tccctgaggc ttaactctgt gaccgccgcg gacacggctg tatattactg tgcgagaccc       300
tcaacatatg actacagtat tgggcgctgg ggccagggaa ccctggtcac cgtctcctca       360
g                                                                      361
```

```
<210> SEQ ID NO 36
<211> LENGTH: 334
<212> TYPE: DNA
<213> ORGANISM: Artificial Sequence
<220> FEATURE:
<223> OTHER INFORMATION: RVA144 light chain nuc

<400> SEQUENCE: 36
cagtccgtgc tgacgcagcc gccctcagtg tctcgggccc cagggcagag ggtcaccatc      60
tcctgcactg ggagcagctc caacatcggg gcaggttatg atgtccactg gtaccagcaa     120
cttccaggaa cagcccccaa actcctcatc tatggtaaca ccaagcggcc ctcaggggtc     180
cctgaccgat tctctggctc caagtctggc acctcagcct ccctggccat cactgggctc     240
ctgactgagg atgaggctga ttattactgc cagtcctttg acagcagcct gagtgcttgg     300
gtattcggcg agggaccaa actgaccgtc ctgg                                  334

<210> SEQ ID NO 37
<211> LENGTH: 10
<212> TYPE: PRT
<213> ORGANISM: Artificial Sequence
<220> FEATURE:
<223> OTHER INFORMATION: RVB185 CDRH1 aa

<400> SEQUENCE: 37

Gly Ala Pro Val Ser Gly Val Asn Ser Tyr
1               5                   10

<210> SEQ ID NO 38
<211> LENGTH: 7
<212> TYPE: PRT
<213> ORGANISM: Artificial Sequence
<220> FEATURE:
<223> OTHER INFORMATION: RVB185 CDRH2 aa

<400> SEQUENCE: 38

Ile Lys Tyr Ser Gly Ser Thr
1               5

<210> SEQ ID NO 39
<211> LENGTH: 11
<212> TYPE: PRT
<213> ORGANISM: Artificial Sequence
<220> FEATURE:
<223> OTHER INFORMATION: RVB185 CDRH3 aa

<400> SEQUENCE: 39

Ala Arg Gln Ser Thr Met Thr Gly Arg Asp Tyr
1               5                   10

<210> SEQ ID NO 40
<211> LENGTH: 8
<212> TYPE: PRT
<213> ORGANISM: Artificial Sequence
<220> FEATURE:
<223> OTHER INFORMATION: RVB185 CDRL1 aa

<400> SEQUENCE: 40

Arg Ser Asn Ile Gly Ser His Pro
1               5

<210> SEQ ID NO 41

<400> SEQUENCE: 41

000
```

<210> SEQ ID NO 42
<211> LENGTH: 9
<212> TYPE: PRT
<213> ORGANISM: Artificial Sequence
<220> FEATURE:
<223> OTHER INFORMATION: RVB185 CDRL2 long aa

<400> SEQUENCE: 42

Leu Ile Tyr Gly Asp Ser Gln Arg Pro
1               5

<210> SEQ ID NO 43
<211> LENGTH: 12
<212> TYPE: PRT
<213> ORGANISM: Artificial Sequence
<220> FEATURE:
<223> OTHER INFORMATION: RVB185 CDRL3 aa

<400> SEQUENCE: 43

Ala Ala Trp Asp Asp Ser Leu Ser Gly Leu Trp Val
1               5                   10

<210> SEQ ID NO 44
<211> LENGTH: 30
<212> TYPE: DNA
<213> ORGANISM: Artificial Sequence
<220> FEATURE:
<223> OTHER INFORMATION: RVB185 CDRH1 nuc

<400> SEQUENCE: 44 ggtgccccccg tcagtggtgt taactcctac                                    30

<210> SEQ ID NO 45
<211> LENGTH: 21
<212> TYPE: DNA
<213> ORGANISM: Artificial Sequence
<220> FEATURE:
<223> OTHER INFORMATION: RVB185 CDRH2 nuc

<400> SEQUENCE: 45
atcaagtaca gtgggagcac c                                              21

<210> SEQ ID NO 46
<211> LENGTH: 33
<212> TYPE: DNA
<213> ORGANISM: Artificial Sequence
<220> FEATURE:
<223> OTHER INFORMATION: RVB185 CDRH3 nuc

<400> SEQUENCE: 46
gccagacaaa gtactatgac gggccgggac tac                                 33

<210> SEQ ID NO 47
<211> LENGTH: 24
<212> TYPE: DNA
<213> ORGANISM: Artificial Sequence
<220> FEATURE:
<223> OTHER INFORMATION: RVB185 CDRL1 nuc

<400> SEQUENCE: 47
agatccaaca tcggaagcca tcct                                           24

<210> SEQ ID NO 48

<400> SEQUENCE: 48

000

<210> SEQ ID NO 49
<211> LENGTH: 27
<212> TYPE: DNA
<213> ORGANISM: Artificial Sequence
<220> FEATURE:
<223> OTHER INFORMATION: RVB185 CDRL2 long nuc

<400> SEQUENCE: 49
ctcatctatg gtgatagtca gcgaccc                                          27

<210> SEQ ID NO 50
<211> LENGTH: 36
<212> TYPE: DNA
<213> ORGANISM: Artificial Sequence
<220> FEATURE:
<223> OTHER INFORMATION: RVB185 CDRL3 nuc

<400> SEQUENCE: 50
gcagcatggg atgacagcct gagtggcctt tgggtg                                36

<210> SEQ ID NO 51
<211> LENGTH: 119
<212> TYPE: PRT
<213> ORGANISM: Artificial Sequence
<220> FEATURE:
<223> OTHER INFORMATION: RVB185 heavy chain aa

<400> SEQUENCE: 51

Gln Val Gln Leu Gln Glu Ser Gly Pro Gly Leu Val Lys Pro Ser Glu
1               5                   10                  15

Thr Leu Ser Leu Thr Cys Ser Val Ser Gly Ala Pro Val Ser Gly Val
            20                  25                  30

Asn Ser Tyr Trp Val Trp Ile Arg Gln Pro Pro Gly Lys Gly Leu Glu
        35                  40                  45

Trp Ile Ala Thr Ile Lys Tyr Ser Gly Ser Thr His Arg Ser Pro Ser
    50                  55                  60

Leu Arg Ser Arg Val Thr Ile Ser Val Asp Thr Ser Lys Asn Gln Phe
65                  70                  75                  80

Ser Leu Glu Leu Ser Ser Val Thr Ala Ala Asp Thr Ala Val Tyr Tyr
                85                  90                  95

Cys Ala Arg Gln Ser Thr Met Thr Gly Arg Asp Tyr Trp Gly Gln Gly
            100                 105                 110

Thr Leu Val Thr Val Ser Ser
        115

<210> SEQ ID NO 52
<211> LENGTH: 111
<212> TYPE: PRT
<213> ORGANISM: Artificial Sequence
<220> FEATURE:
<223> OTHER INFORMATION: RVB185 light chain aa

<400> SEQUENCE: 52

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Ser His
            20                  25                  30

Pro Val Asn Trp Tyr Gln Gln Leu Pro Gly Ala Ala Pro Lys Leu Leu
        35                  40                  45

Ile Tyr Gly Asp Ser Gln Arg Pro Ser Gly Val Pro Asp Arg Phe Ser
            50                  55                  60

Gly Ser Lys Ser Gly Pro Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                85                  90                  95

Ser Gly Leu Trp Val Phe Gly Gly Gly Thr Lys Leu Thr Val Leu
            100                 105                 110

<210> SEQ ID NO 53
<211> LENGTH: 358
<212> TYPE: DNA
<213> ORGANISM: Artificial Sequence
<220> FEATURE:
<223> OTHER INFORMATION: RVB185 heavy chain nuc

<400> SEQUENCE: 53
caggtgcagc tgcaggagtc gggcccagga ctggtgaagc cttcggagac cctgtccctc     60
acctgcagtg tctccggtgc ccccgtcagt ggtgttaact cctactgggt gtggatccgc    120 cagcccccccg ggaaggggct ggagtggatt gcgactatca agtacagtgg gagcacccac    180
cgtagcccgt cgctcaggag tcgagtcacc atatccgtag acacgtccaa gaatcagttc    240
tccctggagc tgagctctgt gaccgccgct gacacggctg tatattactg tgccagacaa    300
agtactatga cgggccggga ctactgggc agggaaccc tggtcaccgt ctcctcag        358

<210> SEQ ID NO 54
<211> LENGTH: 334
<212> TYPE: DNA
<213> ORGANISM: Artificial Sequence
<220> FEATURE:
<223> OTHER INFORMATION: RVB185 light chain nuc

<400> SEQUENCE: 54
cagtctgtgc tgactcagcc accctcagcg tctgggaccc ccgggcagag ggtcaccatc     60
tcttgttctg gaagcagatc caacatcgga agccatcctg taaactggta ccagcagctc    120
ccgggagcgg cccccaagct cctcatctat ggtgatagta gcgaccctc agggtccct     180 gaccgattct ctggctccaa gtctggcccc tcagcctccc tggccatcag tggactccag    240
tctgaagatg aggctgatta ttactgtgca gcatgggatg acagcctgag tggccttggg    300
gtgttcggcg gagggaccaa gctgaccgtc ctaa                                334

<210> SEQ ID NO 55
<211> LENGTH: 8
<212> TYPE: PRT
<213> ORGANISM: Artificial Sequence
<220> FEATURE:
<223> OTHER INFORMATION: RVB492 CDRH1 aa

<400> SEQUENCE: 55

Gly Phe Ser Phe Ser Ser Tyr Ala
 1               5

<210> SEQ ID NO 56
<211> LENGTH: 8
<212> TYPE: PRT
<213> ORGANISM: Artificial Sequence
<220> FEATURE:
<223> OTHER INFORMATION: RVB492 CDRH2 aa

<400> SEQUENCE: 56

```
Leu Asn Ser Ile Asp His Arg Thr
1               5

<210> SEQ ID NO 57
<211> LENGTH: 18
<212> TYPE: PRT
<213> ORGANISM: Artificial Sequence
<220> FEATURE:
<223> OTHER INFORMATION: RVB492 CDRH3 aa

<400> SEQUENCE: 57

Ala Arg Gly Val Gly Leu Trp Phe Gly Glu Leu Ser Trp Asn Tyr Phe
1               5                   10                  15

Asp Tyr

<210> SEQ ID NO 58
<211> LENGTH: 9
<212> TYPE: PRT
<213> ORGANISM: Artificial Sequence
<220> FEATURE:
<223> OTHER INFORMATION: RVB492 CDRL1 aa

<400> SEQUENCE: 58

Ser Asn Asp Ile Gly Gly Tyr Asn Tyr
1               5

<210> SEQ ID NO 59

<400> SEQUENCE: 59

000

<210> SEQ ID NO 60
<211> LENGTH: 9
<212> TYPE: PRT
<213> ORGANISM: Artificial Sequence
<220> FEATURE:
<223> OTHER INFORMATION: RVB492 CDRL2 long aa

<400> SEQUENCE: 60

Met Ile Phe Tyr Val Asn Lys Arg Pro
1               5

<210> SEQ ID NO 61
<211> LENGTH: 9
<212> TYPE: PRT
<213> ORGANISM: Artificial Sequence
<220> FEATURE:
<223> OTHER INFORMATION: RVB492 CDRL3 aa

<400> SEQUENCE: 61

Cys Ser Phe Ala Gly Ser Tyr Ser Leu
1               5

<210> SEQ ID NO 62
<211> LENGTH: 24
<212> TYPE: DNA
<213> ORGANISM: Artificial Sequence
<220> FEATURE:
<223> OTHER INFORMATION: RVB492 CDRH1 nuc

<400> SEQUENCE: 62
ggattcagct ttagcagcta tgcc                                          24

<210> SEQ ID NO 63
```

```
<211> LENGTH: 24
<212> TYPE: DNA
<213> ORGANISM: Artificial Sequence
<220> FEATURE:
<223> OTHER INFORMATION: RVB492 CDRH2 nuc

<400> SEQUENCE: 63
cttaattcta ttgatcatag aaca                                          24

<210> SEQ ID NO 64
<211> LENGTH: 54
<212> TYPE: DNA
<213> ORGANISM: Artificial Sequence
<220> FEATURE:
<223> OTHER INFORMATION: RVB492 CDRH3 nuc

<400> SEQUENCE: 64
gctcgggggg tgggactatg gttcggtgaa ttatcctgga attactttga ctac         54

<210> SEQ ID NO 65
<211> LENGTH: 27
<212> TYPE: DNA
<213> ORGANISM: Artificial Sequence
<220> FEATURE:
<223> OTHER INFORMATION: RVB492 CDRL1 nuc

<400> SEQUENCE: 65
agcaatgata ttggtggtta taactat                                       27

<210> SEQ ID NO 66

<400> SEQUENCE: 66

000

<210> SEQ ID NO 67
<211> LENGTH: 27
<212> TYPE: DNA
<213> ORGANISM: Artificial Sequence
<220> FEATURE:
<223> OTHER INFORMATION: RVB492 CDRL2 long nuc

<400> SEQUENCE: 67 atgattttt atgtcaataa gcggccc                                        27

<210> SEQ ID NO 68
<211> LENGTH: 27
<212> TYPE: DNA
<213> ORGANISM: Artificial Sequence
<220> FEATURE:
<223> OTHER INFORMATION: RVB492 CDRL3 nuc

<400> SEQUENCE: 68
tgctcatttg caggcagtta ctcctta                                       27

<210> SEQ ID NO 69
<211> LENGTH: 125
<212> TYPE: PRT
<213> ORGANISM: Artificial Sequence
<220> FEATURE:
<223> OTHER INFORMATION: RVB492 heavy chain variant 1 aa

<400> SEQUENCE: 69

Glu Val Gln Leu Met Glu Ser Gly Gly Gly Leu Val Gln Pro Gly Gly
1               5                   10                  15

Ser Met Arg Leu Tyr Cys Ala Ala Ser Gly Phe Ser Phe Ser Ser Tyr
```

```
                20                  25                  30
Ala Met Ser Trp Val Arg Gln Ala Pro Gly Lys Gly Leu Glu Trp Val
            35                  40                  45

Ser Ser Leu Asn Ser Ile Asp His Arg Thr Asp Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Val Glu Asp Ser Ala Met Tyr Tyr Cys
                85                  90                  95

Ala Arg Gly Val Gly Leu Trp Phe Gly Glu Leu Ser Trp Asn Tyr Phe
            100                 105                 110

Asp Tyr Trp Gly Gln Gly Thr Leu Val Thr Val Ser Ser
        115                 120                 125

<210> SEQ ID NO 70
<211> LENGTH: 125
<212> TYPE: PRT
<213> ORGANISM: Artificial Sequence
<220> FEATURE:
<223> OTHER INFORMATION: RVB492 heavy chain variant 2 aa

<400> SEQUENCE: 70

Glu Val Gln Leu Val Gln Ser Gly Gly Gly Leu Val Gln Pro Gly Gly
1               5                   10                  15

Ser Met Arg Leu Tyr Cys Ala Ala Ser Gly Phe Ser Phe Ser Ser Tyr
                20                  25                  30

Ala Met Ser Trp Val Arg Gln Ala Pro Gly Lys Gly Leu Glu Trp Val
            35                  40                  45

Ser Ser Leu Asn Ser Ile Asp His Arg Thr Asp Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Val Glu Asp Ser Ala Met Tyr Tyr Cys
                85                  90                  95

Ala Arg Gly Val Gly Leu Trp Phe Gly Glu Leu Ser Trp Asn Tyr Phe
            100                 105                 110

Asp Tyr Trp Gly Gln Gly Thr Leu Val Thr Val Ser Ser
        115                 120                 125

<210> SEQ ID NO 71
<211> LENGTH: 109
<212> TYPE: PRT
<213> ORGANISM: Artificial Sequence
<220> FEATURE:
<223> OTHER INFORMATION: RVB492 light chain aa

<400> SEQUENCE: 71

Gln Ser Ala Leu Thr Gln Pro Arg Ser Val Ser Gly Ser Pro Gly Gln
1               5                   10                  15

Ser Val Thr Ile Ser Cys Thr Gly Thr Ser Asn Asp Ile Gly Gly Tyr
                20                  25                  30

Asn Tyr Val Ser Trp Tyr Gln Gln His Pro Gly Lys Ala Pro Lys Leu
            35                  40                  45

Met Ile Phe Tyr Val Asn Lys Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80
```

Gln Ala Glu Asp Glu Ala Asp Tyr Tyr Cys Cys Ser Phe Ala Gly Ser
            85                  90                  95

Tyr Ser Leu Phe Gly Arg Gly Thr Lys Leu Thr Val Leu
        100                 105

<210> SEQ ID NO 72
<211> LENGTH: 376
<212> TYPE: DNA
<213> ORGANISM: Artificial Sequence
<220> FEATURE:
<223> OTHER INFORMATION: RVB492 heavy chain variant 1 nuc

<400> SEQUENCE: 72
gaggtgcagc tgatggagtc tggggagggc ctggtacagc cggggggtc catgagactc      60 tactgtgcag cctctggatt cagctttagc agctatgcca tgagctgggt ccgccaggct    120
ccagggaagg ggctcgagtg gtctcaagt cttaattcta ttgatcatag aacagactat    180
gcagactccg tgaagggccg gttcaccatc tccagagaca attccaagaa caccctgtat    240
ttacaaatgg acagcctgag agtcgaggac tcggccatgt attactgtgc tcgggggtg    300 ggactatggt tcggtgaatt atcctggaat tactttgact actggggcca gggaaccctg    360
gtcaccgtct cctcag                                                    376

<210> SEQ ID NO 73
<211> LENGTH: 376
<212> TYPE: DNA
<213> ORGANISM: Artificial Sequence
<220> FEATURE:
<223> OTHER INFORMATION: RVB492 heavy chain variant 2 nuc

<400> SEQUENCE: 73
gaggtgcagc tggtgcagtc tggggagggc ctggtacagc cggggggtc catgagactc      60 tactgtgcag cctctggatt cagctttagc agctatgcca tgagctgggt ccgccaggct    120
ccagggaagg ggctcgagtg gtctcaagt cttaattcta ttgatcatag aacagactat    180
gcagactccg tgaagggccg gttcaccatc tccagagaca attccaagaa caccctgtat    240
ttacaaatgg acagcctgag agtcgaggac tcggccatgt attactgtgc tcgggggtg    300 ggactatggt tcggtgaatt atcctggaat tactttgact actggggcca gggaaccctg    360
gtcaccgtct cctcag                                                    376

<210> SEQ ID NO 74
<211> LENGTH: 328
<212> TYPE: DNA
<213> ORGANISM: Artificial Sequence
<220> FEATURE:
<223> OTHER INFORMATION: RVB492 light chain nuc

<400> SEQUENCE: 74
cagtctgccc tgactcagcc tcgctcagtg tccgggtctc ctggacagtc agtcaccatc      60
tcctgcactg gaaccagcaa tgatattggt ggttataact atgtctcctg gtaccaacaa    120
cacccaggca aagcccccaa actcatgatt ttttatgtca ataagcggcc ctcaggggtc    180
cctgatcgct tctctggctc caagtctggc aacacggcct ccctgaccat ctctgggctc    240
caggctgagg atgaagctga ttattactgc tgctcatttg caggcagtta ctccttattc    300
ggcagaggga ccaagctgac cgtcctag                                        328

<210> SEQ ID NO 75
<211> LENGTH: 8

```
<212> TYPE: PRT
<213> ORGANISM: Artificial Sequence
<220> FEATURE:
<223> OTHER INFORMATION: RVC3 CDRH1 aa

<400> SEQUENCE: 75

Thr Phe Thr Phe Arg Asn Tyr Ala
1               5

<210> SEQ ID NO 76
<211> LENGTH: 8
<212> TYPE: PRT
<213> ORGANISM: Artificial Sequence
<220> FEATURE:
<223> OTHER INFORMATION: RVC3 CDRH2 aa

<400> SEQUENCE: 76

Ile Ser Ala Ser Gly Ser Ser Thr
1               5

<210> SEQ ID NO 77
<211> LENGTH: 16
<212> TYPE: PRT
<213> ORGANISM: Artificial Sequence
<220> FEATURE:
<223> OTHER INFORMATION: RVC3 CDRH3 aa

<400> SEQUENCE: 77

Ala Lys Phe Ala His Asp Phe Trp Ser Gly Tyr Ser Tyr Phe Asp Ser
1               5                   10                  15

<210> SEQ ID NO 78
<211> LENGTH: 6
<212> TYPE: PRT
<213> ORGANISM: Artificial Sequence
<220> FEATURE:
<223> OTHER INFORMATION: RVC3 CDRL1 aa

<400> SEQUENCE: 78

Gln Ser Val Asn Ser Asn
1               5

<210> SEQ ID NO 79

<400> SEQUENCE: 79

000

<210> SEQ ID NO 80
<211> LENGTH: 9
<212> TYPE: PRT
<213> ORGANISM: Artificial Sequence
<220> FEATURE:
<223> OTHER INFORMATION: RVC3 CDRL2 long aa

<400> SEQUENCE: 80

Leu Ile Tyr Gly Ala Ser Thr Arg Ala
1               5

<210> SEQ ID NO 81
<211> LENGTH: 10
<212> TYPE: PRT
<213> ORGANISM: Artificial Sequence
<220> FEATURE:
<223> OTHER INFORMATION: RVC3 CDRL3 aa

<400> SEQUENCE: 81
```

```
Gln Gln Tyr Asn Asn Trp Val Ser Ile Thr
1               5                   10
```

<210> SEQ ID NO 82
<211> LENGTH: 24
<212> TYPE: DNA
<213> ORGANISM: Artificial Sequence
<220> FEATURE:
<223> OTHER INFORMATION: RVC3 CDRH1 nuc

<400> SEQUENCE: 82
acattcacgt ttagaaacta tgcc                                          24

<210> SEQ ID NO 83
<211> LENGTH: 24
<212> TYPE: DNA
<213> ORGANISM: Artificial Sequence
<220> FEATURE:
<223> OTHER INFORMATION: RVC3 CDRH2 nuc

<400> SEQUENCE: 83
attagtgcta gtggtagtag cacg                                          24

<210> SEQ ID NO 84
<211> LENGTH: 48
<212> TYPE: DNA
<213> ORGANISM: Artificial Sequence
<220> FEATURE:
<223> OTHER INFORMATION: RVC3 CDRH3 nuc

<400> SEQUENCE: 84
gcgaaatttg ctcacgattt ttggagtggt tattcttact ttgactcc                48

<210> SEQ ID NO 85
<211> LENGTH: 18
<212> TYPE: DNA
<213> ORGANISM: Artificial Sequence
<220> FEATURE:
<223> OTHER INFORMATION: RVC3 CDRL1 nuc

<400> SEQUENCE: 85
cagagtgtta acagcaac                                                 18

<210> SEQ ID NO 86

<400> SEQUENCE: 86

000

<210> SEQ ID NO 87
<211> LENGTH: 27
<212> TYPE: DNA
<213> ORGANISM: Artificial Sequence
<220> FEATURE:
<223> OTHER INFORMATION: RVC3 CDRL2 long nuc

<400> SEQUENCE: 87
ctcatctatg gtgcatccac cagggcc                                       27

<210> SEQ ID NO 88
<211> LENGTH: 30
<212> TYPE: DNA
<213> ORGANISM: Artificial Sequence
<220> FEATURE:
<223> OTHER INFORMATION: RVC3 CDRL3 nuc

<400> SEQUENCE: 88
cagcagtata ataattgggt ttcgatcacc                                          30

<210> SEQ ID NO 89
<211> LENGTH: 123
<212> TYPE: PRT
<213> ORGANISM: Artificial Sequence
<220> FEATURE:
<223> OTHER INFORMATION: RVC3 heavy chain aa

<400> SEQUENCE: 89

Glu Val Gln Leu Leu Glu Ser Gly Gly Gly Leu Val Gln Pro Gly Gly
1               5                   10                  15

Ser Leu Arg Leu Ser Cys Ala Ala Ser Thr Phe Thr Phe Arg Asn Tyr
            20                  25                  30

Ala Met Ser Trp Val Arg Gln Ala Pro Gly Lys Gly Leu Asp Trp Val
        35                  40                  45

Ser Gly Ile Ser Ala Ser Gly Ser Ser Thr Asn Tyr Ala Ala Ser Leu
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Ala His Asp Phe Trp Ser Gly Tyr Ser Tyr Phe Asp Ser
            100                 105                 110

Trp Gly Gln Gly Thr Leu Val Thr Val Ser Ser
        115                 120

<210> SEQ ID NO 90
<211> LENGTH: 108
<212> TYPE: PRT
<213> ORGANISM: Artificial Sequence
<220> FEATURE:
<223> OTHER INFORMATION: RVC3 light chain aa

<400> SEQUENCE: 90

Glu Ile Val Met Thr Gln Ser Pro Ala Thr Leu Ser Val Ser Pro Gly
1               5                   10                  15

Glu Arg Ala Thr Leu Ser Cys Arg Ala Gly Gln Ser Val Asn Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Val Ser
                85                  90                  95

Ile Thr Phe Gly Gln Gly Thr Arg Leu Glu Ile Lys
            100                 105

<210> SEQ ID NO 91
<211> LENGTH: 370
<212> TYPE: DNA
<213> ORGANISM: Artificial Sequence
<220> FEATURE:
<223> OTHER INFORMATION: RVC3 heavy chain nuc

<400> SEQUENCE: 91
gaggtgcagc tgttggagtc tgggggaggc ctggtgcagc cggggggtc cctgagactc      60

```
tcctgtgcag cctctacatt cacgtttaga aactatgcca tgtcctgggt ccgccaggct      120
ccagggaagg ggctggactg ggtctcaggg attagtgcta gtggtagtag cacgaattat      180
gcagcctccc tgaagggccg atttaccatc tccagagaca attccaagaa cacattgtat      240
ctgcaaatga acagcctgag agccgaggac acggccgtct attactgtgc gaaatttgct      300
cacgattttt ggagtggtta ttcttacttt gactcctggg gccagggaac cctggtcacc      360
gtctcctcag                                                            370

<210> SEQ ID NO 92
<211> LENGTH: 325
<212> TYPE: DNA
<213> ORGANISM: Artificial Sequence
<220> FEATURE:
<223> OTHER INFORMATION: RVC3 light chain nuc

<400> SEQUENCE: 92
gaaatagtga tgacgcagtc tccagccacc ctgtctgtgt ctccagggga aagagccacc       60
ctctcctgca gggccggtca gagtgttaac agcaacttag cctggtacca gcagaaacct      120
gggcaggctc ccagactcct catctatggt gcatccacca gggccactgg tatcccagcc      180
aggttcagtg gcagtgggtc tgggacagag ttcactctca ccatcagcag cctgcagtct      240
gaagattttg cagtttatta ctgtcagcag tataataatt gggtttcgat caccttcggc      300
caagggacac gactggagat taaac                                            325

<210> SEQ ID NO 93
<211> LENGTH: 10
<212> TYPE: PRT
<213> ORGANISM: Artificial Sequence
<220> FEATURE:
<223> OTHER INFORMATION: RVC20 CDRH1 aa

<400> SEQUENCE: 93

Gly Gly Ser Phe Ser Ser Gly Ser Tyr Ser
1               5                   10

<210> SEQ ID NO 94
<211> LENGTH: 7
<212> TYPE: PRT
<213> ORGANISM: Artificial Sequence
<220> FEATURE:
<223> OTHER INFORMATION: RVC20 CDRH2 aa

<400> SEQUENCE: 94

Ile Tyr Tyr Ser Gly Ser Thr
1               5

<210> SEQ ID NO 95
<211> LENGTH: 16
<212> TYPE: PRT
<213> ORGANISM: Artificial Sequence
<220> FEATURE:
<223> OTHER INFORMATION: RVC20 CDRH3 aa

<400> SEQUENCE: 95

Ala Arg Gly Thr Tyr Ser Asp Phe Trp Ser Gly Ser Pro Leu Asp Tyr
1               5                   10                  15

<210> SEQ ID NO 96
<211> LENGTH: 6
<212> TYPE: PRT
<213> ORGANISM: Artificial Sequence
```

```
<220> FEATURE:
<223> OTHER INFORMATION: RVC20 CDRL1 aa

<400> SEQUENCE: 96

Gln Gly Ile Ser Asn Tyr
1               5

<210> SEQ ID NO 97

<400> SEQUENCE: 97

000

<210> SEQ ID NO 98
<211> LENGTH: 9
<212> TYPE: PRT
<213> ORGANISM: Artificial Sequence
<220> FEATURE:
<223> OTHER INFORMATION: RVC20 CDRL2 long aa

<400> SEQUENCE: 98

Leu Ile Tyr Ala Ala Ser Ser Leu Gln
1               5

<210> SEQ ID NO 99
<211> LENGTH: 9
<212> TYPE: PRT
<213> ORGANISM: Artificial Sequence
<220> FEATURE:
<223> OTHER INFORMATION: RVC20 CDRL3 aa

<400> SEQUENCE: 99

Gln Gln Tyr Asp Thr Tyr Pro Leu Thr
1               5

<210> SEQ ID NO 100
<211> LENGTH: 30
<212> TYPE: DNA
<213> ORGANISM: Artificial Sequence
<220> FEATURE:
<223> OTHER INFORMATION: RVC20 CDRH1 nuc

<400> SEQUENCE: 100
ggtggctcct tcagcagtgg aagttactcc                                      30

<210> SEQ ID NO 101
<211> LENGTH: 21
<212> TYPE: DNA
<213> ORGANISM: Artificial Sequence
<220> FEATURE:
<223> OTHER INFORMATION: RVC20 CDRH2 nuc

<400> SEQUENCE: 101
atctattaca gtgggagcac t                                               21

<210> SEQ ID NO 102
<211> LENGTH: 48
<212> TYPE: DNA
<213> ORGANISM: Artificial Sequence
<220> FEATURE:
<223> OTHER INFORMATION: RVC20 CDRH3 nuc

<400> SEQUENCE: 102
gcgagaggca cgtattccga tttttggagt ggttcccctt tagactac                  48

<210> SEQ ID NO 103
```

```
<211> LENGTH: 18
<212> TYPE: DNA
<213> ORGANISM: Artificial Sequence
<220> FEATURE:
<223> OTHER INFORMATION: RVC20 CDRL1 nuc

<400> SEQUENCE: 103
cagggcatta gcaattat                                                    18

<210> SEQ ID NO 104

<400> SEQUENCE: 104

000

<210> SEQ ID NO 105
<211> LENGTH: 27
<212> TYPE: DNA
<213> ORGANISM: Artificial Sequence
<220> FEATURE:
<223> OTHER INFORMATION: RVC20 CDRL2 long nuc

<400> SEQUENCE: 105
ctgatctatg ctgcatccag tttgcaa                                          27

<210> SEQ ID NO 106
<211> LENGTH: 27
<212> TYPE: DNA
<213> ORGANISM: Artificial Sequence
<220> FEATURE:
<223> OTHER INFORMATION: RVC20 CDRL3 nuc

<400> SEQUENCE: 106
caacagtatg atacttaccc tctcact                                          27

<210> SEQ ID NO 107
<211> LENGTH: 124
<212> TYPE: PRT
<213> ORGANISM: Artificial Sequence
<220> FEATURE:
<223> OTHER INFORMATION: RVC20 heavy chain aa

<400> SEQUENCE: 107

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Phe Ser Ser Gly
            20                  25                  30

Ser Tyr Ser Trp Asn Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Met Ser Val His Thr Ser Lys Asn Gln Phe
65                  70                  75                  80

Ser Leu Lys Leu Asn Ser Ile Thr Ala Ala Asp Thr Ala Val Tyr Tyr
                85                  90                  95

Cys Ala Arg Gly Thr Tyr Ser Asp Phe Trp Ser Gly Ser Pro Leu Asp
            100                 105                 110

Tyr Trp Gly Gln Gly Thr Leu Val Thr Val Ser Ser
        115                 120

<210> SEQ ID NO 108
<211> LENGTH: 107
<212> TYPE: PRT
```

<213> ORGANISM: Artificial Sequence
<220> FEATURE:
<223> OTHER INFORMATION: RVC20 light chain aa

<400> SEQUENCE: 108

```
Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Val Thr Tyr Phe Cys Gln Gln Tyr Asp Thr Tyr Pro Leu
                85                  90                  95

Thr Phe Gly Gly Gly Thr Lys Val Glu Ile Lys
            100                 105
```

<210> SEQ ID NO 109
<211> LENGTH: 373
<212> TYPE: DNA
<213> ORGANISM: Artificial Sequence
<220> FEATURE:
<223> OTHER INFORMATION: RVC20 heavy chain nuc

<400> SEQUENCE: 109

```
caggtgcagc tgcaggagtc gggcccagga ctggtgaagc cttcacagac cctgtccctc        60
acctgcactg tctccggtgg ctccttcagc agtggaagtt actcctggaa ctggatccgc       120
cagcacccag ggaagggcct ggagtggatt gggtacatct attacagtgg gagcacttat       180
tacaacccgt ccctcaagag tcgagttacc atgtcagtac acacgtctaa gaaccagttc       240
tccctgaagc tgaactctat aactgccgcg gacacggccg tgtattactg tcgagaggc       300
acgtattccg atttttggag tggttcccct ttagactact ggggccaggg aaccctggtc       360
accgtctcct cag                                                          373
```

<210> SEQ ID NO 110
<211> LENGTH: 322
<212> TYPE: DNA
<213> ORGANISM: Artificial Sequence
<220> FEATURE:
<223> OTHER INFORMATION: RVC20 light chain nuc

<400> SEQUENCE: 110

```
gacatccaga tgacccagtc tccatcctca ctgtctgcat ctgtaggaga cagagtcacc        60
atcacttgtc gggcgagtca gggcattagc aattatttag cctggtttca gcagaaacca       120
gggaaagccc ctaagtccct gatctatgct gcatccagtt tgcaaagtgg ggtcccatca       180
aggttcagcg gcagtggatc tgggacagat ttcactctca ccatcaacag cctgcagcct       240
gaagattttg taacttattt ctgccaacag tatgatactt accctctcac tttcggcgga       300
gggaccaagg tggagatcaa ac                                                322
```

<210> SEQ ID NO 111
<211> LENGTH: 10
<212> TYPE: PRT
<213> ORGANISM: Artificial Sequence
<220> FEATURE:

<223> OTHER INFORMATION: RVC21 CDRH1 aa

<400> SEQUENCE: 111

Gly Gly Ser Ile Ser Asn Pro Asn Tyr Tyr
1               5                   10

<210> SEQ ID NO 112
<211> LENGTH: 7
<212> TYPE: PRT
<213> ORGANISM: Artificial Sequence
<220> FEATURE:
<223> OTHER INFORMATION: RVC21 CDRH2 aa

<400> SEQUENCE: 112

Ile Tyr Tyr Asn Gly Tyr Thr
1               5

<210> SEQ ID NO 113
<211> LENGTH: 13
<212> TYPE: PRT
<213> ORGANISM: Artificial Sequence
<220> FEATURE:
<223> OTHER INFORMATION: RVC21 CDRH3 aa

<400> SEQUENCE: 113

Ala Thr Gln Ser Thr Met Thr Thr Ile Ala Gly His Tyr
1               5                   10

<210> SEQ ID NO 114
<211> LENGTH: 8
<212> TYPE: PRT
<213> ORGANISM: Artificial Sequence
<220> FEATURE:
<223> OTHER INFORMATION: RVC21 CDRL1 aa

<400> SEQUENCE: 114

Thr Ser Asn Ile Gly Asn Ser Tyr
1               5

<210> SEQ ID NO 115

<400> SEQUENCE: 115

000

<210> SEQ ID NO 116
<211> LENGTH: 9
<212> TYPE: PRT
<213> ORGANISM: Artificial Sequence
<220> FEATURE:
<223> OTHER INFORMATION: RVC21 CDRL2 long aa

<400> SEQUENCE: 116

Leu Ile Tyr Asp Asn Asn Lys Arg Pro
1               5

<210> SEQ ID NO 117
<211> LENGTH: 11
<212> TYPE: PRT
<213> ORGANISM: Artificial Sequence
<220> FEATURE:
<223> OTHER INFORMATION: RVC21 CDRL3 aa

<400> SEQUENCE: 117

Gly Thr Trp Asp Ser Ser Leu Asn Ala Tyr Val
1               5                   10

<210> SEQ ID NO 118
<211> LENGTH: 30
<212> TYPE: DNA
<213> ORGANISM: Artificial Sequence
<220> FEATURE:
<223> OTHER INFORMATION: RVC21 CDRH1 nuc

<400> SEQUENCE: 118
ggtggctcca tcagcaaccc taactactac                              30

<210> SEQ ID NO 119
<211> LENGTH: 21
<212> TYPE: DNA
<213> ORGANISM: Artificial Sequence
<220> FEATURE:
<223> OTHER INFORMATION: RVC21 CDRH2 nuc

<400> SEQUENCE: 119
atctattata atgggtacac c                                       21

<210> SEQ ID NO 120
<211> LENGTH: 39
<212> TYPE: DNA
<213> ORGANISM: Artificial Sequence
<220> FEATURE:
<223> OTHER INFORMATION: RVC21 CDRH3 nuc

<400> SEQUENCE: 120
gcgacgcaat ctacgatgac taccatagcg ggccactac                    39

<210> SEQ ID NO 121
<211> LENGTH: 24
<212> TYPE: DNA
<213> ORGANISM: Artificial Sequence
<220> FEATURE:
<223> OTHER INFORMATION: RVC21 CDRL1 nuc

<400> SEQUENCE: 121
acatccaaca ttgggaattc ttat                                    24

<210> SEQ ID NO 122

<400> SEQUENCE: 122

000

<210> SEQ ID NO 123
<211> LENGTH: 27
<212> TYPE: DNA
<213> ORGANISM: Artificial Sequence
<220> FEATURE:
<223> OTHER INFORMATION: RVC21 CDRL2 long nuc

<400> SEQUENCE: 123
ctcatttatg acaataataa gcgaccc                                 27

<210> SEQ ID NO 124
<211> LENGTH: 33
<212> TYPE: DNA
<213> ORGANISM: Artificial Sequence
<220> FEATURE:
<223> OTHER INFORMATION: RVC21 CDRL3 nuc

<400> SEQUENCE: 124
ggaacatggg acagcagcct gaatgcttat gtc                          33

<210> SEQ ID NO 125
<211> LENGTH: 121
<212> TYPE: PRT
<213> ORGANISM: Artificial Sequence
<220> FEATURE:
<223> OTHER INFORMATION: RVC21 heavy chain aa

<400> SEQUENCE: 125

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Pro
            20                  25                  30

Asn Tyr Tyr Trp Gly Trp Ile Arg Gln Pro Pro Gly Lys Gly Leu Glu
        35                  40                  45

Trp Ile Gly Ser Ile Tyr Tyr Asn Gly Tyr Thr Tyr Tyr Asn Pro Ser
    50                  55                  60

Leu Lys Ser Arg Val Thr Ile Ser Val Asp Lys Ser Lys Asp Gln Phe
65                  70                  75                  80

Phe Leu Lys Met Thr Ser Leu Thr Ala Ala Asp Thr Ala Val Tyr Tyr
                85                  90                  95

Cys Ala Thr Gln Ser Thr Met Thr Thr Ile Ala Gly His Tyr Trp Gly
            100                 105                 110

Gln Gly Thr Leu Val Thr Val Ser Ser
        115                 120
```

<210> SEQ ID NO 126
<211> LENGTH: 110
<212> TYPE: PRT
<213> ORGANISM: Artificial Sequence
<220> FEATURE:
<223> OTHER INFORMATION: RVC21 light chain aa

<400> SEQUENCE: 126

```
Gln Ser Val Leu Thr Gln Ala Pro Ser Val Ser Ala Ala Pro Gly Leu
1               5                   10                  15

Lys Val Thr Ile Ser Cys Ser Gly Ser Thr Ser Asn Ile Gly Asn Ser
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Asp Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Asn Ala Tyr Val Phe Gly Thr Gly Thr Lys Val Thr Val Leu
            100                 105                 110
```

<210> SEQ ID NO 127
<211> LENGTH: 364
<212> TYPE: DNA
<213> ORGANISM: Artificial Sequence
<220> FEATURE:
<223> OTHER INFORMATION: RVC21 heavy chain nuc

<400> SEQUENCE: 127

```
cagctgcagc tgcaggagtc gggcccagga ctggtgaagc cttcggagac cctgtccctc    60
acgtgcactg tctctggtgg ctccatcagc aaccctaact actactgggg ctggatccgc   120
```

-continued

```
cagcccccag ggaagggtct ggaatggatt gggagtatct attataatgg gtacacctac    180
tacaacccgt ccctcaagag tcgagttacc atatccgtgg acaagtccaa ggaccagttc    240
tttctgaaga tgacctctct gaccgccgca gacacggctg tgtattactg tgcgacgcaa    300
tctacgatga ctaccatagc gggccactac tggggccagg aaccctggt caccgtctcc    360 tcag                                                                 364
```

<210> SEQ ID NO 128
<211> LENGTH: 331
<212> TYPE: DNA
<213> ORGANISM: Artificial Sequence
<220> FEATURE:
<223> OTHER INFORMATION: RVC21 light chain nuc

<400> SEQUENCE: 128

```
cagtctgtat tgacgcaggc gccctcagtg tctgcggccc caggactaaa ggtcaccatc     60
tcctgctctg gaagcacatc caacattggg aattcttatg tatcctggta ccagcagctc    120
ccaggaacag ccccaaaact cctcatttat gacaataata gcgaccctc agggattcct    180 gaccgattct ctggctccaa gtctgacacg tcagccaccc tgggcatcac cggactccag    240
actggggacg aggccgatta ttactgcgga acatgggaca gcagcctgaa tgcttatgtc    300
ttcggaactg ggaccaaggt caccgtccta g                                   331
```

<210> SEQ ID NO 129
<211> LENGTH: 8
<212> TYPE: PRT
<213> ORGANISM: Artificial Sequence
<220> FEATURE:
<223> OTHER INFORMATION: RVC38 CDRH1 aa

<400> SEQUENCE: 129

Gly Gly Thr Phe Ser Ser Tyr Ala
1               5

<210> SEQ ID NO 130
<211> LENGTH: 8
<212> TYPE: PRT
<213> ORGANISM: Artificial Sequence
<220> FEATURE:
<223> OTHER INFORMATION: RVC38 CDRH2 aa

<400> SEQUENCE: 130

Ile Met Pro Met Phe Val Ala Ala
1               5

<210> SEQ ID NO 131
<211> LENGTH: 14
<212> TYPE: PRT
<213> ORGANISM: Artificial Sequence
<220> FEATURE:
<223> OTHER INFORMATION: RVC38 CDRH3 aa

<400> SEQUENCE: 131

Ala Arg Gly Asp Gly Tyr Asn Tyr Lys Trp Tyr Phe Asp Leu
1               5                   10

<210> SEQ ID NO 132
<211> LENGTH: 6
<212> TYPE: PRT
<213> ORGANISM: Artificial Sequence
<220> FEATURE:
<223> OTHER INFORMATION: RVC38 CDRL1 aa

```
<400> SEQUENCE: 132

Gln Asp Ile Ser Asn Tyr
1               5

<210> SEQ ID NO 133

<400> SEQUENCE: 133

000

<210> SEQ ID NO 134
<211> LENGTH: 9
<212> TYPE: PRT
<213> ORGANISM: Artificial Sequence
<220> FEATURE:
<223> OTHER INFORMATION: RVC38 CDRL2 long aa

<400> SEQUENCE: 134

Leu Ile Tyr Ala Ala Ser Thr Leu Gln
1               5

<210> SEQ ID NO 135
<211> LENGTH: 10
<212> TYPE: PRT
<213> ORGANISM: Artificial Sequence
<220> FEATURE:
<223> OTHER INFORMATION: RVC38 CDRL3 aa

<400> SEQUENCE: 135

Gln Gln Leu Asp Thr Tyr Val Ala Leu Thr
1               5                   10

<210> SEQ ID NO 136
<211> LENGTH: 24
<212> TYPE: DNA
<213> ORGANISM: Artificial Sequence
<220> FEATURE:
<223> OTHER INFORMATION: RVC38 CDRH1 nuc

<400> SEQUENCE: 136
ggaggcacct tcagcagcta tgcc                                          24

<210> SEQ ID NO 137
<211> LENGTH: 24
<212> TYPE: DNA
<213> ORGANISM: Artificial Sequence
<220> FEATURE:
<223> OTHER INFORMATION: RVC38 CDRH2 nuc

<400> SEQUENCE: 137
atcatgccta tgtttgtggc ggca                                          24

<210> SEQ ID NO 138
<211> LENGTH: 42
<212> TYPE: DNA
<213> ORGANISM: Artificial Sequence
<220> FEATURE:
<223> OTHER INFORMATION: RVC38 CDRH3 nuc

<400> SEQUENCE: 138
gcgagagggg atggctacaa ttacaagtgg tattttgacc tt                      42

<210> SEQ ID NO 139
<211> LENGTH: 18
<212> TYPE: DNA
<213> ORGANISM: Artificial Sequence
```

<220> FEATURE:
<223> OTHER INFORMATION: RVC38 CDRL1 nuc

<400> SEQUENCE: 139
caggacatta gtaattat                                                    18

<210> SEQ ID NO 140

<400> SEQUENCE: 140

000

<210> SEQ ID NO 141
<211> LENGTH: 27
<212> TYPE: DNA
<213> ORGANISM: Artificial Sequence
<220> FEATURE:
<223> OTHER INFORMATION: RVC38 CDRL2 long nuc

<400> SEQUENCE: 141
ctgatctatg ctgcatccac tttgcaa                                          27

<210> SEQ ID NO 142
<211> LENGTH: 30
<212> TYPE: DNA
<213> ORGANISM: Artificial Sequence
<220> FEATURE:
<223> OTHER INFORMATION: RVC38 CDRL3 nuc

<400> SEQUENCE: 142
caacagcttg atacttacgt cgcgctcact                                       30

<210> SEQ ID NO 143
<211> LENGTH: 121
<212> TYPE: PRT
<213> ORGANISM: Artificial Sequence
<220> FEATURE:
<223> OTHER INFORMATION: RVC38 heavy chain aa

<400> SEQUENCE: 143

Glu Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Ser Tyr
            20                  25                  30

Ala Ile Ser Trp Val Arg Gln Ala Pro Gly Leu Gly Leu Glu Trp Met
        35                  40                  45

Gly Gly Ile Met Pro Met Phe Val Ala Ala Asn Tyr Ala Gln Asn Phe
    50                  55                  60

Gln Gly Arg Val Thr Val Ser Val Asp Lys Ser Thr Asn Thr Ala Tyr
65                  70                  75                  80

Met Glu Met His Asn Leu Arg Ser Asp Asp Thr Ala Met Tyr Tyr Cys
                85                  90                  95

Ala Arg Gly Asp Gly Tyr Asn Tyr Lys Trp Tyr Phe Asp Leu Trp Gly
            100                 105                 110

Gln Gly Thr Leu Val Thr Val Ser Ser
        115                 120

<210> SEQ ID NO 144
<211> LENGTH: 108
<212> TYPE: PRT
<213> ORGANISM: Artificial Sequence
<220> FEATURE:
<223> OTHER INFORMATION: RVC38 light chain aa

<400> SEQUENCE: 144

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Pro Pro Lys Leu Leu Ile
        35                  40                  45

Tyr Ala Ala Ser Thr Leu Gln Arg Gly Val Pro Ser Arg Phe Ser Gly
    50                  55                  60

Ser Gly Ser Gly Ser Glu Phe Thr Leu Thr Ile Ser Ser Leu Gln Pro
65                  70                  75                  80

Glu Asp Phe Ala Thr Tyr Tyr Cys Gln Gln Leu Asp Thr Tyr Val Ala
                85                  90                  95

Leu Thr Phe Gly Gly Gly Thr Lys Val Glu Ile Lys
            100                 105

<210> SEQ ID NO 145
<211> LENGTH: 364
<212> TYPE: DNA
<213> ORGANISM: Artificial Sequence
<220> FEATURE:
<223> OTHER INFORMATION: RVC38 heavy chain nuc

<400> SEQUENCE: 145
gaggtgcagc tggtgcagtc tggggctgag gtgaagaagc ctgggtcctc ggtgagggtc    60
tcctgcaagg cttctggagg caccttcagc agctatgcca tcagctgggt gcgacaggcc   120
cctgggctag gcttgagtg gatgggaggg atcatgccta tgtttgtggc ggcaaactac   180
gcacagaact tccagggcag agtcacggtt tctgtggaca atccacgaa caccgcctat   240 atggagatgc acaacctgag atctgacgac acggccatgt attactgtgc gagaggggat   300
ggctacaatt acaagtggta ttttgacctt tggggccagg gaaccctagt caccgtctcc   360
tcag                                                                364

<210> SEQ ID NO 146
<211> LENGTH: 325
<212> TYPE: DNA
<213> ORGANISM: Artificial Sequence
<220> FEATURE:
<223> OTHER INFORMATION: RVC38 light chain nuc

<400> SEQUENCE: 146
gacatccagt tgacccagtc tccatccttc ctgtctgcat ctgtaggaga cagagtcacc    60
atcacttgcc gggccagtca ggacattagt aattatttag cctggtatca gcaaaaacca   120
gggaagcccc ctaaactcct gatctatgct gcatccactt tgcaaagggg ggtcccatca   180
aggttcagtg gcagtggatc tgggtcagaa ttcactctca caatcagcag cctgcagcct   240
gaagattttg caacttatta ctgtcaacag cttgatactt acgtcgcgct cactttcggc   300
ggagggacca aggtggagat caaac                                         325

<210> SEQ ID NO 147
<211> LENGTH: 8
<212> TYPE: PRT
<213> ORGANISM: Artificial Sequence
<220> FEATURE:
<223> OTHER INFORMATION: RVC44 CDRH1 aa

<400> SEQUENCE: 147

```
Gly Phe Thr Phe Ser Ser Tyr Ser
1               5
```

<210> SEQ ID NO 148
<211> LENGTH: 8
<212> TYPE: PRT
<213> ORGANISM: Artificial Sequence
<220> FEATURE:
<223> OTHER INFORMATION: RVC44 CDRH2 aa

<400> SEQUENCE: 148

```
Ile Ser Thr Thr Gly Thr Tyr Ile
1               5
```

<210> SEQ ID NO 149
<211> LENGTH: 17
<212> TYPE: PRT
<213> ORGANISM: Artificial Sequence
<220> FEATURE:
<223> OTHER INFORMATION: RVC44 CDRH3 aa

<400> SEQUENCE: 149

```
Ala Arg Arg Ser Ala Ile Ala Leu Ala Gly Thr Gln Arg Ala Phe Asp
1               5                   10                  15

Ile
```

<210> SEQ ID NO 150
<211> LENGTH: 6
<212> TYPE: PRT
<213> ORGANISM: Artificial Sequence
<220> FEATURE:
<223> OTHER INFORMATION: RVC44 CDRL1 aa

<400> SEQUENCE: 150

```
Gln Asn Ile Asn Asn Tyr
1               5
```

<210> SEQ ID NO 151

<400> SEQUENCE: 151

000

<210> SEQ ID NO 152
<211> LENGTH: 9
<212> TYPE: PRT
<213> ORGANISM: Artificial Sequence
<220> FEATURE:
<223> OTHER INFORMATION: RVC44 CDRL2 long aa

<400> SEQUENCE: 152

```
Leu Ile Tyr Ala Ala Ser Ser Leu His
1               5
```

<210> SEQ ID NO 153
<211> LENGTH: 9
<212> TYPE: PRT
<213> ORGANISM: Artificial Sequence
<220> FEATURE:
<223> OTHER INFORMATION: RVC44 CDRL3 aa

<400> SEQUENCE: 153

```
Gln Gln Ser Tyr Ser Asn Pro Trp Thr
1               5
```

```
<210> SEQ ID NO 154
<211> LENGTH: 24
<212> TYPE: DNA
<213> ORGANISM: Artificial Sequence
<220> FEATURE:
<223> OTHER INFORMATION: RVC44 CDRH1 nuc

<400> SEQUENCE: 154
ggcttcacct ttagtagtta tagt                                              24

<210> SEQ ID NO 155
<211> LENGTH: 24
<212> TYPE: DNA
<213> ORGANISM: Artificial Sequence
<220> FEATURE:
<223> OTHER INFORMATION: RVC44 CDRH2 nuc

<400> SEQUENCE: 155
atcagtacta ctggtactta cata                                              24

<210> SEQ ID NO 156
<211> LENGTH: 51
<212> TYPE: DNA
<213> ORGANISM: Artificial Sequence
<220> FEATURE:
<223> OTHER INFORMATION: RVC44 CDRH3 nuc

<400> SEQUENCE: 156
gcgagacggt cggccatagc actggctggt acgcagcgtg cttttgatat c                51

<210> SEQ ID NO 157
<211> LENGTH: 18
<212> TYPE: DNA
<213> ORGANISM: Artificial Sequence
<220> FEATURE:
<223> OTHER INFORMATION: RVC44 CDRL1 nuc

<400> SEQUENCE: 157
cagaacatta acaactat                                                     18

<210> SEQ ID NO 158

<400> SEQUENCE: 158

000

<210> SEQ ID NO 159
<211> LENGTH: 27
<212> TYPE: DNA
<213> ORGANISM: Artificial Sequence
<220> FEATURE:
<223> OTHER INFORMATION: RVC44 CDRL2 long nuc

<400> SEQUENCE: 159
ctgatctatg ctgcatccag tttacat                                           27

<210> SEQ ID NO 160
<211> LENGTH: 27
<212> TYPE: DNA
<213> ORGANISM: Artificial Sequence
<220> FEATURE:
<223> OTHER INFORMATION: RVC44 CDRL3 nuc

<400> SEQUENCE: 160
caacagagtt acagtaaccc ttggacg                                           27
```

-continued

```
<210> SEQ ID NO 161
<211> LENGTH: 124
<212> TYPE: PRT
<213> ORGANISM: Artificial Sequence
<220> FEATURE:
<223> OTHER INFORMATION: RVC44 heavy chain aa

<400> SEQUENCE: 161
```

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Ser Ile Ser Thr Thr Gly Thr Tyr Ile Tyr Tyr Ala Asp Ser Val
    50                  55                  60

Glu Gly Arg Phe Ser Ile Ser Arg Asp Ser Ala Arg Ser Ser Leu Phe
65                  70                  75                  80

Leu Gln Met Asn Ser Leu Arg Ala Glu Asp Thr Ala Val Tyr Tyr Cys
                85                  90                  95

Ala Arg Arg Ser Ala Ile Ala Leu Ala Gly Thr Gln Arg Ala Phe Asp
            100                 105                 110

Ile Trp Gly Pro Gly Thr Asn Val Ile Val Ser Ser
        115                 120

```
<210> SEQ ID NO 162
<211> LENGTH: 107
<212> TYPE: PRT
<213> ORGANISM: Artificial Sequence
<220> FEATURE:
<223> OTHER INFORMATION: RVC44 light chain aa

<400> SEQUENCE: 162
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Asn Asn Tyr
            20                  25                  30

Leu Asn Trp Tyr Gln Gln Lys Leu Gly Lys Ala Pro Lys Leu Leu Ile
        35                  40                  45

Tyr Ala Ala Ser Ser Leu His Ser Gly Val Pro Ser Arg Phe Ser Ala
    50                  55                  60

Ser Gly Ser Gly Thr Asp Phe Ile Leu Thr Ile Ser Asn Leu Gln Pro
65                  70                  75                  80

Glu Asp Cys Ala Thr Tyr Tyr Cys Gln Gln Ser Tyr Ser Asn Pro Trp
                85                  90                  95

Thr Phe Gly Gln Gly Thr Lys Val Glu Ile Lys
            100                 105

```
<210> SEQ ID NO 163
<211> LENGTH: 373
<212> TYPE: DNA
<213> ORGANISM: Artificial Sequence
<220> FEATURE:
<223> OTHER INFORMATION: RVC44 heavy chain nuc

<400> SEQUENCE: 163
```
gaggtgcagc tggtgcagtc tggggggaggc ctggtcaagc ctgggggggtc cctgagactc      60 tcctgtgcag cctctggctt cacctttagt agttatagta tgagttgggt ccgccaggct     120
ccagggaagg gcctggagtg ggtctcatcc atcagtacta ctggtactta catatactac     180

```
gcagactcag tggagggccg attctccatt tccagagaca gcgccaggag ctctctgttt    240
ctgcaaatga acagcctgag agccgaggac acggctgtct attactgtgc gagacggtcg    300
gccatagcac tggctggtac gcagcgtgct tttgatatct ggggcccagg gacaaacgtc    360
atcgtctctt cag                                                       373

<210> SEQ ID NO 164
<211> LENGTH: 322
<212> TYPE: DNA
<213> ORGANISM: Artificial Sequence
<220> FEATURE:
<223> OTHER INFORMATION: RVC44 light chain nuc

<400> SEQUENCE: 164
gacatccaga tgacccagtc tccatcttcc ctgtctgcat ctgtaggaga cagagtcacc     60
atcacttgcc gggcaagtca gaacattaac aactatttaa attggtatca gcagaaacta    120
gggaaagccc ctaagctcct gatctatgct gcatccagtt tacatagtgg ggtcccatca    180
aggttcagtg ccagtggatc tgggacagat ttcattctga ccatcagtaa tctgcaacct    240
gaagattgtg caacttacta ctgtcaacag agttacagta acccttggac gttcggccaa    300
gggaccaagg tggaaatcaa ac                                             322

<210> SEQ ID NO 165
<211> LENGTH: 8
<212> TYPE: PRT
<213> ORGANISM: Artificial Sequence
<220> FEATURE:
<223> OTHER INFORMATION: RVC58 CDRH1 aa

<400> SEQUENCE: 165

Gly Phe Thr Phe Ser Thr Tyr Ala
1               5

<210> SEQ ID NO 166
<211> LENGTH: 8
<212> TYPE: PRT
<213> ORGANISM: Artificial Sequence
<220> FEATURE:
<223> OTHER INFORMATION: RVC58 CDRH2 aa

<400> SEQUENCE: 166

Ile Ser Asp Arg Gly Gly Ser Arg
1               5

<210> SEQ ID NO 167
<211> LENGTH: 17
<212> TYPE: PRT
<213> ORGANISM: Artificial Sequence
<220> FEATURE:
<223> OTHER INFORMATION: RVC58 CDRH3 aa

<400> SEQUENCE: 167

Ala Arg Asp Ile Ala Pro Pro Tyr Asn Tyr Tyr Phe Tyr Gly Met Asp
1               5                   10                  15
Val

<210> SEQ ID NO 168
<211> LENGTH: 9
<212> TYPE: PRT
<213> ORGANISM: Artificial Sequence
<220> FEATURE:
<223> OTHER INFORMATION: RVC58 CDRL1 aa
```

<400> SEQUENCE: 168

Ser Ser Asp Ile Gly Ala Phe Asn Tyr
1               5

<210> SEQ ID NO 169

<400> SEQUENCE: 169

000

<210> SEQ ID NO 170
<211> LENGTH: 9
<212> TYPE: PRT
<213> ORGANISM: Artificial Sequence
<220> FEATURE:
<223> OTHER INFORMATION: RVC58 CDRL2 long aa

<400> SEQUENCE: 170

Ile Ile Tyr Glu Val Ser Asn Arg Pro
1               5

<210> SEQ ID NO 171
<211> LENGTH: 10
<212> TYPE: PRT
<213> ORGANISM: Artificial Sequence
<220> FEATURE:
<223> OTHER INFORMATION: RVC58 CDRL3 aa

<400> SEQUENCE: 171

Asn Ser Tyr Thr Ser Ser Ser Thr Gln Leu
1               5                   10

<210> SEQ ID NO 172
<211> LENGTH: 24
<212> TYPE: DNA
<213> ORGANISM: Artificial Sequence
<220> FEATURE:
<223> OTHER INFORMATION: RVC58 CDRH1 nuc

<400> SEQUENCE: 172
ggattcacct ttagcaccta tgcc                                              24

<210> SEQ ID NO 173
<211> LENGTH: 24
<212> TYPE: DNA
<213> ORGANISM: Artificial Sequence
<220> FEATURE:
<223> OTHER INFORMATION: RVC58 CDRH2 nuc

<400> SEQUENCE: 173
attagtgata gaggtggtag taga                                              24

<210> SEQ ID NO 174
<211> LENGTH: 51
<212> TYPE: DNA
<213> ORGANISM: Artificial Sequence
<220> FEATURE:
<223> OTHER INFORMATION: RVC58 CDRH3 nuc

<400> SEQUENCE: 174
gcgagagata ttgccccccc atataactac tacttctacg gtatggacgt c                51

<210> SEQ ID NO 175
<211> LENGTH: 27
<212> TYPE: DNA

<213> ORGANISM: Artificial Sequence
<220> FEATURE:
<223> OTHER INFORMATION: RVC58 CDRL1 nuc

<400> SEQUENCE: 175
agcagtgaca ttggtgcttt taactat      27

<210> SEQ ID NO 176

<400> SEQUENCE: 176

000

<210> SEQ ID NO 177
<211> LENGTH: 27
<212> TYPE: DNA
<213> ORGANISM: Artificial Sequence
<220> FEATURE:
<223> OTHER INFORMATION: RVC58 CDRL2 long nuc

<400> SEQUENCE: 177
ataatttatg aggtcagtaa tcggccc      27

<210> SEQ ID NO 178
<211> LENGTH: 30
<212> TYPE: DNA
<213> ORGANISM: Artificial Sequence
<220> FEATURE:
<223> OTHER INFORMATION: RVC58 CDRL3 nuc

<400> SEQUENCE: 178
aactcatata caagcagcag cactcagtta      30

<210> SEQ ID NO 179
<211> LENGTH: 124
<212> TYPE: PRT
<213> ORGANISM: Artificial Sequence
<220> FEATURE:
<223> OTHER INFORMATION: RVC58 heavy chain aa

<400> SEQUENCE: 179

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Gly Ile Ser Asp Arg Gly Gly Ser Arg Tyr Tyr Ala Gly Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Ile Ala Pro Pro Tyr Asn Tyr Tyr Phe Tyr Gly Met Asp
            100                 105                 110

Val Trp Gly Arg Gly Thr Thr Val Thr Val Ser Ser
        115                 120

<210> SEQ ID NO 180
<211> LENGTH: 110
<212> TYPE: PRT
<213> ORGANISM: Artificial Sequence
<220> FEATURE:

<223> OTHER INFORMATION: RVC58 light chain aa

<400> SEQUENCE: 180

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Ala Phe
            20                  25                  30

Asn Tyr Val Ser Trp Tyr Gln Gln His Pro Gly Lys Ala Pro Lys Leu
        35                  40                  45

Ile Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Ser
                85                  90                  95

Ser Thr Gln Leu Phe Gly Gly Gly Thr Lys Leu Thr Val Leu
            100                 105                 110

<210> SEQ ID NO 181
<211> LENGTH: 373
<212> TYPE: DNA
<213> ORGANISM: Artificial Sequence
<220> FEATURE:
<223> OTHER INFORMATION: RVC58 heavy chain nuc

<400> SEQUENCE: 181

```
gaggtgcagc tggtggagtc tgggggaggc ttggtacagc ctggggggtc cctgagactc      60
tcctgtgcgg cctctggatt cacctttagc acctatgcca tgaattgggt ccgccaggct     120
ccagggaagg gctggagtg gtctcaggt attagtgata aggtggtag tagatactac        180
gcaggctccg tgaagggccg gttcaccatc tccagagaca attccaagaa cacgctgttt     240
ctgcaaatga acagcctgag agccgaggac acggccgtat attactgtgc gagagatatt    300
gccccccat ataactacta cttctacggt atggacgtct ggggccgagg gaccacggtc     360
accgtctcct cag                                                        373
```

<210> SEQ ID NO 182
<211> LENGTH: 331
<212> TYPE: DNA
<213> ORGANISM: Artificial Sequence
<220> FEATURE:
<223> OTHER INFORMATION: RVC58 light chain nuc

<400> SEQUENCE: 182

```
cagtctgccc tgactcagcc tgcctccgtg tctgggtctc ctggacagtc gatcaccatc      60
tcctgcactg gtaccagcag tgacattggt gcttttaact atgtctcttg gtaccaacag     120
cacccaggca agcccccaa actcataatt tatgaggtca gtaatcggcc ctcaggggtt     180
tctaatcgct tctctggctc caagtctggc aacacggcct ccctgaccat ctctgggctc     240
caggctgagg acgaggctga ttattactgc aactcatata caagcagcag cactcagtta    300
ttcggcggag ggaccaagct gaccgtccta g                                    331
```

<210> SEQ ID NO 183
<211> LENGTH: 8
<212> TYPE: PRT
<213> ORGANISM: Artificial Sequence
<220> FEATURE:
<223> OTHER INFORMATION: RVC68 CDRH1 aa

```
<400> SEQUENCE: 183

Gly Gly Ser Ile Ser Glu His His
1               5

<210> SEQ ID NO 184
<211> LENGTH: 7
<212> TYPE: PRT
<213> ORGANISM: Artificial Sequence
<220> FEATURE:
<223> OTHER INFORMATION: RVC68 CDRH2 aa

<400> SEQUENCE: 184

Ile Phe His Ser Gly Ser Thr
1               5

<210> SEQ ID NO 185
<211> LENGTH: 14
<212> TYPE: PRT
<213> ORGANISM: Artificial Sequence
<220> FEATURE:
<223> OTHER INFORMATION: RVC68 CDRH3 aa

<400> SEQUENCE: 185

Ala Arg Ala Val Ser Thr Tyr Tyr Tyr Tyr Tyr Ile Asp Val
1               5                   10

<210> SEQ ID NO 186
<211> LENGTH: 6
<212> TYPE: PRT
<213> ORGANISM: Artificial Sequence
<220> FEATURE:
<223> OTHER INFORMATION: RVC68 CDRL1 aa

<400> SEQUENCE: 186

Gln Asp Ile Ser Asn Trp
1               5

<210> SEQ ID NO 187

<400> SEQUENCE: 187

000

<210> SEQ ID NO 188
<211> LENGTH: 9
<212> TYPE: PRT
<213> ORGANISM: Artificial Sequence
<220> FEATURE:
<223> OTHER INFORMATION: RVC68 CDRL2 long aa

<400> SEQUENCE: 188

Leu Ile Tyr Ala Ala Ser Ser Leu Gln
1               5

<210> SEQ ID NO 189
<211> LENGTH: 9
<212> TYPE: PRT
<213> ORGANISM: Artificial Sequence
<220> FEATURE:
<223> OTHER INFORMATION: RVC68 CDRL3 aa

<400> SEQUENCE: 189

Gln Gln Ala Lys Ser Phe Pro Leu Thr
1               5

<210> SEQ ID NO 190
```

```
<211> LENGTH: 24
<212> TYPE: DNA
<213> ORGANISM: Artificial Sequence
<220> FEATURE:
<223> OTHER INFORMATION: RVC68 CDRH1 nuc

<400> SEQUENCE: 190
ggtggctcca ttagtgagca ccac                                          24

<210> SEQ ID NO 191
<211> LENGTH: 21
<212> TYPE: DNA
<213> ORGANISM: Artificial Sequence
<220> FEATURE:
<223> OTHER INFORMATION: RVC68 CDRH2 nuc

<400> SEQUENCE: 191
atctttcaca gtgggagtac c                                             21

<210> SEQ ID NO 192
<211> LENGTH: 42
<212> TYPE: DNA
<213> ORGANISM: Artificial Sequence
<220> FEATURE:
<223> OTHER INFORMATION: RVC68 CDRH3 nuc

<400> SEQUENCE: 192
gcgagagcgg tgtctactta ctactactat tacatagacg tc                      42

<210> SEQ ID NO 193
<211> LENGTH: 18
<212> TYPE: DNA
<213> ORGANISM: Artificial Sequence
<220> FEATURE:
<223> OTHER INFORMATION: RVC68 CDRL1 nuc

<400> SEQUENCE: 193
caggatatta gcaactgg                                                 18

<210> SEQ ID NO 194

<400> SEQUENCE: 194

000

<210> SEQ ID NO 195
<211> LENGTH: 27
<212> TYPE: DNA
<213> ORGANISM: Artificial Sequence
<220> FEATURE:
<223> OTHER INFORMATION: RVC68 CDRL2 long nuc

<400> SEQUENCE: 195
ctgatctatg ctgcgtccag tttgcaa                                       27

<210> SEQ ID NO 196
<211> LENGTH: 27
<212> TYPE: DNA
<213> ORGANISM: Artificial Sequence
<220> FEATURE:
<223> OTHER INFORMATION: RVC68 CDRL3 nuc

<400> SEQUENCE: 196
caacaggcta agagtttccc tcttact                                       27

<210> SEQ ID NO 197
```

-continued

```
<211> LENGTH: 120
<212> TYPE: PRT
<213> ORGANISM: Artificial Sequence
<220> FEATURE:
<223> OTHER INFORMATION: RVC68 heavy chain aa

<400> SEQUENCE: 197

Gln Val Gln Leu Gln Glu Ser Gly Pro Arg Leu Val Lys Pro Ser Glu
1               5                   10                  15

Thr Leu Ser Leu Thr Cys Thr Phe Ser Gly Gly Ser Ile Ser Glu His
            20                  25                  30

His Trp Ser Trp Leu Arg Gln Ser Pro Gly Lys Gly Leu Glu Trp Ile
        35                  40                  45

Gly Tyr Ile Phe His Ser Gly Ser Thr Asn Tyr Asn Pro Ser Leu Lys
    50                  55                  60

Ser Arg Val Asn Ile Ser Leu Asp Lys Ser Lys Asn Gln Phe Ser Leu
65                  70                  75                  80

Lys Leu Ser Ser Val Thr Ala Ala Asp Thr Ala Val Tyr Phe Cys Ala
                85                  90                  95

Arg Ala Val Ser Thr Tyr Tyr Tyr Tyr Ile Asp Val Trp Gly Gln
            100                 105                 110

Gly Thr Thr Val Thr Val Ser Ser
        115                 120

<210> SEQ ID NO 198
<211> LENGTH: 107
<212> TYPE: PRT
<213> ORGANISM: Artificial Sequence
<220> FEATURE:
<223> OTHER INFORMATION: RVC68 light chain aa

<400> SEQUENCE: 198

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Asn Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Ile Ser Ser Arg Phe Ser Gly
    50                  55                  60

Gly Gly Ser Gly Thr Asp Phe Thr Leu Thr Ile Ser Ser Leu Gln Pro
65                  70                  75                  80

Glu Asp Phe Ala Ser Tyr Tyr Cys Gln Gln Ala Lys Ser Phe Pro Leu
                85                  90                  95

Thr Phe Gly Gln Gly Thr Lys Leu Glu Ile Lys
            100                 105

<210> SEQ ID NO 199
<211> LENGTH: 361
<212> TYPE: DNA
<213> ORGANISM: Artificial Sequence
<220> FEATURE:
<223> OTHER INFORMATION: RVC68 heavy chain nuc

<400> SEQUENCE: 199
caggtgcagc tacaggagtc gggcccaaga ctggtgaagc cctcggagac cctgtccctc     60
acctgcactt tctctggtgg ctccattagt gagcaccact ggagctggct ccggcagtcc    120
ccagggaagg gactggagtg gattggatat atctttcaca gtgggagtac caactacaac    180
```

```
ccctcccctca agagtcgagt caacatatca ttagacaagt ccaagaacca gttctccctg    240
aagctgagtt ctgtgaccgc tgcggacacg gccgtgtatt tctgtgcgag agcggtgtct    300
acttactact actattacat agacgtctgg ggccaaggga ccacggtcac cgtctcctca    360
g                                                                   361
```

```
<210> SEQ ID NO 200
<211> LENGTH: 322
<212> TYPE: DNA
<213> ORGANISM: Artificial Sequence
<220> FEATURE:
<223> OTHER INFORMATION: RVC68 light chain nuc

<400> SEQUENCE: 200
gacatccaga tgacccagtc tccatcttcc gtgtctgcat ctgtaggaga cagagtcacc     60
atcacttgtc gggcgagtca ggatattagc aactggttag cctggtatca gcagaaacca    120
gggaaagccc ctaaactcct gatctatgct gcgtccagtt tgcaaagtgg gatctcatct    180
aggttcagcg gcggtggctc tgggacagat ttcactctca ccatcagcag cctgcagcct    240
gaagattttg caagttacta ctgtcaacag gctaagagtt ccctcttac ttttggccag    300 gggaccaagc tggagatcaa ac                                             322
```

```
<210> SEQ ID NO 201
<211> LENGTH: 8
<212> TYPE: PRT
<213> ORGANISM: Artificial Sequence
<220> FEATURE:
<223> OTHER INFORMATION: RVC111 CDRH1 aa

<400> SEQUENCE: 201

Gly Phe Ser Phe Ser Ser Tyr Val
1               5
```

```
<210> SEQ ID NO 202
<211> LENGTH: 8
<212> TYPE: PRT
<213> ORGANISM: Artificial Sequence
<220> FEATURE:
<223> OTHER INFORMATION: RVC111 CDRH2 aa

<400> SEQUENCE: 202

Ile Ser Tyr Asp Gly Ser Asn Lys
1               5
```

```
<210> SEQ ID NO 203
<211> LENGTH: 13
<212> TYPE: PRT
<213> ORGANISM: Artificial Sequence
<220> FEATURE:
<223> OTHER INFORMATION: RVC111 CDRH3 aa

<400> SEQUENCE: 203

Ala Arg Gly Ser Gly Thr Gln Thr Pro Leu Phe Asp Tyr
1               5                   10
```

```
<210> SEQ ID NO 204
<211> LENGTH: 6
<212> TYPE: PRT
<213> ORGANISM: Artificial Sequence
<220> FEATURE:
<223> OTHER INFORMATION: RVC111 CDRL1 aa

<400> SEQUENCE: 204
```

Gln Ser Ile Thr Ser Trp
1               5

<210> SEQ ID NO 205

<400> SEQUENCE: 205

000

<210> SEQ ID NO 206
<211> LENGTH: 9
<212> TYPE: PRT
<213> ORGANISM: Artificial Sequence
<220> FEATURE:
<223> OTHER INFORMATION: RVC111 CDRL2 long aa

<400> SEQUENCE: 206

Leu Ile Tyr Asp Asp Ser Thr Leu Glu
1               5

<210> SEQ ID NO 207
<211> LENGTH: 9
<212> TYPE: PRT
<213> ORGANISM: Artificial Sequence
<220> FEATURE:
<223> OTHER INFORMATION: RVC111 CDRL3 aa

<400> SEQUENCE: 207

Gln Gln Tyr Glu Ser Tyr Ser Gly Thr
1               5

<210> SEQ ID NO 208
<211> LENGTH: 24
<212> TYPE: DNA
<213> ORGANISM: Artificial Sequence
<220> FEATURE:
<223> OTHER INFORMATION: RVC111 CDRH1 nuc

<400> SEQUENCE: 208
ggattctcct tcagtagcta tgtt                                          24

<210> SEQ ID NO 209
<211> LENGTH: 24
<212> TYPE: DNA
<213> ORGANISM: Artificial Sequence
<220> FEATURE:
<223> OTHER INFORMATION: RVC111 CDRH2 nuc

<400> SEQUENCE: 209
atatcatatg atggaagtaa taaa                                          24

<210> SEQ ID NO 210
<211> LENGTH: 39
<212> TYPE: DNA
<213> ORGANISM: Artificial Sequence
<220> FEATURE:
<223> OTHER INFORMATION: RVC111 CDRH3 nuc

<400> SEQUENCE: 210
gcgagagggt ccggaaccca aactcccctc tttgactac                          39

<210> SEQ ID NO 211
<211> LENGTH: 18
<212> TYPE: DNA
<213> ORGANISM: Artificial Sequence
<220> FEATURE:
<223> OTHER INFORMATION: RVC111 CDRL1 nuc

<400> SEQUENCE: 211
cagagtatta ctagctgg                                                      18

<210> SEQ ID NO 212

<400> SEQUENCE: 212

000

<210> SEQ ID NO 213
<211> LENGTH: 27
<212> TYPE: DNA
<213> ORGANISM: Artificial Sequence
<220> FEATURE:
<223> OTHER INFORMATION: RVC111 CDRL2 long nuc

<400> SEQUENCE: 213
ctgatctatg atgactccac tttggaa                                            27

<210> SEQ ID NO 214
<211> LENGTH: 27
<212> TYPE: DNA
<213> ORGANISM: Artificial Sequence
<220> FEATURE:
<223> OTHER INFORMATION: RVC111 CDRL3 nuc

<400> SEQUENCE: 214
caacagtatg agagttattc agggacg                                            27

<210> SEQ ID NO 215
<211> LENGTH: 120
<212> TYPE: PRT
<213> ORGANISM: Artificial Sequence
<220> FEATURE:
<223> OTHER INFORMATION: RVC111 heavy chain aa

<400> SEQUENCE: 215

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Val Met Tyr Trp Val Arg Gln Ala Pro Gly Lys Gly Leu Glu Trp Val
        35                  40                  45

Thr Ile Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Gly Thr Gln Thr Pro Leu Phe Asp Tyr Trp Gly Gln
            100                 105                 110

Gly Thr Leu Val Thr Val Ser Ser
        115                 120

<210> SEQ ID NO 216
<211> LENGTH: 107
<212> TYPE: PRT
<213> ORGANISM: Artificial Sequence
<220> FEATURE:
<223> OTHER INFORMATION: RVC111 light chain aa

<400> SEQUENCE: 216

Asp Ile Gln Met Thr Gln Ser Pro Ser Thr Leu Ser Ala Ser Val Gly
1               5                   10                  15

Asp Arg Val Thr Ile Thr Cys Arg Ala Asn Gln Ser Ile Thr Ser Trp
            20                  25                  30

Val Ala Trp Tyr Gln Gln Met Pro Gly Arg Ala Pro Lys Leu Leu Ile
        35                  40                  45

Tyr Asp Asp Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Glu Ser Tyr Ser Gly
            85                  90                  95

Thr Phe Gly Gln Gly Thr Lys Val Glu Ile Lys
            100                 105

<210> SEQ ID NO 217
<211> LENGTH: 361
<212> TYPE: DNA
<213> ORGANISM: Artificial Sequence
<220> FEATURE:
<223> OTHER INFORMATION: RVC111 heavy chain nuc

<400> SEQUENCE: 217
caggtgcaac tggtggagtc tgggggaggc gtggtccagc ctggggaggtc cctgagactc      60 tcctgtgcag cctctggatt ctccttcagt agctatgtta tgtactgggt ccgccaggct    120
ccaggcaagg ggctggagtg ggtgacaatt atatcatatg atggaagtaa taaatactac    180
gcagactccg tgaagggccg attcaccatc tccagagaca attccaagaa cacgctgtat    240
ctgcaaatga acagcctgag agctgaggac acggctgtct attactgtgc gagagggtcc    300
ggaacccaaa ctcccctctt tgactactgg ggccagggaa ccctggtcac cgtctcctca    360
g                                                                    361

<210> SEQ ID NO 218
<211> LENGTH: 322
<212> TYPE: DNA
<213> ORGANISM: Artificial Sequence
<220> FEATURE:
<223> OTHER INFORMATION: RVC111 light chain nuc

<400> SEQUENCE: 218
gacatccaga tgacccagtc tccttccacc ctgtctgcat ctgtgggaga cagagtcacc      60
atcacttgcc gggccaatca gagtattact agctgggtgg cctggtatca gcagatgcca    120
gggagagccc ctaaactcct gatctatgat gactccactt ggaaagtgg ggtcccatca      180 aggttcagcg gcagtggatc tgggacagaa ttcactctca ccatcagcag cctgcagcct    240
gatgattttg caacttatta ctgccaacag tatgagagtt attcagggac gttcggccaa    300
gggaccaagg tggaaatcaa ac                                              322